United States Patent
Montenegro et al.

(10) Patent No.: US 9,812,648 B2
(45) Date of Patent: *Nov. 7, 2017

(54) SPIROBIFLUORENE COMPOUNDS FOR ORGANIC ELECTROLUMINESCENT DEVICES

(71) Applicant: Merck Patent GmbH, Darmstadt (DE)

(72) Inventors: Elvira Montenegro, Weinheim (DE); Amir H. Parham, Frankfurt am Main (DE); Philipp Stoessel, Frankfurt am Main (DE); Teresa Mujica-Fernaud, Darmstadt (DE); Frank Voges, Bad Duerkheim (DE); Arne Buesing, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/378,529

(22) PCT Filed: Jan. 21, 2013

(86) PCT No.: PCT/EP2013/000177
§ 371 (c)(1),
(2) Date: Aug. 13, 2014

(87) PCT Pub. No.: WO2013/120577
PCT Pub. Date: Aug. 22, 2013

(65) Prior Publication Data
US 2015/0065730 A1   Mar. 5, 2015

Related U.S. Application Data

(60) Provisional application No. 61/716,810, filed on Oct. 22, 2012.

(30) Foreign Application Priority Data

Feb. 14, 2012 (EP) .................................... 12000929

(51) Int. Cl.
| | | |
|---|---|---|
| *C07D 279/22* | (2006.01) | |
| *C07D 333/76* | (2006.01) | |
| *C07D 209/88* | (2006.01) | |
| *C07D 307/91* | (2006.01) | |
| *C07D 209/86* | (2006.01) | |

(Continued)

(52) U.S. Cl.
CPC ........ *H01L 51/0058* (2013.01); *C07C 211/54* (2013.01); *C07C 211/58* (2013.01); *C07C 211/61* (2013.01); *C07D 209/86* (2013.01); *C07D 209/88* (2013.01); *C07D 265/38* (2013.01); *C07D 279/22* (2013.01); *C07D 307/91* (2013.01); *C07D 333/76* (2013.01); *C09K 11/06* (2013.01); *H01L 51/006* (2013.01); *H01L 51/0061* (2013.01); *H01L 51/0072* (2013.01); *H01L 51/0073* (2013.01); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *H01L 51/0067* (2013.01); *H01L 51/5012* (2013.01); *H01L 51/5016* (2013.01);

(Continued)

(58) Field of Classification Search
CPC .. C07D 279/22; C07D 333/76; C07D 209/88; C07D 307/91; C07D 209/86; C07D 265/38; C07C 211/54; C07C 211/58; C07C 211/61

See application file for complete search history.

(56) References Cited

U.S. PATENT DOCUMENTS

| 6,933,063 B2 | 8/2005 | Lee et al. |
| 7,781,579 B2 * | 8/2010 | Park ...................... C07C 211/54 544/101 |

(Continued)

FOREIGN PATENT DOCUMENTS

| CN | 103108859 A | 5/2013 | |
| DE | WO 2012034627 A1 * | 3/2012 | ........... C07C 211/61 |

(Continued)

OTHER PUBLICATIONS

Chemical Abstract Service (CAS) STN Registry No. (RN) 1291081-78-1 [entered STN: May 6, 2011].*

(Continued)

*Primary Examiner* — Michael Barker
*Assistant Examiner* — Amanda L Aguirre

(57) ABSTRACT

Spirobifluroene compounds of the formula (1) which are suitable for use in electronic devices, formula (1)

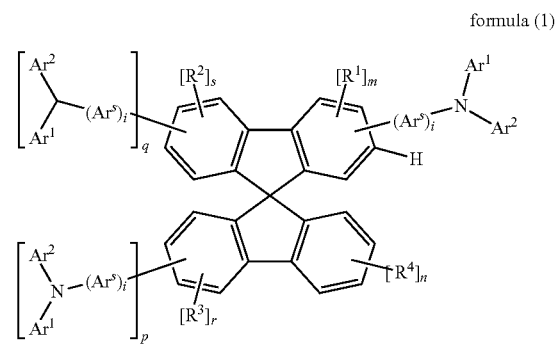

and in particular organic electroluminescent devices, and to electronic devices that include the spirobifluorene compounds.

10 Claims, No Drawings

(51) Int. Cl.
| | |
|---|---|
| *C07D 265/38* | (2006.01) |
| *C07C 211/61* | (2006.01) |
| *C07C 211/58* | (2006.01) |
| *H01L 51/00* | (2006.01) |
| *C09K 11/06* | (2006.01) |
| *C07C 211/54* | (2006.01) |
| *H01L 51/50* | (2006.01) |

(52) U.S. Cl.
CPC ...... *H01L 51/5056* (2013.01); *H01L 51/5096* (2013.01); *Y02E 10/549* (2013.01)

(56) References Cited

U.S. PATENT DOCUMENTS

| | | | | |
|---|---|---|---|---|
| 7,816,668 | B2 * | 10/2010 | Kawakami | ............ C07C 211/61 257/40 |
| 9,312,495 | B2 | 4/2016 | Pflumm et al. | |
| 2002/0061419 | A1 | 5/2002 | Woo et al. | |
| 2006/0063027 | A1 | 3/2006 | Vestweber et al. | |
| 2007/0252516 | A1 * | 11/2007 | Kondakova | ......... H01L 51/5016 313/504 |
| 2008/0220285 | A1 * | 9/2008 | Vestweber | ............... C07C 13/62 428/690 |
| 2009/0167161 | A1 * | 7/2009 | Yabunouchi | .......... C07C 211/61 313/504 |
| 2010/0084647 | A1 * | 4/2010 | Kondakova | ......... H01L 51/0058 257/40 |
| 2010/0108997 | A1 * | 5/2010 | Kim | ...................... C07C 211/54 257/40 |
| 2011/0232763 | A1 | 9/2011 | Kang et al. | |
| 2012/0126179 | A1 | 5/2012 | Parham et al. | |
| 2012/0228552 | A1 | 9/2012 | Parham et al. | |
| 2014/0203216 | A1 | 7/2014 | Parham et al. | |

FOREIGN PATENT DOCUMENTS

| | | | | |
|---|---|---|---|---|
| JP | 2006-063036 | A | | 3/2006 |
| JP | 2006-511939 | A | | 4/2006 |
| JP | 2011/173973 | A * | | 9/2011 |
| JP | 2011173973 | A * | | 9/2011 |
| JP | 2011173973 | A | | 9/2011 |
| KR | 2003-0008993 | A | | 1/2003 |
| KR | 2003-0041996 | A | | 5/2003 |
| KR | 2004-0082849 | A | | 9/2004 |
| KR | 1029082 | B1 * | | 4/2011 |
| KR | 101029082 | B1 * | 4/2011 | ........... C07D 307/91 |
| KR | WO2011049325 | A2 * | | 4/2011 |
| WO | WO-2011006574 | A1 | | 1/2011 |
| WO | WO-2011060877 | A2 | | 5/2011 |
| WO | WO-2013017192 | A1 | | 2/2013 |

OTHER PUBLICATIONS

English machine translation of Tanaka et al. JP 2011-173973 A (Sep. 8, 2011).*
WO 2012034627 A1 English Machine Translation. [online] [retrieved on Nov. 9, 2016]. Retrieved from: Google Patents.*
KR 101029082 B1 English Machine Traslation. [online] [retrieved on Feb. 22, 2017]. Retrieved from: Korean Intellectual Property Office.*
Choi et al. KR 1029082 B1 (Apr. 12, 2011) English machine translation obtained from the Korean Intellectual Property Office.*
International Search Report for PCT/EP2013/000177 dated May 22, 2013.
Chinese Office Action with English Translation for Application No. 201510570760.0, dated Mar. 6, 2017.
Jiang, Z., et al., "Novel Oligo-9,9'-spirabifluorenes through ortho-Linkage as Full Hydrocarbon Host for Highly Efficient Phosphorescent OLEDs", Organic Letters, 2009, vol. 11, No. 12, pp. 2607-2610.
Uoyama, H., "Highly efficient organic light-emitting diodes from delayed fluorescence", Nature, 2012, vol. 492, pp. 234-238.
Chinese Office Action dated Mar. 14, 2017 in Application No. 201480017424.7.

* cited by examiner

SPIROBIFLUORENE COMPOUNDS FOR ORGANIC ELECTROLUMINESCENT DEVICES

CROSS-REFERENCE TO RELATED APPLICATIONS

This application is a national stage application (under 35 U.S.C. §371) of PCT/EP2013/000177, filed Jan. 21, 2013, which claims benefit of European Application No. 12000929.5, filed Feb. 14, 2012 and U.S. Provisional Application 61/716, 810, filed Oct. 22, 2012, which are incorporated herein by reference in their entirety.

The present invention relates to materials for use in electronic devices, in particular in organic electroluminescent devices, and to electronic devices comprising these materials.

The structure of organic electroluminescent devices (OLEDs) in which organic semiconductors are employed as functional materials is described, for example, in U.S. Pat. Nos. 4,539,507, 5,151,629, EP 0676461 and WO 98/27136. The emitting materials employed here are increasingly organometallic complexes which exhibit phosphorescence instead of fluorescence (M. A. Baldo et al., *Appl. Phys. Lett.* 1999, 75, 4-6).

In accordance with the prior art, the hole-transport materials used in the hole-transport layer or in the hole-injection layer are, in particular, triarylamine derivatives which frequently contain at least two triarylamino groups or at least one triarylamino group and at least one carbazole group. These compounds are frequently derived from diarylamino-substituted triphenylamines (TPA type), from diarylamino-substituted biphenyl derivatives (TAD type) or combinations of these base compounds. Furthermore, for example, use is made of spirobifluorene derivatives which are substituted in the 2,7- or 2,2',7,7-position by two or four diarylamino groups (for example in accordance with EP 676461 or U.S. Pat. No. 7,714,145). Furthermore known are spirobifluorene derivatives which are substituted in the 4,4'-position in each case by diphenylamino groups. In the case of these compounds, there is furthermore a need for improvement both in the case of fluorescent and in the case of phosphorescent OLEDs, in particular with respect to efficiency, lifetime and operating voltage on use in an organic electroluminescent device.

The object of the present invention is to provide compounds which are suitable for use in a fluorescent or phosphorescent OLED, in particular a phosphorescent OLED, for example as hole-transport material in a hole-transport or exciton-blocking layer or as matrix material in an emitting layer. Surprisingly, it has been found that certain compounds described below in greater detail achieve this object and result in significant improvements in the organic electroluminescent device, in particular with respect to the lifetime, the efficiency and the operating voltage. This applies to phosphorescent and fluorescent electroluminescent devices, especially on use of the compounds according to the invention as hole-transport material or as matrix material. The materials generally have high thermal stability and can therefore be sublimed without decomposition and without a residue. The present invention therefore relates to these materials and to electronic devices which comprise compounds of this type.

In particular, it is a surprising result that very good results are also obtained, in particular, with aromatic monoamines, since hole-transport materials containing at least two nitrogen atoms are generally employed in organic electroluminescent devices.

The present invention therefore relates to a compound of the following formula (1):

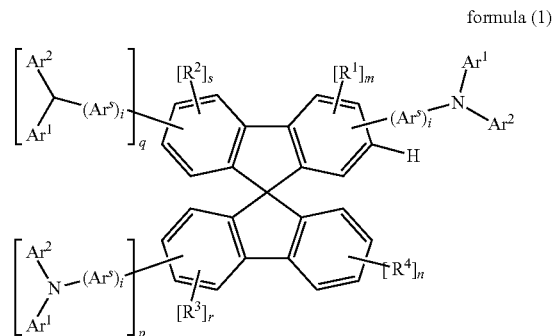

formula (1)

where the following applies to the symbols and indices used:

$Ar^1$ is on each occurrence, identically or differently, an aromatic or heteroaromatic ring system having 6 to 60 C atoms, selected from the group consisting of fluorene, spirobifluorene, biphenyl, terphenyl, quaterphenyl, carbazole, dibenzofuran and dibenzothiophene, each of which may also be substituted by one or more radicals $R^5$; $Ar^1$ and $Ar^2$ here may also be connected to one another by a group E;

$Ar^2$ is on each occurrence, identically or differently, an aromatic or heteroaromatic ring system having 6 to 60 C atoms, which may in each case also be substituted by one or more radicals $R^5$; $Ar^1$ and $Ar^2$ here may also be connected to one another by a group E;

$Ar^5$ is on each occurrence, identically or differently, an aromatic or heteroaromatic ring system having 6 to 60 C atoms, which may in each case also be substituted by one or more radicals $R^5$;

E is on each occurrence, identically or differently, a single bond, $C(R^5)_2$, $NR^5$, O or S;

$R^1$, $R^2$, $R^3$, $R^4$ are selected on each occurrence, identically or differently, from the group consisting of H, D, F, Cl, Br, I, CN, $Si(R^6)_3$, a straight-chain alkyl, alkoxy or thioalkyl group having 1 to 40 C atoms or a branched or cyclic alkyl, alkoxy or thioalkyl group having 3 to 40 C atoms, each of which may be substituted by one or more radicals $R^6$, where in each case one or more non-adjacent $CH_2$ groups may be replaced by $Si(R^6)_2$, $C=NR^6$, $P(=O)(R^6)$, SO, $SO_2$, $NR^6$, O, S or $CONR^6$ and where one or more H atoms may be replaced by D, F, Cl, Br or I, an aromatic or heteroaromatic ring system having 6 to 60 C atoms, which may in each case be substituted by one or more radicals $R^6$, an aryloxy or heteroaryloxy group having 5 to 60 aromatic ring atoms, which may be substituted by one or more radicals $R^6$, or an aralkyl or heteroaralkyl group having 5 to 60 aromatic ring atoms, which may in each case be substituted by one or more radicals $R^6$, where two or more adjacent substituents $R^1$ or $R^2$ or $R^3$ or $R^4$ may optionally form a mono- or polycyclic, aliphatic ring system, which may be substituted by one or more radicals $R^6$;

$R^5$ is selected on each occurrence, identically or differently, from the group consisting of H, D, F, Cl, Br, I, CN, $Si(R^6)_3$, a straight-chain alkyl, alkoxy or thioalkyl group having 1 to 40 C atoms or a branched or cyclic alkyl, alkoxy or thioalkyl group having 3 to 40 C atoms, each of which may be substituted by one or more radicals $R^6$, where in each case one or more non-adjacent $CH_2$ groups may be replaced by $Si(R^6)_2$, $C=NR^6$, $P(=O)(R^6)$, SO, $SO_2$, $NR^6$, O, S or $CONR^6$ and where one or more H atoms may be replaced by D, F, Cl, Br or I, an aromatic or heteroaromatic ring system having 6 to 60 C atoms, which may in each case be substituted by one or more radicals $R^6$, an aryloxy or heteroaryloxy group having 5 to 60 aromatic ring atoms, which may be substituted by one or more radicals $R^6$, or an aralkyl or heteroaralkyl group having 5 to 60 aromatic ring atoms, which may in each case be substituted by one or more radicals $R^6$, where two or more adjacent substituents $R^5$ may optionally form a mono- or polycyclic, aliphatic ring system, which may be substituted by one or more radicals $R^6$;

$R^6$ is selected from the group consisting of H, D, F, an aliphatic hydrocarbon radical having 1 to 20 C atoms or an aromatic or heteroaromatic ring system having 5 to 30 C atoms, in which one or more H atoms may be replaced by D or F, where two or more adjacent substituents $R^6$ may form a mono- or polycyclic, aliphatic ring system with one another;

i is on each occurrence, identically or differently, 0 or 1;
m is 0, 1 or 2;
n is on each occurrence, identically or differently, 0, 1, 2, 3 or 4;
p, q are on each occurrence, identically or differently, 0 or 1;
r, s are on each occurrence, identically or differently, 0, 1, 2, 3 or 4, where p+r≤4 and q+s≤4.

In addition, the present invention relates to a compound of a formula (1), with the proviso that the following definitions apply to groups $Ar^1$ and $Ar^2$ instead of the definitions above:
groups $Ar^1$ and $Ar^2$ are connected to each other via a group E, as defined above, and
groups $Ar^1$ and $Ar^2$ are, identically or differently on each occurrence, an aromatic or heteroaromatic ring system having 6 to 60 C atoms, which may in each case also be substituted by one or more radicals $R^5$.

An aryl group in the sense of this invention is taken to mean either a simple aromatic ring, i.e. benzene, or a condensed (anellated) aryl group, for example naphthalene or phenanthrene. By contrast, aromatic groups linked to one another by a single bond, such as, for example, biphenyl or fluorene, are not referred to as an aryl group, but instead as an aromatic ring system.

A heteroaryl group in the sense of the present invention comprises at least one heteroatom in the aromatic ring, preferably a heteroatom selected from N, O and S. A heteroaryl group may comprise only a simple heteroaromatic ring, such as e.g. pyridine, triazine, or thiophene, or it may be a condensed (anellated) heteroaryl group, such as quinoline or carbazole.

An aromatic ring system in the sense of this invention contains 6 to 60 C atoms in the ring system, where the aromatic ring system may be built up e.g. from benzene, naphthalene, phenanthrene, fluorene and spirobifluorene or combinations of these groups. An aromatic ring system in the sense of this invention is, in particular, also intended to be taken to mean a system in which, in addition, a plurality of aryl groups is linked to one another directly or via a carbon atom. Thus, for example, systems such as biphenyl, terphenyl, quaterphenyl, fluorene, 9,9'-spirobifluorene, 9,9-diarylfluorene, etc., in particular, are also intended to be taken to be aromatic ring systems in the sense of this invention. The aromatic ring system here by definition contains no amino groups. Triarylamino groups are thus not covered by the definition of an aromatic ring system.

An analogous definition applies to the term heteroaromatic ring system, which is to be understood to be a combination of two or more interconnected aryl or heteroaryl groups, at least one of them being a heteroaryl group.

An aralkyl group is to be understood to be an alkyl group which is substituted by an aryl group, where the aryl group is defined as above, and the alkyl group may have 1 to 20 C atoms, and may be substituted as defined above for alkyl groups, and may have one or more $CH_2$ groups replaced as defined above for alkyl groups. In the aralkyl group, the alkyl group is the group which bonds to the rest of the compound. An analogous definition applies to the term heteroaralkyl group, only that a heteroaryl group is present instead of an aryl group.

An aryloxy group is to be understood to be an aryl group bonded via a divalent (ether) oxygen atom. An analogous definition applies to the term heteroaryloxy group, only that a heteroaryl group is present instead of an aryl group.

For the purposes of the present invention, an aliphatic hydrocarbon radical or an alkyl group or an alkenyl or alkynyl group, which may typically contain 1 to 40 or also 1 to 20 C atoms and in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl.

An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy or 2,2,2-trifluoroethoxy.

A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

In general, alkyl, alkoxy or thioalkyl groups in accordance with the present invention can be straight-chain, branched or cyclic, where one or more non-adjacent $CH_2$ groups may be replaced by the above-mentioned groups; furthermore, one or more H atoms may also be replaced by D, F, Cl, Br, I, CN or $NO_2$, preferably F, Cl or CN, further preferably F or CN, particularly preferably CN.

In a preferred embodiment of the invention, p+q=0 or 1. The compound according to the invention thus preferably contains one or two diarylamino groups.

In a preferred embodiment, m, s, r, and n are identically or differently on each occurrence 0 or 1, more preferably 0.

According to a further preferred embodiment of the invention, not more than one index i in the formula (1) is 1. More preferably, the index i is generally equal to 0. For the case that the index i is 0, it is to be understood that the spirobifluorene and the nitrogen atom are directly connected.
In a preferred embodiment of the invention, the compound of the formula (1) is selected from the compounds of the following formulae (2) to (10),
formula (2)
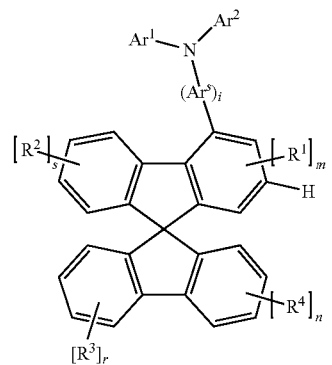
formula (3)
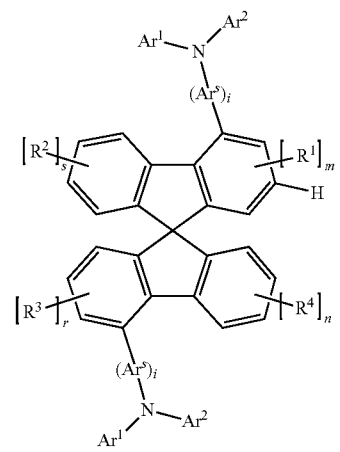
formula (4)
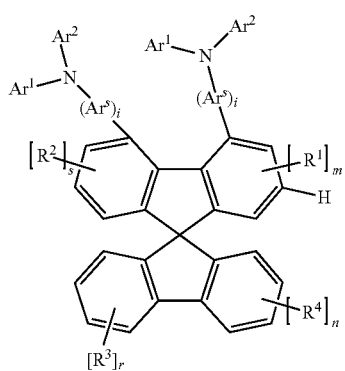
formula (5)
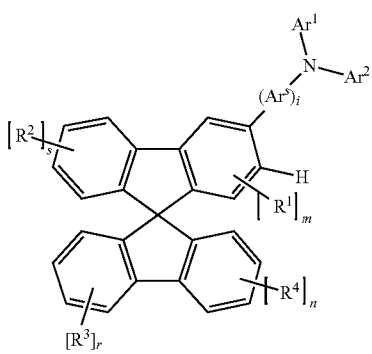
formula (6)
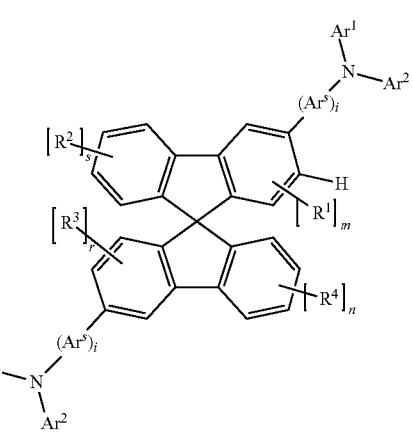
formula (7)
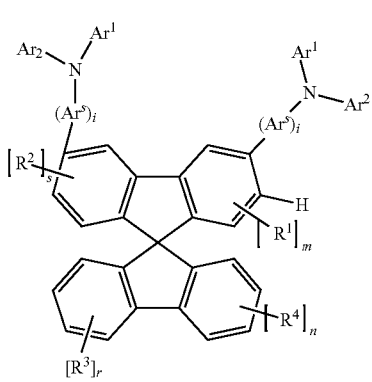
formula (8)
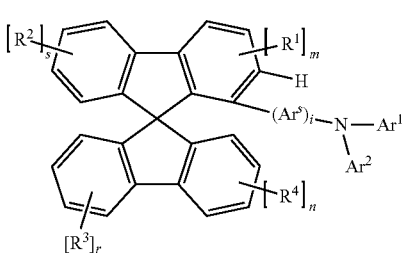

formula (9)

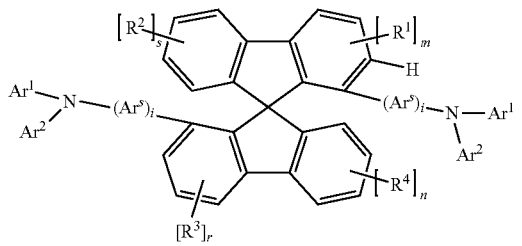

formula (10)

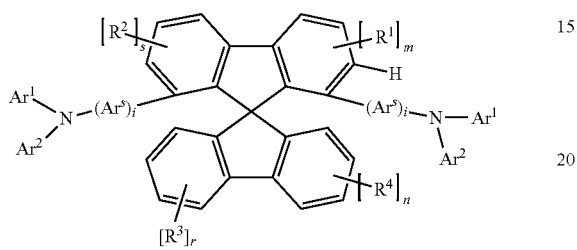

where the symbols and indices used have the meanings given above.

For the compounds according to formulae (2) to (10) above, it is preferred that i=0.

In a particularly preferred embodiment of the invention, the compounds of the formulae (2) to (10) are selected from the compounds of the following formulae (2a) to (10a), formula (2a)

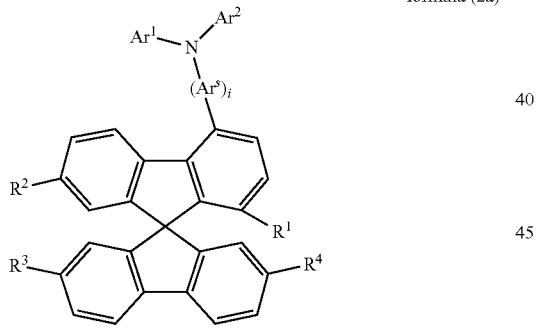

formula (3a)

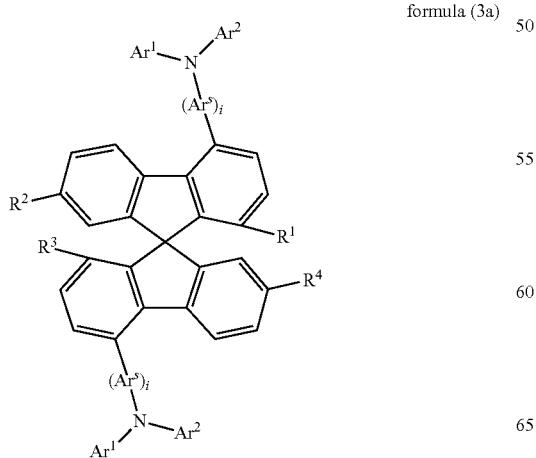

formula (4a)

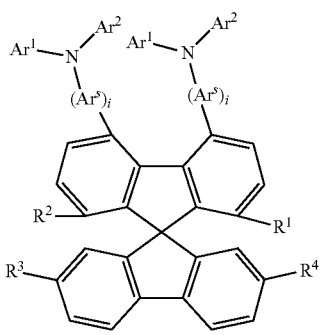

formula (5a)

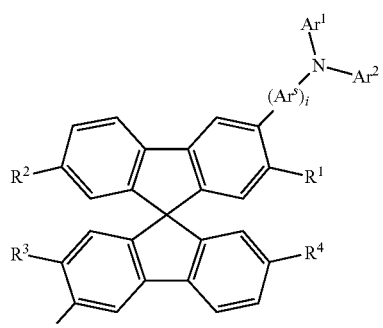

formula (6a)

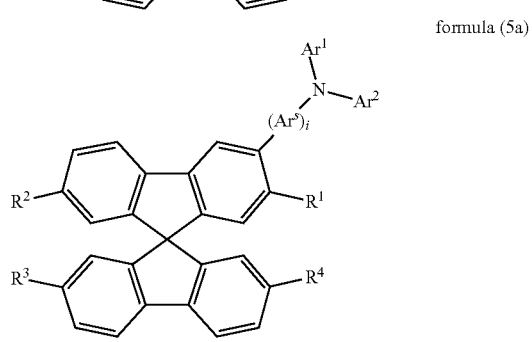

formula (7a)

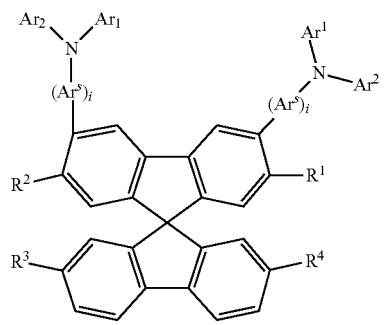

formula (8a)

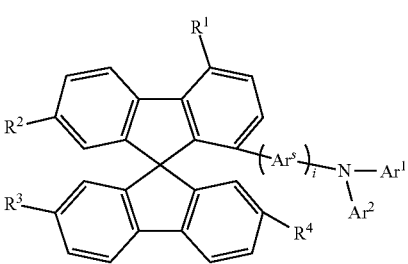

formula (9a)
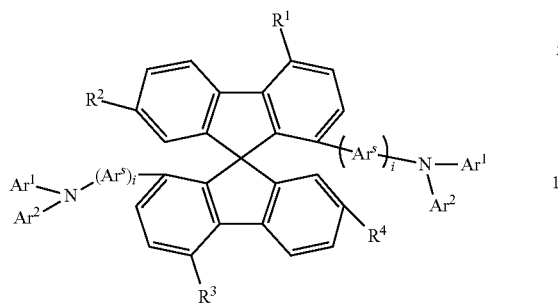
formula (10a)
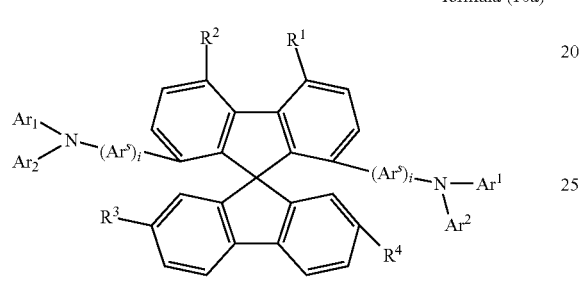
where the symbols and indices used have the meanings given above.
For the compounds according to formulae (2a) to (10a) above, it is preferred that i=0.
Very particular preference is given to the compounds of the following formulae (2b) to (10b),
formula (2b)
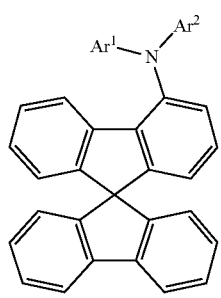
formula (3b)
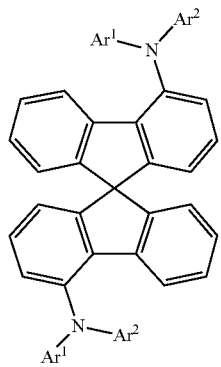
formula (4b)
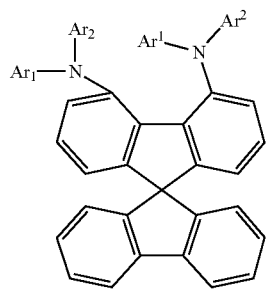
formula (5b)
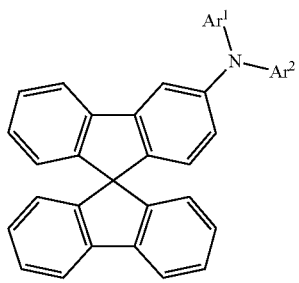
formula (6b)
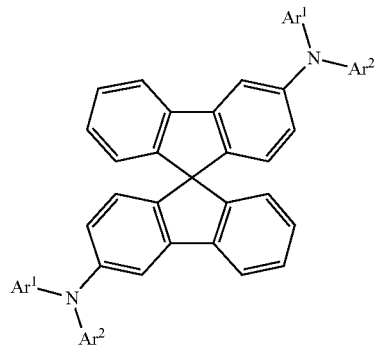
formula (7b)
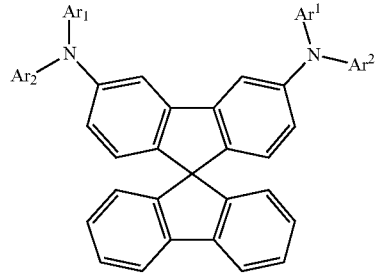
formula (8b)
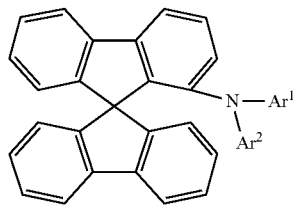
formula (9b)
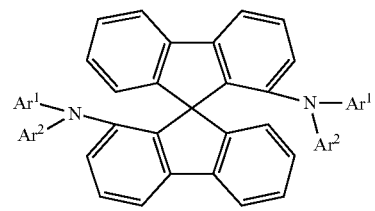

-continued

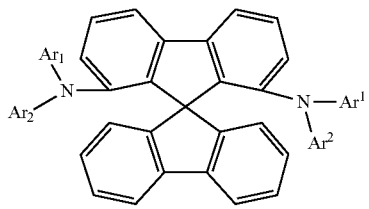

formula (10b)

where the symbols used have the meanings given above.

In a particularly preferred embodiment of the invention, the compound according to the invention contains only one diarylamino group —NAr$^1$Ar$^2$. This thus preferably relates to compounds of the formulae (2), (5) and (8) or (2a), (5a) and (8a) or (2b), (5b) and (8b).

In a further preferred embodiment of the invention, the diarylamino groups —NAr$^1$Ar$^2$ are bonded in the 4-position or in the 4- and 4'-position of the spirobifluorene. This thus preferably relates to the compounds of the formulae (2) and (3) or (2a) and (3a) or (2b) and (3b).

Very particular preference is given to the compounds of the formula (2) or (2a) or (2b).

In a further preferred embodiment of the invention, Ar$^2$ is selected, identically or differently, from the group consisting of fluorene, spirobifluorene, biphenyl, terphenyl, quaterphenyl, carbazole, dibenzofuran and dibenzothiophene, each of which may be substituted by one or more radicals R$^5$.

The groups Ar$^1$ and Ar$^2$ here are preferably selected, identically or differently on each occurrence, from the groups of the following formulae (11) to (66),

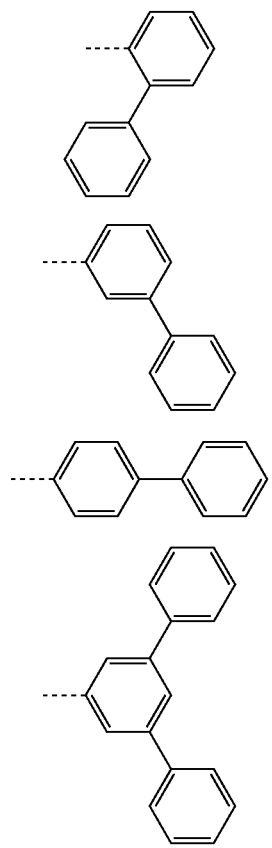

formula (11)

formula (12)

formula (13)

formula (14)

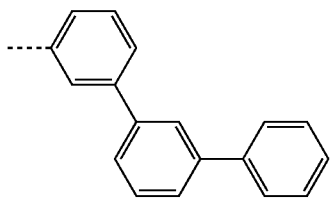

formula (15)

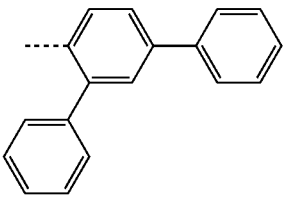

formula (16)

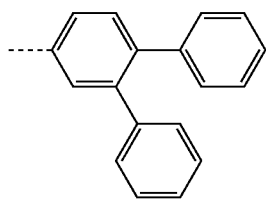

formula (17)

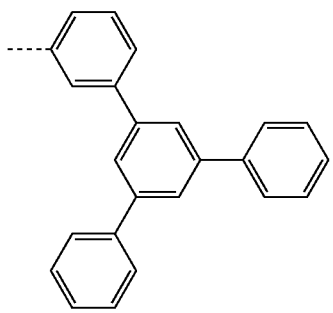

formula (18)

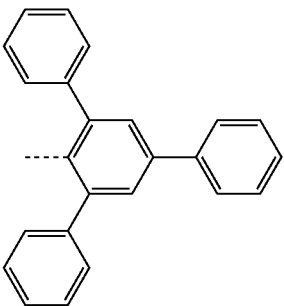

formula (19)

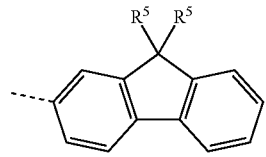

formula (20)

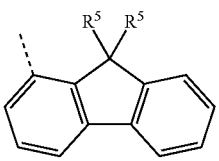

formula (21)

-continued
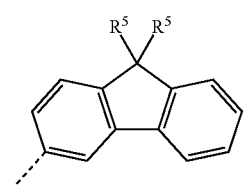
formula (22)
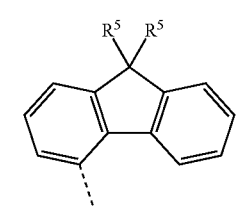
formula (23)
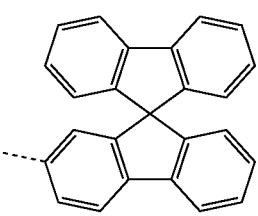
formula (24)
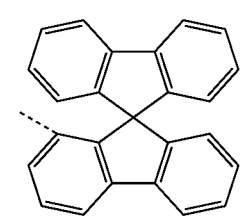
formula (25)
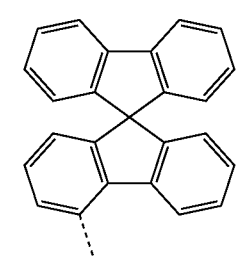
formula (26)
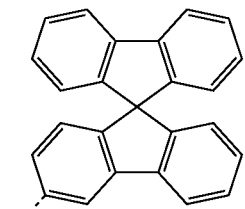
formula (27)
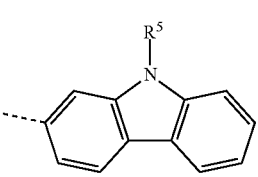
formula (28)
-continued
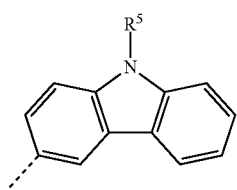
formula (29)
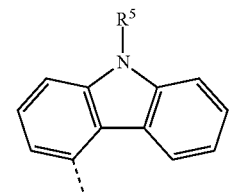
formula (30)
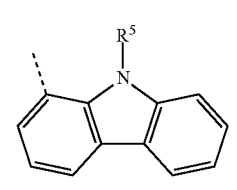
formula (31)
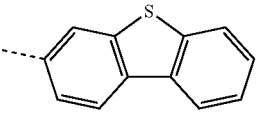
formula (32)
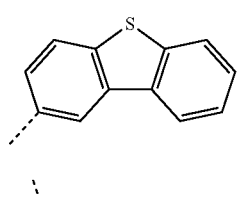
formula (33)
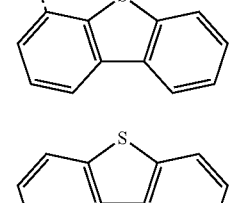
formula (34)
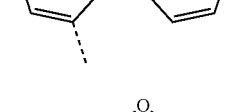
formula (35)
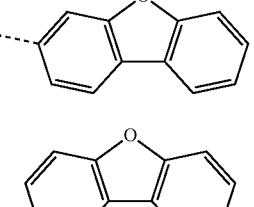
formula (36)
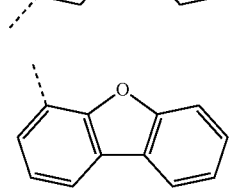
formula (37)
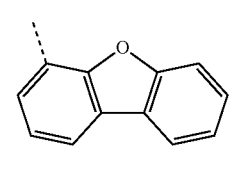
formula (38)

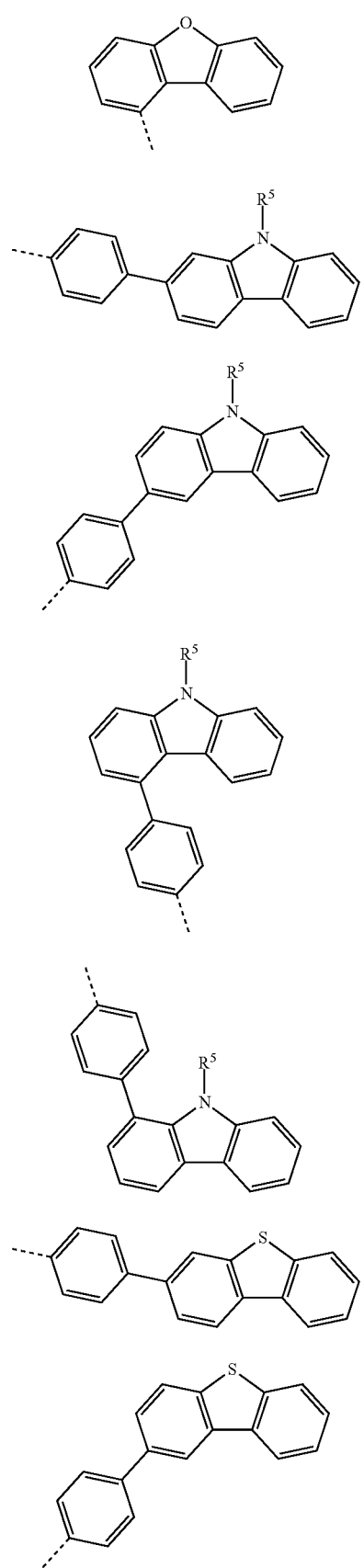
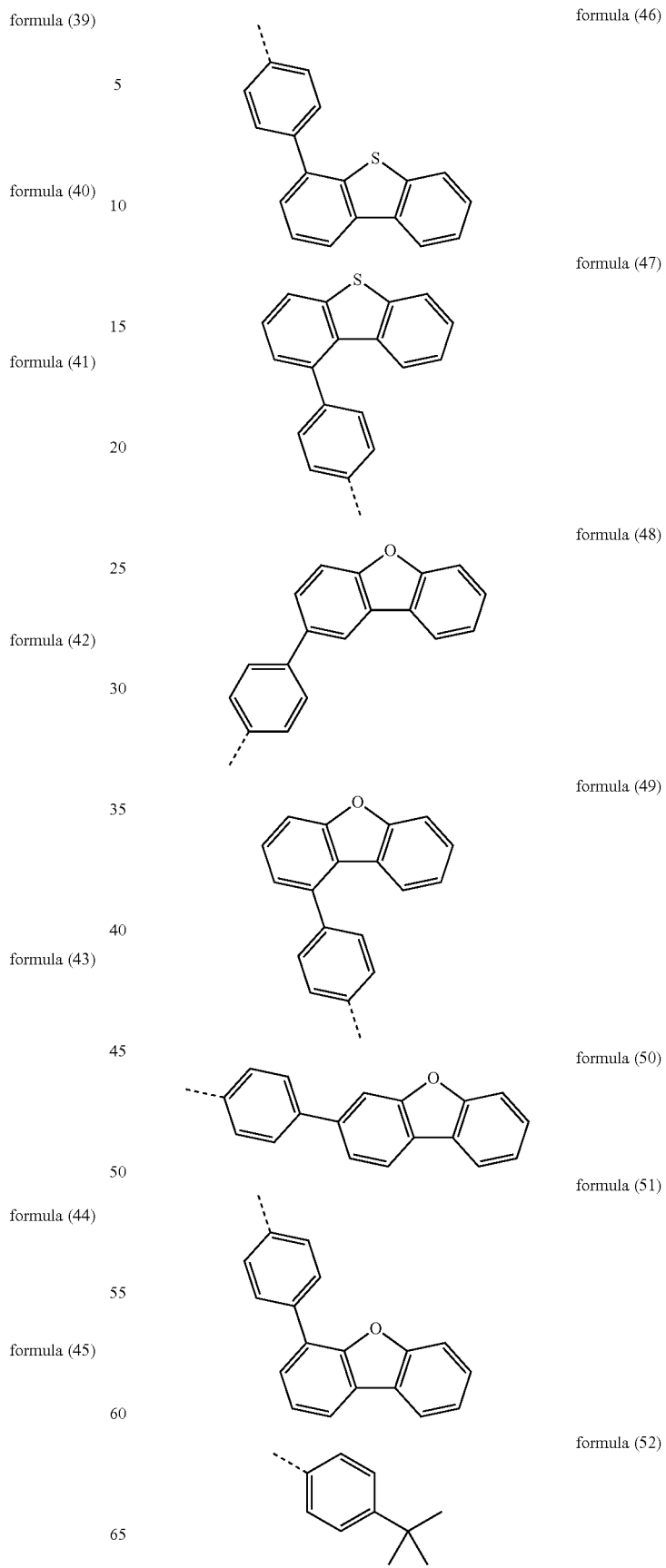

formula (53)
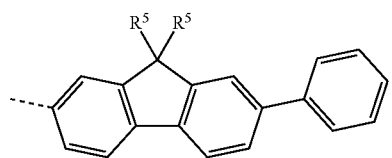
formula (54)
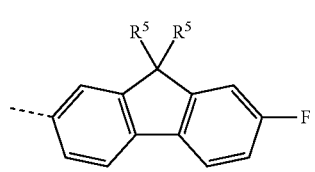
formula (55)
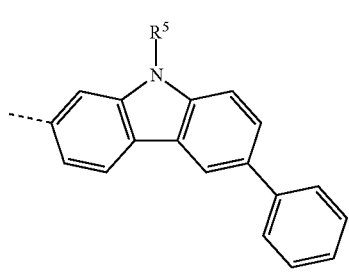
formula (56)
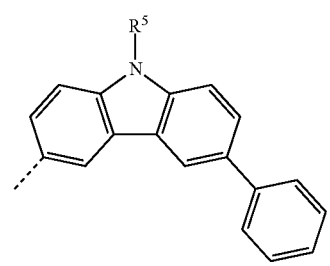
formula (57)
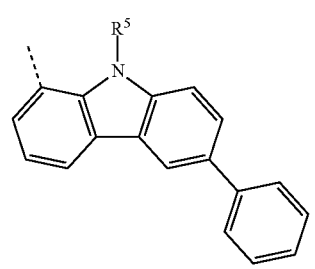
formula (58)
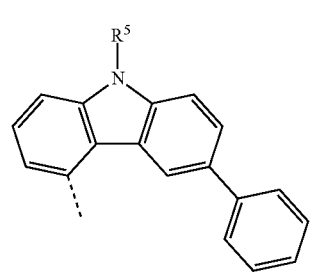
formula (59)
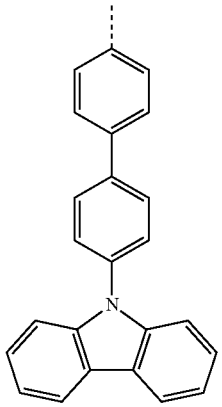
formula (60)
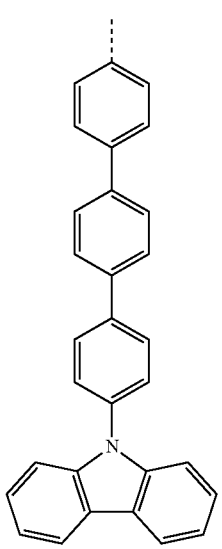
formula (61)
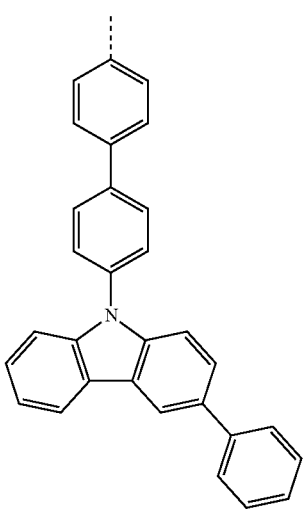

-continued formula (62)

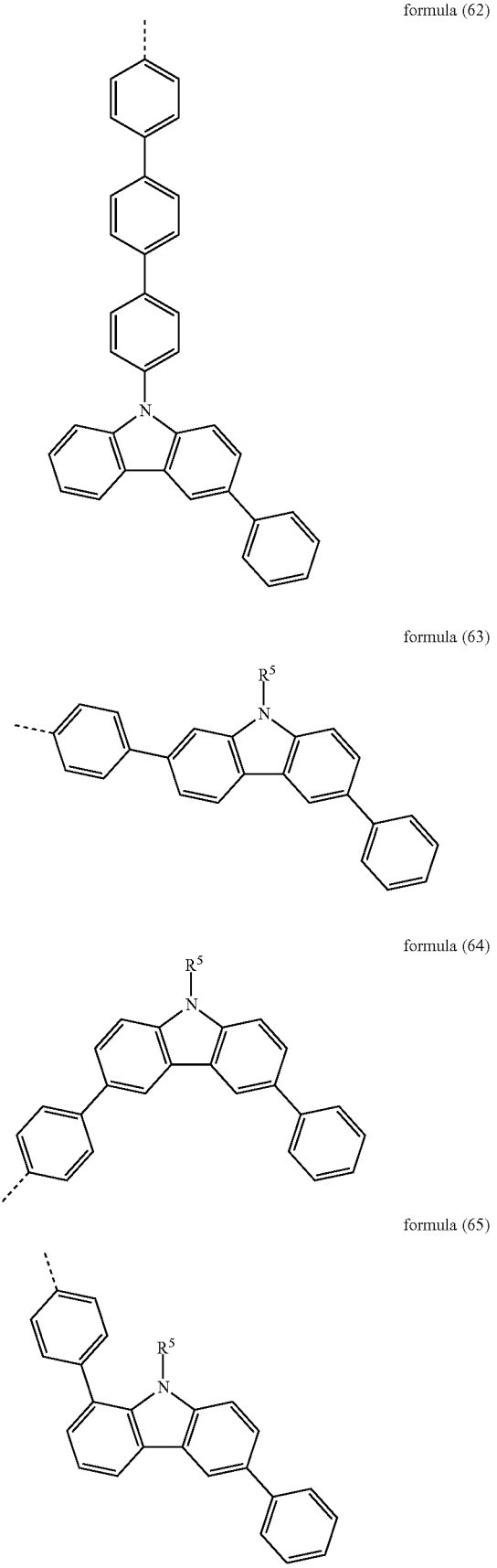

formula (63)

formula (64)

formula (65)

-continued formula (66)

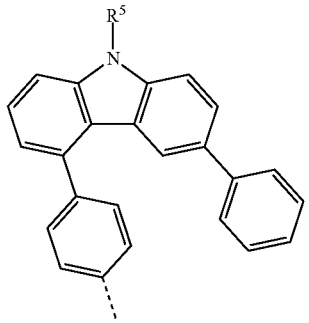

where the dashed bond indicates the bond to the nitrogen, and the groups may be substituted by one or more radicals $R^5$, but are preferably unsubstituted.

$R^5$ in the groups of the formulae (20) to (23), (53) and (54) preferably stands, identically or differently, for an alkyl group having 1 to 10 C atoms, in particular for methyl, or a phenyl group, which may be substituted by one or more radicals $R^6$.

Preferred groups $Ar^1$ and $Ar^2$ are selected, identically or differently on each occurrence, from the group consisting of the above-mentioned formulae (11), (13), (16), (20), (28), (29), (33), (34), (35), (37), (38), (39), (40), (44), (48), (49), (51) and (59). All possible combinations of these groups are equally possible here.

Particularly preferred is that $Ar^1$ and $Ar^2$ are selected, identically or differently on each occurrence, from the group consisting of the above-mentioned formulae (11), (13), (20), (29), (35), (38), (39), (49), (51) and (59).

Furthermore, $R^5$ in the groups of the formulae (28) to (31) and (40) to (43) and (55) to (58) and (63) to (66) preferably stands for a phenyl group, an ortho-biphenyl group, a meta-biphenyl group, a para-biphenyl group, a terphenyl group, a 1-naphthyl group, or a 2-naphthyl group which may be substituted by one or more radicals $R^6$.

Preferably, $Ar^1$ and $Ar^2$ are selected, identically or differently on each occurrence, from the groups of the formulae (11), (20) and (24), which may be substituted by one or more radicals $R^5$.

At least one of the groups $Ar^1$ and $Ar^2$ is particularly preferably a group of the formula (11) or (20). Very particularly preferably, $Ar^1$ stands for a group of the formula (11) and $Ar^2$ stands for a group of the formula (20).

The two groups $Ar^1$ and $Ar^2$ of the above-mentioned formulae (11) to (66) which are bonded to the nitrogen may be combined with one another as desired.

In a preferred embodiment of the invention, the groups $Ar^1$ and $Ar^2$ are selected differently from one another.

If the groups $Ar^1$ and $Ar^2$ in the compounds of the formula (1) and (2) to (10) or the preferred embodiments are linked to one another by a group E, the group —$NAr^1Ar^2$ preferably has the structure of one of the following formulae (67) to (74), formula (67)
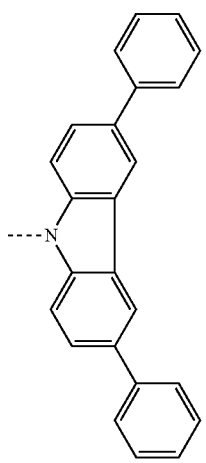
formula (68)
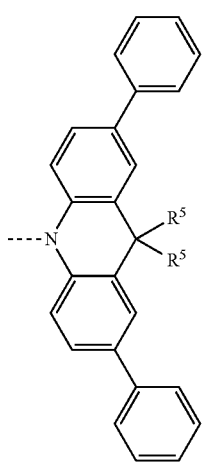
formula (69)
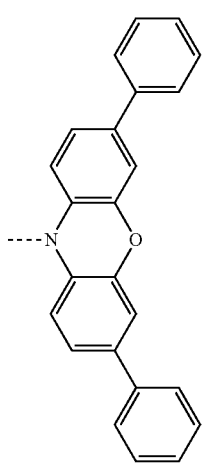
formula (70)
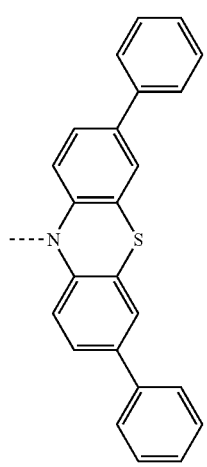
formula (71)
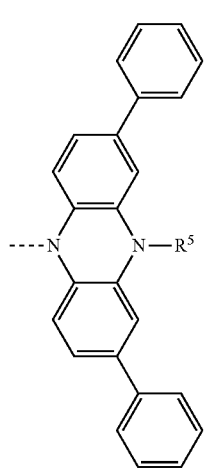
formula (72)
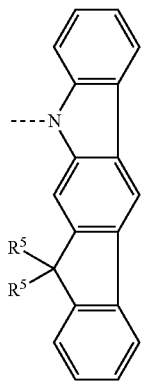

-continued

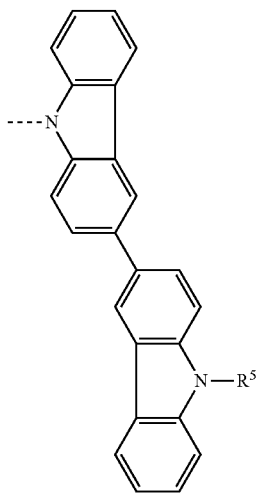
formula (73)

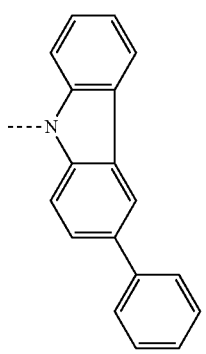
formula (74)

where the symbols used have the meanings given above, and the dashed bond indicates the bond to the spirobifluorene. These groups may also be substituted by one or more radicals $R^5$, but are preferably unsubstituted.

$R^5$ in the group of the formula (68) and (72) preferably stands, identically or differently, for an alkyl group having 1 to 10 C atoms, in particular for methyl, or a phenyl group, which may be substituted by one or more radicals $R^6$.

Furthermore, $R^5$ in the group of the formula (71) and (73) preferably stands for a phenyl group, which may be substituted by one or more radicals $R^6$.

Preferred substituted embodiments of the formula (13) are the following formulae (13a) to (13f), a preferred embodiment of the formula (16) are the formulae (16a) and (16b), preferred embodiments of the formula (20) are the following formulae (20a) to (20l), preferred embodiments of the formula (21) are the following formulae (21a) to (21g), preferred embodiments of the formula (22) are the following formulae (22a), (22b), (22c) and (22d), and preferred embodiments of the formula (23) are the following formulae (23a), (23b), (23c) and (23d),

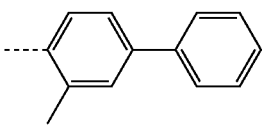
formula (13a)

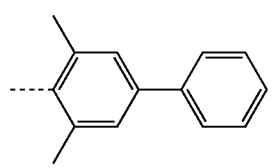
formula (13b)

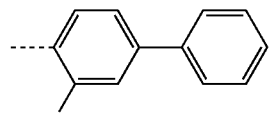
formula (13c)

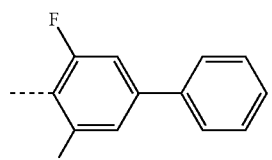
formula (13d)

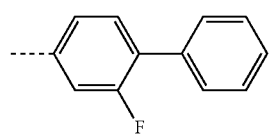
formula (13e)

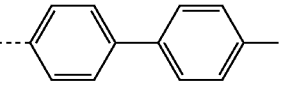
formula (13f)

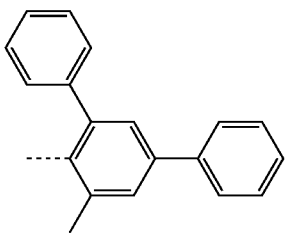
formula (16a)

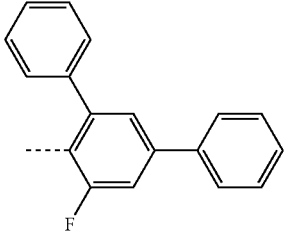
formula (16b)

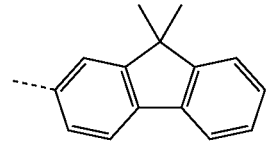
formula (20a)

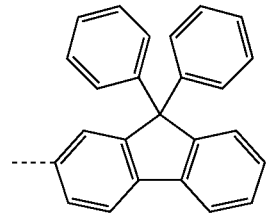
formula (20b)

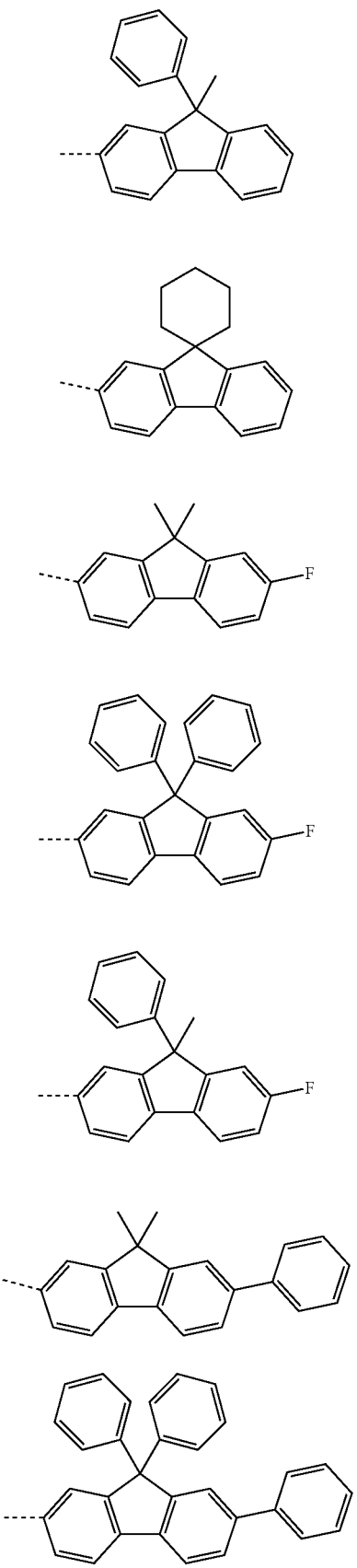
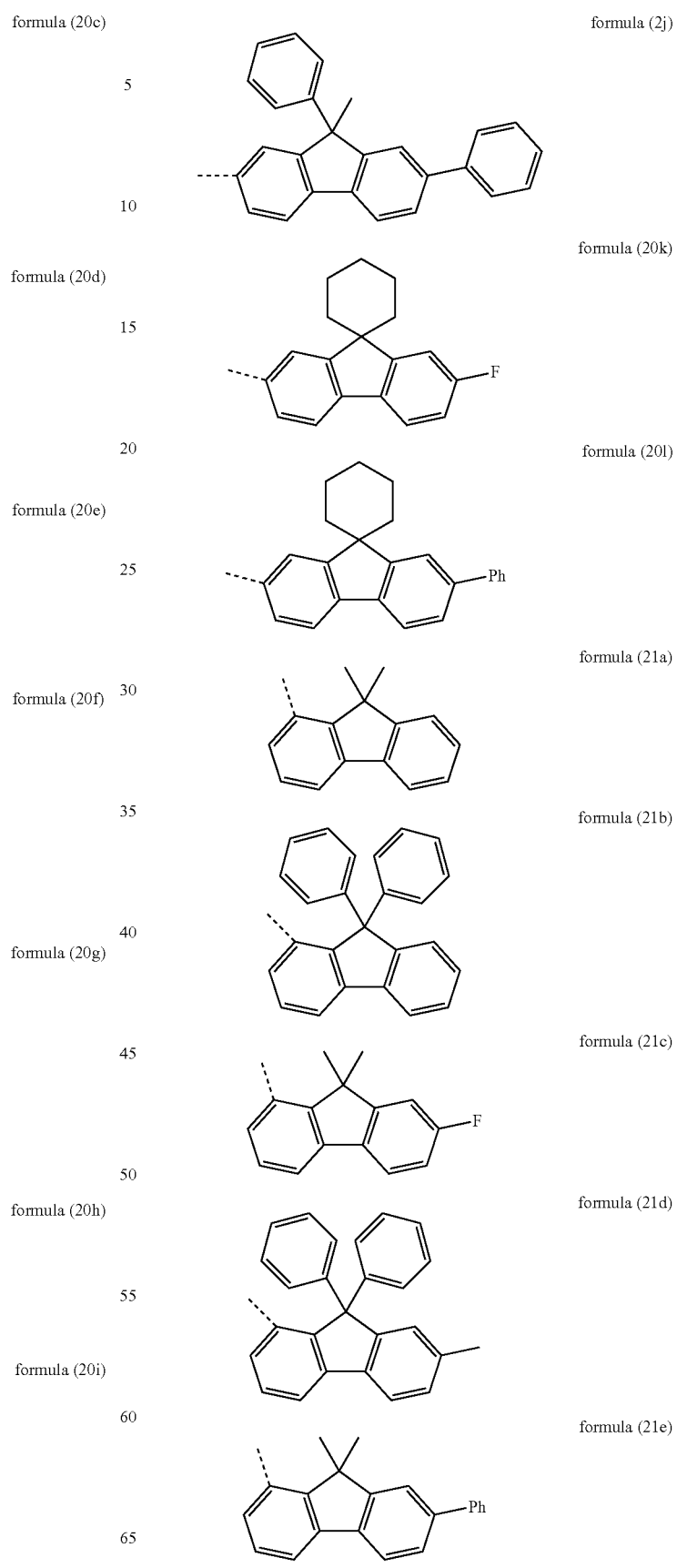

formula (21f)

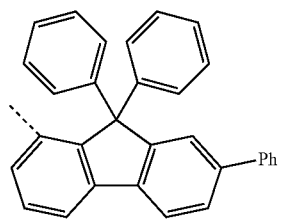

formula (21g)

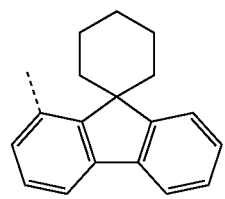

formula (22a)

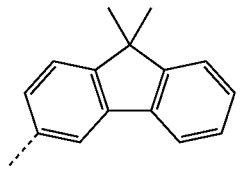

formula (22b)

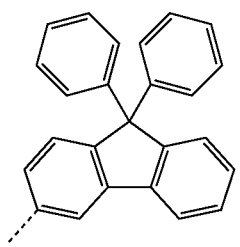

formula (22c)

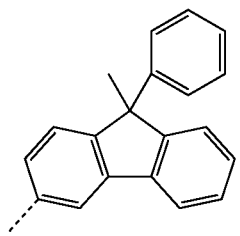

formula (22d)

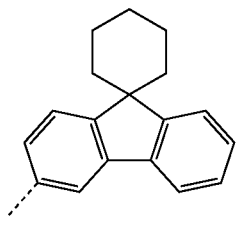

formula (23a)

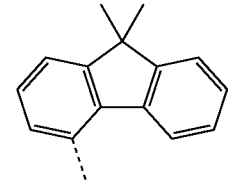

formula (23b)

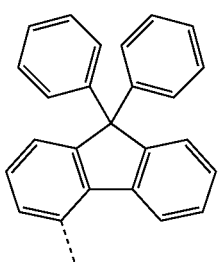

formula (23c)

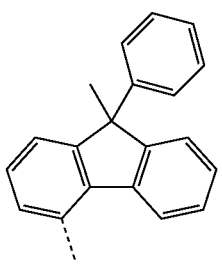

formula (23d)

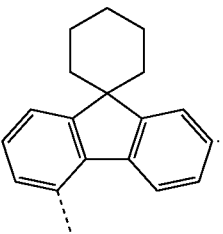

where the dashed bond indicates the bond to the nitrogen.

Group $Ar^S$ is preferably, identically or differently on each occurrence, selected from aromatic or heteroaromatic ring systems having 6 to 18 aromatic ring atoms, which may in each case also be substituted by one or more radicals $R^5$.

Particularly preferable groups $Ar^S$ are selected from the groups of formulae $(Ar^S\text{-}1)$ to $(Ar^S\text{-}15)$ below:

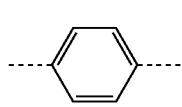

Ar$^s$-1

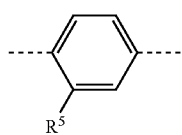

Ar$^s$-2

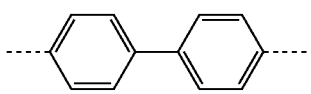

Ar$^s$-3

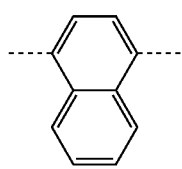

Ar$^s$-4

Ar<sup>s</sup>-5 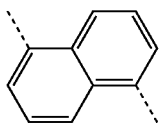

Ar<sup>s</sup>-6 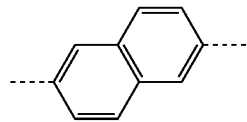

Ar<sup>s</sup>-7 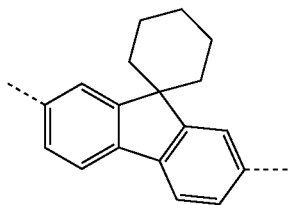

Ar<sup>s</sup>-8 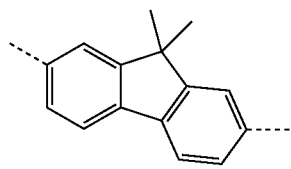

Ar<sup>s</sup>-9 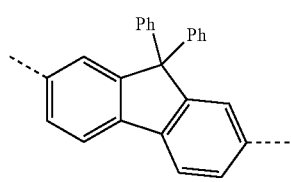

Ar<sup>s</sup>-10 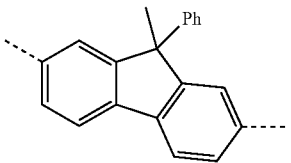

Ar<sup>s</sup>-11 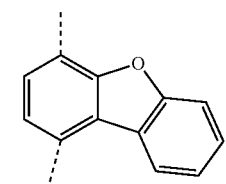

Ar<sup>s</sup>-12 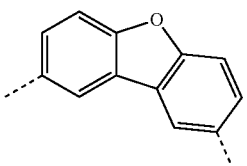

Ar<sup>s</sup>-13 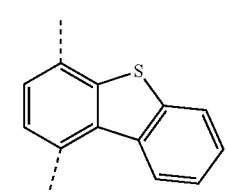

Ar<sup>s</sup>-14 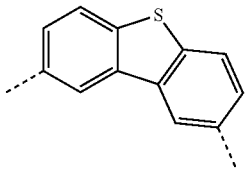

Ar<sup>s</sup>-15 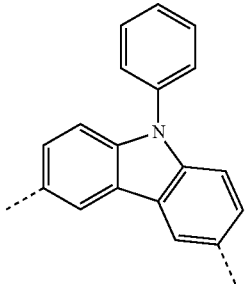

where the dashed bonds indicates the bonds to the spirobifluorene and to the amine, and where the groups may be substituted at each free position by a group R⁵ but are preferably unsubstituted.

In a preferred embodiment of the invention, R¹ to R⁴ are selected, identically or differently on each occurrence, from the group consisting of H, F, CN, a straight-chain alkyl or alkoxy group having 1 to 10 C atoms or a branched or cyclic alkyl or alkoxy group having 3 to 10 C atoms, each of which may be substituted by one or more radicals R⁶, where one or more non-adjacent CH₂ groups may be replaced by O and where one or more H atoms may be replaced by F, an aromatic or heteroaromatic ring system having 6 to 24 aromatic ring atoms, which may in each case be substituted by one or more radicals R⁶.

In a particularly preferred embodiment of the invention, R¹ to R⁴ are selected on each occurrence, identically or differently, from the group consisting of H, F, a straight-chain alkyl group having 1 to 5 C atoms or a branched or cyclic alkyl group having 3 to 6 C atoms, an aromatic or heteroaromatic ring system having 5 to 18 aromatic ring atoms, which may in each case be substituted by one or more radicals R⁶.

Most preferably, R¹ to R⁴ are selected, identically or differently, from H, F, phenyl, methyl and tert-butyl.

R¹ to R⁴ in the compounds of the formulae (1) and (2) to (10) and (2a) to (10a) are very particularly preferably selected, identically or differently on each occurrence, from the group consisting of H, F, methyl, tert-butyl, and phenyl.

In a further preferred embodiment of the invention, the radical R⁵ which is bonded to Ar¹ or Ar² or Ar<sup>S</sup> is selected, identically or differently on each occurrence, from the group consisting of H, F, CN, a straight-chain alkyl group having 1 to 10 C atoms, a branched or cyclic alkyl group having 3 to 10 C atoms or an aromatic or heteroaromatic ring system having 5 to 24 aromatic ring atoms, each of which may be substituted by one or more radicals R⁶.

In a particularly preferred embodiment of the invention, the radical R⁵ which is bonded to Ar¹ or Ar² or Ar<sup>S</sup> is selected, identically or differently on each occurrence, from the group consisting of H, a straight-chain alkyl group having 1 to 5 C atoms, a branched or cyclic alkyl group having 3 to 6 C atoms or an aromatic or heteroaromatic ring system having 5 to 24 aromatic ring atoms, each of which may be substituted by one or more radicals R⁶.

The radicals $R^1$ to $R^6$ here preferably contain no condensed aryl or heteroaryl groups in which more than two aromatic or heteroaromatic six-membered rings are condensed directly onto one another, i.e., for example, no anthracene or pyrene groups. The radicals $R^1$ to $R^6$ particularly preferably contain absolutely no condensed aryl or heteroaryl groups in which aromatic or heteroaromatic six-membered rings are condensed directly onto one another, i.e. also, for example, no naphthalene groups.

It may furthermore be preferred for the two substituents $R^5$ in the 9-position of a fluorene together to form a cycloalkyl ring, preferably having 3 to 8 C atoms, particularly preferably having 5 or 6 C atoms.

Likewise, the two substituents $R^5$ in formula (68) and (72) may form a ring system with one another and thus form a spiro system, for example a cycloalkyl ring, preferably having 3 to 8 C atoms, particularly preferably having 5 or 6 C atoms.

For compounds which are processed by vacuum evaporation, the alkyl groups preferably have not more than four C atoms, particularly preferably not more than 1 C atom. For compounds which are processed from solution, suitable compounds are also those which are substituted by linear, branched or cyclic alkyl groups having up to 10 C atoms or which are substituted by oligoarylene groups, for example ortho-, meta-, para- or branched terphenyl or quaterphenyl groups.

In a preferred embodiment of the invention, $R^6$ is selected, identically or differently on each occurrence, from the group consisting of H, a straight-chain alkyl group having 1 to 10 C atoms or a branched or cyclic alkyl group having 3 to 10 C atoms or an aromatic ring system having 6 to 24 C atoms. $R^6$ is particularly preferably, identically or differently on each occurrence, H or a methyl group, very particularly preferably H.

Particular preference is given to compounds of the formulae (1) and (2) to (10) and (2a) to (10a) and (2b) to (10b), in which the preferred embodiments mentioned above occur simultaneously. Particular preference is therefore given to compounds for which:

$Ar^1$, $Ar^2$ are, identically or differently, a group of one of the formulae (11) to (66); or —$NAr^1Ar^2$ stands for a group of one of the formulae (67) to (74);

E is on each occurrence, identically or differently, a single bond or $C(R^1)_2$, $N(R^1)$, O or S;

$R^1$ to $R^4$ are selected, identically or differently on each occurrence, from the group consisting of H, F, CN, a straight-chain alkyl or alkoxy group having 1 to 10 C atoms or a branched or cyclic alkyl or alkoxy group having 3 to 10 C atoms, each of which may be substituted by one or more radicals $R^6$, where one or more non-adjacent $CH_2$ groups may be replaced by O and where one or more H atoms may be replaced by F, an aromatic or heteroaromatic ring system having 6 to 24 aromatic ring atoms, which may in each case be substituted by one or more radicals $R^6$;

$R^5$ is, if the radical $R^5$ is bonded to $Ar^1$ or $Ar^2$ or $Ar^S$, selected, identically or differently on each occurrence, from the group consisting of H, F, CN, a straight-chain alkyl group having 1 to 10 C atoms, a branched or cyclic alkyl group having 3 to 10 C atoms or an aromatic or heteroaromatic ring system having 5 to 24 aromatic ring atoms, each of which may be substituted by one or more radicals $R^6$;

or $R^5$ which is bonded to the carbon bridge in the formulae (20) to (23), (53), (54), (68) and (72) is, identically or differently, an alkyl group having 1 to 10 C atoms, in particular methyl, or a phenyl group, which may be substituted by one or more radicals $R^6$; or $R^5$ which is bonded to the nitrogen bridge in the formulae (28) to (31), (40) to (43) or (55) to (58), (63) to (66), (71) and (73) is a phenyl group, which may be substituted by one or more radicals $R^6$;

$R^6$ is selected on each occurrence, identically or differently, from the group consisting of H, a straight-chain alkyl group having 1 to 10 C atoms or a branched or cyclic alkyl group having 3 to 10 C atoms or an aromatic ring system having 6 to 24 C atoms;

i is 0;
m is 0 or 1, preferably 0;
n is 0 or 1;
p+q is 0 or 1;
r is 0 or 1;
s is 0 or 1.

Examples for preferred structures for compounds according to formula (1) are listed in the following. The compounds are based on the basic structures of formulae (2a), (5a) and (8a).

| Formula | basic structure of formula | i = | $Ar^1$ of formula | $Ar^2$ of formula |
| --- | --- | --- | --- | --- |
| (2a-1-1) | (2a) | 0 | (11) | (11) |
| (2a-1-2) | (2a) | 0 | (11) | (13) |
| (2a-1-3) | (2a) | 0 | (11) | (20) |
| (2a-1-4) | (2a) | 0 | (11) | (29) |
| (2a-1-5) | (2a) | 0 | (11) | (35) |
| (2a-1-6) | (2a) | 0 | (11) | (38) |
| (2a-1-7) | (2a) | 0 | (11) | (39) |
| (2a-1-8) | (2a) | 0 | (11) | (49) |
| (2a-1-9) | (2a) | 0 | (11) | (51) |
| (2a-1-10) | (2a) | 0 | (11) | (59) |
| (2a-1-11) | (2a) | 0 | (13) | (13) |
| (2a-1-12) | (2a) | 0 | (13) | (20) |
| (2a-1-13) | (2a) | 0 | (13) | (29) |
| (2a-1-14) | (2a) | 0 | (13) | (35) |
| (2a-1-15) | (2a) | 0 | (13) | (38) |
| (2a-1-16) | (2a) | 0 | (13) | (39) |
| (2a-1-17) | (2a) | 0 | (13) | (49) |
| (2a-1-18) | (2a) | 0 | (13) | (51) |
| (2a-1-19) | (2a) | 0 | (13) | (59) |
| (2a-1-20) | (2a) | 0 | (20) | (20) |
| (2a-1-21) | (2a) | 0 | (20) | (29) |
| (2a-1-22) | (2a) | 0 | (20) | (35) |
| (2a-1-23) | (2a) | 0 | (20) | (38) |
| (2a-1-24) | (2a) | 0 | (20) | (39) |
| (2a-1-25) | (2a) | 0 | (20) | (49) |
| (2a-1-26) | (2a) | 0 | (20) | (51) |
| (2a-1-27) | (2a) | 0 | (20) | (59) |
| (2a-1-28) | (2a) | 0 | (29) | (29) |
| (2a-1-29) | (2a) | 0 | (29) | (35) |
| (2a-1-30) | (2a) | 0 | (29) | (38) |
| (2a-1-31) | (2a) | 0 | (29) | (39) |
| (2a-1-32) | (2a) | 0 | (29) | (49) |
| (2a-1-33) | (2a) | 0 | (29) | (51) |
| (2a-1-34) | (2a) | 0 | (29) | (59) |
| (2a-1-35) | (2a) | 0 | (35) | (35) |
| (2a-1-36) | (2a) | 0 | (35) | (38) |
| (2a-1-37) | (2a) | 0 | (35) | (39) |
| (2a-1-38) | (2a) | 0 | (35) | (49) |
| (2a-1-39) | (2a) | 0 | (35) | (51) |
| (2a-1-40) | (2a) | 0 | (35) | (59) |
| (2a-1-41) | (2a) | 0 | (38) | (38) |
| (2a-1-42) | (2a) | 0 | (38) | (39) |
| (2a-1-43) | (2a) | 0 | (38) | (49) |
| (2a-1-44) | (2a) | 0 | (38) | (51) |
| (2a-1-45) | (2a) | 0 | (38) | (59) |
| (2a-1-46) | (2a) | 0 | (39) | (39) |
| (2a-1-47) | (2a) | 0 | (39) | (49) |
| (2a-1-48) | (2a) | 0 | (39) | (51) |
| (2a-1-49) | (2a) | 0 | (39) | (59) |
| (2a-1-50) | (2a) | 0 | (49) | (49) |

| Formula | basic structure of formula | i = | Ar¹ of formula | Ar² of formula | Formula | basic structure of formula | i = | Ar¹ of formula | Ar² of formula |
| --- | --- | --- | --- | --- | --- | --- | --- | --- | --- |
| (2a-1-51) | (2a) | 0 | (49) | (51) | (5a-1-17) | (5a) | 0 | (13) | (49) |
| (2a-1-52) | (2a) | 0 | (49) | (59) | (5a-1-18) | (5a) | 0 | (13) | (51) |
| (2a-1-53) | (2a) | 0 | (51) | (51) | (5a-1-19) | (5a) | 0 | (13) | (59) |
| (2a-1-54) | (2a) | 0 | (51) | (59) | (5a-1-20) | (5a) | 0 | (20) | (20) |
| (2a-1-55) | (2a) | 0 | (59) | (59) | (5a-1-21) | (5a) | 0 | (20) | (29) |
| (2a-2-1) | (2a) | 1 | (11) | (11) | (5a-1-22) | (5a) | 0 | (20) | (35) |
| (2a-2-2) | (2a) | 1 | (11) | (13) | (5a-1-23) | (5a) | 0 | (20) | (38) |
| (2a-2-3) | (2a) | 1 | (11) | (20) | (5a-1-24) | (5a) | 0 | (20) | (39) |
| (2a-2-4) | (2a) | 1 | (11) | (29) | (5a-1-25) | (5a) | 0 | (20) | (49) |
| (2a-2-5) | (2a) | 1 | (11) | (35) | (5a-1-26) | (5a) | 0 | (20) | (51) |
| (2a-2-6) | (2a) | 1 | (11) | (38) | (5a-1-27) | (5a) | 0 | (20) | (59) |
| (2a-2-7) | (2a) | 1 | (11) | (39) | (5a-1-28) | (5a) | 0 | (29) | (29) |
| (2a-2-8) | (2a) | 1 | (11) | (49) | (5a-1-29) | (5a) | 0 | (29) | (35) |
| (2a-2-9) | (2a) | 1 | (11) | (51) | (5a-1-30) | (5a) | 0 | (29) | (38) |
| (2a-2-10) | (2a) | 1 | (11) | (59) | (5a-1-31) | (5a) | 0 | (29) | (39) |
| (2a-2-11) | (2a) | 1 | (13) | (13) | (5a-1-32) | (5a) | 0 | (29) | (49) |
| (2a-2-12) | (2a) | 1 | (13) | (20) | (5a-1-33) | (5a) | 0 | (29) | (51) |
| (2a-2-13) | (2a) | 1 | (13) | (29) | (5a-1-34) | (5a) | 0 | (29) | (59) |
| (2a-2-14) | (2a) | 1 | (13) | (35) | (5a-1-35) | (5a) | 0 | (35) | (35) |
| (2a-2-15) | (2a) | 1 | (13) | (38) | (5a-1-36) | (5a) | 0 | (35) | (38) |
| (2a-2-16) | (2a) | 1 | (13) | (39) | (5a-1-37) | (5a) | 0 | (35) | (39) |
| (2a-2-17) | (2a) | 1 | (13) | (49) | (5a-1-38) | (5a) | 0 | (35) | (49) |
| (2a-2-18) | (2a) | 1 | (13) | (51) | (5a-1-39) | (5a) | 0 | (35) | (51) |
| (2a-2-19) | (2a) | 1 | (13) | (59) | (5a-1-40) | (5a) | 0 | (35) | (59) |
| (2a-2-20) | (2a) | 1 | (20) | (20) | (5a-1-41) | (5a) | 0 | (38) | (38) |
| (2a-2-21) | (2a) | 1 | (20) | (29) | (5a-1-42) | (5a) | 0 | (38) | (39) |
| (2a-2-22) | (2a) | 1 | (20) | (35) | (5a-1-43) | (5a) | 0 | (38) | (49) |
| (2a-2-23) | (2a) | 1 | (20) | (38) | (5a-1-44) | (5a) | 0 | (38) | (51) |
| (2a-2-24) | (2a) | 1 | (20) | (39) | (5a-1-45) | (5a) | 0 | (38) | (59) |
| (2a-2-25) | (2a) | 1 | (20) | (49) | (5a-1-46) | (5a) | 0 | (39) | (39) |
| (2a-2-26) | (2a) | 1 | (20) | (51) | (5a-1-47) | (5a) | 0 | (39) | (49) |
| (2a-2-27) | (2a) | 1 | (20) | (59) | (5a-1-48) | (5a) | 0 | (39) | (51) |
| (2a-2-28) | (2a) | 1 | (29) | (29) | (5a-1-49) | (5a) | 0 | (39) | (59) |
| (2a-2-29) | (2a) | 1 | (29) | (35) | (5a-1-50) | (5a) | 0 | (49) | (49) |
| (2a-2-30) | (2a) | 1 | (29) | (38) | (5a-1-51) | (5a) | 0 | (49) | (51) |
| (2a-2-31) | (2a) | 1 | (29) | (39) | (5a-1-52) | (5a) | 0 | (49) | (59) |
| (2a-2-32) | (2a) | 1 | (29) | (49) | (5a-1-53) | (5a) | 0 | (51) | (51) |
| (2a-2-33) | (2a) | 1 | (29) | (51) | (5a-1-54) | (5a) | 0 | (51) | (59) |
| (2a-2-34) | (2a) | 1 | (29) | (59) | (5a-1-55) | (5a) | 0 | (59) | (59) |
| (2a-2-35) | (2a) | 1 | (35) | (35) | (5a-2-1) | (5a) | 1 | (11) | (11) |
| (2a-2-36) | (2a) | 1 | (35) | (38) | (5a-2-2) | (5a) | 1 | (11) | (13) |
| (2a-2-37) | (2a) | 1 | (35) | (39) | (5a-2-3) | (5a) | 1 | (11) | (20) |
| (2a-2-38) | (2a) | 1 | (35) | (49) | (5a-2-4) | (5a) | 1 | (11) | (29) |
| (2a-2-39) | (2a) | 1 | (35) | (51) | (5a-2-5) | (5a) | 1 | (11) | (35) |
| (2a-2-40) | (2a) | 1 | (35) | (59) | (5a-2-6) | (5a) | 1 | (11) | (38) |
| (2a-2-41) | (2a) | 1 | (38) | (38) | (5a-2-7) | (5a) | 1 | (11) | (39) |
| (2a-2-42) | (2a) | 1 | (38) | (39) | (5a-2-8) | (5a) | 1 | (11) | (49) |
| (2a-2-43) | (2a) | 1 | (38) | (49) | (5a-2-9) | (5a) | 1 | (11) | (51) |
| (2a-2-44) | (2a) | 1 | (38) | (51) | (5a-2-10) | (5a) | 1 | (11) | (59) |
| (2a-2-45) | (2a) | 1 | (38) | (59) | (5a-2-11) | (5a) | 1 | (13) | (13) |
| (2a-2-46) | (2a) | 1 | (39) | (39) | (5a-2-12) | (5a) | 1 | (13) | (20) |
| (2a-2-47) | (2a) | 1 | (39) | (49) | (5a-2-13) | (5a) | 1 | (13) | (29) |
| (2a-2-48) | (2a) | 1 | (39) | (51) | (5a-2-14) | (5a) | 1 | (13) | (35) |
| (2a-2-49) | (2a) | 1 | (39) | (59) | (5a-2-15) | (5a) | 1 | (13) | (38) |
| (2a-2-50) | (2a) | 1 | (49) | (49) | (5a-2-16) | (5a) | 1 | (13) | (39) |
| (2a-2-51) | (2a) | 1 | (49) | (51) | (5a-2-17) | (5a) | 1 | (13) | (49) |
| (2a-2-52) | (2a) | 1 | (49) | (59) | (5a-2-18) | (5a) | 1 | (13) | (51) |
| (2a-2-53) | (2a) | 1 | (51) | (51) | (5a-2-19) | (5a) | 1 | (13) | (59) |
| (2a-2-54) | (2a) | 1 | (51) | (59) | (5a-2-20) | (5a) | 1 | (20) | (20) |
| (2a-2-55) | (2a) | 1 | (59) | (59) | (5a-2-21) | (5a) | 1 | (20) | (29) |
| (5a-1-1) | (5a) | 0 | (11) | (11) | (5a-2-22) | (5a) | 1 | (20) | (35) |
| (5a-1-2) | (5a) | 0 | (11) | (13) | (5a-2-23) | (5a) | 1 | (20) | (38) |
| (5a-1-3) | (5a) | 0 | (11) | (20) | (5a-2-24) | (5a) | 1 | (20) | (39) |
| (5a-1-4) | (5a) | 0 | (11) | (29) | (5a-2-25) | (5a) | 1 | (20) | (49) |
| (5a-1-5) | (5a) | 0 | (11) | (35) | (5a-2-26) | (5a) | 1 | (20) | (51) |
| (5a-1-6) | (5a) | 0 | (11) | (38) | (5a-2-27) | (5a) | 1 | (20) | (59) |
| (5a-1-7) | (5a) | 0 | (11) | (39) | (5a-2-28) | (5a) | 1 | (29) | (29) |
| (5a-1-8) | (5a) | 0 | (11) | (49) | (5a-2-29) | (5a) | 1 | (29) | (35) |
| (5a-1-9) | (5a) | 0 | (11) | (51) | (5a-2-30) | (5a) | 1 | (29) | (38) |
| (5a-1-10) | (5a) | 0 | (11) | (59) | (5a-2-31) | (5a) | 1 | (29) | (39) |
| (5a-1-11) | (5a) | 0 | (13) | (13) | (5a-2-32) | (5a) | 1 | (29) | (49) |
| (5a-1-12) | (5a) | 0 | (13) | (20) | (5a-2-33) | (5a) | 1 | (29) | (51) |
| (5a-1-13) | (5a) | 0 | (13) | (29) | (5a-2-34) | (5a) | 1 | (29) | (59) |
| (5a-1-14) | (5a) | 0 | (13) | (35) | (5a-2-35) | (5a) | 1 | (35) | (35) |
| (5a-1-15) | (5a) | 0 | (13) | (38) | (5a-2-36) | (5a) | 1 | (35) | (38) |
| (5a-1-16) | (5a) | 0 | (13) | (39) | (5a-2-37) | (5a) | 1 | (35) | (39) |

| Formula | basic structure of formula | i = | Ar¹ of formula | Ar² of formula |
|---|---|---|---|---|
| (5a-2-38) | (5a) | 1 | (35) | (49) |
| (5a-2-39) | (5a) | 1 | (35) | (51) |
| (5a-2-40) | (5a) | 1 | (35) | (59) |
| (5a-2-41) | (5a) | 1 | (38) | (38) |
| (5a-2-42) | (5a) | 1 | (38) | (39) |
| (5a-2-43) | (5a) | 1 | (38) | (49) |
| (5a-2-44) | (5a) | 1 | (38) | (51) |
| (5a-2-45) | (5a) | 1 | (38) | (59) |
| (5a-2-46) | (5a) | 1 | (39) | (39) |
| (5a-2-47) | (5a) | 1 | (39) | (49) |
| (5a-2-48) | (5a) | 1 | (39) | (51) |
| (5a-2-49) | (5a) | 1 | (39) | (59) |
| (5a-2-50) | (5a) | 1 | (49) | (49) |
| (5a-2-51) | (5a) | 1 | (49) | (51) |
| (5a-2-52) | (5a) | 1 | (49) | (59) |
| (5a-2-53) | (5a) | 1 | (51) | (51) |
| (5a-2-54) | (5a) | 1 | (51) | (59) |
| (5a-2-55) | (5a) | 1 | (59) | (59) |
| (8a-1-1) | (8a) | 0 | (11) | (11) |
| (8a-1-2) | (8a) | 0 | (11) | (13) |
| (8a-1-3) | (8a) | 0 | (11) | (20) |
| (8a-1-4) | (8a) | 0 | (11) | (29) |
| (8a-1-5) | (8a) | 0 | (11) | (35) |
| (8a-1-6) | (8a) | 0 | (11) | (38) |
| (8a-1-7) | (8a) | 0 | (11) | (39) |
| (8a-1-8) | (8a) | 0 | (11) | (49) |
| (8a-1-9) | (8a) | 0 | (11) | (51) |
| (8a-1-10) | (8a) | 0 | (11) | (59) |
| (8a-1-11) | (8a) | 0 | (13) | (13) |
| (8a-1-12) | (8a) | 0 | (13) | (20) |
| (8a-1-13) | (8a) | 0 | (13) | (29) |
| (8a-1-14) | (8a) | 0 | (13) | (35) |
| (8a-1-15) | (8a) | 0 | (13) | (38) |
| (8a-1-16) | (8a) | 0 | (13) | (39) |
| (8a-1-17) | (8a) | 0 | (13) | (49) |
| (8a-1-18) | (8a) | 0 | (13) | (51) |
| (8a-1-19) | (8a) | 0 | (13) | (59) |
| (8a-1-20) | (8a) | 0 | (20) | (20) |
| (8a-1-21) | (8a) | 0 | (20) | (29) |
| (8a-1-22) | (8a) | 0 | (20) | (35) |
| (8a-1-23) | (8a) | 0 | (20) | (38) |
| (8a-1-24) | (8a) | 0 | (20) | (39) |
| (8a-1-25) | (8a) | 0 | (20) | (49) |
| (8a-1-26) | (8a) | 0 | (20) | (51) |
| (8a-1-27) | (8a) | 0 | (20) | (59) |
| (8a-1-28) | (8a) | 0 | (29) | (29) |
| (8a-1-29) | (8a) | 0 | (29) | (35) |
| (8a-1-30) | (8a) | 0 | (29) | (38) |
| (8a-1-31) | (8a) | 0 | (29) | (39) |
| (8a-1-32) | (8a) | 0 | (29) | (49) |
| (8a-1-33) | (8a) | 0 | (29) | (51) |
| (8a-1-34) | (8a) | 0 | (29) | (59) |
| (8a-1-35) | (8a) | 0 | (35) | (35) |
| (8a-1-36) | (8a) | 0 | (35) | (38) |
| (8a-1-37) | (8a) | 0 | (35) | (39) |
| (8a-1-38) | (8a) | 0 | (35) | (49) |
| (8a-1-39) | (8a) | 0 | (35) | (51) |
| (8a-1-40) | (8a) | 0 | (35) | (59) |
| (8a-1-41) | (8a) | 0 | (38) | (38) |
| (8a-1-42) | (8a) | 0 | (38) | (39) |
| (8a-1-43) | (8a) | 0 | (38) | (49) |
| (8a-1-44) | (8a) | 0 | (38) | (51) |
| (8a-1-45) | (8a) | 0 | (38) | (59) |
| (8a-1-46) | (8a) | 0 | (39) | (39) |
| (8a-1-47) | (8a) | 0 | (39) | (49) |
| (8a-1-48) | (8a) | 0 | (39) | (51) |
| (8a-1-49) | (8a) | 0 | (39) | (59) |
| (8a-1-50) | (8a) | 0 | (49) | (49) |
| (8a-1-51) | (8a) | 0 | (49) | (51) |
| (8a-1-52) | (8a) | 0 | (49) | (59) |
| (8a-1-53) | (8a) | 0 | (51) | (51) |
| (8a-1-54) | (8a) | 0 | (51) | (59) |
| (8a-1-55) | (8a) | 0 | (59) | (59) |
| (8a-2-1) | (8a) | 1 | (11) | (11) |
| (8a-2-2) | (8a) | 1 | (11) | (13) |
| (8a-2-3) | (8a) | 1 | (11) | (20) |
| (8a-2-4) | (8a) | 1 | (11) | (29) |
| (8a-2-5) | (8a) | 1 | (11) | (35) |
| (8a-2-6) | (8a) | 1 | (11) | (38) |
| (8a-2-7) | (8a) | 1 | (11) | (39) |
| (8a-2-8) | (8a) | 1 | (11) | (49) |
| (8a-2-9) | (8a) | 1 | (11) | (51) |
| (8a-2-10) | (8a) | 1 | (11) | (59) |
| (8a-2-11) | (8a) | 1 | (13) | (13) |
| (8a-2-12) | (8a) | 1 | (13) | (20) |
| (8a-2-13) | (8a) | 1 | (13) | (29) |
| (8a-2-14) | (8a) | 1 | (13) | (35) |
| (8a-2-15) | (8a) | 1 | (13) | (38) |
| (8a-2-16) | (8a) | 1 | (13) | (39) |
| (8a-2-17) | (8a) | 1 | (13) | (49) |
| (8a-2-18) | (8a) | 1 | (13) | (51) |
| (8a-2-19) | (8a) | 1 | (13) | (59) |
| (8a-2-20) | (8a) | 1 | (20) | (20) |
| (8a-2-21) | (8a) | 1 | (20) | (29) |
| (8a-2-22) | (8a) | 1 | (20) | (35) |
| (8a-2-23) | (8a) | 1 | (20) | (38) |
| (8a-2-24) | (8a) | 1 | (20) | (39) |
| (8a-2-25) | (8a) | 1 | (20) | (49) |
| (8a-2-26) | (8a) | 1 | (20) | (51) |
| (8a-2-27) | (8a) | 1 | (20) | (59) |
| (8a-2-28) | (8a) | 1 | (29) | (29) |
| (8a-2-29) | (8a) | 1 | (29) | (35) |
| (8a-2-30) | (8a) | 1 | (29) | (38) |
| (8a-2-31) | (8a) | 1 | (29) | (39) |
| (8a-2-32) | (8a) | 1 | (29) | (49) |
| (8a-2-33) | (8a) | 1 | (29) | (51) |
| (8a-2-34) | (8a) | 1 | (29) | (59) |
| (8a-2-35) | (8a) | 1 | (35) | (35) |
| (8a-2-36) | (8a) | 1 | (35) | (38) |
| (8a-2-37) | (8a) | 1 | (35) | (39) |
| (8a-2-38) | (8a) | 1 | (35) | (49) |
| (8a-2-39) | (8a) | 1 | (35) | (51) |
| (8a-2-40) | (8a) | 1 | (35) | (59) |
| (8a-2-41) | (8a) | 1 | (38) | (38) |
| (8a-2-42) | (8a) | 1 | (38) | (39) |
| (8a-2-43) | (8a) | 1 | (38) | (49) |
| (8a-2-44) | (8a) | 1 | (38) | (51) |
| (8a-2-45) | (8a) | 1 | (38) | (59) |
| (8a-2-46) | (8a) | 1 | (39) | (39) |
| (8a-2-47) | (8a) | 1 | (39) | (49) |
| (8a-2-48) | (8a) | 1 | (39) | (51) |
| (8a-2-49) | (8a) | 1 | (39) | (59) |
| (8a-2-50) | (8a) | 1 | (49) | (49) |
| (8a-2-51) | (8a) | 1 | (49) | (51) |
| (8a-2-52) | (8a) | 1 | (49) | (59) |
| (8a-2-53) | (8a) | 1 | (51) | (51) |
| (8a-2-54) | (8a) | 1 | (51) | (59) |
| (8a-2-55) | (8a) | 1 | (59) | (59) |

The compounds of the list above have preferably as $Ar^S$ and $R^1$ to $R^4$ the preferred embodiments of these groups which have been described above. More preferably, in the compounds listed above, $Ar^S$ is selected from groups $Ar^S$-1 to $Ar^S$-15, as defined above. More preferably, in the compounds listed above, $R^1$ to $R^4$ is selected, identically or differently, from H, F, phenyl, methyl and tert-butyl.

Examples of suitable compounds according to the invention are the compounds shown in the following table:

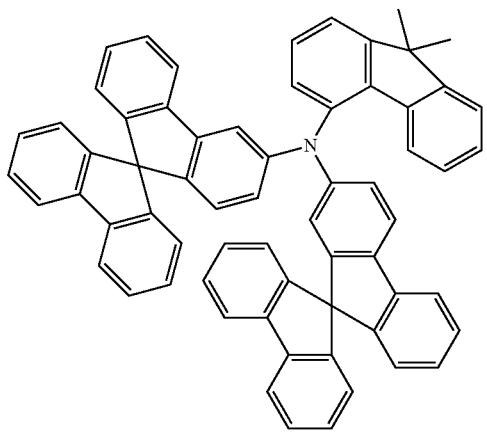 [SMILES: CC1(C)c2ccccc2-c2c(N(c3ccc4c(c3)-c3ccccc3C43c4ccccc4-c4ccccc43)c3ccc4c(c3)C3(c5ccccc5-c5ccccc53)c3ccccc3-4)cccc21]
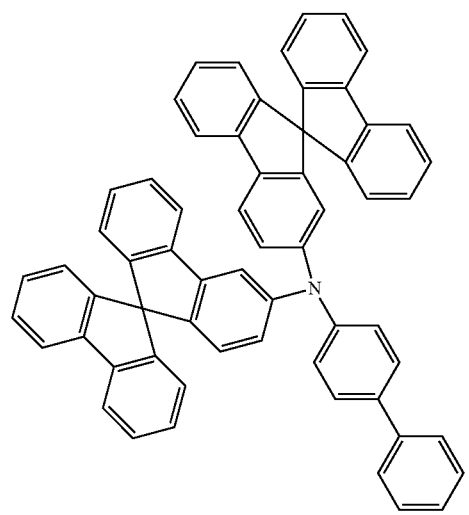 [SMILES: c1ccc(-c2ccc(N(c3ccc4c(c3)-c3ccccc3C43c4ccccc4-c4ccccc43)c3ccc4c(c3)C3(c5ccccc5-c5ccccc53)c3ccccc3-4)cc2)cc1]
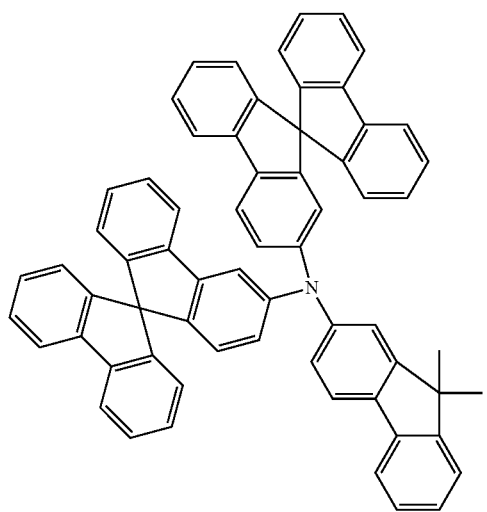 [SMILES: CC1(C)c2ccccc2-c2ccc(N(c3ccc4c(c3)-c3ccccc3C43c4ccccc4-c4ccccc43)c3ccc4c(c3)C3(c5ccccc5-c5ccccc53)c3ccccc3-4)cc21]

-continued
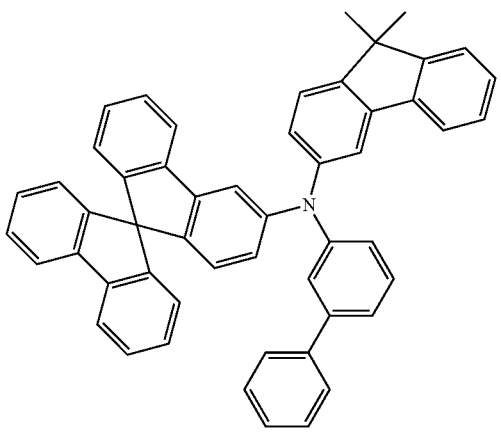 [SMILES: CC1(C)c2ccccc2-c2cc(N(c3cccc(-c4ccccc4)c3)c3ccc4c(c3)-c3ccccc3C43c4ccccc4-c4ccccc43)ccc21]
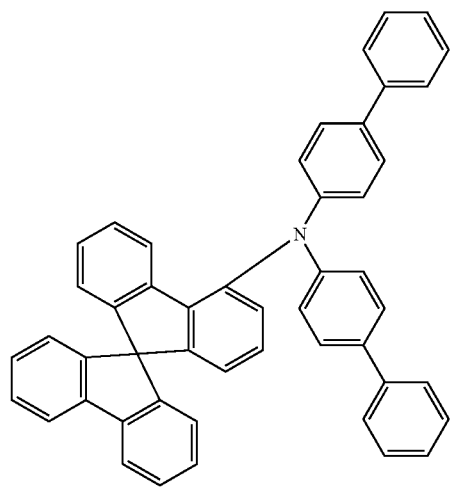 [SMILES: c1ccc(-c2ccc(N(c3ccc(-c4ccccc4)cc3)c3cccc4c3-c3ccccc3C43c4ccccc4-c4ccccc43)cc2)cc1]
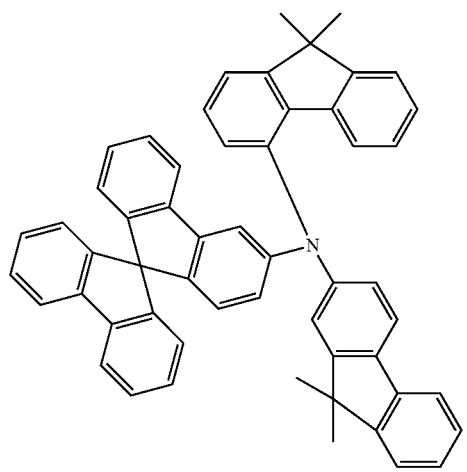 [SMILES: CC1(C)c2ccccc2-c2ccc(N(c3ccc4c(c3)-c3ccccc3C43c4ccccc4-c4ccccc43)c3cccc4c3-c3ccccc3C4(C)C)cc21]

-continued
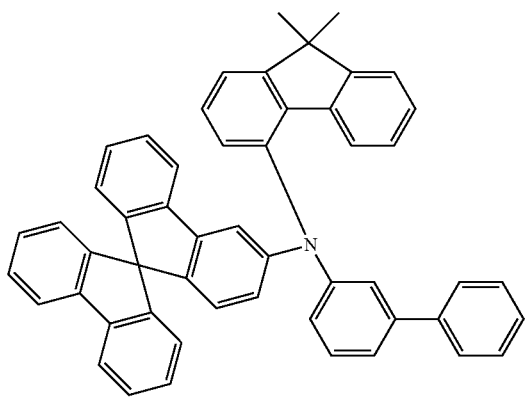 [SMILES: CC1(C)c2ccccc2-c2c(N(c3cccc(-c4ccccc4)c3)c3ccc4c(c3)-c3ccccc3C43c4ccccc4-c4ccccc43)cccc21]
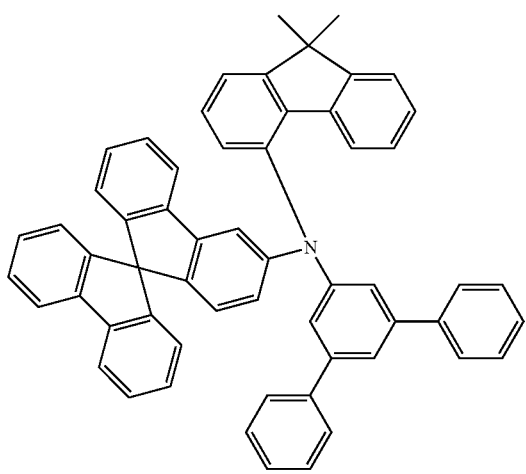 [SMILES: CC1(C)c2ccccc2-c2c(N(c3cc(-c4ccccc4)cc(-c4ccccc4)c3)c3ccc4c(c3)-c3ccccc3C43c4ccccc4-c4ccccc43)cccc21]
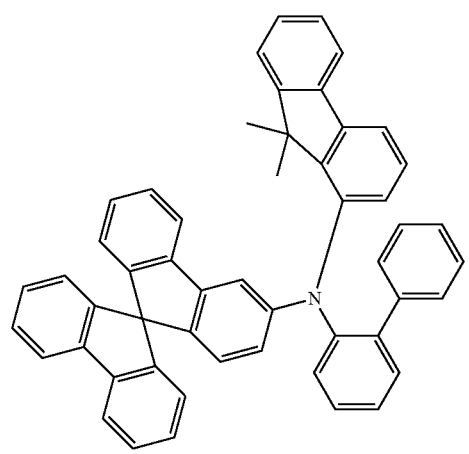 [SMILES: CC1(C)c2ccccc2-c2cccc(N(c3ccc4c(c3)-c3ccccc3C43c4ccccc4-c4ccccc43)c3ccccc3-c3ccccc3)c21]

-continued
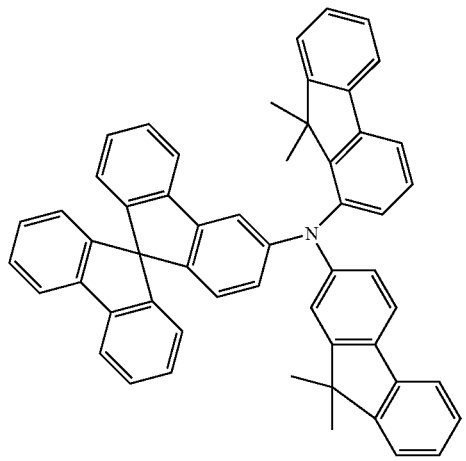 [SMILES: CC1(C)c2ccccc2-c2ccc(N(c3ccc4c(c3)-c3ccccc3C43c4ccccc4-c4ccccc43)c3cccc4c3C(C)(C)c3ccccc3-4)cc21]
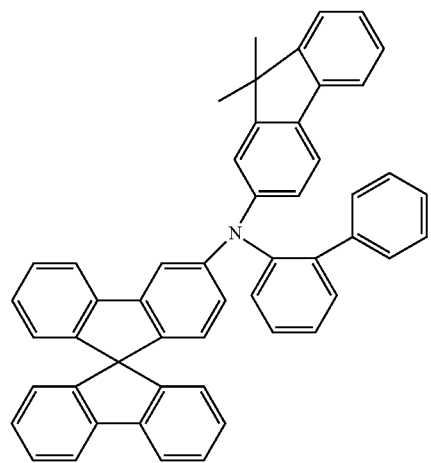 [SMILES: CC1(C)c2ccccc2-c2ccc(N(c3ccc4c(c3)-c3ccccc3C43c4ccccc4-c4ccccc43)c3ccccc3-c3ccccc3)cc21]
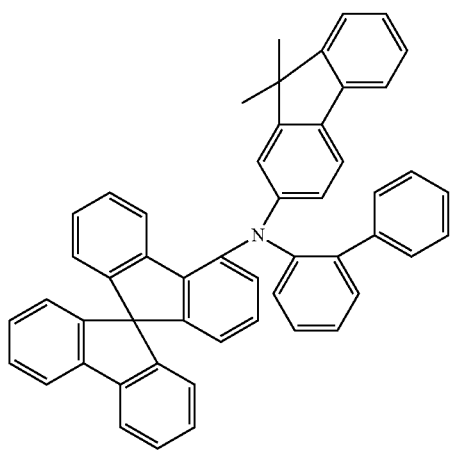 [SMILES: CC1(C)c2ccccc2-c2ccc(N(c3ccccc3-c3ccccc3)c3cccc4c3-c3ccccc3C43c4ccccc4-c4ccccc43)cc21]

-continued
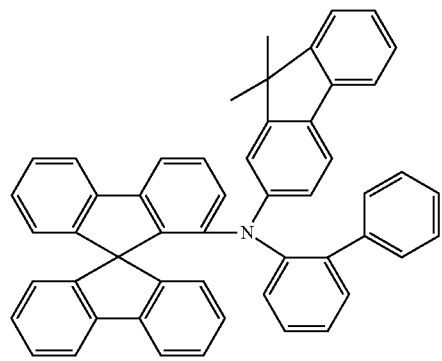 [SMILES: CC1(C)c2ccccc2-c2ccc(N(c3ccccc3-c3ccccc3)c3cccc4c3C3(c5ccccc5-c5ccccc53)c3ccccc3-4)cc21]
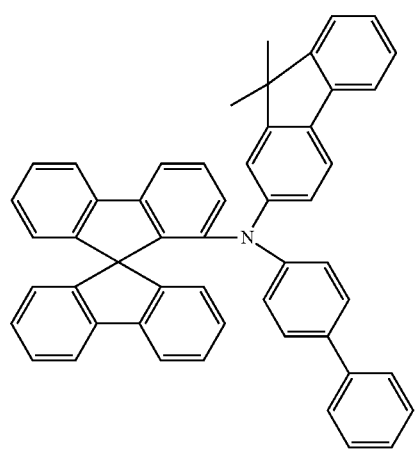 [SMILES: CC1(C)c2ccccc2-c2ccc(N(c3ccc(-c4ccccc4)cc3)c3cccc4c3C3(c5ccccc5-c5ccccc53)c3ccccc3-4)cc21]
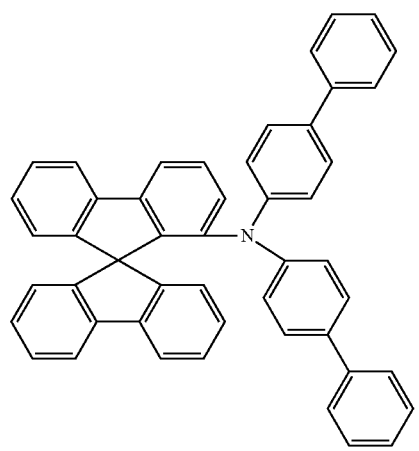 [SMILES: c1ccc(-c2ccc(N(c3ccc(-c4ccccc4)cc3)c3cccc4c3C3(c5ccccc5-c5ccccc53)c3ccccc3-4)cc2)cc1]

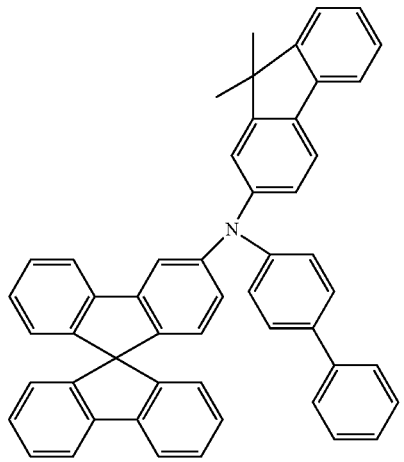 [SMILES: CC1(C)c2ccccc2-c2ccc(N(c3ccc(-c4ccccc4)cc3)c3ccc4c(c3)-c3ccccc3C43c4ccccc4-c4ccccc43)cc21]
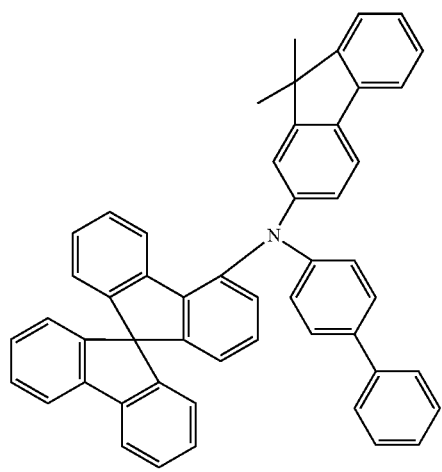 [SMILES: CC1(C)c2ccccc2-c2ccc(N(c3ccc(-c4ccccc4)cc3)c3cccc4c3-c3ccccc3C43c4ccccc4-c4ccccc43)cc21]
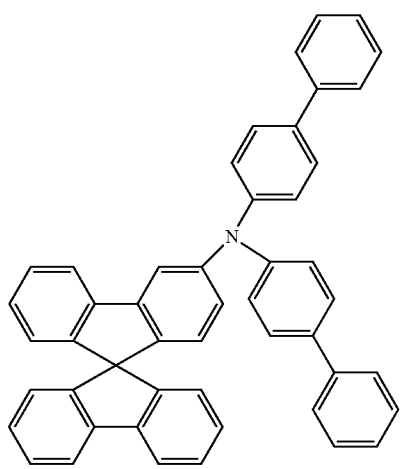 [SMILES: c1ccc(-c2ccc(N(c3ccc(-c4ccccc4)cc3)c3ccc4c(c3)-c3ccccc3C43c4ccccc4-c4ccccc43)cc2)cc1]

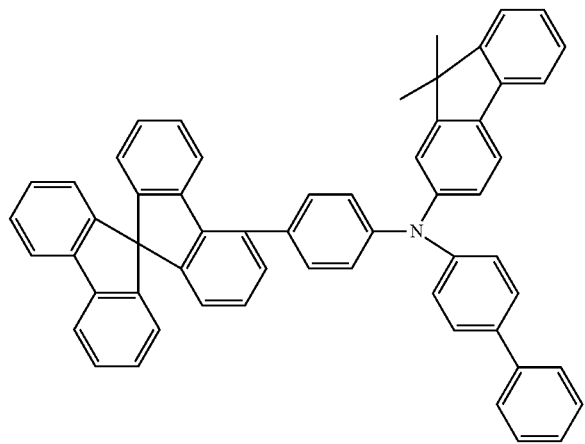 [SMILES: CC1(C)c2ccccc2-c2ccc(N(c3ccc(-c4ccccc4)cc3)c3ccc(-c4cccc5c4-c4ccccc4C54c5ccccc5-c5ccccc54)cc3)cc21]
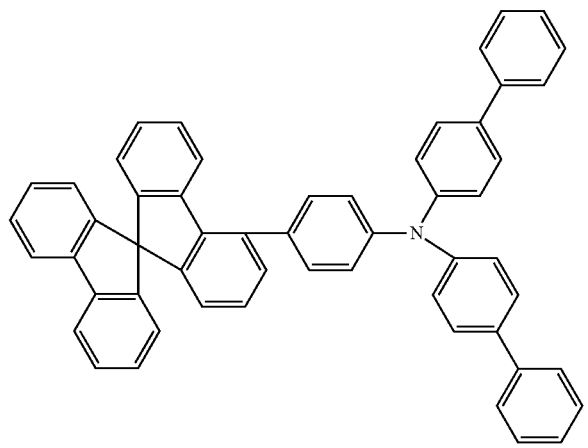 [SMILES: c1ccc(-c2ccc(N(c3ccc(-c4ccccc4)cc3)c3ccc(-c4cccc5c4-c4ccccc4C54c5ccccc5-c5ccccc54)cc3)cc2)cc1]
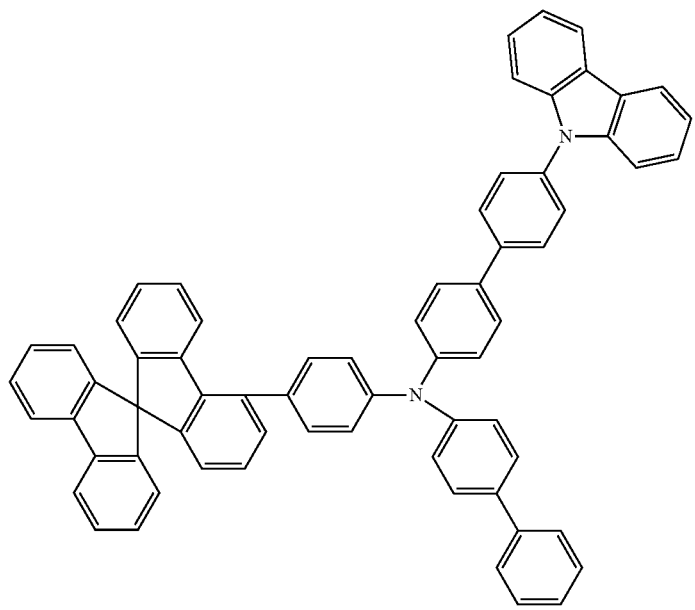 [SMILES: c1ccc(-c2ccc(N(c3ccc(-c4ccc(-n5c6ccccc6c6ccccc65)cc4)cc3)c3ccc(-c4cccc5c4-c4ccccc4C54c5ccccc5-c5ccccc54)cc3)cc2)cc1]

-continued
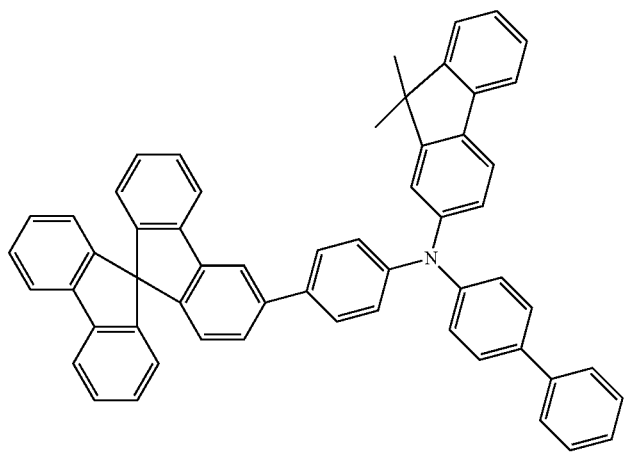 [SMILES: CC1(C)c2ccccc2-c2ccc(N(c3ccc(-c4ccccc4)cc3)c3ccc(-c4ccc5c(c4)-c4ccccc4C54c5ccccc5-c5ccccc54)cc3)cc21]
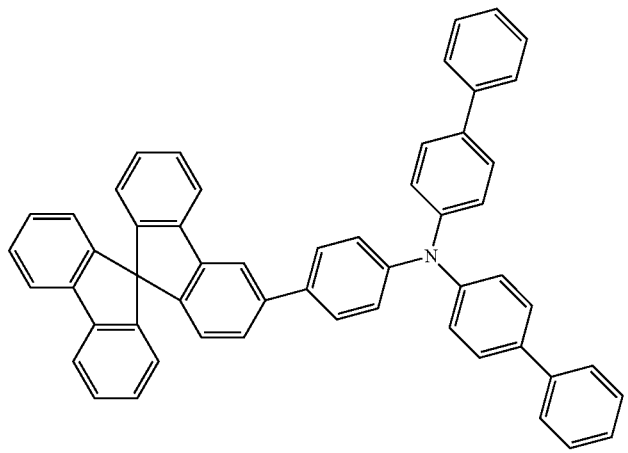 [SMILES: c1ccc(-c2ccc(N(c3ccc(-c4ccccc4)cc3)c3ccc(-c4ccc5c(c4)-c4ccccc4C54c5ccccc5-c5ccccc54)cc3)cc2)cc1]
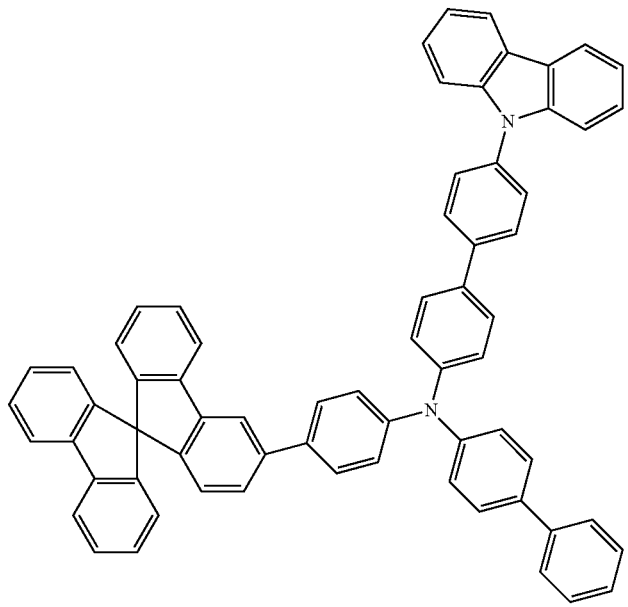 [SMILES: c1ccc(-c2ccc(N(c3ccc(-c4ccc(-n5c6ccccc6c6ccccc65)cc4)cc3)c3ccc(-c4ccc5c(c4)-c4ccccc4C54c5ccccc5-c5ccccc54)cc3)cc2)cc1]

-continued
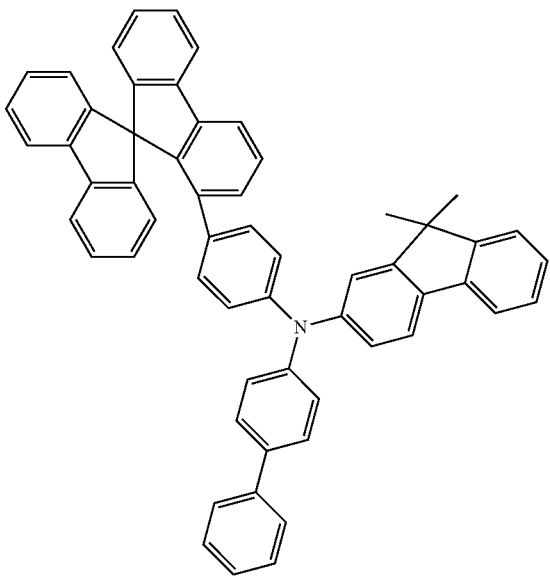 [SMILES: CC1(C)c2ccccc2-c2ccc(N(c3ccc(-c4ccccc4)cc3)c3ccc(-c4cccc5c4C4(c6ccccc6-c6ccccc64)c4ccccc4-5)cc3)cc21]
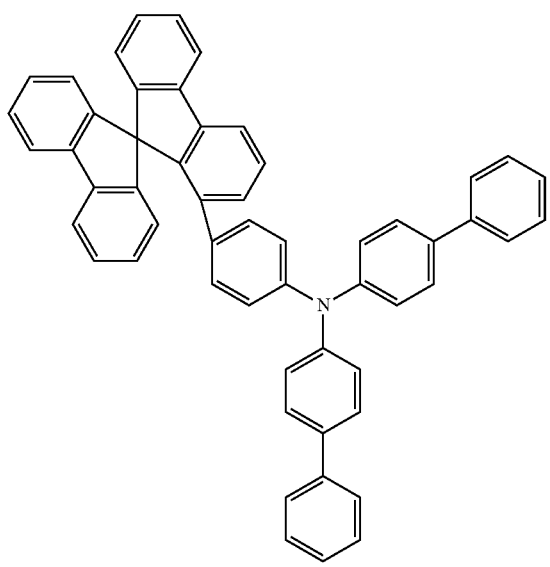 [SMILES: c1ccc(-c2ccc(N(c3ccc(-c4ccccc4)cc3)c3ccc(-c4cccc5c4C4(c6ccccc6-c6ccccc64)c4ccccc4-5)cc3)cc2)cc1]

-continued
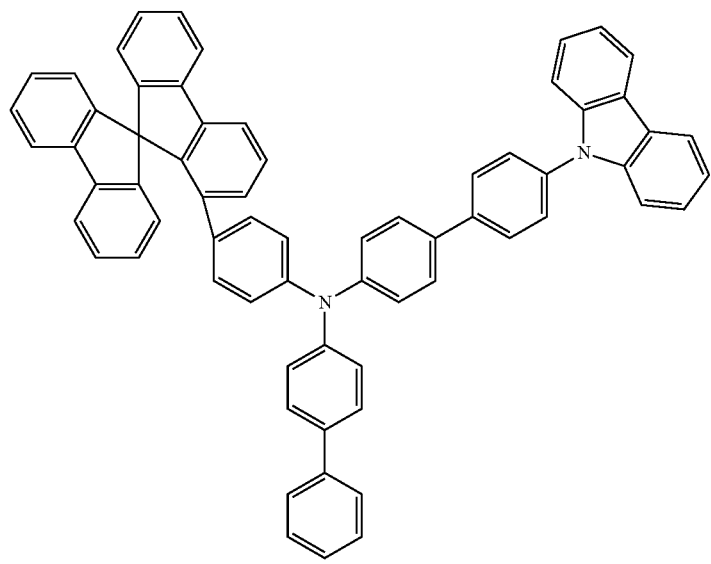 [SMILES: c1ccc(-c2ccc(N(c3ccc(-c4ccc(-n5c6ccccc6c6ccccc65)cc4)cc3)c3ccc(-c4cccc5c4C4(c6ccccc6-c6ccccc64)c4ccccc4-5)cc3)cc2)cc1]
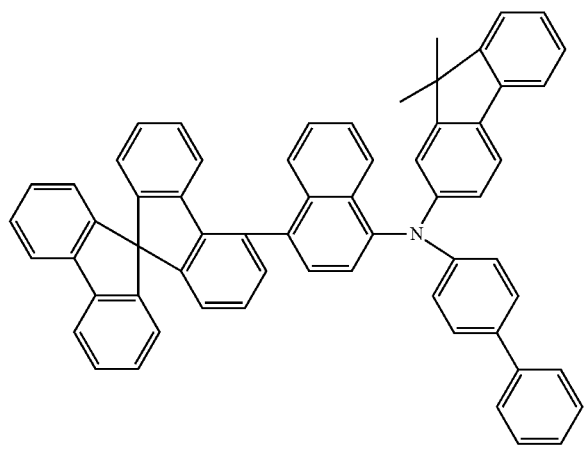 [SMILES: CC1(C)c2ccccc2-c2ccc(N(c3ccc(-c4ccccc4)cc3)c3ccc(-c4cccc5c4-c4ccccc4C54c5ccccc5-c5ccccc54)c4ccccc34)cc21]
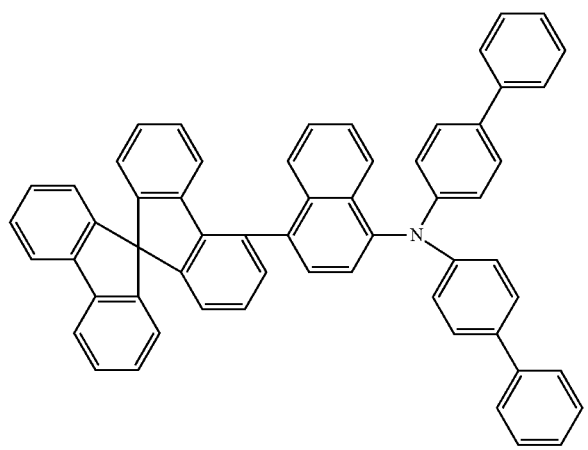 [SMILES: c1ccc(-c2ccc(N(c3ccc(-c4ccccc4)cc3)c3ccc(-c4cccc5c4-c4ccccc4C54c5ccccc5-c5ccccc54)c4ccccc34)cc2)cc1]

-continued
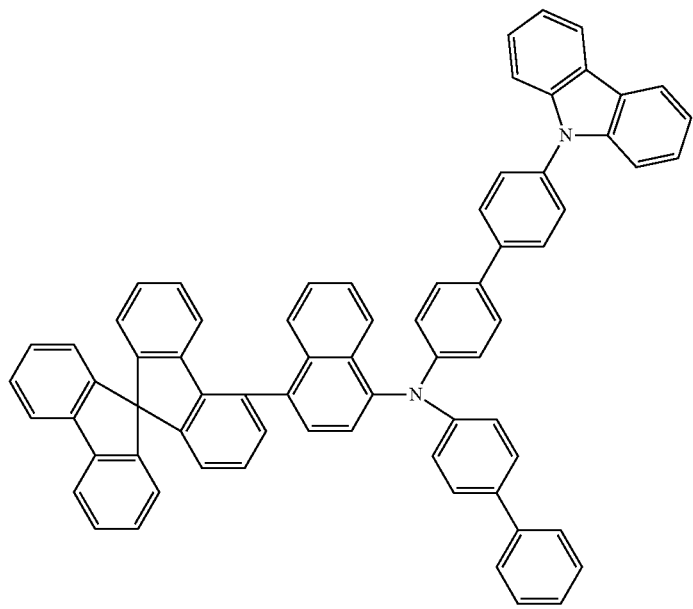 [SMILES: c1ccc(-c2ccc(N(c3ccc(-c4ccc(-n5c6ccccc6c6ccccc65)cc4)cc3)c3ccc(-c4cccc5c4-c4ccccc4C54c5ccccc5-c5ccccc54)c4ccccc34)cc2)cc1]
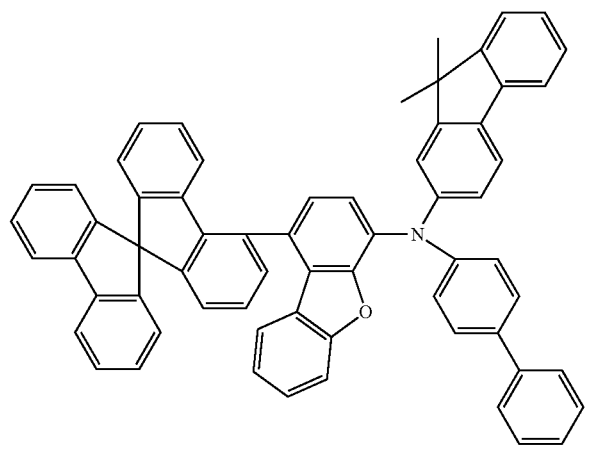 [SMILES: CC1(C)c2ccccc2-c2ccc(N(c3ccc(-c4ccccc4)cc3)c3ccc(-c4cccc5c4-c4ccccc4C54c5ccccc5-c5ccccc54)c4c3oc3ccccc34)cc21]
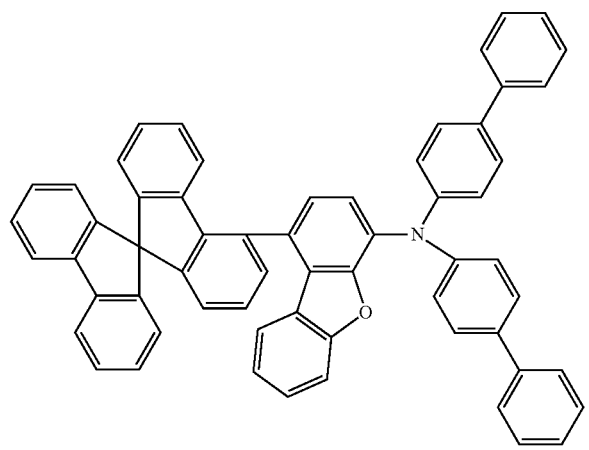 [SMILES: c1ccc(-c2ccc(N(c3ccc(-c4ccccc4)cc3)c3ccc(-c4cccc5c4-c4ccccc4C54c5ccccc5-c5ccccc54)c4c3oc3ccccc34)cc2)cc1]

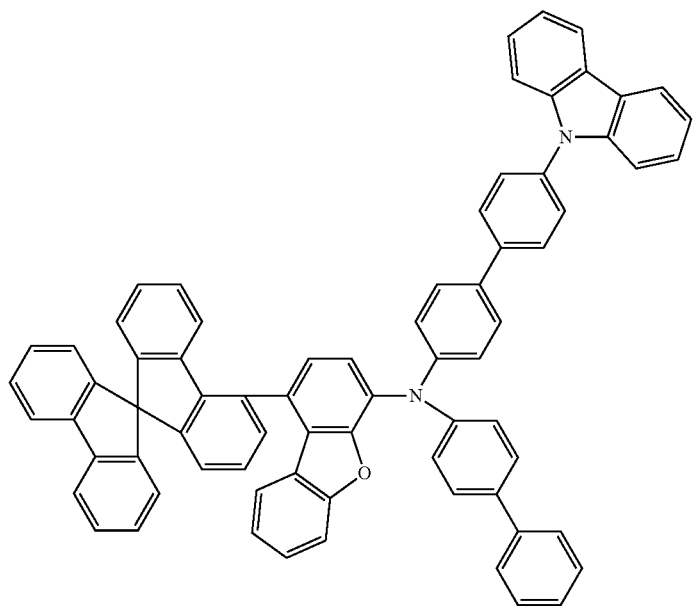 [SMILES: c1ccc(-c2ccc(N(c3ccc(-c4ccc(-n5c6ccccc6c6ccccc65)cc4)cc3)c3ccc(-c4cccc5c4-c4ccccc4C54c5ccccc5-c5ccccc54)c4c3oc3ccccc34)cc2)cc1]
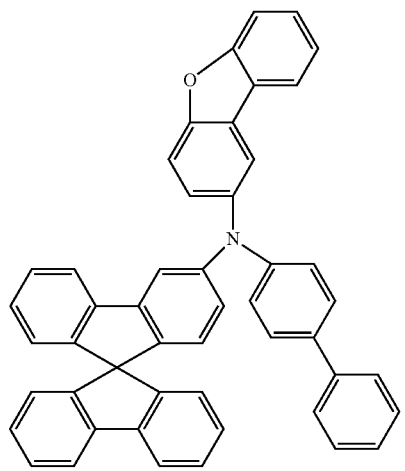
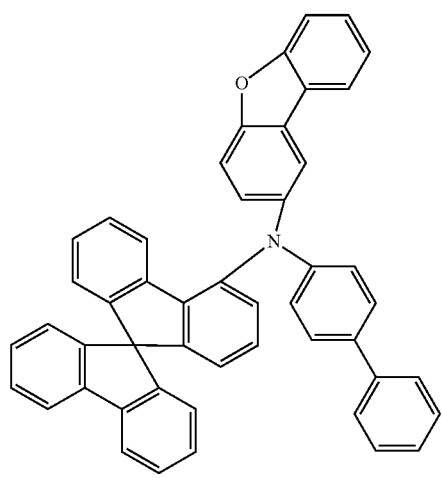 [SMILES: c1ccc(-c2ccc(N(c3ccc4oc5ccccc5c4c3)c3cccc4c3-c3ccccc3C43c4ccccc4-c4ccccc43)cc2)cc1]

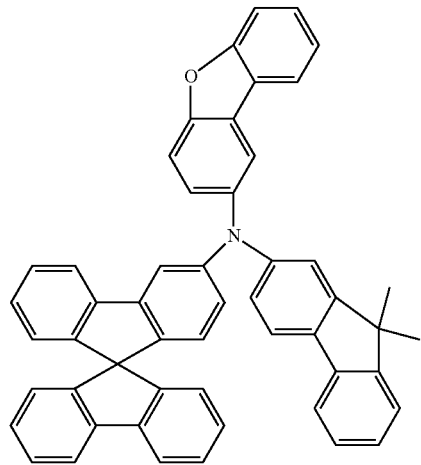 [SMILES: CC1(C)c2ccccc2-c2ccc(N(c3ccc4c(c3)-c3ccccc3C43c4ccccc4-c4ccccc43)c3ccc4oc5ccccc5c4c3)cc21]
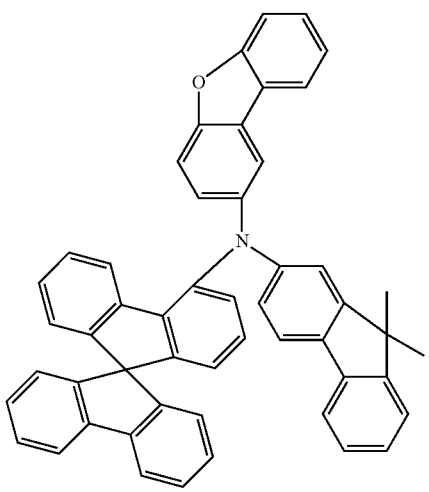
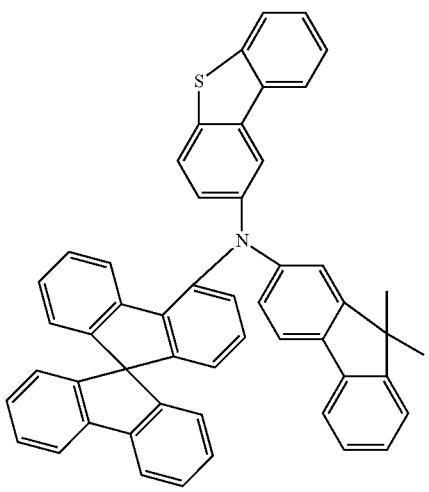 [SMILES: CC1(C)c2ccccc2-c2ccc(N(c3ccc4oc5ccccc5c4c3)c3cccc4c3-c3ccccc3C43c4ccccc4-c4ccccc43)cc21]

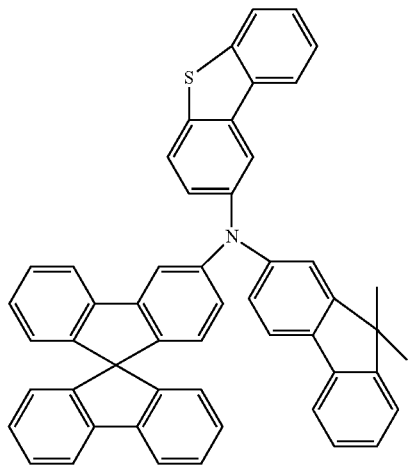 [SMILES: CC1(C)c2ccccc2-c2ccc(N(c3ccc4c(c3)-c3ccccc3C43c4ccccc4-c4ccccc43)c3ccc4sc5ccccc5c4c3)cc21]
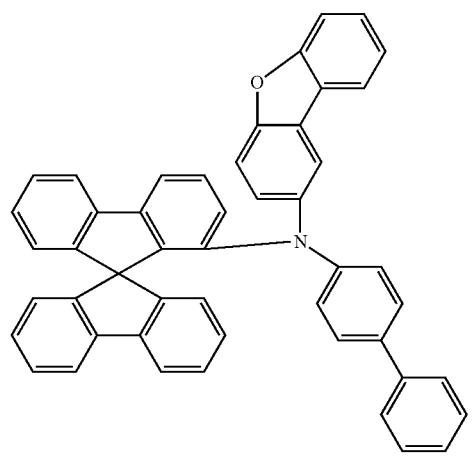 [SMILES: c1ccc(-c2ccc(N(c3ccc4oc5ccccc5c4c3)c3cccc4c3C3(c5ccccc5-c5ccccc53)c3ccccc3-4)cc2)cc1]
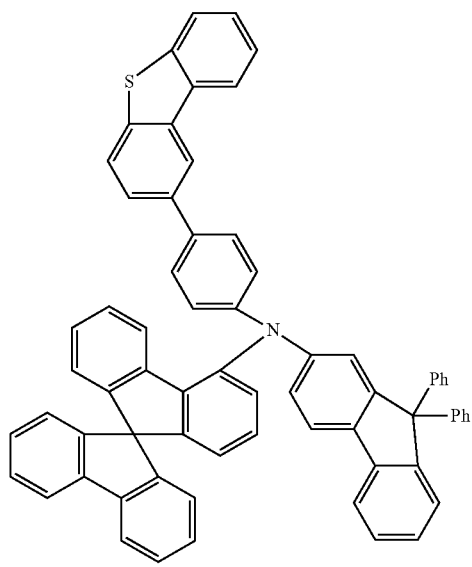 [SMILES: c1ccc(C2(c3ccccc3)c3ccccc3-c3ccc(N(c4ccc(-c5ccc6sc7ccccc7c6c5)cc4)c4cccc5c4-c4ccccc4C54c5ccccc5-c5ccccc54)cc32)cc1]

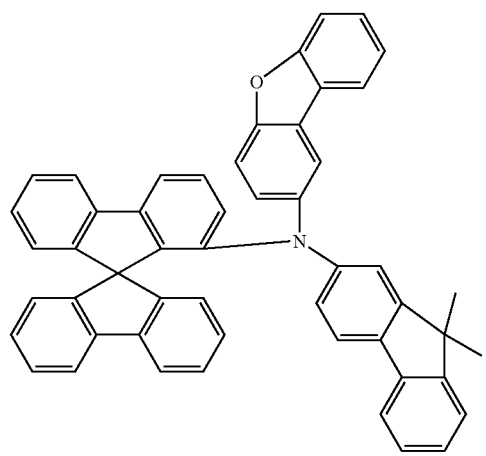 [SMILES: CC1(C)c2ccccc2-c2ccc(N(c3ccc4oc5ccccc5c4c3)c3cccc4c3C3(c5ccccc5-c5ccccc53)c3ccccc3-4)cc21]
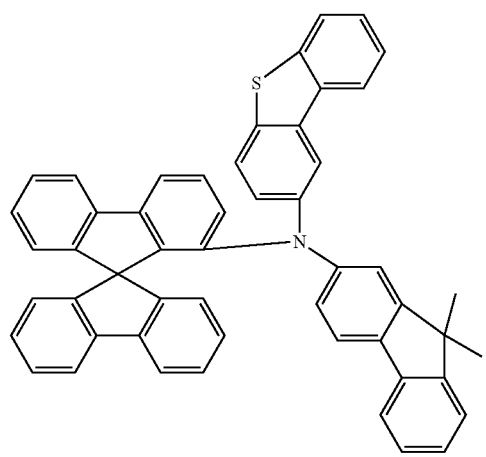 [SMILES: CC1(C)c2ccccc2-c2ccc(N(c3ccc4sc5ccccc5c4c3)c3cccc4c3C3(c5ccccc5-c5ccccc53)c3ccccc3-4)cc21]
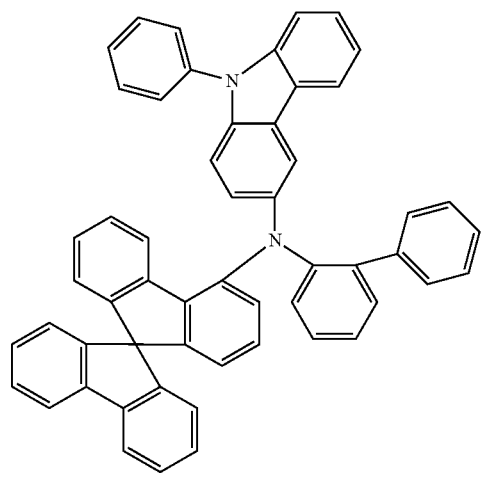 [SMILES: c1ccc(-c2ccccc2N(c2ccc3c(c2)c2ccccc2n3-c2ccccc2)c2cccc3c2-c2ccccc2C32c3ccccc3-c3ccccc32)cc1]

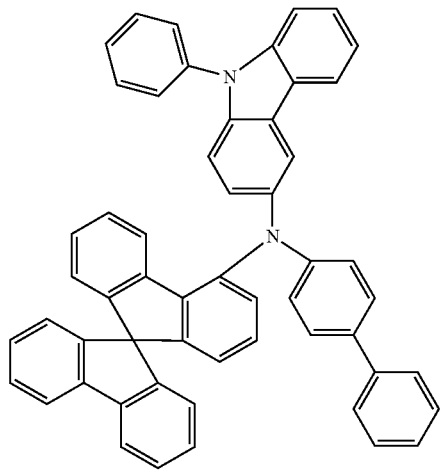 [SMILES: c1ccc(-c2ccc(N(c3ccc4c(c3)c3ccccc3n4-c3ccccc3)c3cccc4c3-c3ccccc3C43c4ccccc4-c4ccccc43)cc2)cc1]
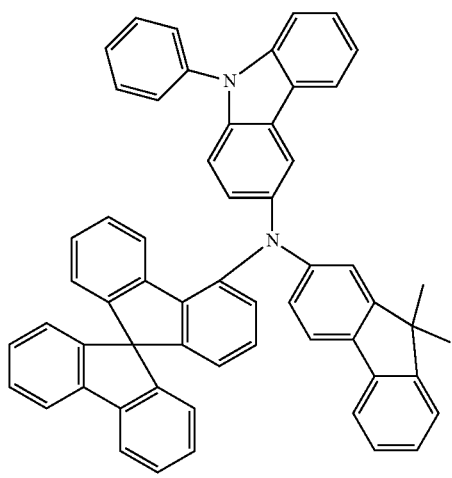 [SMILES: CC1(C)c2ccccc2-c2ccc(N(c3ccc4c(c3)c3ccccc3n4-c3ccccc3)c3cccc4c3-c3ccccc3C43c4ccccc4-c4ccccc43)cc21]
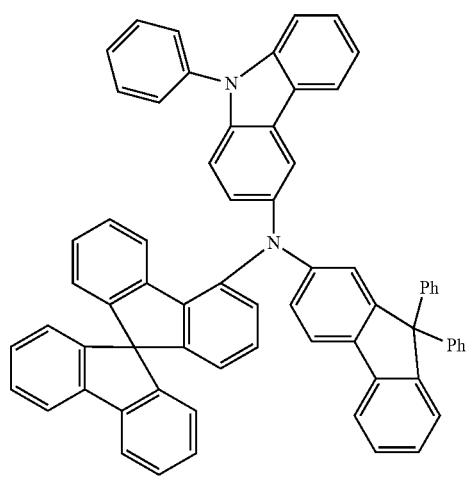 [SMILES: c1ccc(-n2c3ccccc3c3cc(N(c4ccc5c(c4)C(c4ccccc4)(c4ccccc4)c4ccccc4-5)c4cccc5c4-c4ccccc4C54c5ccccc5-c5ccccc54)ccc32)cc1]

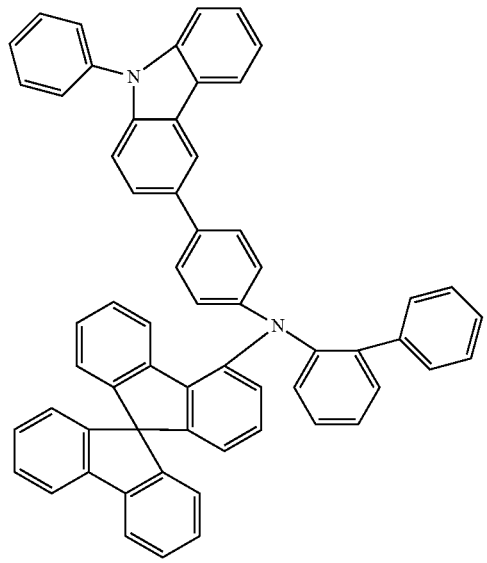 [SMILES: c1ccc(-c2ccccc2N(c2ccc(-c3ccc4c(c3)c3ccccc3n4-c3ccccc3)cc2)c2cccc3c2-c2ccccc2C32c3ccccc3-c3ccccc32)cc1]
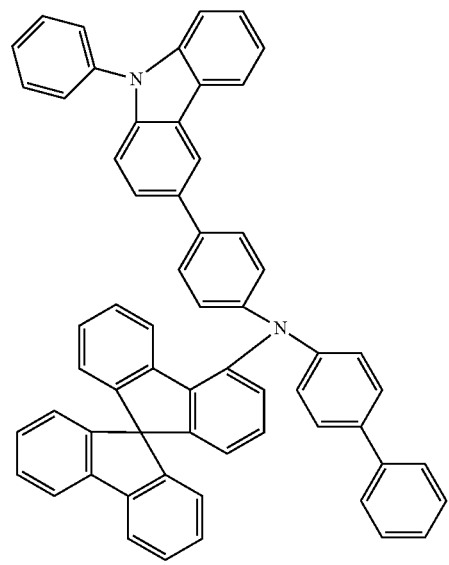 [SMILES: c1ccc(-c2ccc(N(c3ccc(-c4ccc5c(c4)c4ccccc4n5-c4ccccc4)cc3)c3cccc4c3-c3ccccc3C43c4ccccc4-c4ccccc43)cc2)cc1]

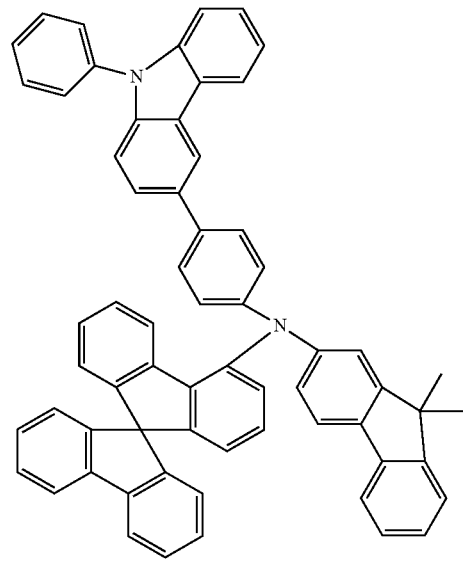 [SMILES: CC1(C)c2ccccc2-c2ccc(N(c3ccc(-c4ccc5c(c4)c4ccccc4n5-c4ccccc4)cc3)c3cccc4c3-c3ccccc3C43c4ccccc4-c4ccccc43)cc21]
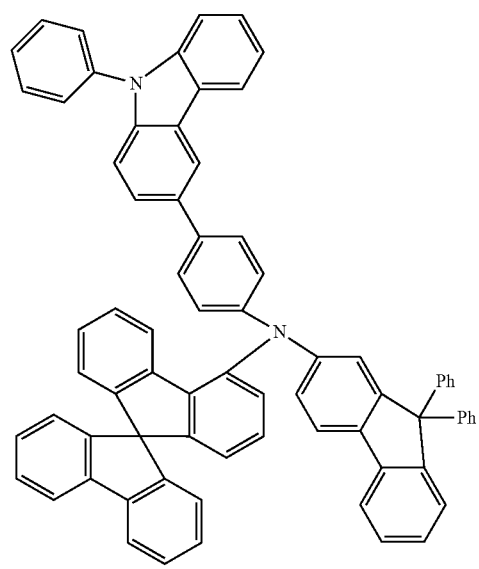 [SMILES: c1ccc(-n2c3ccccc3c3cc(-c4ccc(N(c5ccc6c(c5)C(c5ccccc5)(c5ccccc5)c5ccccc5-6)c5cccc6c5-c5ccccc5C65c6ccccc6-c6ccccc65)cc4)ccc32)cc1]

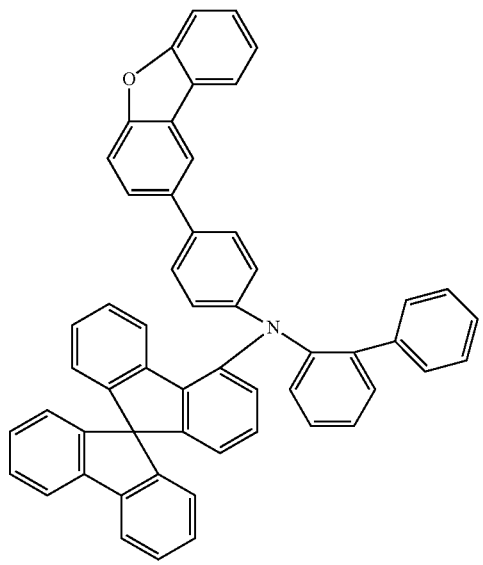 [SMILES: c1ccc(-c2ccccc2N(c2ccc(-c3ccc4oc5ccccc5c4c3)cc2)c2cccc3c2-c2ccccc2C32c3ccccc3-c3ccccc32)cc1]
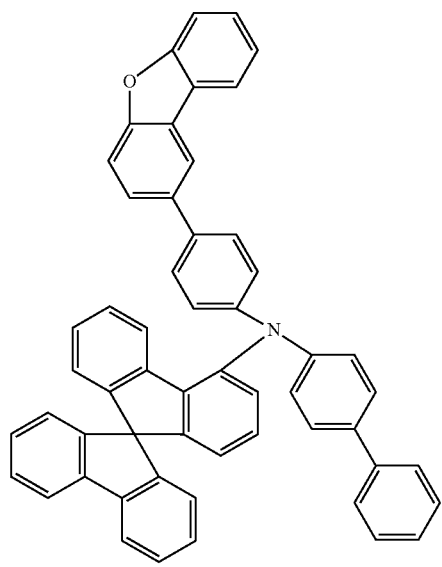 [SMILES: c1ccc(-c2ccc(N(c3ccc(-c4ccc5oc6ccccc6c5c4)cc3)c3cccc4c3-c3ccccc3C43c4ccccc4-c4ccccc43)cc2)cc1]

-continued
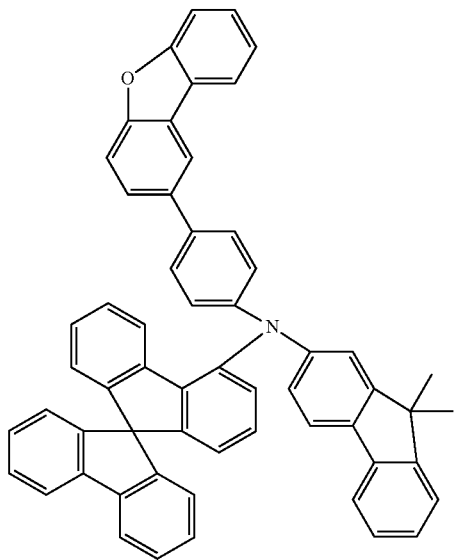 [SMILES: CC1(C)c2ccccc2-c2ccc(N(c3ccc(-c4ccc5oc6ccccc6c5c4)cc3)c3cccc4c3-c3ccccc3C43c4ccccc4-c4ccccc43)cc21]
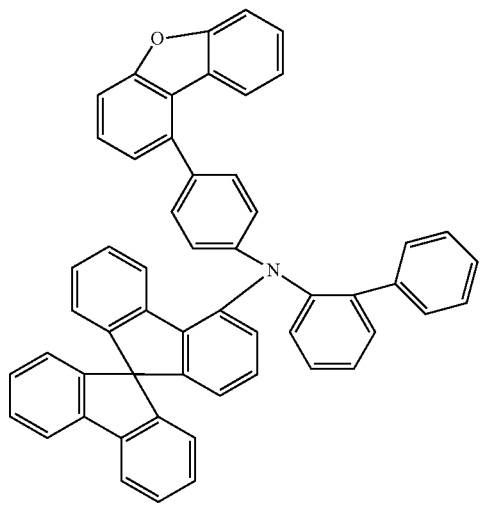 [SMILES: c1ccc(-c2ccccc2N(c2ccc(-c3cccc4oc5ccccc5c34)cc2)c2cccc3c2-c2ccccc2C32c3ccccc3-c3ccccc32)cc1]
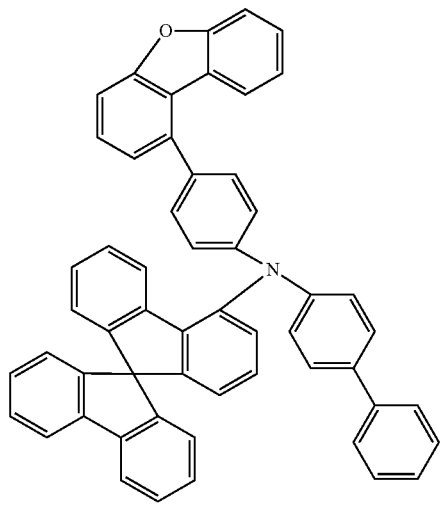 [SMILES: c1ccc(-c2ccc(N(c3ccc(-c4cccc5oc6ccccc6c45)cc3)c3cccc4c3-c3ccccc3C43c4ccccc4-c4ccccc43)cc2)cc1]

-continued
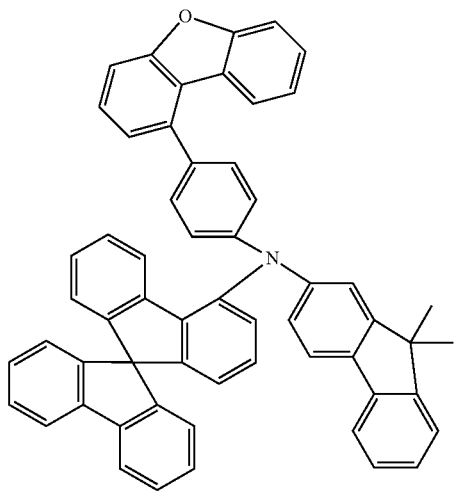 [SMILES: CC1(C)c2ccccc2-c2ccc(N(c3ccc(-c4cccc5oc6ccccc6c45)cc3)c3cccc4c3-c3ccccc3C43c4ccccc4-c4ccccc43)cc21]
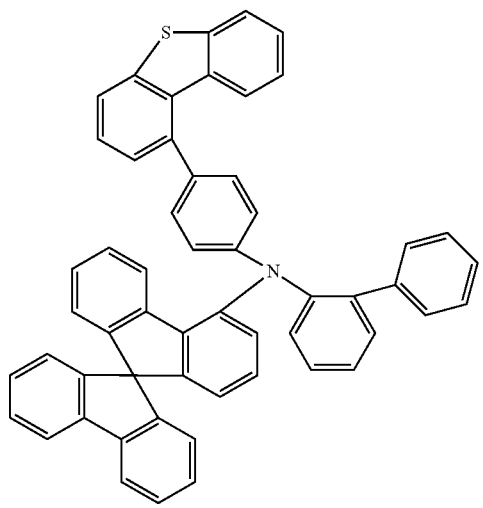 [SMILES: c1ccc(-c2ccccc2N(c2ccc(-c3cccc4sc5ccccc5c34)cc2)c2cccc3c2-c2ccccc2C32c3ccccc3-c3ccccc32)cc1]
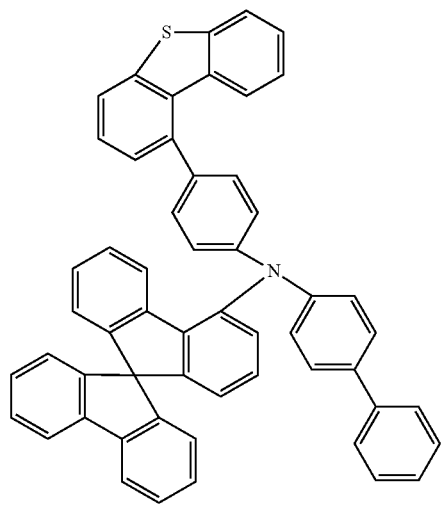 [SMILES: c1ccc(-c2ccc(N(c3ccc(-c4cccc5sc6ccccc6c45)cc3)c3cccc4c3-c3ccccc3C43c4ccccc4-c4ccccc43)cc2)cc1]

-continued
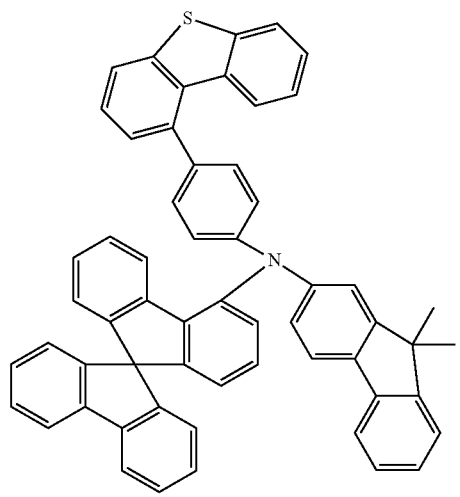 [SMILES: CC1(C)c2ccccc2-c2ccc(N(c3ccc(-c4cccc5sc6ccccc6c45)cc3)c3cccc4c3-c3ccccc3C43c4ccccc4-c4ccccc43)cc21]
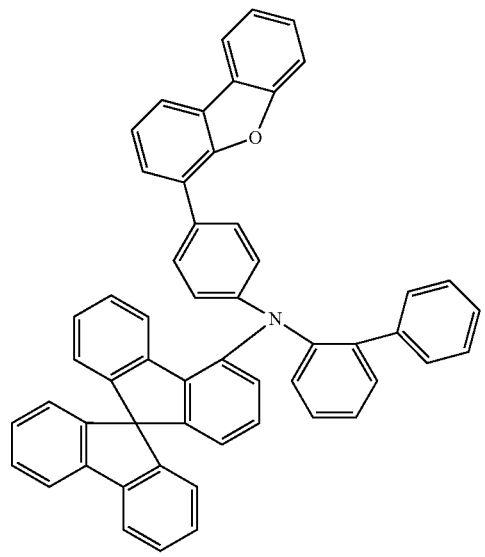 [SMILES: c1ccc(-c2ccccc2N(c2ccc(-c3cccc4c3oc3ccccc34)cc2)c2cccc3c2-c2ccccc2C32c3ccccc3-c3ccccc32)cc1]
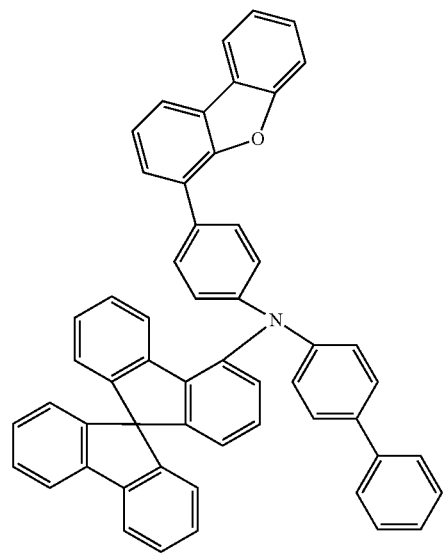 [SMILES: c1ccc(-c2ccc(N(c3ccc(-c4cccc5c4oc4ccccc45)cc3)c3cccc4c3-c3ccccc3C43c4ccccc4-c4ccccc43)cc2)cc1]

-continued
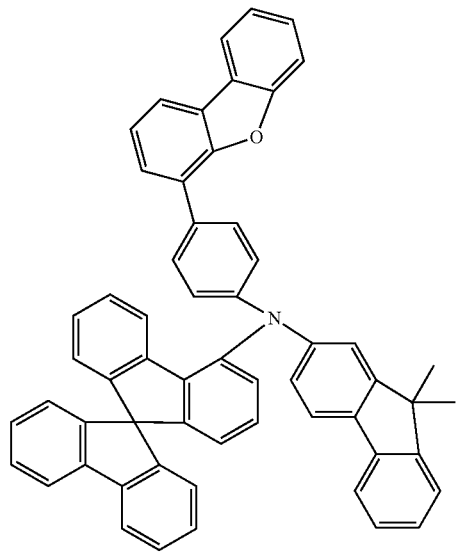 [SMILES: CC1(C)c2ccccc2-c2ccc(N(c3ccc(-c4cccc5c4oc4ccccc45)cc3)c3cccc4c3-c3ccccc3C43c4ccccc4-c4ccccc43)cc21]
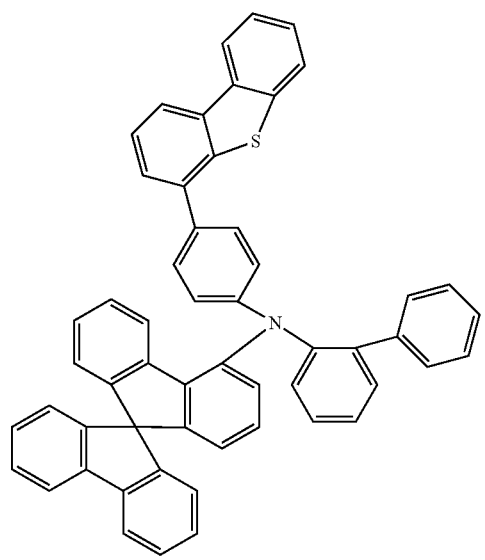 [SMILES: c1ccc(-c2ccccc2N(c2ccc(-c3cccc4c3sc3ccccc34)cc2)c2cccc3c2-c2ccccc2C32c3ccccc3-c3ccccc32)cc1]
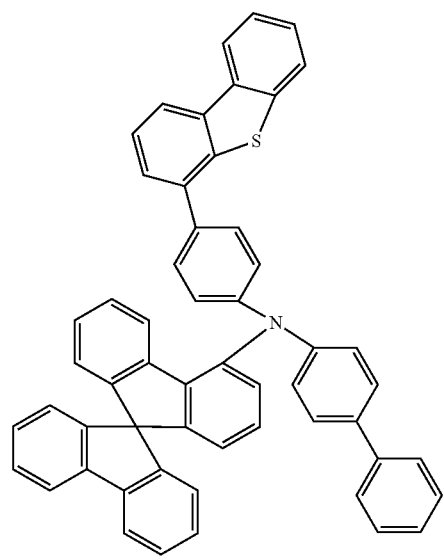 [SMILES: c1ccc(-c2ccc(N(c3ccc(-c4cccc5c4sc4ccccc45)cc3)c3cccc4c3-c3ccccc3C43c4ccccc4-c4ccccc43)cc2)cc1]

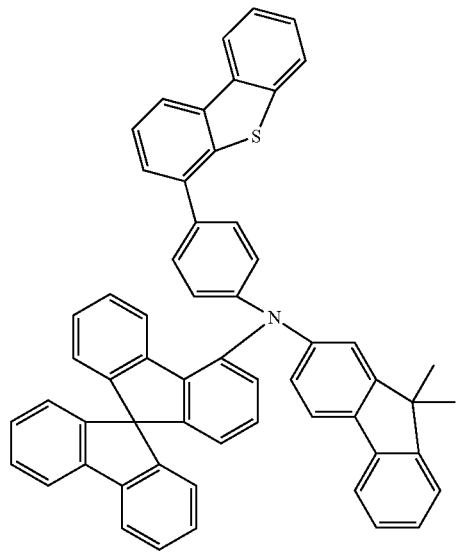 [SMILES: CC1(C)c2ccccc2-c2ccc(N(c3ccc(-c4cccc5c4sc4ccccc45)cc3)c3cccc4c3-c3ccccc3C43c4ccccc4-c4ccccc43)cc21]
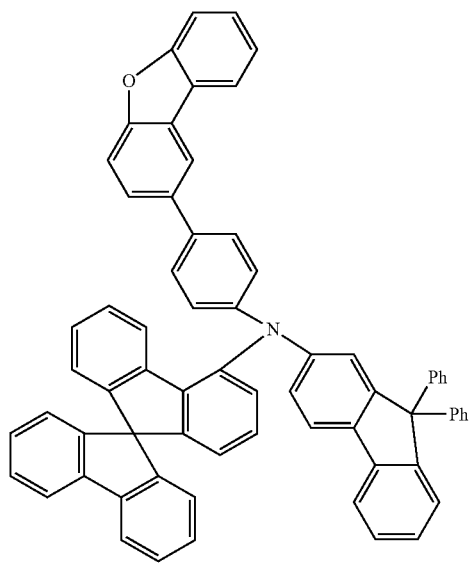 [SMILES: c1ccc(C2(c3ccccc3)c3ccccc3-c3ccc(N(c4ccc(-c5ccc6oc7ccccc7c6c5)cc4)c4cccc5c4-c4ccccc4C54c5ccccc5-c5ccccc54)cc32)cc1]

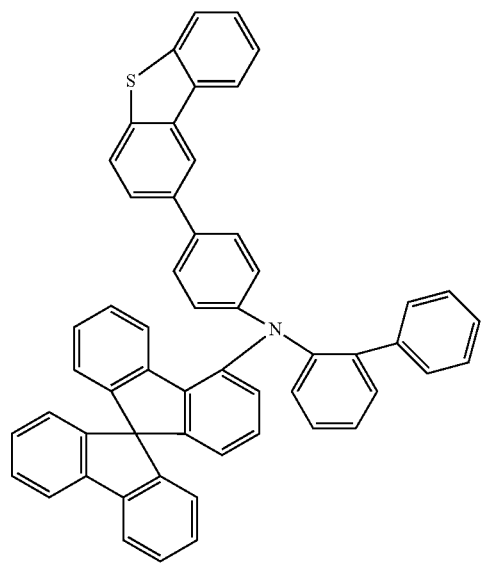 [SMILES: c1ccc(-c2ccccc2N(c2ccc(-c3ccc4sc5ccccc5c4c3)cc2)c2cccc3c2-c2ccccc2C32c3ccccc3-c3ccccc32)cc1]
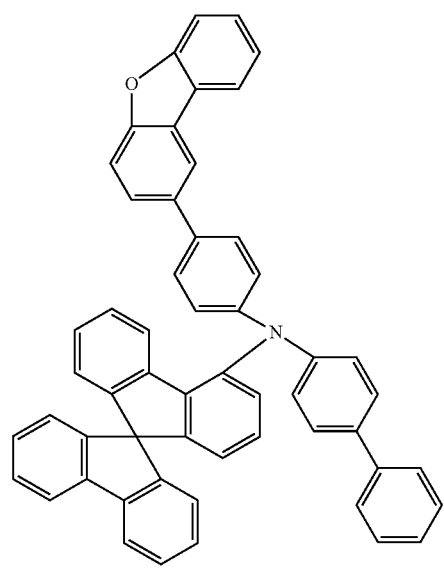 [SMILES: c1ccc(-c2ccc(N(c3ccc(-c4ccc5oc6ccccc6c5c4)cc3)c3cccc4c3-c3ccccc3C43c4ccccc4-c4ccccc43)cc2)cc1]
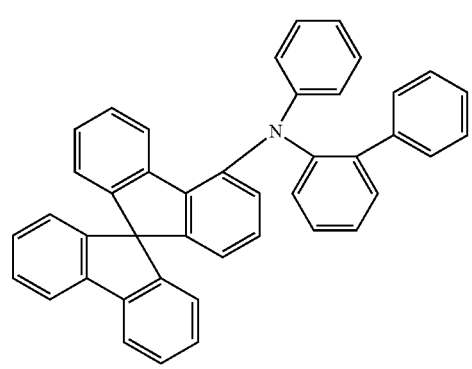 [SMILES: c1ccc(-c2ccccc2N(c2ccccc2)c2cccc3c2-c2ccccc2C32c3ccccc3-c3ccccc32)cc1]

-continued
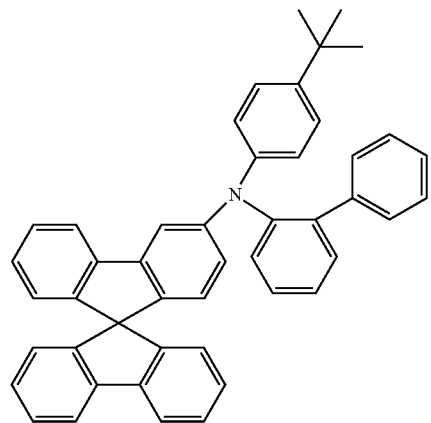 [SMILES: CC(C)(C)c1ccc(N(c2ccc3c(c2)-c2ccccc2C32c3ccccc3-c3ccccc32)c2ccccc2-c2ccccc2)cc1]
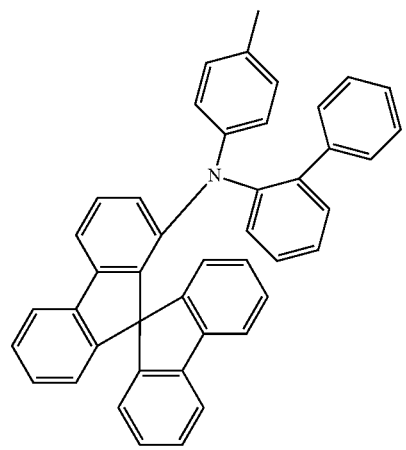 [SMILES: Cc1ccc(N(c2ccccc2-c2ccccc2)c2cccc3c2C2(c4ccccc4-c4ccccc42)c2ccccc2-3)cc1]
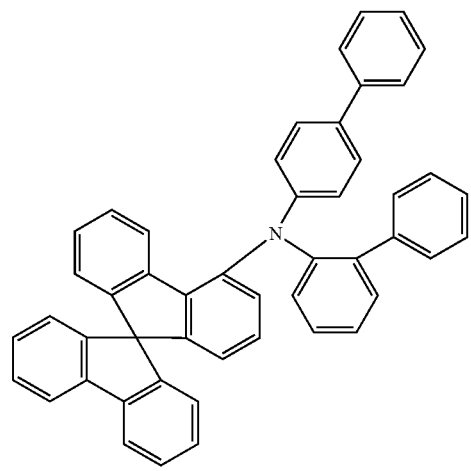 [SMILES: c1ccc(-c2ccc(N(c3ccccc3-c3ccccc3)c3cccc4c3-c3ccccc3C43c4ccccc4-c4ccccc43)cc2)cc1]

-continued
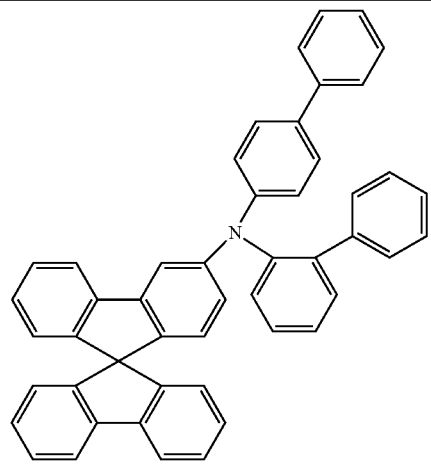
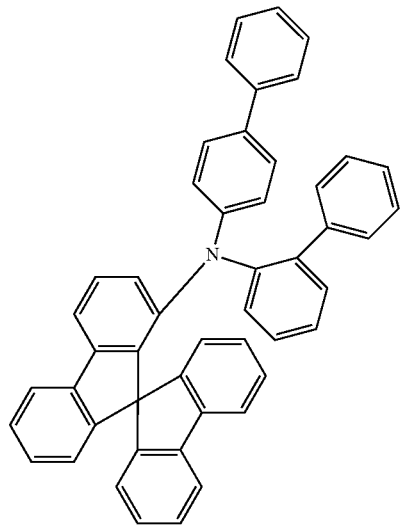 [SMILES: c1ccc(-c2ccc(N(c3ccccc3-c3ccccc3)c3cccc4c3C3(c5ccccc5-c5ccccc53)c3ccccc3-4)cc2)cc1]
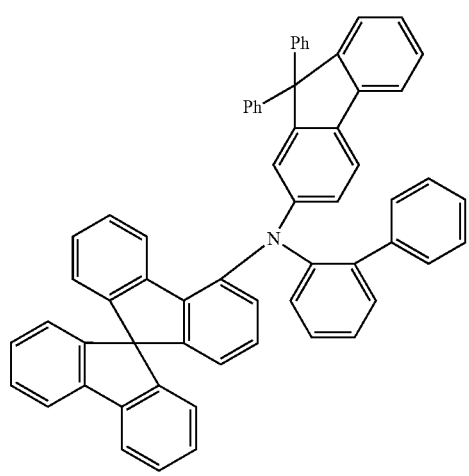 [SMILES: c1ccc(-c2ccccc2N(c2ccc3c(c2)C(c2ccccc2)(c2ccccc2)c2ccccc2-3)c2cccc3c2-c2ccccc2C32c3ccccc3-c3ccccc32)cc1]

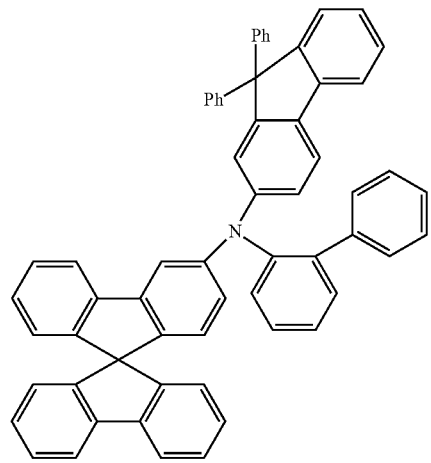 [SMILES: c1ccc(-c2ccccc2N(c2ccc3c(c2)-c2ccccc2C32c3ccccc3-c3ccccc32)c2ccc3c(c2)C(c2ccccc2)(c2ccccc2)c2ccccc2-3)cc1]
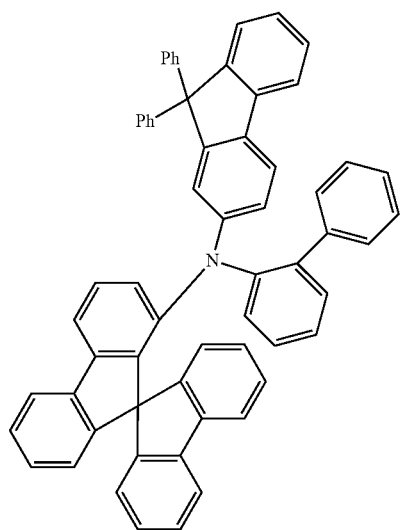 [SMILES: c1ccc(-c2ccccc2N(c2ccc3c(c2)C(c2ccccc2)(c2ccccc2)c2ccccc2-3)c2cccc3c2C2(c4ccccc4-c4ccccc42)c2ccccc2-3)cc1]
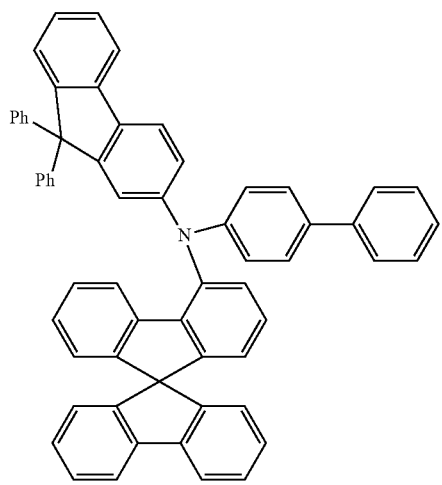 [SMILES: c1ccc(-c2ccc(N(c3ccc4c(c3)C(c3ccccc3)(c3ccccc3)c3ccccc3-4)c3cccc4c3-c3ccccc3C43c4ccccc4-c4ccccc43)cc2)cc1]

-continued
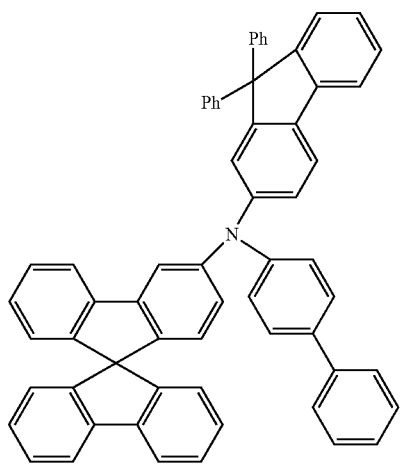
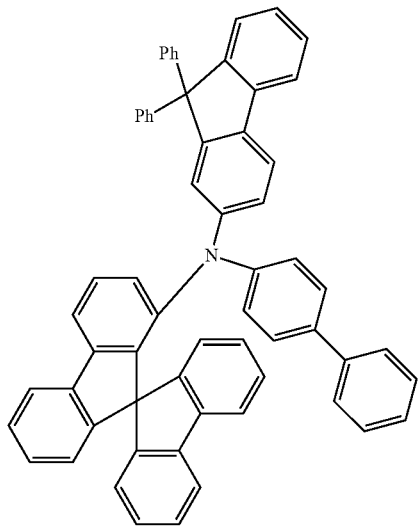 [SMILES: c1ccc(-c2ccc(N(c3ccc4c(c3)C(c3ccccc3)(c3ccccc3)c3ccccc3-4)c3cccc4c3C3(c5ccccc5-c5ccccc53)c3ccccc3-4)cc2)cc1]
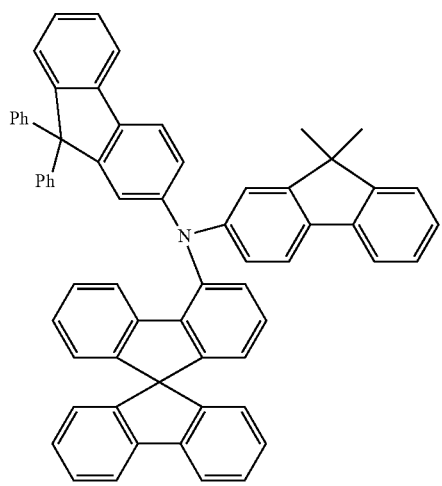 [SMILES: CC1(C)c2ccccc2-c2ccc(N(c3ccc4c(c3)C(c3ccccc3)(c3ccccc3)c3ccccc3-4)c3cccc4c3-c3ccccc3C43c4ccccc4-c4ccccc43)cc21]

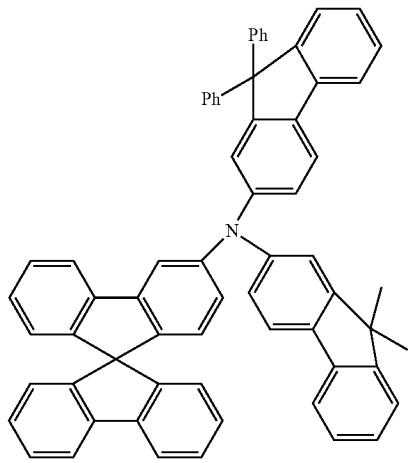 [SMILES: CC1(C)c2ccccc2-c2ccc(N(c3ccc4c(c3)-c3ccccc3C43c4ccccc4-c4ccccc43)c3ccc4c(c3)C(c3ccccc3)(c3ccccc3)c3ccccc3-4)cc21]
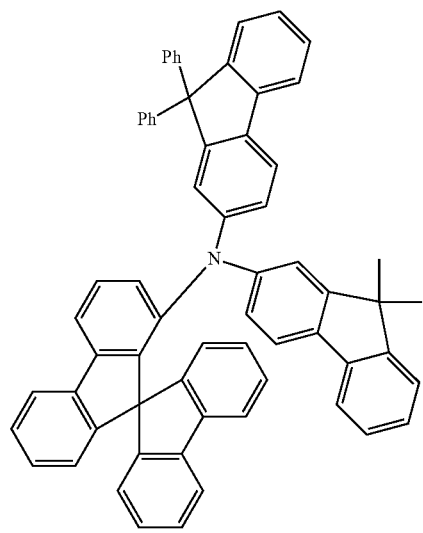 [SMILES: CC1(C)c2ccccc2-c2ccc(N(c3ccc4c(c3)C(c3ccccc3)(c3ccccc3)c3ccccc3-4)c3cccc4c3C3(c5ccccc5-c5ccccc53)c3ccccc3-4)cc21]
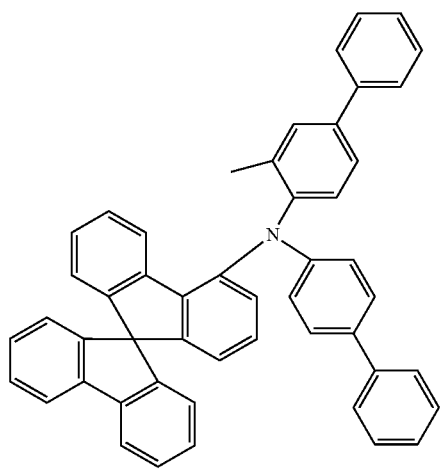 [SMILES: Cc1cc(-c2ccccc2)ccc1N(c1ccc(-c2ccccc2)cc1)c1cccc2c1-c1ccccc1C21c2ccccc2-c2ccccc21]

-continued
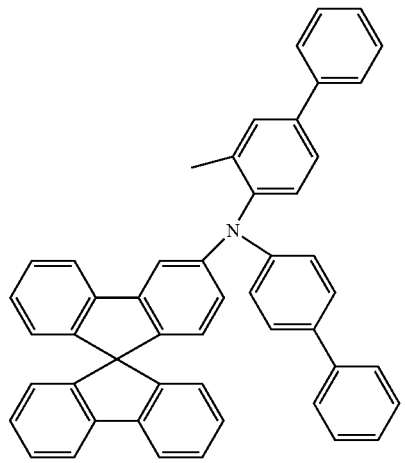 [SMILES: Cc1cc(-c2ccccc2)ccc1N(c1ccc(-c2ccccc2)cc1)c1ccc2c(c1)-c1ccccc1C21c2ccccc2-c2ccccc21]
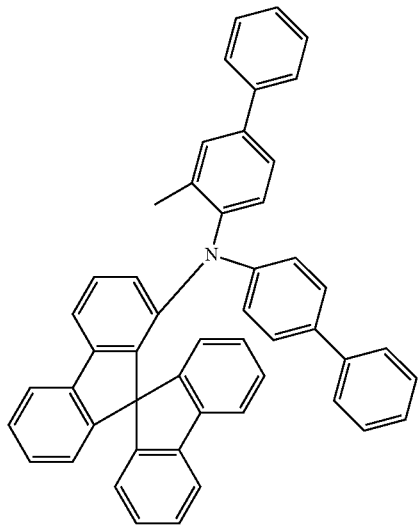 [SMILES: Cc1cc(-c2ccccc2)ccc1N(c1ccc(-c2ccccc2)cc1)c1cccc2c1C1(c3ccccc3-c3ccccc31)c1ccccc1-2]
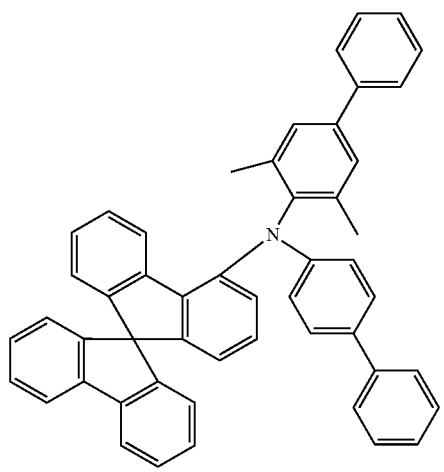 [SMILES: Cc1cc(-c2ccccc2)cc(C)c1N(c1ccc(-c2ccccc2)cc1)c1cccc2c1-c1ccccc1C21c2ccccc2-c2ccccc21]

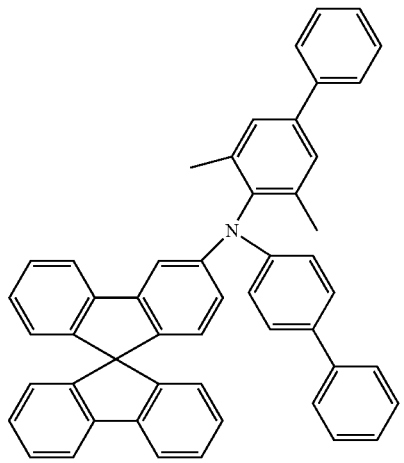 [SMILES: Cc1cc(-c2ccccc2)cc(C)c1N(c1ccc(-c2ccccc2)cc1)c1ccc2c(c1)-c1ccccc1C21c2ccccc2-c2ccccc21]
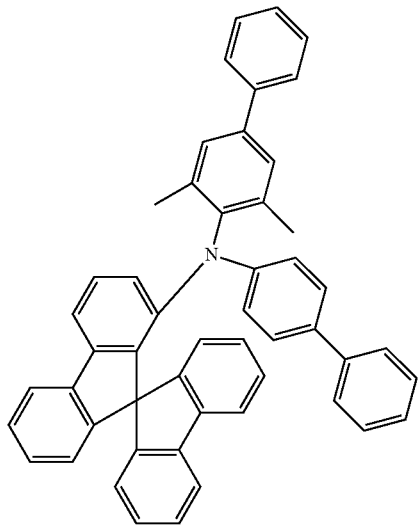 [SMILES: Cc1cc(-c2ccccc2)cc(C)c1N(c1ccc(-c2ccccc2)cc1)c1cccc2c1C1(c3ccccc3-c3ccccc31)c1ccccc1-2]
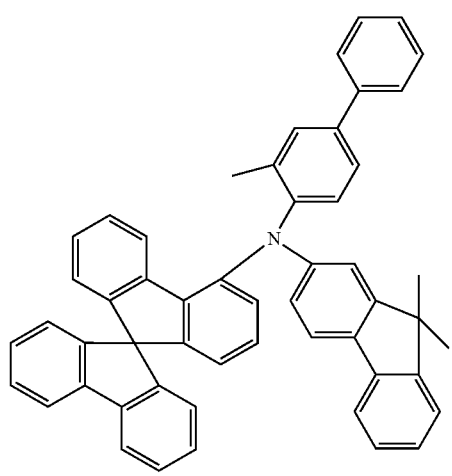 [SMILES: Cc1cc(-c2ccccc2)ccc1N(c1ccc2c(c1)C(C)(C)c1ccccc1-2)c1cccc2c1-c1ccccc1C21c2ccccc2-c2ccccc21]

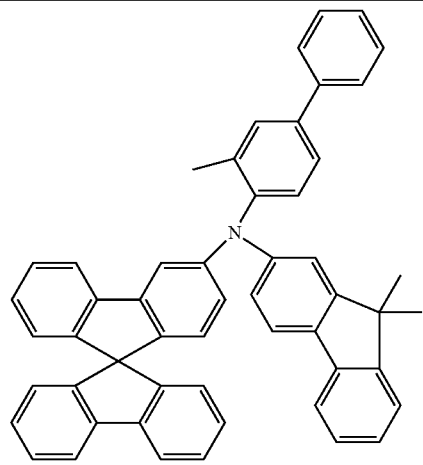
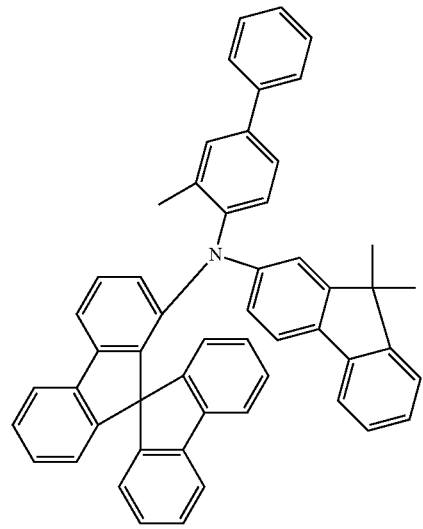 [SMILES: Cc1cc(-c2ccccc2)ccc1N(c1ccc2c(c1)C(C)(C)c1ccccc1-2)c1cccc2c1C1(c3ccccc3-c3ccccc31)c1ccccc1-2]
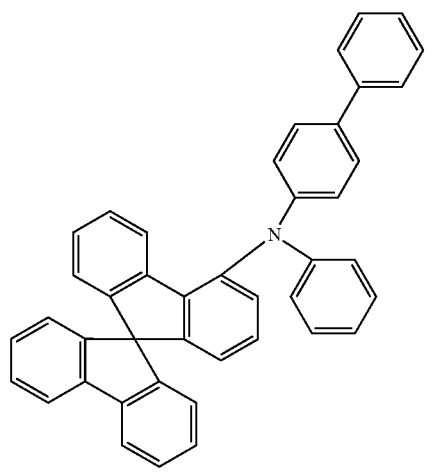 [SMILES: c1ccc(-c2ccc(N(c3ccccc3)c3cccc4c3-c3ccccc3C43c4ccccc4-c4ccccc43)cc2)cc1]

-continued
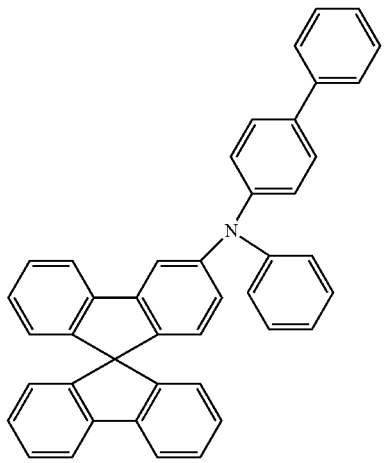 [SMILES: c1ccc(-c2ccc(N(c3ccccc3)c3ccc4c(c3)-c3ccccc3C43c4ccccc4-c4ccccc43)cc2)cc1]
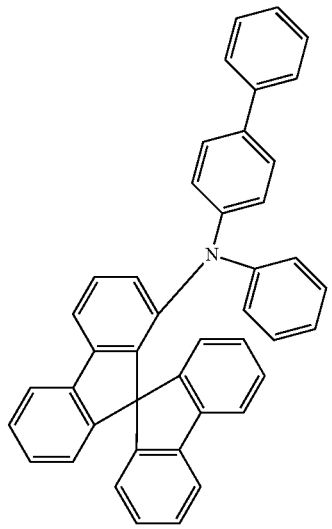 [SMILES: c1ccc(-c2ccc(N(c3ccccc3)c3cccc4c3C3(c5ccccc5-c5ccccc53)c3ccccc3-4)cc2)cc1]
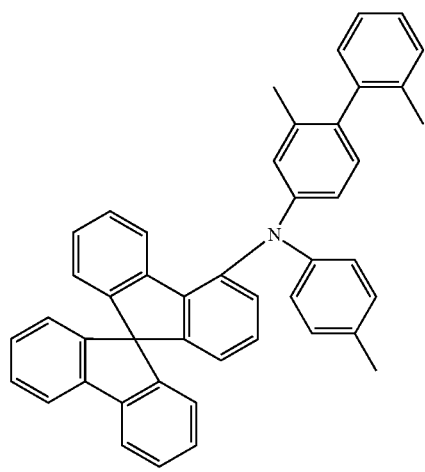 [SMILES: Cc1ccc(N(c2ccc(-c3ccccc3C)c(C)c2)c2cccc3c2-c2ccccc2C32c3ccccc3-c3ccccc32)cc1]

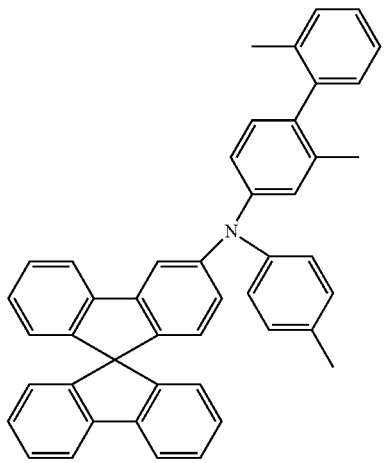 [SMILES: Cc1ccc(N(c2ccc(-c3ccccc3C)c(C)c2)c2ccc3c(c2)-c2ccccc2C32c3ccccc3-c3ccccc32)cc1]
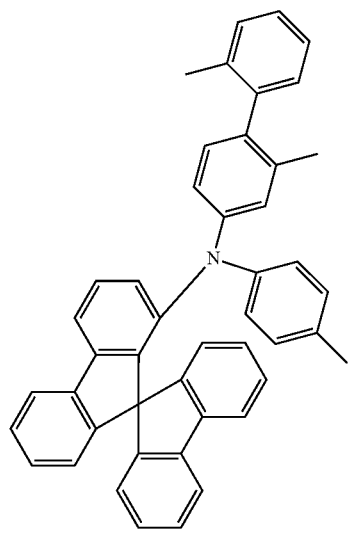 [SMILES: Cc1ccc(N(c2ccc(-c3ccccc3C)c(C)c2)c2cccc3c2C2(c4ccccc4-c4ccccc42)c2ccccc2-3)cc1]
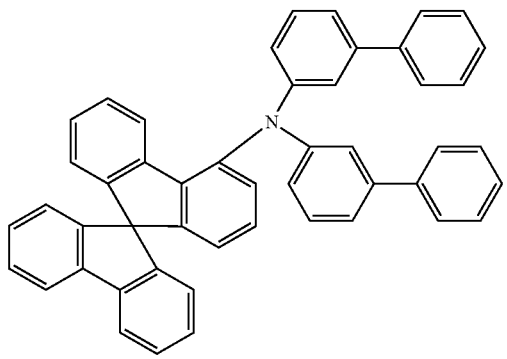 [SMILES: c1ccc(-c2cccc(N(c3cccc(-c4ccccc4)c3)c3cccc4c3-c3ccccc3C43c4ccccc4-c4ccccc43)c2)cc1]

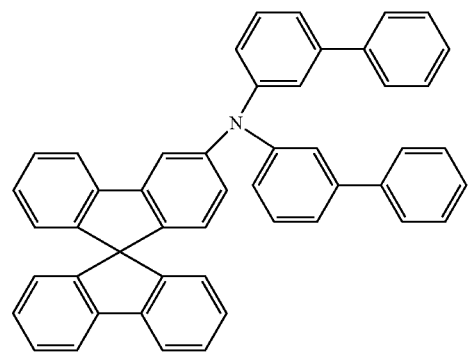 [SMILES: c1ccc(-c2cccc(N(c3cccc(-c4ccccc4)c3)c3ccc4c(c3)-c3ccccc3C43c4ccccc4-c4ccccc43)c2)cc1]
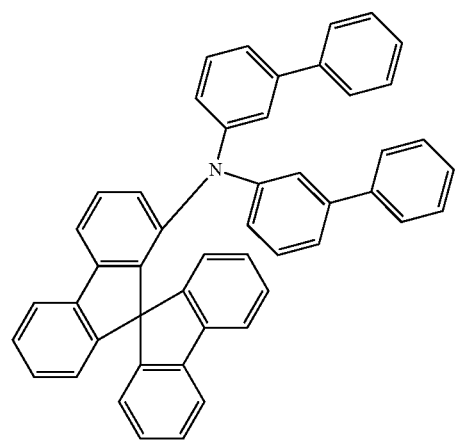 [SMILES: c1ccc(-c2cccc(N(c3cccc(-c4ccccc4)c3)c3cccc4c3C3(c5ccccc5-c5ccccc53)c3ccccc3-4)c2)cc1]
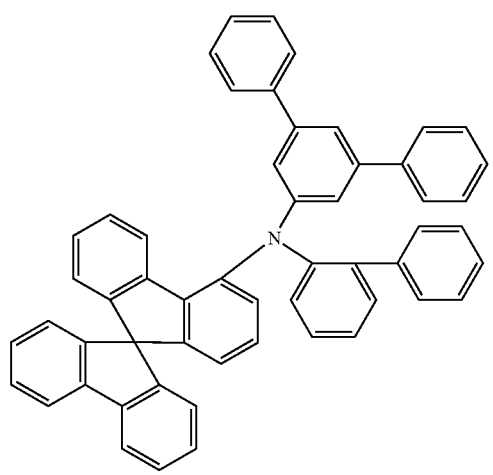 [SMILES: c1ccc(-c2cc(-c3ccccc3)cc(N(c3ccccc3-c3ccccc3)c3cccc4c3-c3ccccc3C43c4ccccc4-c4ccccc43)c2)cc1]

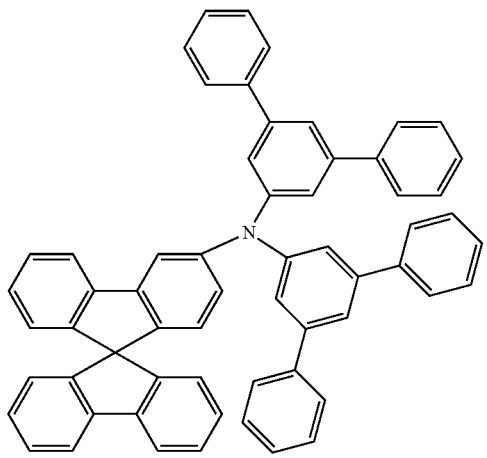 [SMILES: c1ccc(-c2cc(-c3ccccc3)cc(N(c3cc(-c4ccccc4)cc(-c4ccccc4)c3)c3ccc4c(c3)-c3ccccc3C43c4ccccc4-c4ccccc43)c2)cc1]
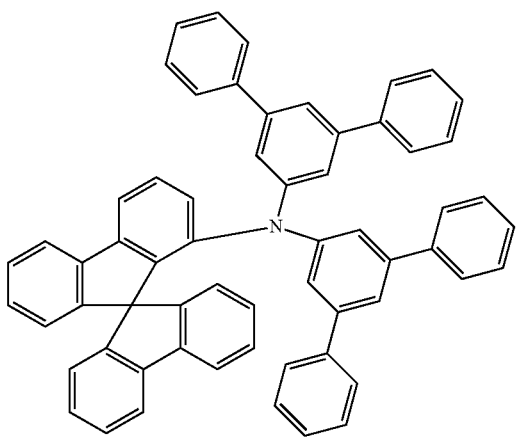 [SMILES: c1ccc(-c2cc(-c3ccccc3)cc(N(c3cc(-c4ccccc4)cc(-c4ccccc4)c3)c3cccc4c3C3(c5ccccc5-c5ccccc53)c3ccccc3-4)c2)cc1]
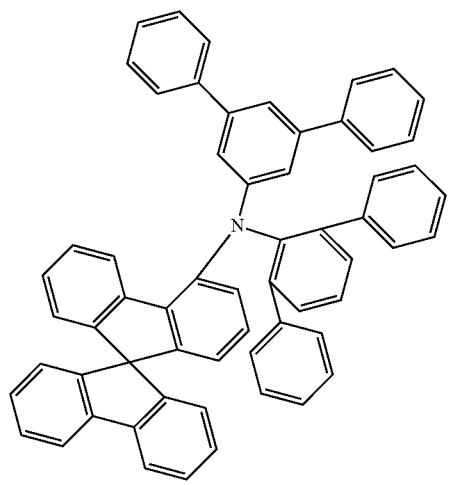 [SMILES: c1ccc(-c2cc(-c3ccccc3)cc(N(c3cccc4c3-c3ccccc3C43c4ccccc4-c4ccccc43)c3c(-c4ccccc4)cccc3-c3ccccc3)c2)cc1]

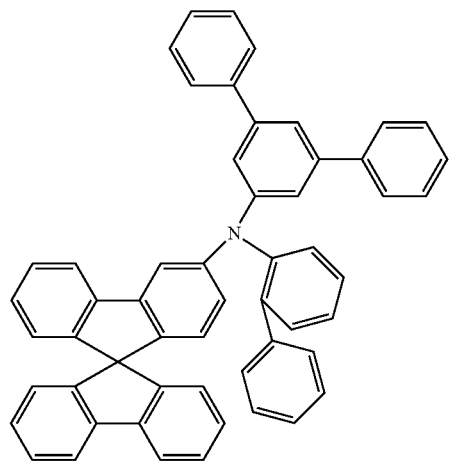 [SMILES: c1ccc(-c2cc(-c3ccccc3)cc(N(c3ccc4c(c3)-c3ccccc3C43c4ccccc4-c4ccccc43)c3ccccc3-c3ccccc3)c2)cc1]
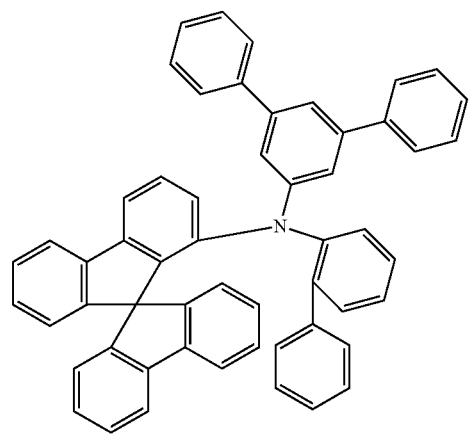 [SMILES: c1ccc(-c2cc(-c3ccccc3)cc(N(c3ccccc3-c3ccccc3)c3cccc4c3C3(c5ccccc5-c5ccccc53)c3ccccc3-4)c2)cc1]
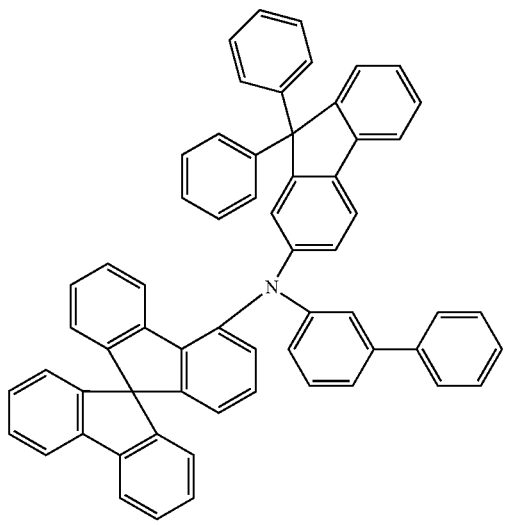 [SMILES: c1ccc(-c2cccc(N(c3ccc4c(c3)C(c3ccccc3)(c3ccccc3)c3ccccc3-4)c3cccc4c3-c3ccccc3C43c4ccccc4-c4ccccc43)c2)cc1]

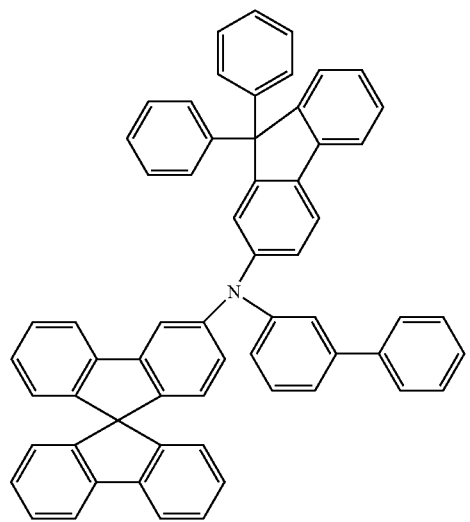 [SMILES: c1ccc(-c2cccc(N(c3ccc4c(c3)-c3ccccc3C43c4ccccc4-c4ccccc43)c3ccc4c(c3)C(c3ccccc3)(c3ccccc3)c3ccccc3-4)c2)cc1]
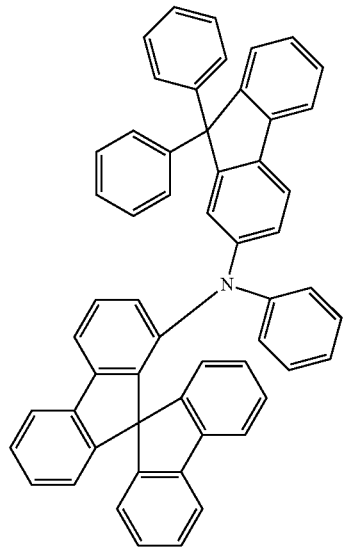 [SMILES: c1ccc(N(c2ccc3c(c2)C(c2ccccc2)(c2ccccc2)c2ccccc2-3)c2cccc3c2C2(c4ccccc4-c4ccccc42)c2ccccc2-3)cc1]
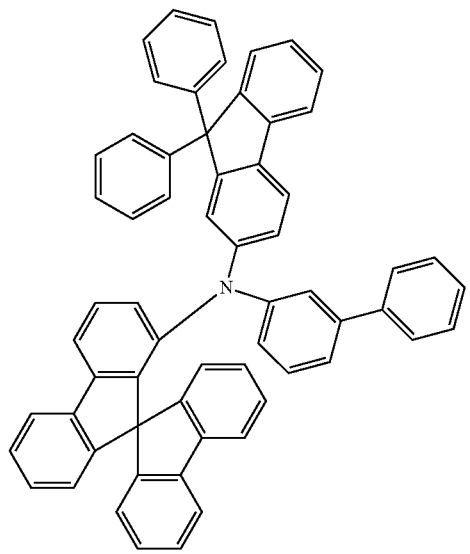 [SMILES: c1ccc(-c2cccc(N(c3ccc4c(c3)C(c3ccccc3)(c3ccccc3)c3ccccc3-4)c3cccc4c3C3(c5ccccc5-c5ccccc53)c3ccccc3-4)c2)cc1]

-continued
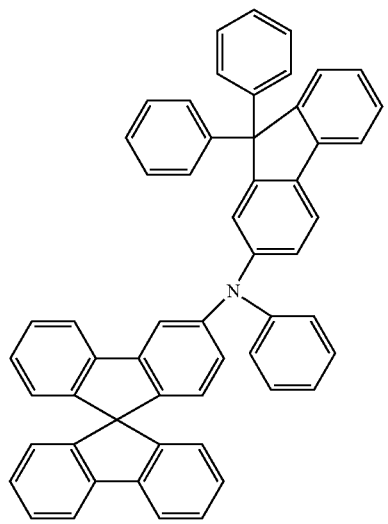 [SMILES: c1ccc(N(c2ccc3c(c2)-c2ccccc2C32c3ccccc3-c3ccccc32)c2ccc3c(c2)C(c2ccccc2)(c2ccccc2)c2ccccc2-3)cc1]
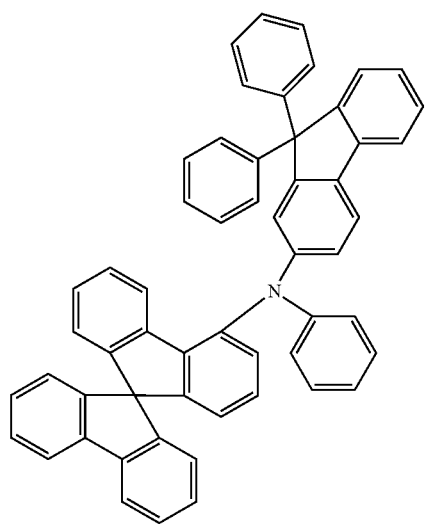 [SMILES: c1ccc(N(c2ccc3c(c2)C(c2ccccc2)(c2ccccc2)c2ccccc2-3)c2cccc3c2-c2ccccc2C32c3ccccc3-c3ccccc32)cc1]
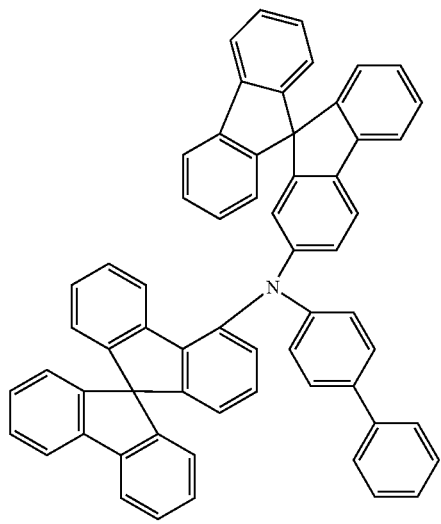 [SMILES: c1ccc(-c2ccc(N(c3ccc4c(c3)C3(c5ccccc5-c5ccccc53)c3ccccc3-4)c3cccc4c3-c3ccccc3C43c4ccccc4-c4ccccc43)cc2)cc1]

-continued
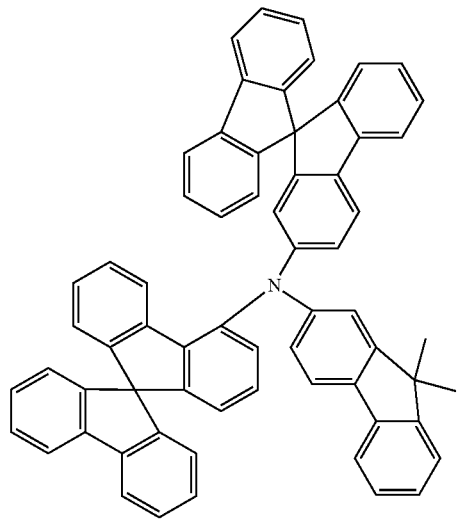 [SMILES: CC1(C)c2ccccc2-c2ccc(N(c3ccc4c(c3)C3(c5ccccc5-c5ccccc53)c3ccccc3-4)c3cccc4c3-c3ccccc3C43c4ccccc4-c4ccccc43)cc21]
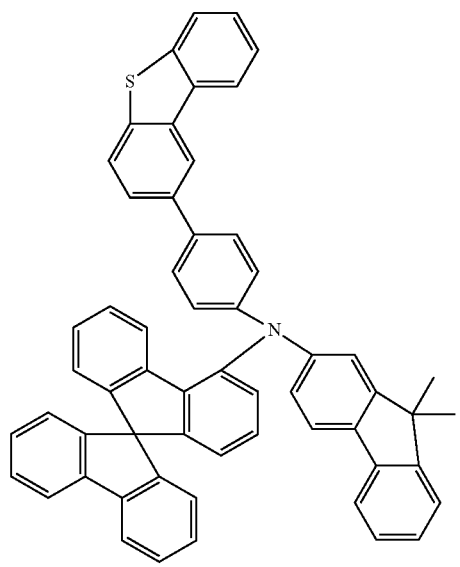 [SMILES: CC1(C)c2ccccc2-c2ccc(N(c3ccc(-c4ccc5sc6ccccc6c5c4)cc3)c3cccc4c3-c3ccccc3C43c4ccccc4-c4ccccc43)cc21]
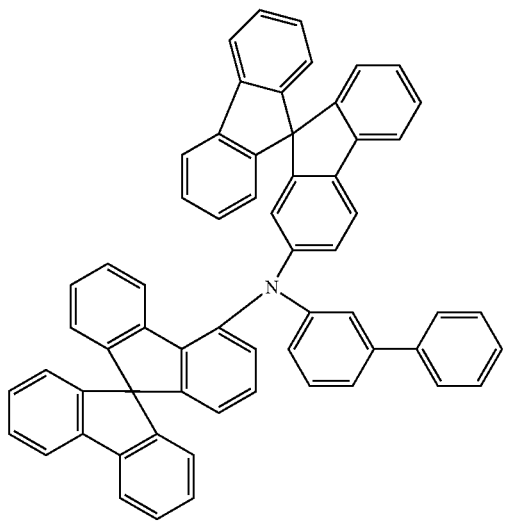 [SMILES: c1ccc(-c2cccc(N(c3ccc4c(c3)C3(c5ccccc5-c5ccccc53)c3ccccc3-4)c3cccc4c3-c3ccccc3C43c4ccccc4-c4ccccc43)c2)cc1]

-continued
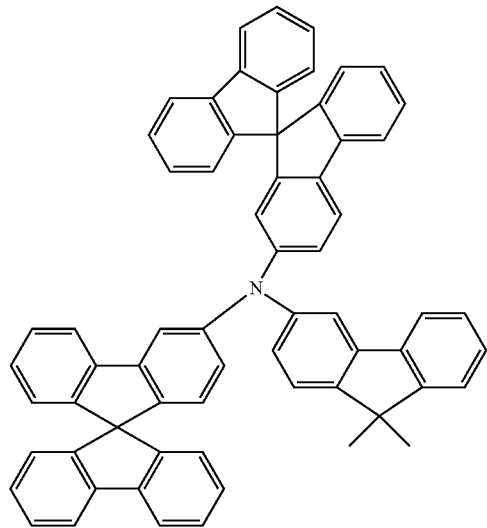 [SMILES: CC1(C)c2ccccc2-c2cc(N(c3ccc4c(c3)-c3ccccc3C43c4ccccc4-c4ccccc43)c3ccc4c(c3)C3(c5ccccc5-c5ccccc53)c3ccccc3-4)ccc21]
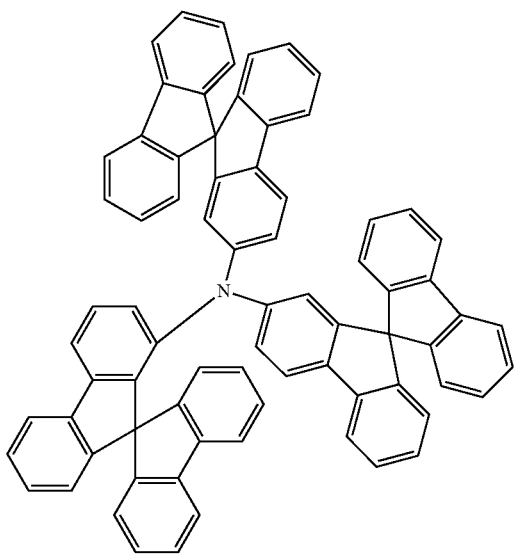 [SMILES: c1ccc2c(c1)-c1ccccc1C21c2ccccc2-c2ccc(N(c3ccc4c(c3)C3(c5ccccc5-c5ccccc53)c3ccccc3-4)c3cccc4c3C3(c5ccccc5-c5ccccc53)c3ccccc3-4)cc21]
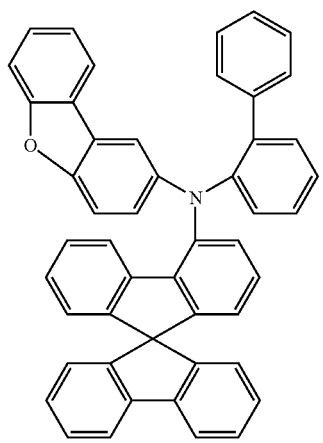 [SMILES: c1ccc(-c2ccccc2N(c2ccc3oc4ccccc4c3c2)c2cccc3c2-c2ccccc2C32c3ccccc3-c3ccccc32)cc1]

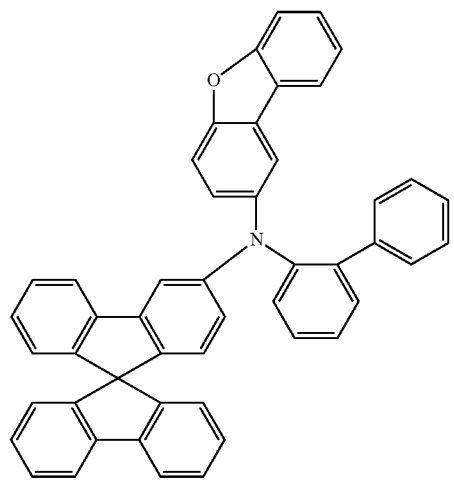 [SMILES: c1ccc(-c2ccccc2N(c2ccc3c(c2)-c2ccccc2C32c3ccccc3-c3ccccc32)c2ccc3oc4ccccc4c3c2)cc1]
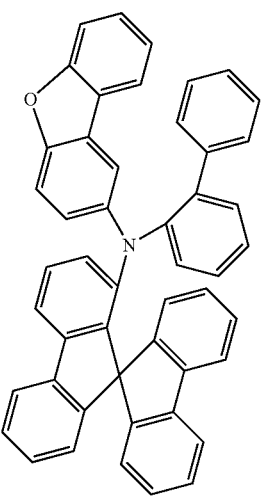 [SMILES: c1ccc(-c2ccccc2N(c2ccc3oc4ccccc4c3c2)c2cccc3c2C2(c4ccccc4-c4ccccc42)c2ccccc2-3)cc1]
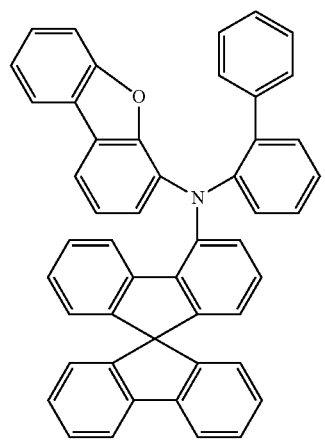 [SMILES: c1ccc(-c2ccccc2N(c2cccc3c2-c2ccccc2C32c3ccccc3-c3ccccc32)c2cccc3c2oc2ccccc23)cc1]

-continued
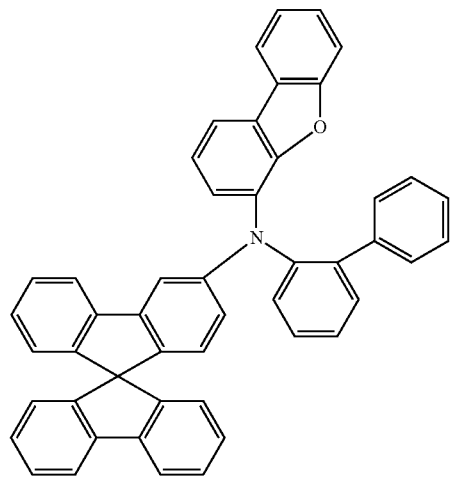 [SMILES: c1ccc(-c2ccccc2N(c2ccc3c(c2)-c2ccccc2C32c3ccccc3-c3ccccc32)c2cccc3c2oc2ccccc23)cc1]
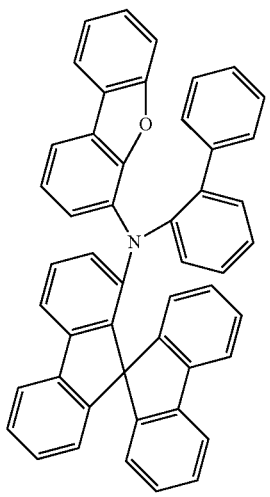 [SMILES: c1ccc(-c2ccccc2N(c2cccc3c2C2(c4ccccc4-c4ccccc42)c2ccccc2-3)c2cccc3c2oc2ccccc23)cc1]
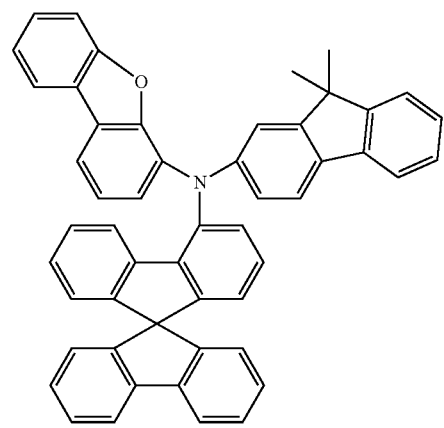 [SMILES: CC1(C)c2ccccc2-c2ccc(N(c3cccc4c3-c3ccccc3C43c4ccccc4-c4ccccc43)c3cccc4c3oc3ccccc34)cc21]

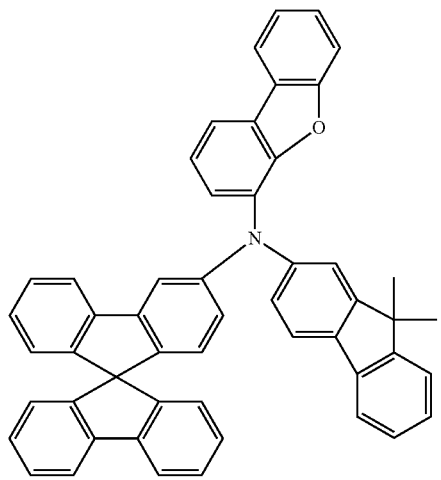 [SMILES: CC1(C)c2ccccc2-c2ccc(N(c3ccc4c(c3)-c3ccccc3C43c4ccccc4-c4ccccc43)c3cccc4c3oc3ccccc34)cc21]
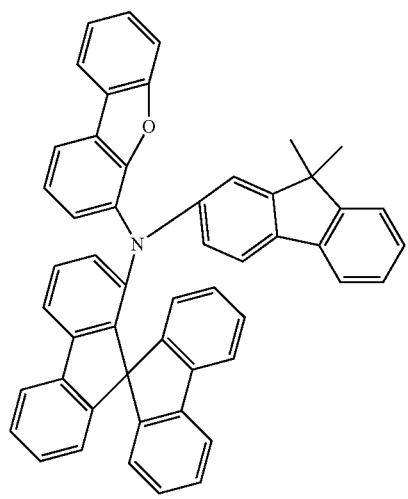 [SMILES: CC1(C)c2ccccc2-c2ccc(N(c3cccc4c3C3(c5ccccc5-c5ccccc53)c3ccccc3-4)c3cccc4c3oc3ccccc34)cc21]
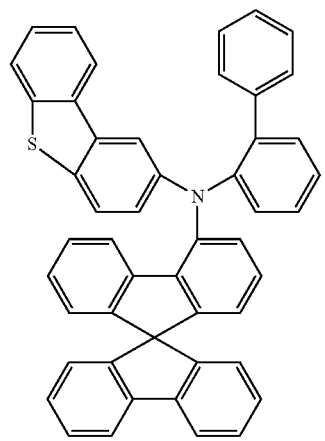 [SMILES: c1ccc(-c2ccccc2N(c2ccc3sc4ccccc4c3c2)c2cccc3c2-c2ccccc2C32c3ccccc3-c3ccccc32)cc1]

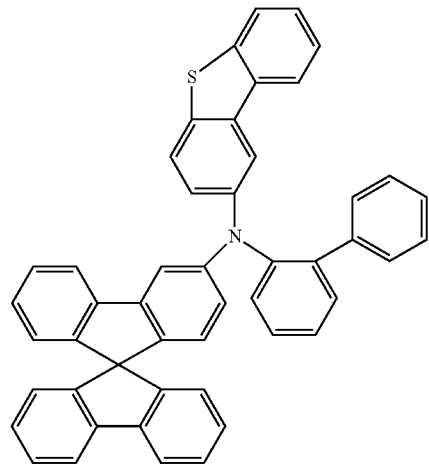 [SMILES: c1ccc(-c2ccccc2N(c2ccc3c(c2)-c2ccccc2C32c3ccccc3-c3ccccc32)c2ccc3sc4ccccc4c3c2)cc1]
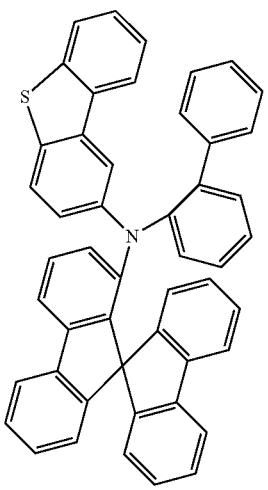 [SMILES: c1ccc(-c2ccccc2N(c2ccc3sc4ccccc4c3c2)c2cccc3c2C2(c4ccccc4-c4ccccc42)c2ccccc2-3)cc1]
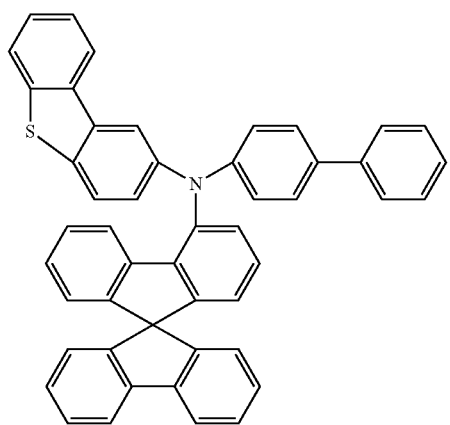 [SMILES: c1ccc(-c2ccc(N(c3ccc4sc5ccccc5c4c3)c3cccc4c3-c3ccccc3C43c4ccccc4-c4ccccc43)cc2)cc1]

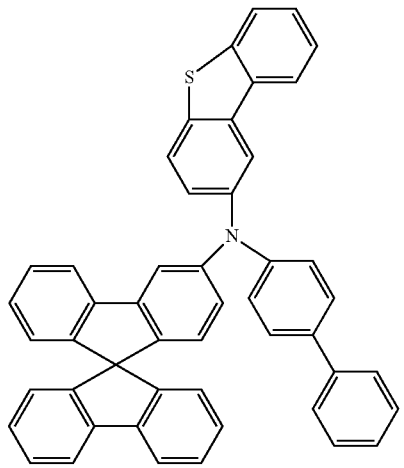 [SMILES: c1ccc(-c2ccc(N(c3ccc4c(c3)-c3ccccc3C43c4ccccc4-c4ccccc43)c3ccc4sc5ccccc5c4c3)cc2)cc1]
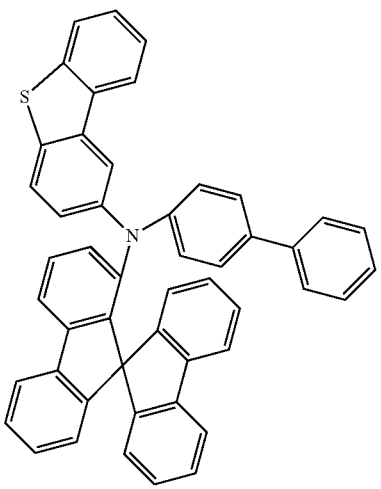 [SMILES: c1ccc(-c2ccc(N(c3ccc4sc5ccccc5c4c3)c3cccc4c3C3(c5ccccc5-c5ccccc53)c3ccccc3-4)cc2)cc1]
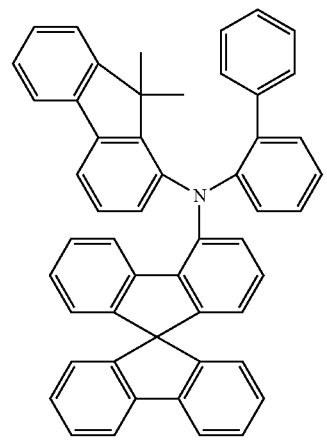

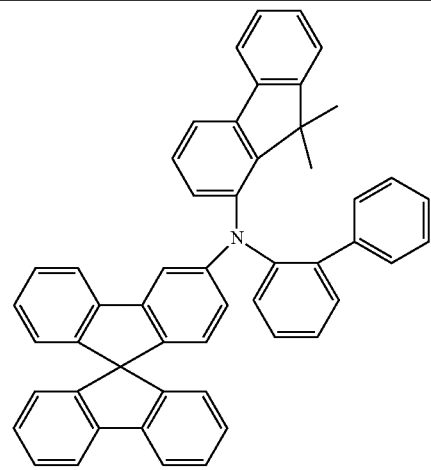
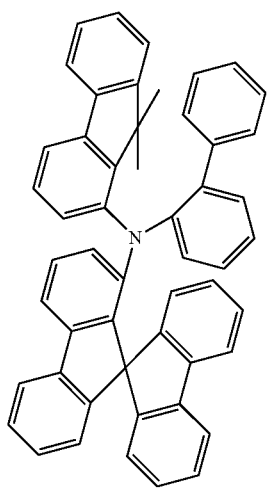 [SMILES: CC1(C)c2ccccc2-c2cccc(N(c3ccccc3-c3ccccc3)c3cccc4c3C3(c5ccccc5-c5ccccc53)c3ccccc3-4)c21]
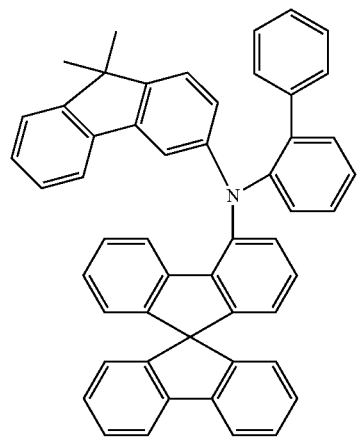 [SMILES: CC1(C)c2ccccc2-c2cc(N(c3ccccc3-c3ccccc3)c3cccc4c3-c3ccccc3C43c4ccccc4-c4ccccc43)ccc21]

-continued
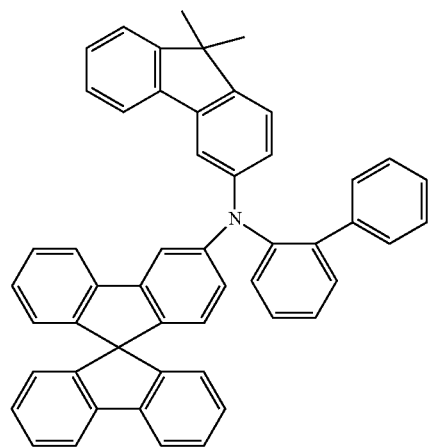 [SMILES: CC1(C)c2ccccc2-c2cc(N(c3ccc4c(c3)-c3ccccc3C43c4ccccc4-c4ccccc43)c3ccccc3-c3ccccc3)ccc21]
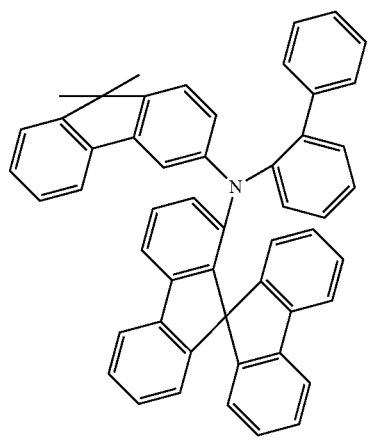 [SMILES: CC1(C)c2ccccc2-c2cc(N(c3ccccc3-c3ccccc3)c3cccc4c3C3(c5ccccc5-c5ccccc53)c3ccccc3-4)ccc21]
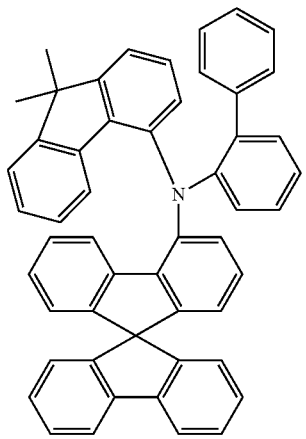 [SMILES: CC1(C)c2ccccc2-c2c(N(c3ccccc3-c3ccccc3)c3cccc4c3-c3ccccc3C43c4ccccc4-c4ccccc43)cccc21]

-continued
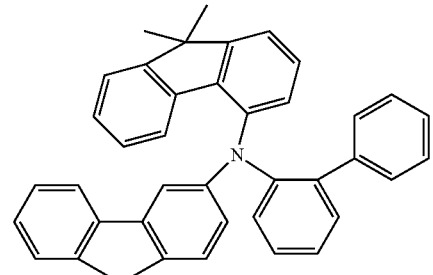
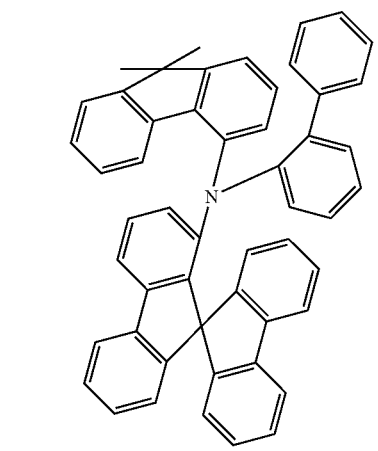 [SMILES: CC1(C)c2ccccc2-c2c(N(c3ccccc3-c3ccccc3)c3cccc4c3C3(c5ccccc5-c5ccccc53)c3ccccc3-4)cccc21]
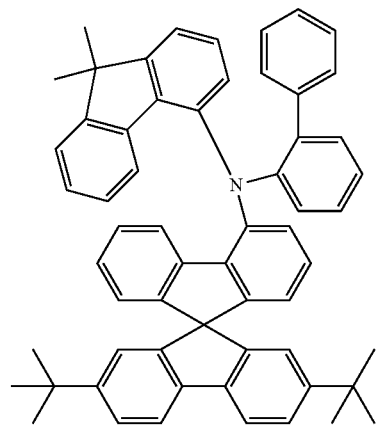 [SMILES: CC(C)(C)c1ccc2c(c1)C1(c3cc(C(C)(C)C)ccc3-2)c2ccccc2-c2c(N(c3ccccc3-c3ccccc3)c3cccc4c3-c3ccccc3C4(C)C)cccc21]
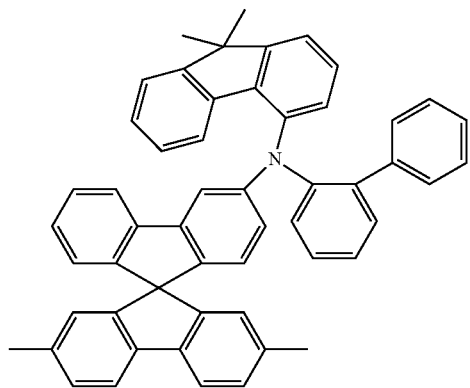 [SMILES: Cc1ccc2c(c1)C1(c3ccccc3-c3cc(N(c4ccccc4-c4ccccc4)c4cccc5c4-c4ccccc4C5(C)C)ccc31)c1cc(C)ccc1-2]

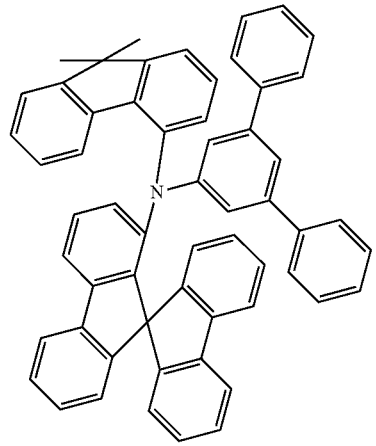 [SMILES: CC1(C)c2ccccc2-c2c(N(c3cc(-c4ccccc4)cc(-c4ccccc4)c3)c3cccc4c3C3(c5ccccc5-c5ccccc53)c3ccccc3-4)cccc21]
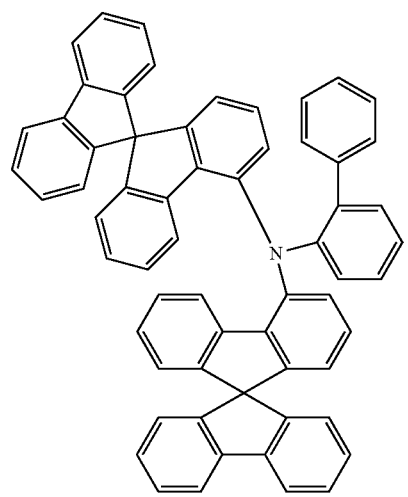 [SMILES: c1ccc(-c2ccccc2N(c2cccc3c2-c2ccccc2C32c3ccccc3-c3ccccc32)c2cccc3c2-c2ccccc2C32c3ccccc3-c3ccccc32)cc1]
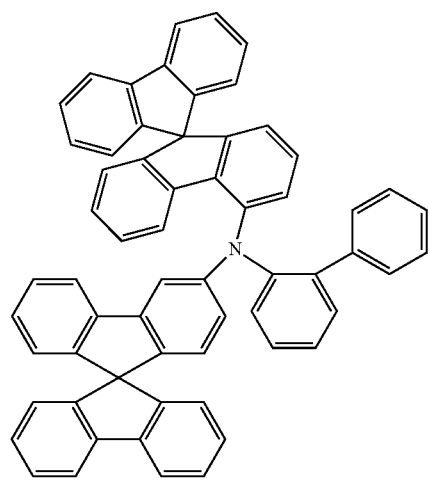 [SMILES: c1ccc(-c2ccccc2N(c2ccc3c(c2)-c2ccccc2C32c3ccccc3-c3ccccc32)c2cccc3c2-c2ccccc2C32c3ccccc3-c3ccccc32)cc1]

-continued
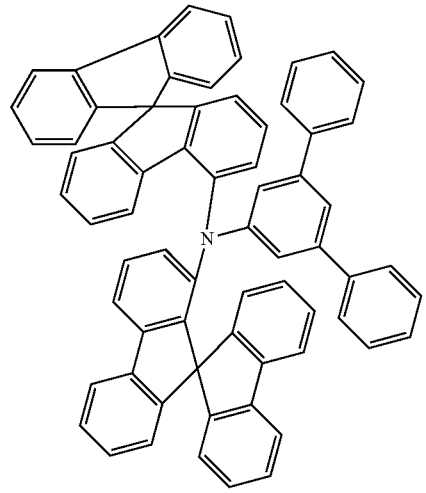 [SMILES: c1ccc(-c2cc(-c3ccccc3)cc(N(c3cccc4c3-c3ccccc3C43c4ccccc4-c4ccccc43)c3cccc4c3C3(c5ccccc5-c5ccccc53)c3ccccc3-4)c2)cc1]
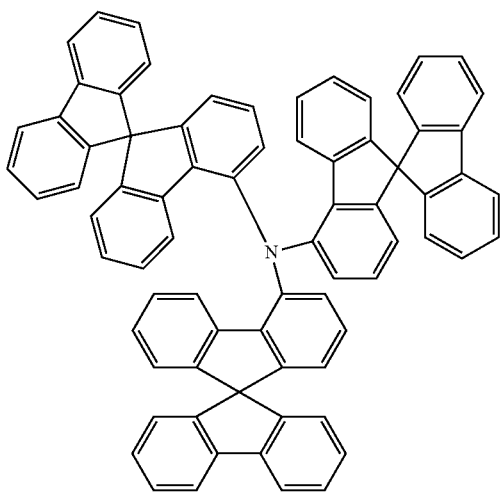 [SMILES: c1ccc2c(c1)-c1ccccc1C21c2ccccc2-c2c(N(c3cccc4c3-c3ccccc3C43c4ccccc4-c4ccccc43)c3cccc4c3-c3ccccc3C43c4ccccc4-c4ccccc43)cccc21]
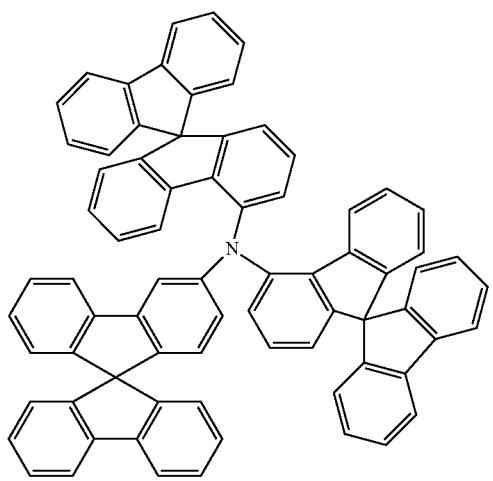 [SMILES: c1ccc2c(c1)-c1ccccc1C21c2ccccc2-c2cc(N(c3cccc4c3-c3ccccc3C43c4ccccc4-c4ccccc43)c3cccc4c3-c3ccccc3C43c4ccccc4-c4ccccc43)ccc21]

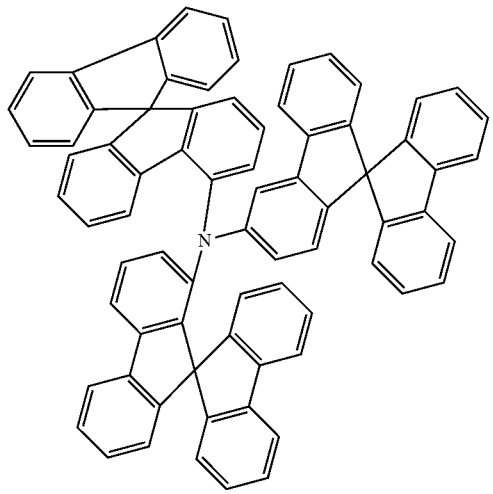 [SMILES: c1ccc2c(c1)-c1ccccc1C21c2ccccc2-c2cc(N(c3cccc4c3-c3ccccc3C43c4ccccc4-c4ccccc43)c3cccc4c3C3(c5ccccc5-c5ccccc53)c3ccccc3-4)ccc21]
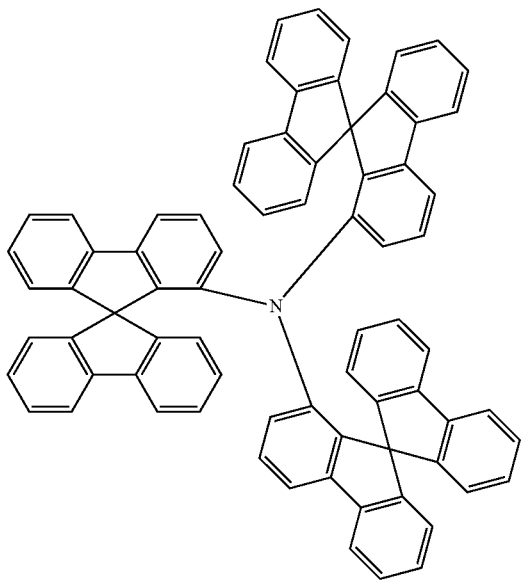 [SMILES: c1ccc2c(c1)-c1ccccc1C21c2ccccc2-c2cccc(N(c3cccc4c3C3(c5ccccc5-c5ccccc53)c3ccccc3-4)c3cccc4c3C3(c5ccccc5-c5ccccc53)c3ccccc3-4)c21]
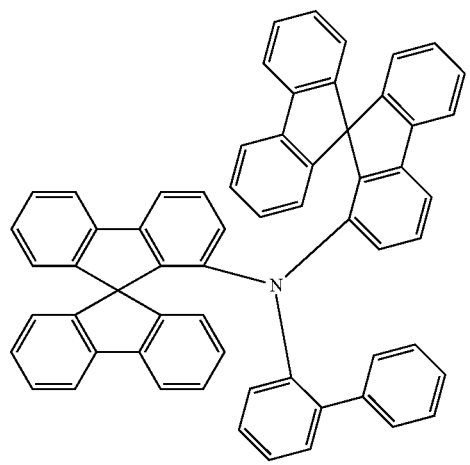 [SMILES: c1ccc(-c2ccccc2N(c2cccc3c2C2(c4ccccc4-c4ccccc42)c2ccccc2-3)c2cccc3c2C2(c4ccccc4-c4ccccc42)c2ccccc2-3)cc1]

-continued
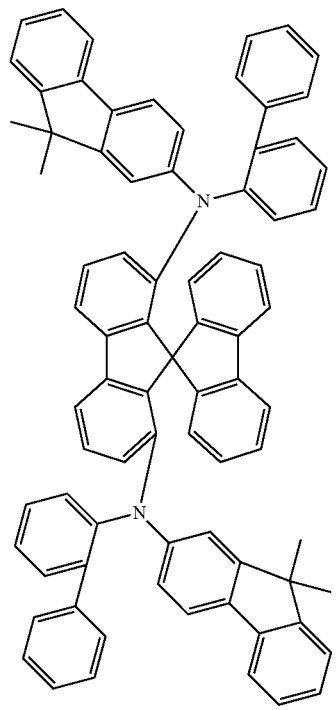 [SMILES: CC1(C)c2ccccc2-c2ccc(N(c3ccccc3-c3ccccc3)c3cccc4c3C3(c5ccccc5-c5ccccc53)c3c-4cccc3N(c3ccc4c(c3)C(C)(C)c3ccccc3-4)c3ccccc3-c3ccccc3)cc21]
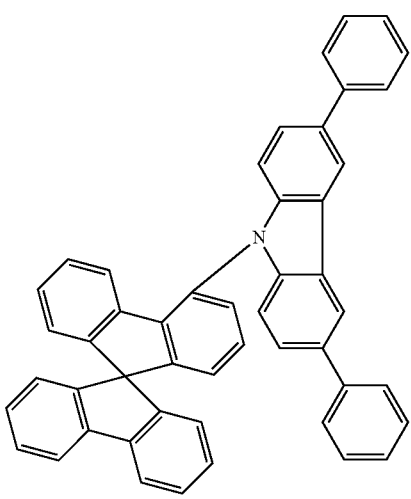 [SMILES: c1ccc(-c2ccc3c(c2)c2cc(-c4ccccc4)ccc2n3-c2cccc3c2-c2ccccc2C32c3ccccc3-c3ccccc32)cc1]

-continued
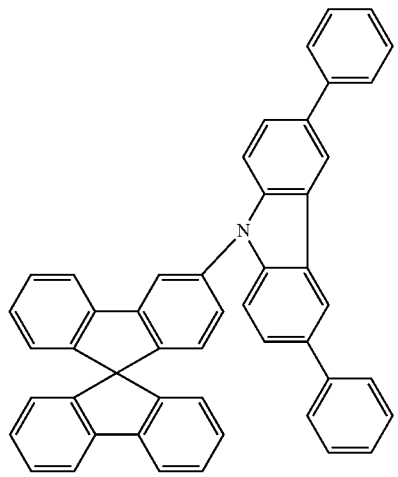 [SMILES: c1ccc(-c2ccc3c(c2)c2cc(-c4ccccc4)ccc2n3-c2ccc3c(c2)-c2ccccc2C32c3ccccc3-c3ccccc32)cc1]
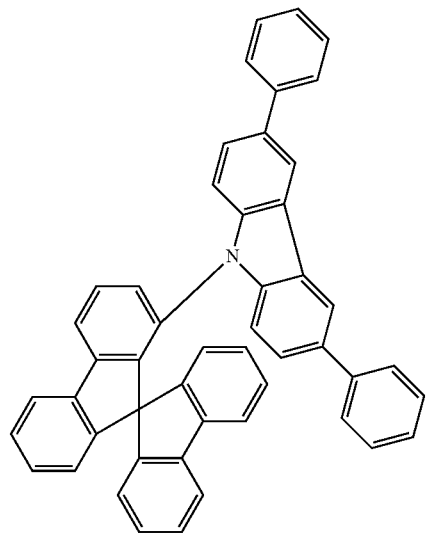 [SMILES: c1ccc(-c2ccc3c(c2)c2cc(-c4ccccc4)ccc2n3-c2cccc3c2C2(c4ccccc4-c4ccccc42)c2ccccc2-3)cc1]
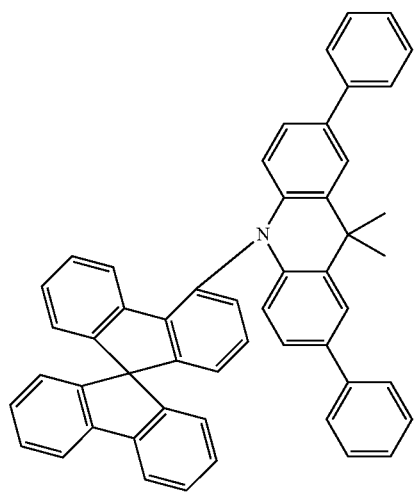 [SMILES: CC1(C)c2cc(-c3ccccc3)ccc2N(c2cccc3c2-c2ccccc2C32c3ccccc3-c3ccccc32)c2ccc(-c3ccccc3)cc21]

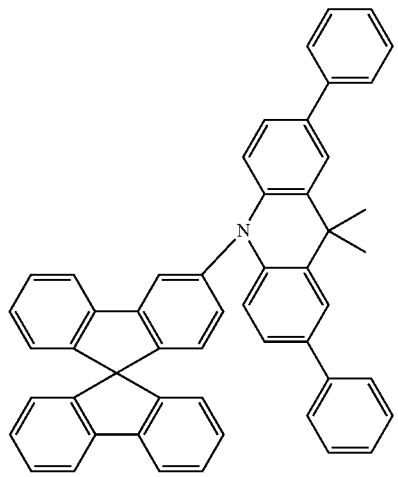 [SMILES: CC1(C)c2cc(-c3ccccc3)ccc2N(c2ccc3c(c2)-c2ccccc2C32c3ccccc3-c3ccccc32)c2ccc(-c3ccccc3)cc21]
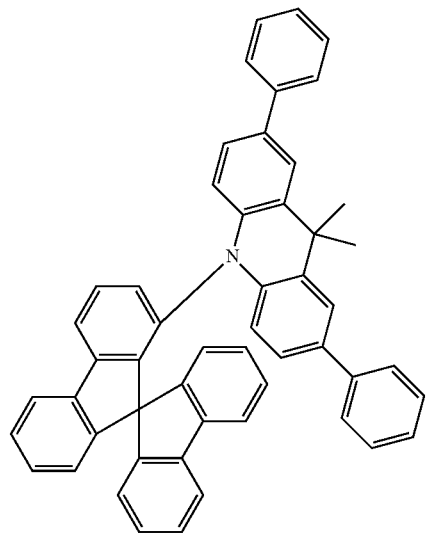 [SMILES: CC1(C)c2cc(-c3ccccc3)ccc2N(c2cccc3c2C2(c4ccccc4-c4ccccc42)c2ccccc2-3)c2ccc(-c3ccccc3)cc21]
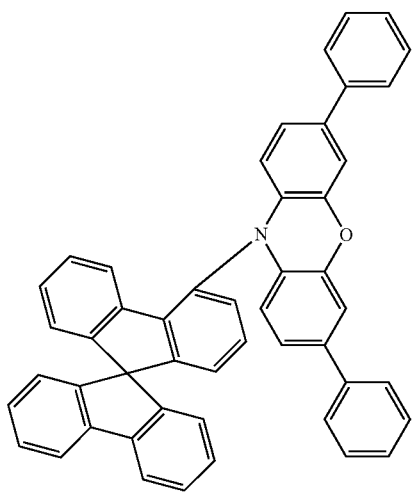 [SMILES: c1ccc(-c2ccc3c(c2)Oc2cc(-c4ccccc4)ccc2N3c2cccc3c2-c2ccccc2C32c3ccccc3-c3ccccc32)cc1]

-continued
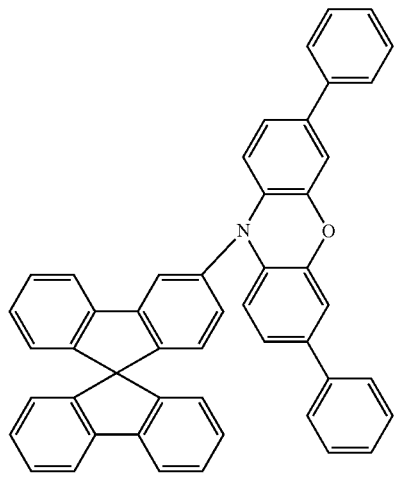 [SMILES: c1ccc(-c2ccc3c(c2)Oc2cc(-c4ccccc4)ccc2N3c2ccc3c(c2)-c2ccccc2C32c3ccccc3-c3ccccc32)cc1]
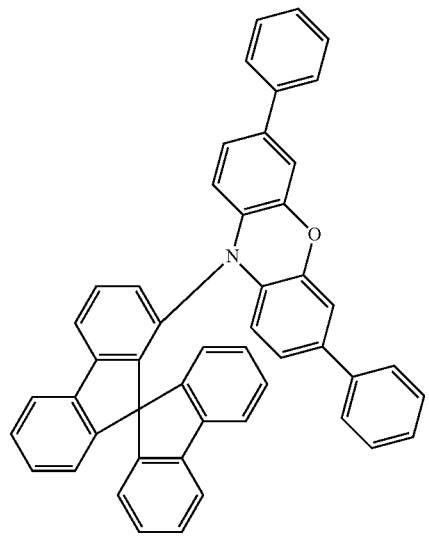 [SMILES: c1ccc(-c2ccc3c(c2)Oc2cc(-c4ccccc4)ccc2N3c2cccc3c2C2(c4ccccc4-c4ccccc42)c2ccccc2-3)cc1]
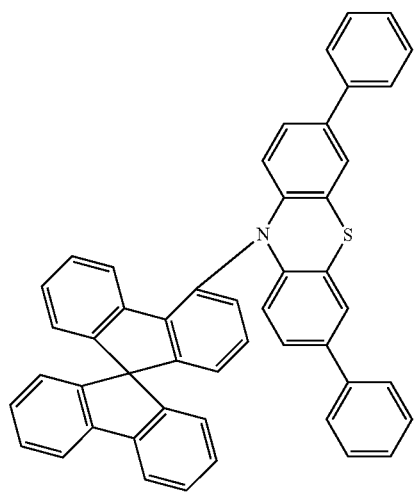 [SMILES: c1ccc(-c2ccc3c(c2)Sc2cc(-c4ccccc4)ccc2N3c2cccc3c2-c2ccccc2C32c3ccccc3-c3ccccc32)cc1]

-continued
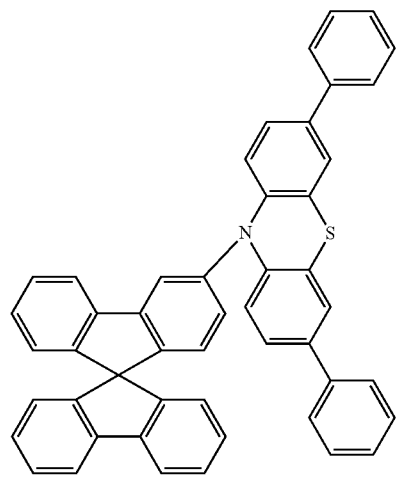
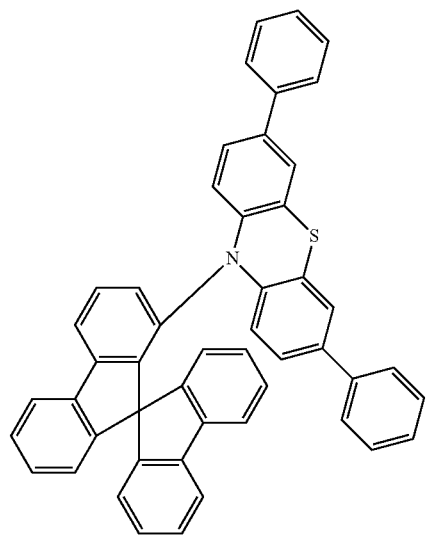 [SMILES: c1ccc(-c2ccc3c(c2)Sc2cc(-c4ccccc4)ccc2N3c2cccc3c2C2(c4ccccc4-c4ccccc42)c2ccccc2-3)cc1]
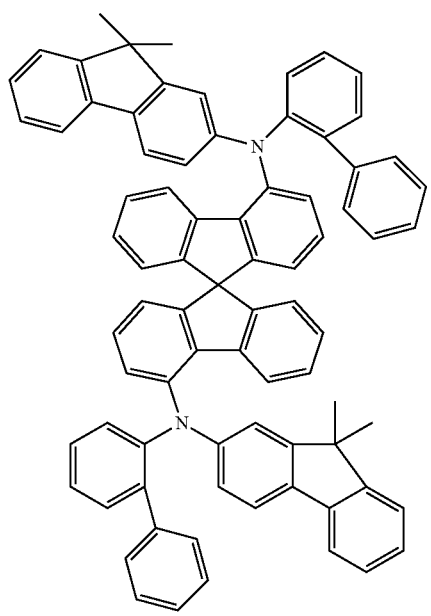 [SMILES: CC1(C)c2ccccc2-c2ccc(N(c3ccccc3-c3ccccc3)c3cccc4c3-c3ccccc3C43c4ccccc4-c4c(N(c5ccc6c(c5)C(C)(C)c5ccccc5-6)c5ccccc5-c5ccccc5)cccc43)cc21]

-continued
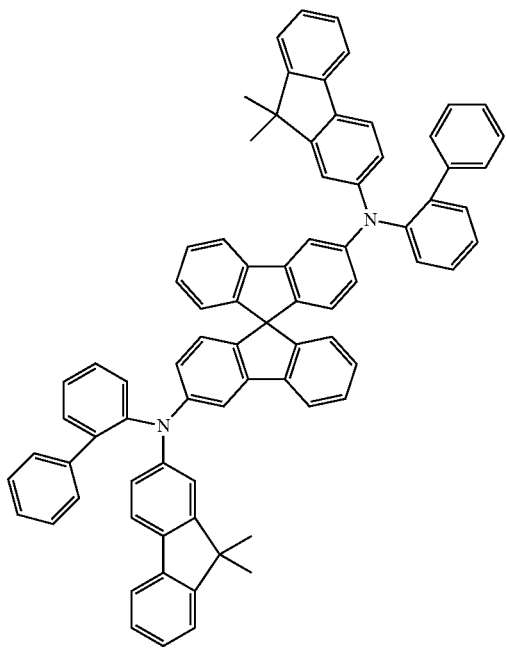 [SMILES: CC1(C)c2ccccc2-c2ccc(N(c3ccc4c(c3)-c3ccccc3C43c4ccccc4-c4cc(N(c5ccc6c(c5)C(C)(C)c5ccccc5-6)c5ccccc5-c5ccccc5)ccc43)c3ccccc3-c3ccccc3)cc21]
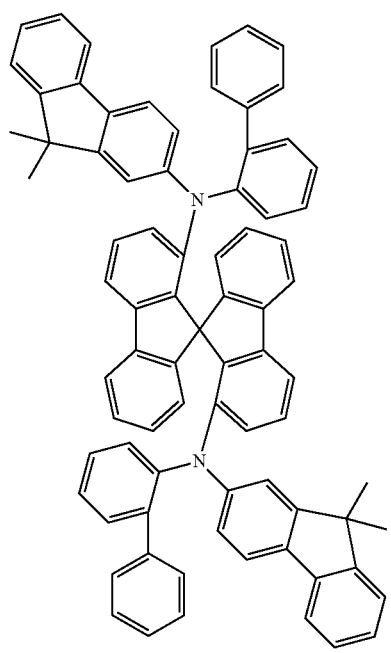

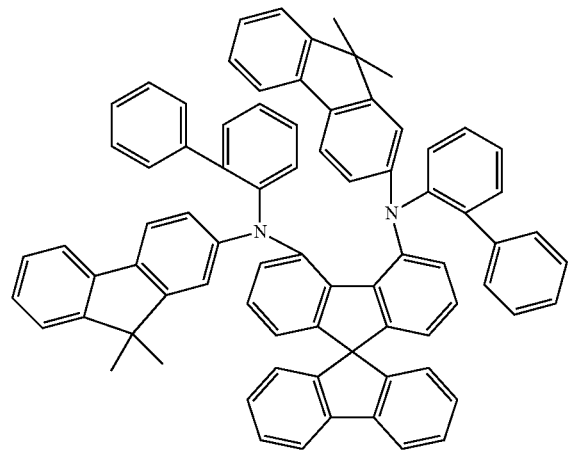 [SMILES: CC1(C)c2ccccc2-c2ccc(N(c3ccccc3-c3ccccc3)c3cccc4c3-c3c(N(c5ccc6c(c5)C(C)(C)c5ccccc5-6)c5ccccc5-c5ccccc5)cccc3C43c4ccccc4-c4ccccc43)cc21]
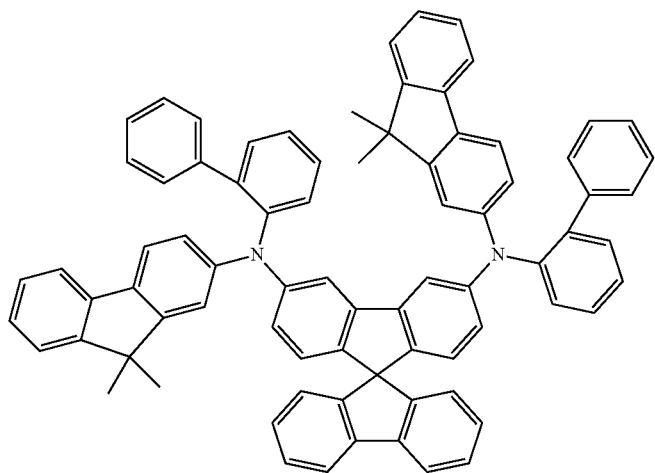 [SMILES: CC1(C)c2ccccc2-c2ccc(N(c3ccc4c(c3)-c3cc(N(c5ccc6c(c5)C(C)(C)c5ccccc5-6)c5ccccc5-c5ccccc5)ccc3C43c4ccccc4-c4ccccc43)c3ccccc3-c3ccccc3)cc21]
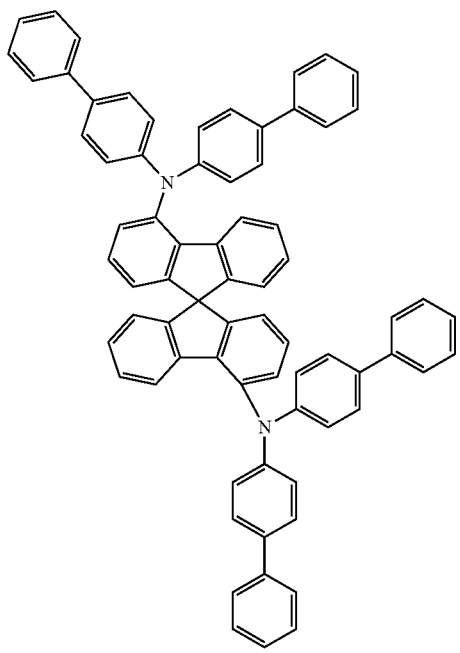 [SMILES: c1ccc(-c2ccc(N(c3ccc(-c4ccccc4)cc3)c3cccc4c3-c3ccccc3C43c4ccccc4-c4c(N(c5ccc(-c6ccccc6)cc5)c5ccc(-c6ccccc6)cc5)cccc43)cc2)cc1]

-continued
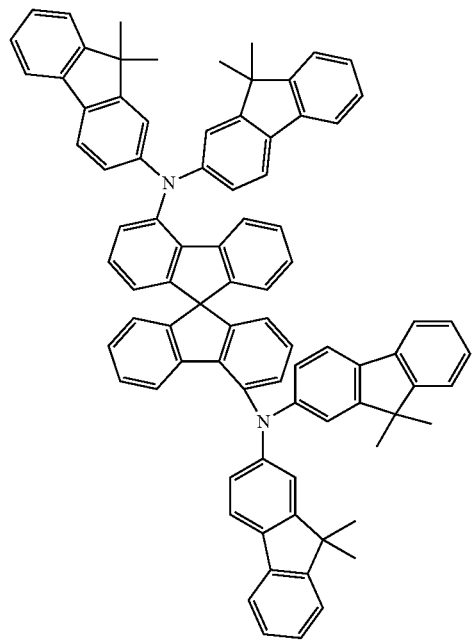 [SMILES: CC1(C)c2ccccc2-c2ccc(N(c3ccc4c(c3)C(C)(C)c3ccccc3-4)c3cccc4c3-c3ccccc3C43c4ccccc4-c4c(N(c5ccc6c(c5)C(C)(C)c5ccccc5-6)c5ccc6c(c5)C(C)(C)c5ccccc5-6)cccc43)cc21]
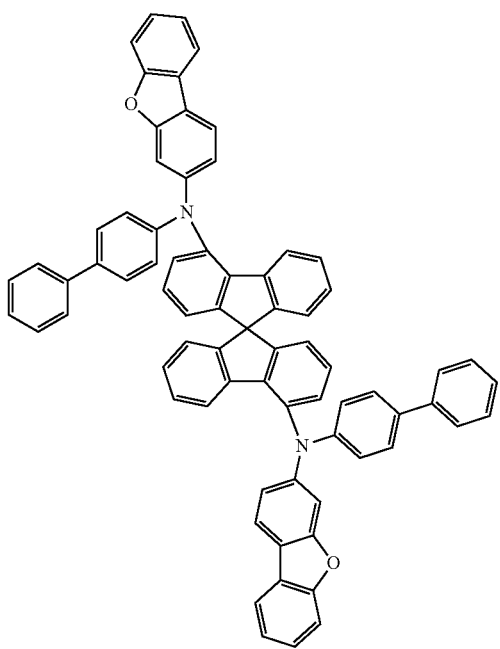 [SMILES: c1ccc(-c2ccc(N(c3ccc4c(c3)oc3ccccc34)c3cccc4c3-c3ccccc3C43c4ccccc4-c4c(N(c5ccc(-c6ccccc6)cc5)c5ccc6c(c5)oc5ccccc56)cccc43)cc2)cc1]

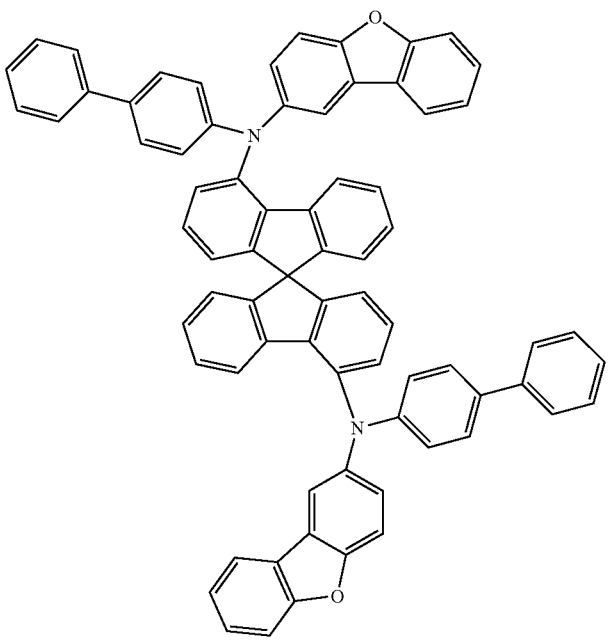 [SMILES: c1ccc(-c2ccc(N(c3ccc4oc5ccccc5c4c3)c3cccc4c3-c3ccccc3C43c4ccccc4-c4c(N(c5ccc(-c6ccccc6)cc5)c5ccc6oc7ccccc7c6c5)cccc43)cc2)cc1]
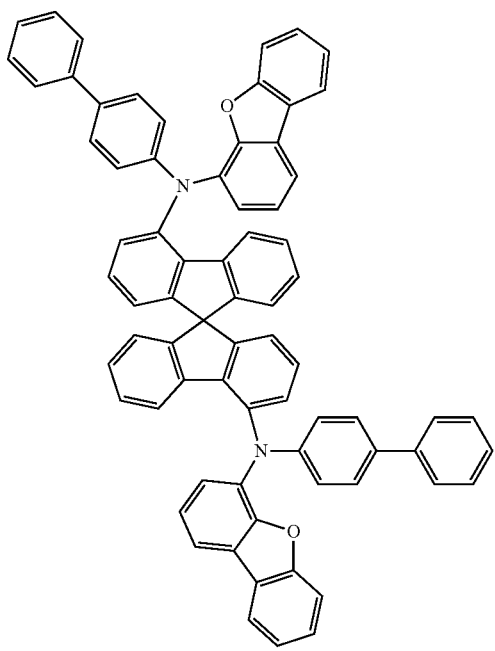 [SMILES: c1ccc(-c2ccc(N(c3cccc4c3-c3ccccc3C43c4ccccc4-c4c(N(c5ccc(-c6ccccc6)cc5)c5cccc6c5oc5ccccc56)cccc43)c3cccc4c3oc3ccccc34)cc2)cc1]

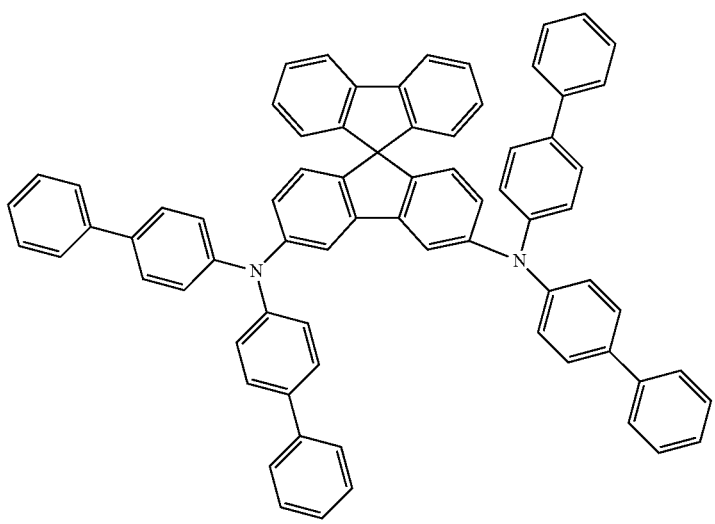 [SMILES: c1ccc(-c2ccc(N(c3ccc(-c4ccccc4)cc3)c3ccc4c(c3)-c3cc(N(c5ccc(-c6ccccc6)cc5)c5ccc(-c6ccccc6)cc5)ccc3C43c4ccccc4-c4ccccc43)cc2)cc1]
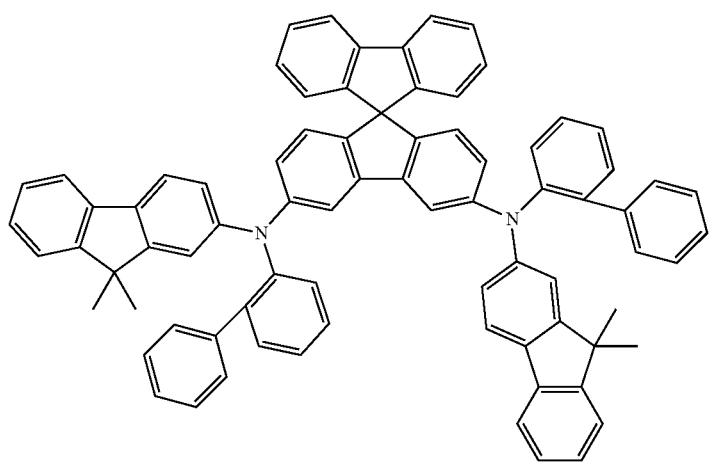 [SMILES: CC1(C)c2ccccc2-c2ccc(N(c3ccc4c(c3)-c3cc(N(c5ccc6c(c5)C(C)(C)c5ccccc5-6)c5ccccc5-c5ccccc5)ccc3C43c4ccccc4-c4ccccc43)c3ccccc3-c3ccccc3)cc21]
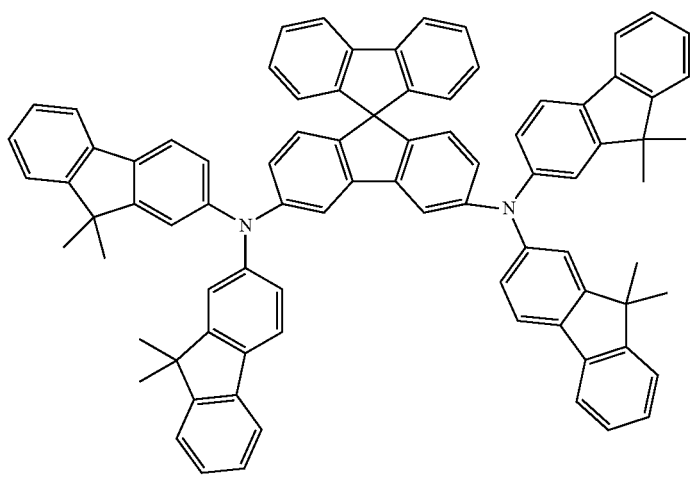 [SMILES: CC1(C)c2ccccc2-c2ccc(N(c3ccc4c(c3)-c3cc(N(c5ccc6c(c5)C(C)(C)c5ccccc5-6)c5ccc6c(c5)C(C)(C)c5ccccc5-6)ccc3C43c4ccccc4-c4ccccc43)c3ccc4c(c3)C(C)(C)c3ccccc3-4)cc21]

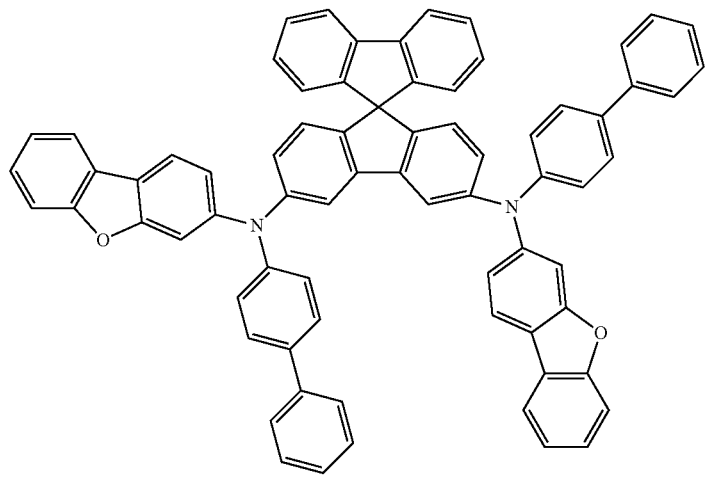 [SMILES: c1ccc(-c2ccc(N(c3ccc4c(c3)-c3cc(N(c5ccc(-c6ccccc6)cc5)c5ccc6c(c5)oc5ccccc56)ccc3C43c4ccccc4-c4ccccc43)c3ccc4c(c3)oc3ccccc34)cc2)cc1]
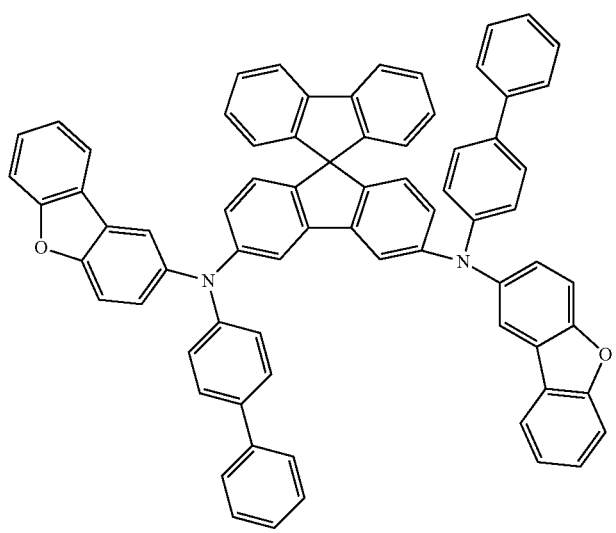 [SMILES: c1ccc(-c2ccc(N(c3ccc4c(c3)-c3cc(N(c5ccc(-c6ccccc6)cc5)c5ccc6oc7ccccc7c6c5)ccc3C43c4ccccc4-c4ccccc43)c3ccc4oc5ccccc5c4c3)cc2)cc1]
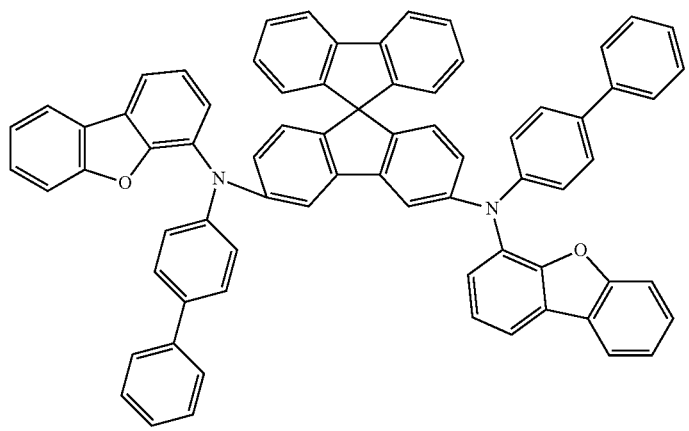 [SMILES: c1ccc(-c2ccc(N(c3ccc4c(c3)-c3cc(N(c5ccc(-c6ccccc6)cc5)c5cccc6c5oc5ccccc56)ccc3C43c4ccccc4-c4ccccc43)c3cccc4c3oc3ccccc34)cc2)cc1]

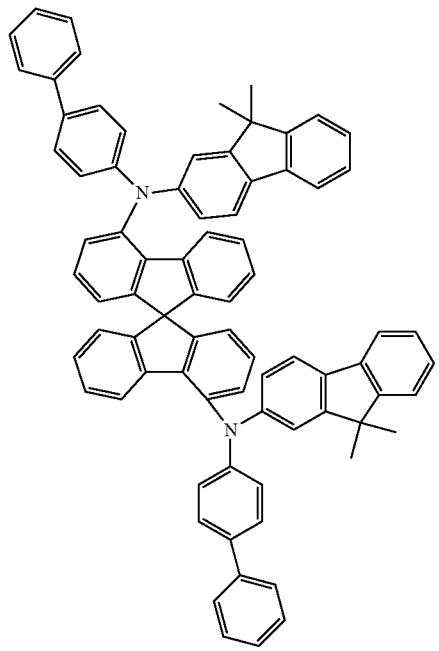 [SMILES: CC1(C)c2ccccc2-c2ccc(N(c3ccc(-c4ccccc4)cc3)c3cccc4c3-c3ccccc3C43c4ccccc4-c4c(N(c5ccc(-c6ccccc6)cc5)c5ccc6c(c5)C(C)(C)c5ccccc5-6)cccc43)cc21]
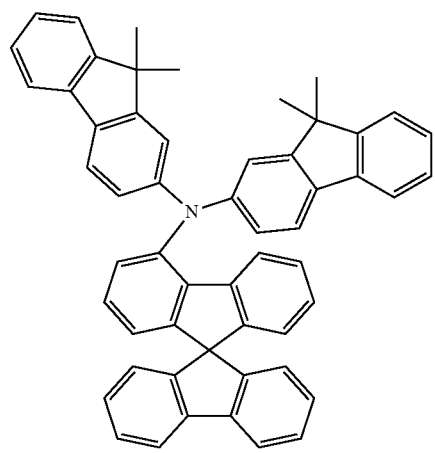 [SMILES: CC1(C)c2ccccc2-c2ccc(N(c3ccc4c(c3)C(C)(C)c3ccccc3-4)c3cccc4c3-c3ccccc3C43c4ccccc4-c4ccccc43)cc21]
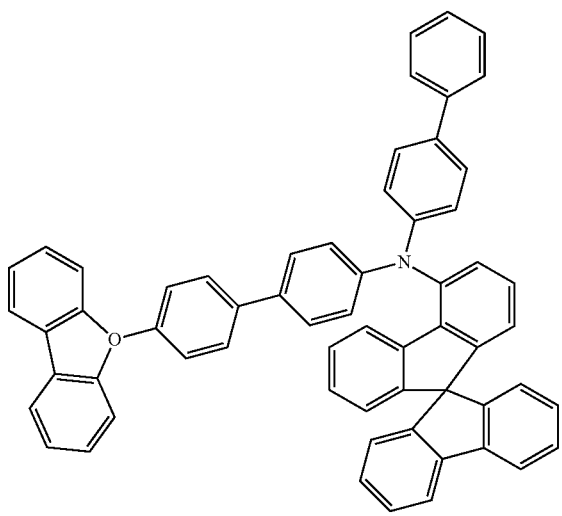

-continued
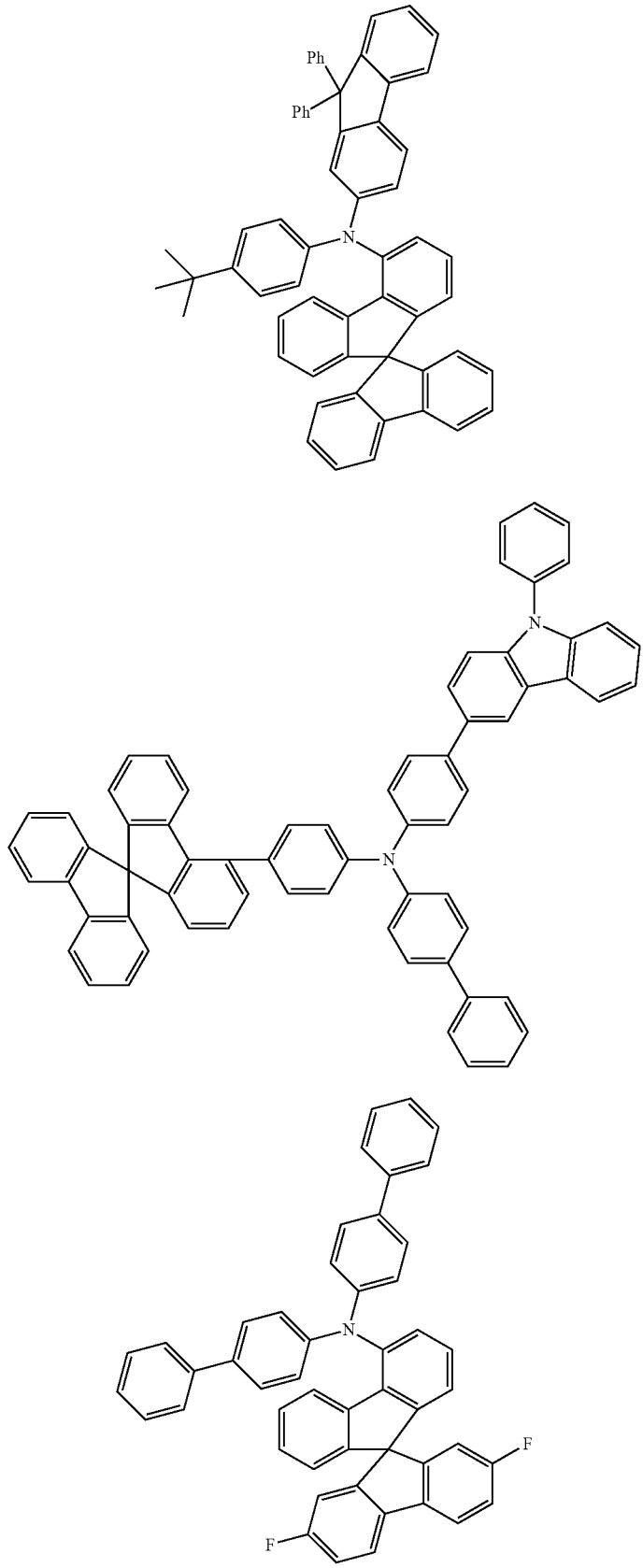

-continued
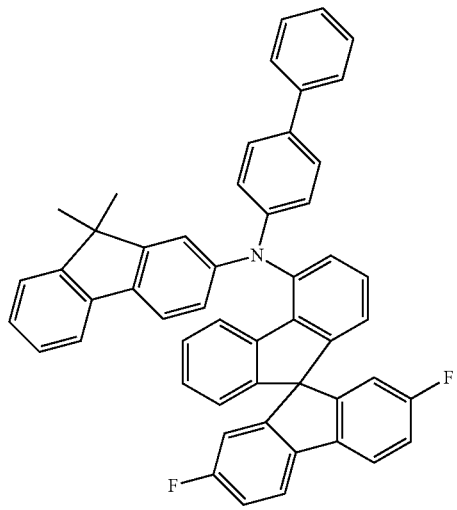 [SMILES: CC1(C)c2ccccc2-c2ccc(N(c3ccc(-c4ccccc4)cc3)c3cccc4c3-c3ccccc3C43c4cc(F)ccc4-c4ccc(F)cc43)cc21]
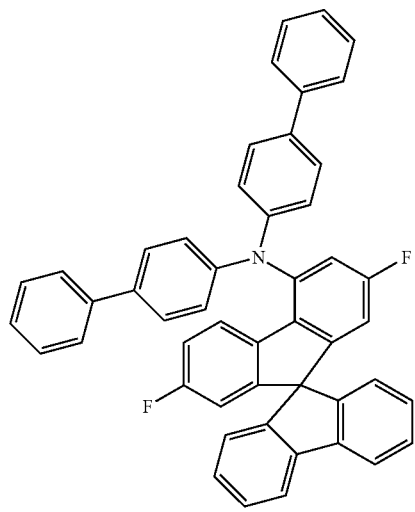 [SMILES: Fc1ccc2c(c1)C1(c3ccccc3-c3ccccc31)c1cc(F)cc(N(c3ccc(-c4ccccc4)cc3)c3ccc(-c4ccccc4)cc3)c1-2]
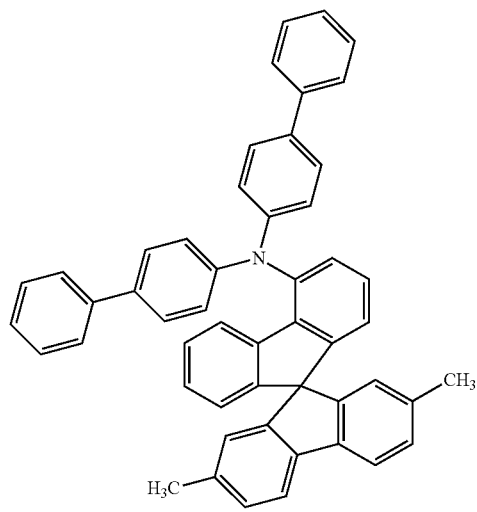 [SMILES: Cc1ccc2c(c1)C1(c3cc(C)ccc3-2)c2ccccc2-c2c(N(c3ccc(-c4ccccc4)cc3)c3ccc(-c4ccccc4)cc3)cccc21]

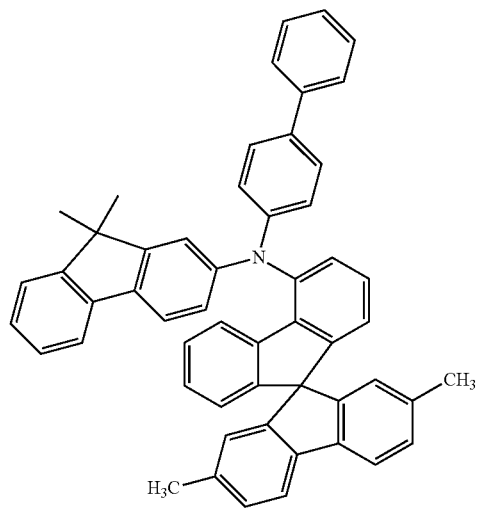 [SMILES: Cc1ccc2c(c1)C1(c3cc(C)ccc3-2)c2ccccc2-c2c(N(c3ccc(-c4ccccc4)cc3)c3ccc4c(c3)C(C)(C)c3ccccc3-4)cccc21]
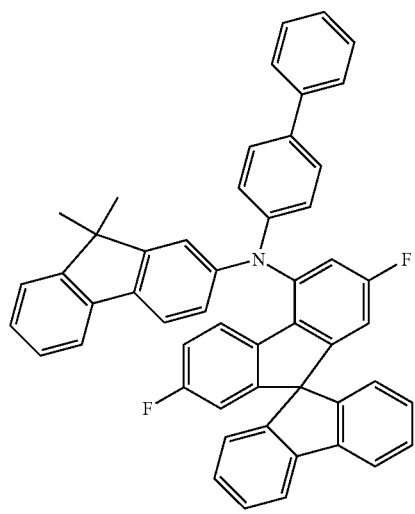 [SMILES: CC1(C)c2ccccc2-c2ccc(N(c3ccc(-c4ccccc4)cc3)c3cc(F)cc4c3-c3ccc(F)cc3C43c4ccccc4-c4ccccc43)cc21]
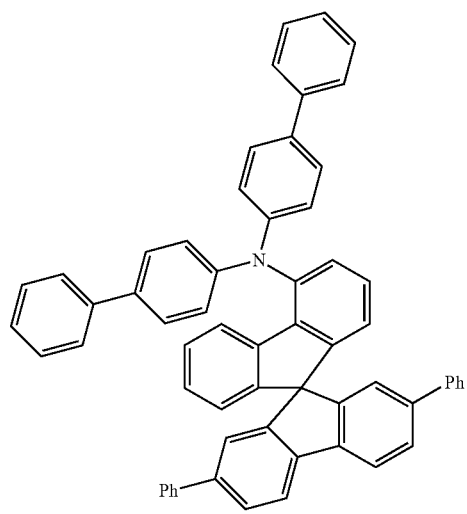 [SMILES: c1ccc(-c2ccc(N(c3ccc(-c4ccccc4)cc3)c3cccc4c3-c3ccccc3C43c4cc(-c5ccccc5)ccc4-c4ccc(-c5ccccc5)cc43)cc2)cc1]

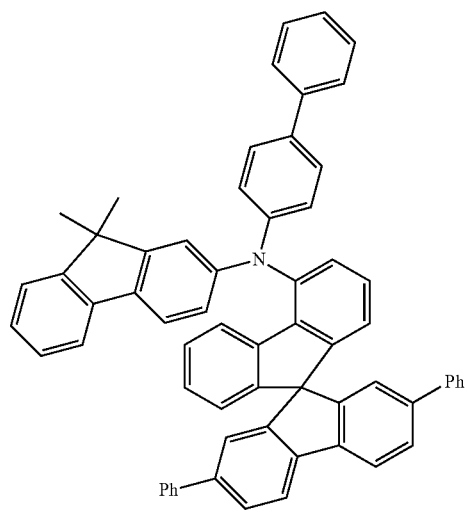 [SMILES: CC1(C)c2ccccc2-c2ccc(N(c3ccc(-c4ccccc4)cc3)c3cccc4c3-c3ccccc3C43c4cc(-c5ccccc5)ccc4-c4ccc(-c5ccccc5)cc43)cc21]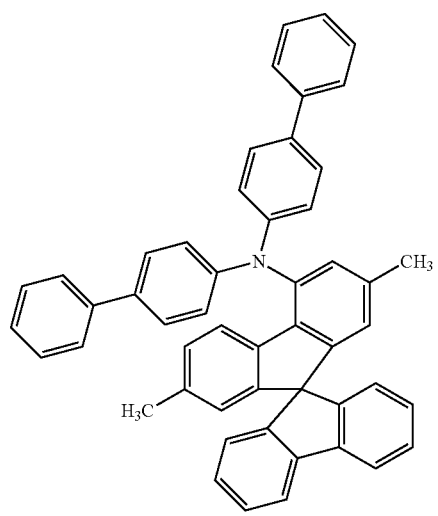 [SMILES: Cc1ccc2c(c1)C1(c3ccccc3-c3ccccc31)c1cc(C)cc(N(c3ccc(-c4ccccc4)cc3)c3ccc(-c4ccccc4)cc3)c1-2]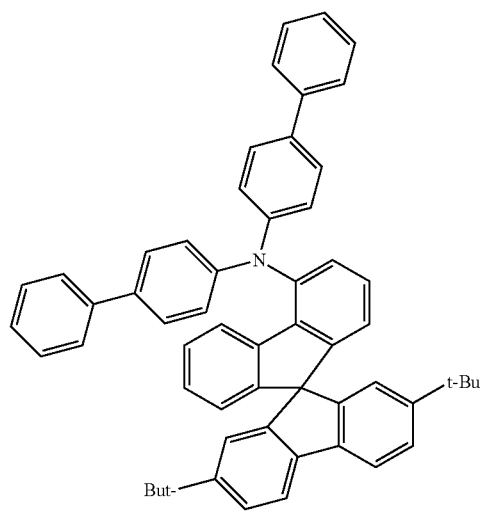

-continued
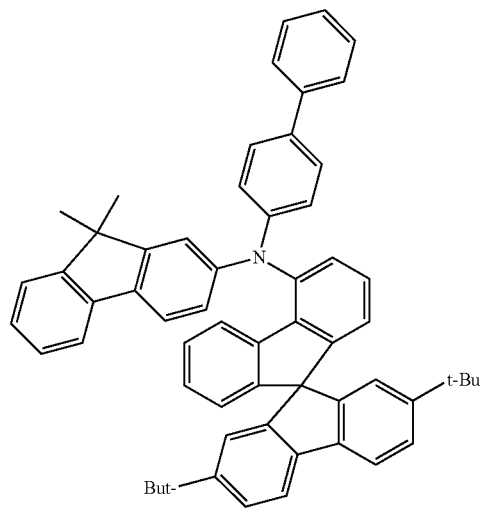
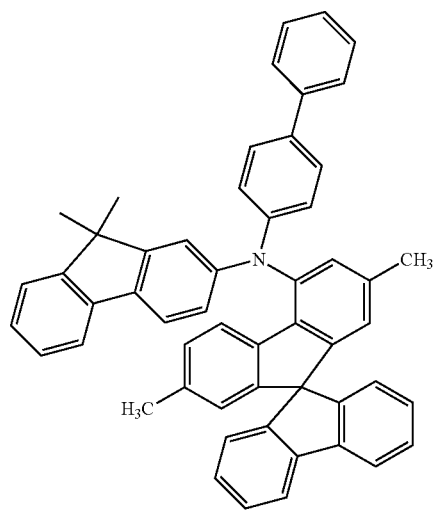 [SMILES: Cc1ccc2c(c1)C1(c3ccccc3-c3ccccc31)c1cc(C)cc(N(c3ccc(-c4ccccc4)cc3)c3ccc4c(c3)C(C)(C)c3ccccc3-4)c1-2]
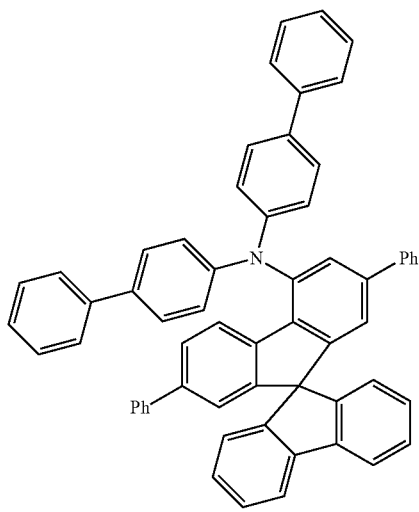 [SMILES: c1ccc(-c2ccc(N(c3ccc(-c4ccccc4)cc3)c3cc(-c4ccccc4)cc4c3-c3ccc(-c5ccccc5)cc3C43c4ccccc4-c4ccccc43)cc2)cc1]

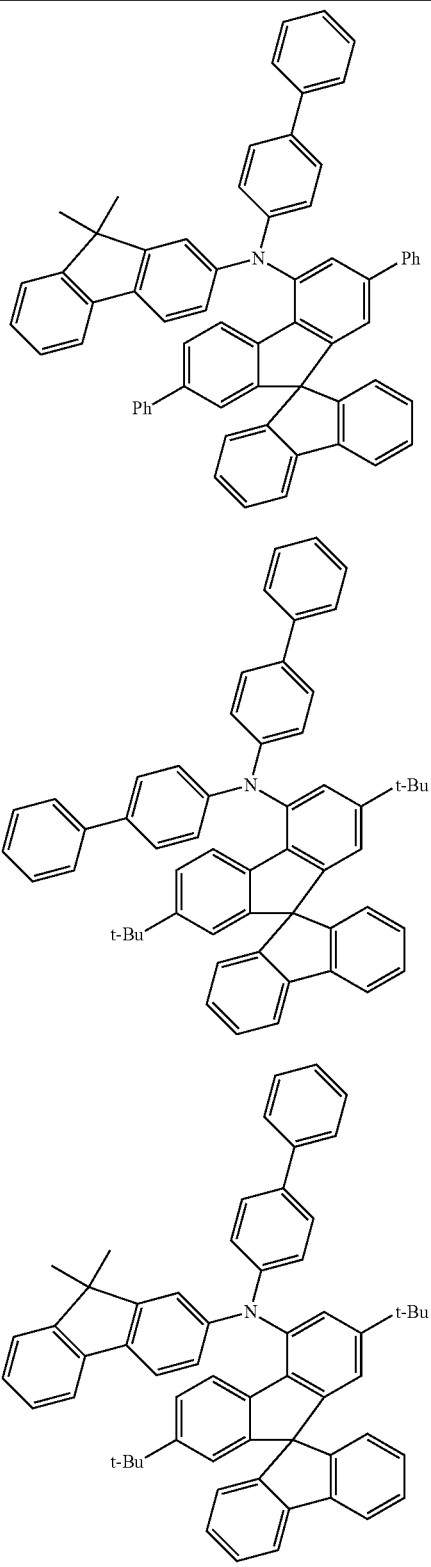

The compounds according to the invention can be prepared by synthetic steps known to the person skilled in the art, such as, for example, bromination, Ullmann arylation, Hartwig-Buchwald coupling, etc.

The syntheses generally start from the 1-, 3- or 4-halogenated, in particular brominated, spirobifluorene derivatives, followed by a C—N coupling reaction, for example a Hartwig-Buchwald coupling or an Ullmann coupling, for introduction of the diarylamino group. Analogously, another suitable leaving group, for example tosylate or triflate, can be used instead of the halogen. The synthesis of 1-diarylaminospirobifluorene is shown in Scheme 1, where two different access routes to the brominated starting compound are shown.

Scheme 1:

a) Classical spiro synthesis:

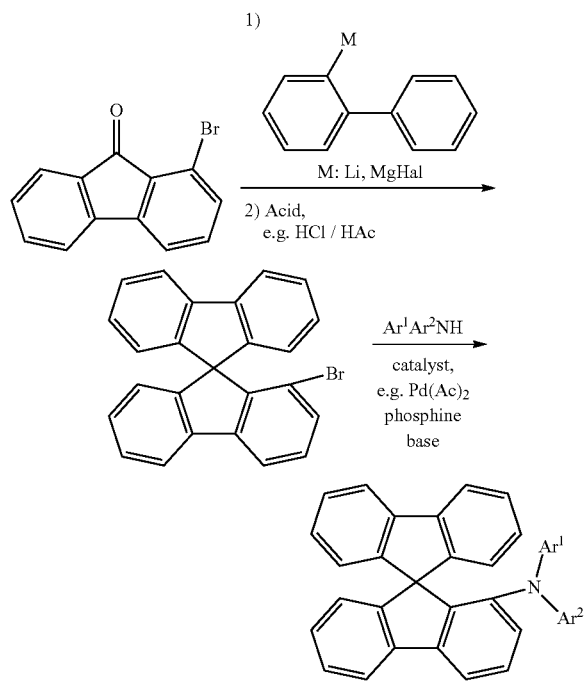

b) Directional lithiation of fluorenol:

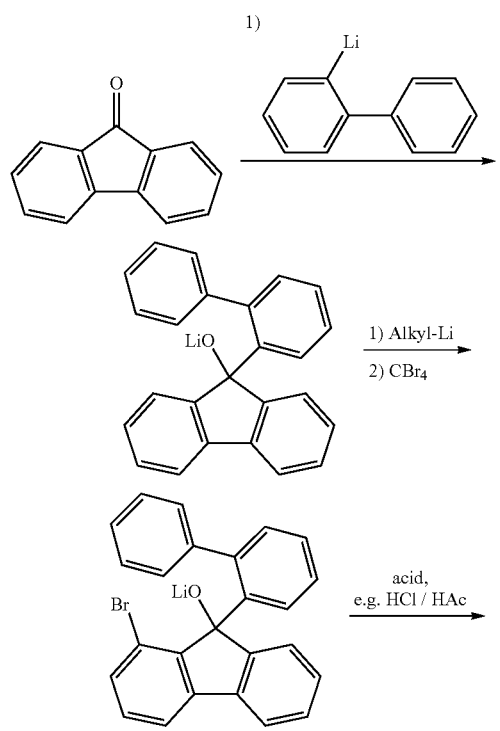

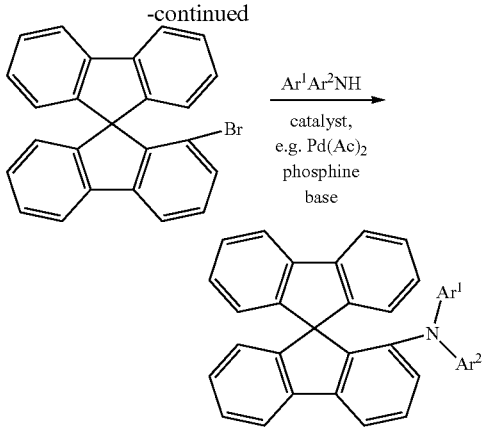

Analogously to the classical Spiro synthesis shown above, the corresponding spirobifluorene derivatives which are halogenated in the 3- or 4-position can be synthesised by employing the corresponding 3- or 4-halogen-substituted fluorenone as starting material. Likewise, corresponding substituted structures can also be synthesised entirely analogously.

In a modification of the process shown in Scheme 1a, it is likewise possible to perform the Buchwald coupling in a first step on the fluorenone, and then perform the addition of the metalated biphenyl and the ring closure to the spirobifluorene afterwards. For further details, such synthesis process is shown in the working examples.

Spirobifluorene-carbazole compounds can be synthesized by Buchwald coupling of a carbazole with a halogen-substituted spirobifluorene, as shown in the working examples.

The present invention therefore furthermore relates to a process for the preparation of a compound of the formula (1), characterised in that the diarylamino group is introduced by a C—N coupling reaction between a 1- or 3- or 4-halogenated spirobifluorene and a diarylamine.

The compounds according to the invention described above, in particular compounds which are substituted by reactive leaving groups, such as bromine, iodine, boronic acid or boronic acid ester, can be used as monomers for the preparation of corresponding oligomers, dendrimers or polymers. The oligomerisation or polymerisation here is preferably carried out via the halogen functionality or the boronic acid functionality.

The invention therefore furthermore relates to oligomers, polymers or dendrimers comprising one or more compounds of the formula (1), where the bond(s) to the polymer, oligomer or dendrimer may be localised at any desired positions in formula (1) substituted by $R^1$ to $R^5$. Depending on the linking of the compound of the formula (1), the compound is part of a side chain of the oligomer or polymer or part of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (1) may be linked directly to one another or linked to one another via a divalent group, for example via a substituted or unsubstituted alkylene group, via a heteroatom or via a divalent aromatic or heteroaromatic group. In branched and dendritic structures, three or more units of the formula (1) may, for example, be linked via a trivalent or polyvalent group, for example via a trivalent or polyvalent aromatic or heteroaromatic group, to give a branched or dendritic oligomer or polymer. The same preferences as described above for compounds of the formula (1) apply to the recurring units of the formula (1) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689 or WO 07/006,383), cis- and trans-indenofluorenes (for example in accordance with WO 04/041901 or WO 04/113412), ketones (for example in accordance with WO 05/040302), phenanthrenes (for example in accordance with WO 05/104264 or WO 07/017,066) or also a plurality of these units. The polymers, oligomers and dendrimers usually also contain further units, for example emitting (fluorescent or phosphorescent) units, such as, for example, vinyltriarylamines (for example in accordance with WO 07/068,325) or phosphorescent metal complexes (for example in accordance with WO 06/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula (1) in the polymer. Suitable polymerisation reactions are known to the person skilled in the art and are described in the literature. Particularly suitable and preferred polymerisation reactions which result in C—C or C—N links are the following:
(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 02/067343 A1 and WO 2005/026144 A1.

The compounds according to the invention are suitable for use in an electronic device. An electronic device here is taken to mean a device which comprises at least one layer which comprises at least one organic compound. However, the component here may also comprise inorganic materials or also layers built up entirely from inorganic materials.

The present invention therefore furthermore relates to the use of the compounds according to the invention in an electronic device, in particular in an organic electroluminescent device.

The present invention still furthermore relates to an electronic device comprising at least one compound according to the invention. The preferences stated above likewise apply to the electronic devices.

The electronic device is preferably selected from the group consisting of organic electroluminescent devices (organic light-emitting diodes, OLEDs), organic integrated circuits (O—ICs), organic field-effect transistors (O-FETs), organic thin-film transistors (O-TFTs), organic light-emitting transistors (O-LETs), organic solar cells (O-SCs), organic dye-sensitised solar cells (ODSSCs), organic optical detectors, organic photoreceptors, organic field-quench devices (O-FQDs), light-emitting electrochemical cells (LECs), organic laser diodes (O-lasers) and organic plasmon emitting devices (D. M. Koller et al., Nature Photonics 2008, 1-4), but preferably organic electroluminescent devices (OLEDs), particularly preferably phosphorescent OLEDs.

The organic electroluminescent devices and the light-emitting electrochemical cells can be employed for various applications, for example for monochromatic or polychromatic displays, for lighting applications or for medical and/or cosmetic applications, for example in phototherapy.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. Interlayers, which have, for example, an exciton-blocking function, may likewise be introduced between two emitting layers. However, it should be pointed out that each of these layers does not necessarily have to be present.

The organic electroluminescent device here may comprise one emitting layer or a plurality of emitting layers. If a plurality of emission layers is present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). It is possible here for all emitting layers to be fluorescent or for all emitting layers to be phosphorescent or for one or more emitting layers to be fluorescent and one or more other layers to be phosphorescent.

The compound according to the invention in accordance with the embodiments indicated above can be employed here in different layers, depending on the precise structure. Preference is given to an organic electroluminescent device comprising a compound of the formula (1) or the preferred embodiments as hole-transport material in a hole-transport or hole-injection or exciton-blocking or electron-blocking layer or as matrix material for fluorescent or phosphorescent emitters in an emitting layer, in particular for phosphorescent emitters. The preferred embodiments indicated above also apply to the use of the materials in organic electronic devices.

In a preferred embodiment of the invention, the compound of the formula (1) or the preferred embodiments is employed as hole-transport or hole-injection material in a hole-transport or hole-injection layer. The emitting layer here can be fluorescent or phosphorescent. A hole-injection layer in the sense of the present invention is a layer which is directly adjacent to the anode. A hole-transport layer in the sense of the present invention is a layer which is located between a hole-injection layer and an emitting layer.

In still a further preferred embodiment of the invention, the compound of the formula (1) or the preferred embodiments is employed in an exciton-blocking layer. An exciton-blocking layer is taken to mean a layer which is directly adjacent to an emitting layer on the anode side.

The compound of the formula (1) or the preferred embodiments is particularly preferably employed in a hole-transport or exciton-blocking layer.

In an embodiment of the invention, the compound of the formula (1) or the preferred embodiments is used in a hole-transport or -injection layer in combination with a layer which comprises a hexaazatriphenylene derivative, in particular hexacyanohexaazatriphenylene (for example in accordance with EP 1175470). Thus, for example, preference is given to a combination which looks as follows: anode-hexaazatriphenylene derivative-hole-transport layer, where the hole-transport layer comprises one or more compounds of the formula (1) or the preferred embodiments. It is likewise possible in this structure to use a plurality of successive hole-transport layers, where at least one hole-transport layer comprises at least one compound of the formula (1) or the preferred embodiments. A further preferred combination looks as follows: anode-hole-transport layer-hexaazatriphenylene derivative-hole-transport layer, where at least one of the two hole-transport layers comprises one or more compounds of the formula (1) or the preferred embodiments. It is likewise possible in this structure to use a plurality of successive hole-transport layers instead of one hole-transport layer, where at least one hole-transport layer comprises at least one compound of the formula (1) or the preferred embodiments.

If the compound according to formula (1) is employed as a hole transporting material in a hole transporting layer, a hole injection layer, an exciton blocking layer or an electron blocking layer, the compound may be used as a pure material, i.e. in a proportion of 100% in the layer, or it may be used in combination with one or more other materials. According to a preferred embodiment, in this case, the one or other compound which is used in combination with the compound according to formula (1) is a p-dopant. Preferred p-dopants to be used are electron acceptor compounds, preferably such electron acceptor compounds which can oxidize one or more of the other compounds of the mixture.

The p-dopant is preferably present in a concentration of 0.1 to 20 Vol-%, preferably 0.5 to 12 Vol-%, more preferably 1 to 8 Vol-% and most preferably 2 to 6 Vol-% in the layer comprising the compound according to the invention.

Particularly preferred p-dopants to be used in combination with the compounds according to the invention are the compounds disclosed in one or more of the following documents: WO 2011/073149, EP 1968131, EP 2276085, EP 2213662, EP 1722602, EP 2045848, DE 102007031220, U.S. Pat. Nos. 8,044,390, 8,057,712, WO 2009/003455, WO 2010/094378, WO 2011/120709, US 2010/0096600 and WO 2012/095143.

Highly preferred p-dopants to be used in the devices according to the invention are quinodimethanes, azaindenofluorendiones, azaphenalenes, azatriphenylenes, $I_2$, metal halogenides, preferably transition metal halogenides, metal oxides, preferably transition metal oxides or metal oxides comprising at least one metal of the third main group, and transition metal complexes, preferably complexes of Cu, Co, Ni, Pd or Pt with ligands having at least one binding oxygen atom. Preferred are furthermore transition metal oxides such as rhenium oxides, molybdenum oxides and tungsten oxides, more preferably $Re_2O_7$, $MoO_3$, $WO_3$ and $ReO_3$.

Preferred p-dopants are furthermore the following compounds:

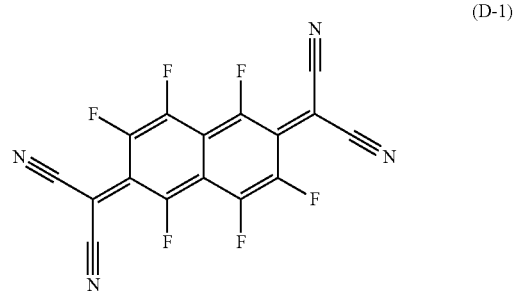

(D-1)

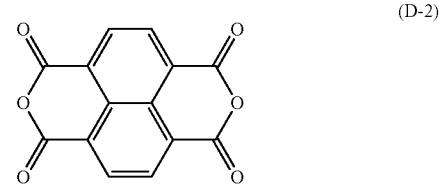

(D-2)

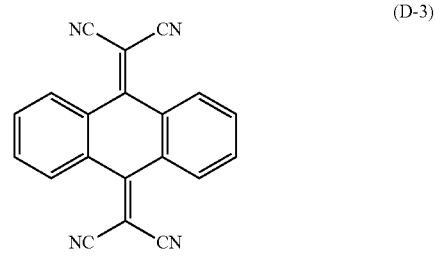

(D-3)

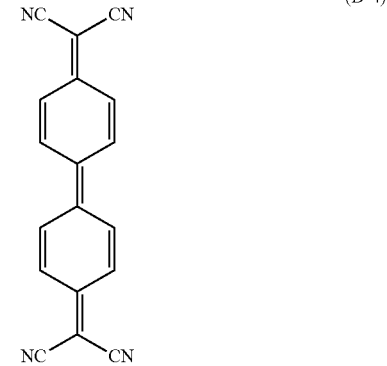

(D-4)

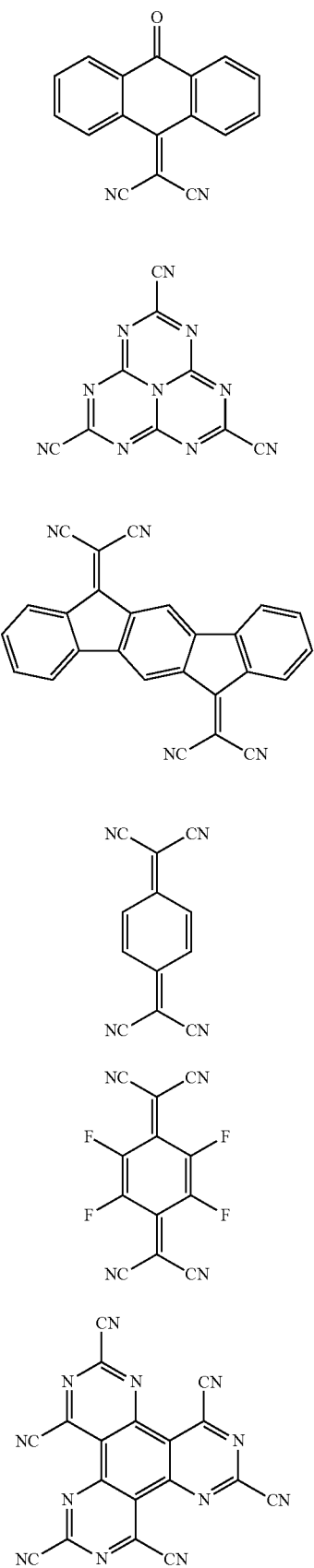
(D-5)
(D-6)
(D-7)
(D-8)
(D-9)
(D-10)

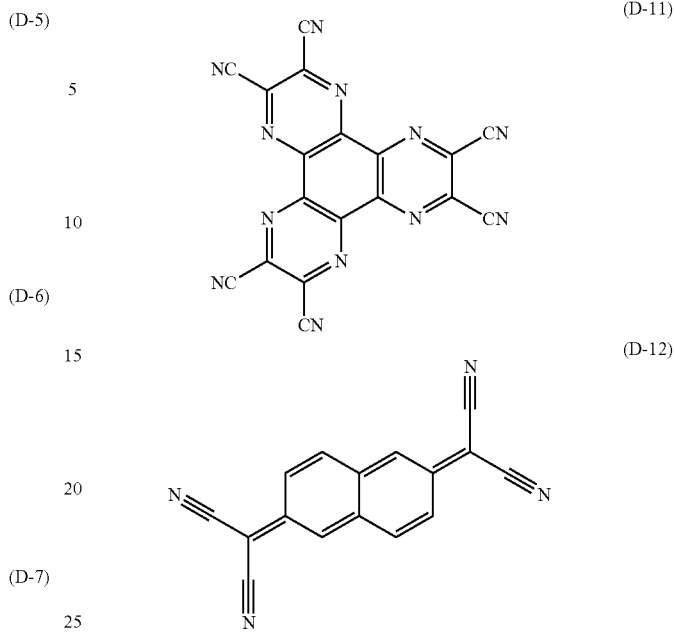
(D-11)
(D-12)

In a further preferred embodiment of the invention, the compound of the formula (1) or the preferred embodiments is employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

If the compound of the formula (1) or the preferred embodiments is employed as matrix material for an emitting compound in an emitting layer, it is preferably employed in combination with one or more phosphorescent materials (triplet emitters). Phosphorescence in the sense of this invention is taken to mean the luminescence from an excited state having a spin multiplicity >1, in particular from an excited triplet state. For the purposes of this application, all luminescent complexes containing transition metals or lanthanoids, in particular all luminescent iridium, platinum and copper complexes, are to be regarded as phosphorescent compounds.

The mixture comprising the compound of the formula (1) or the preferred embodiments and the emitting compound comprises between 99.9 and 1% by weight, preferably between 99 and 10% by weight, particularly preferably between 97 and 60% by weight, in particular between 95 and 80% by weight, of the compound of the formula (1) or the preferred embodiments, based on the entire mixture comprising emitter and matrix material. Correspondingly, the mixture comprises between 0.1 and 99% by weight, preferably between 1 and 90% by weight, particularly preferably between 3 and 40% by weight, in particular between 5 and 20% by weight, of the emitter, based on the entire mixture comprising emitter and matrix material. The limits indicated above apply, in particular, if the layer is applied from solution: If the layer is applied by vacuum evaporation, the same numerical values apply, with the percentage in this case being indicated in % by vol. in each case.

A particularly preferred embodiment of the present invention is the use of the compound of the formula (1) or the preferred embodiments as matrix material for a phosphorescent emitter in combination with a further matrix material. Particularly suitable matrix materials which can be employed in combination with the compounds of the formula (1) or the preferred embodiments are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl), m-CBP or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109 or WO 2011/000455, aza-carbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 08/056,746, zinc complexes, for example in accordance with EP 652273 or WO 2009/062578, fluorene derivatives, for example in accordance with WO 2009/124627, diazasilole or tetraazasilole derivatives, for example in accordance with WO 2010/054729, diazaphosphole derivatives, for example in accordance with WO 2010/054730, or bridged carbazole derivatives, for example in accordance with US 2009/0136779, WO 2010/050778, WO 2011/042107 or WO 2011/088877. It is furthermore possible to use an electronically neutral co-host which has neither hole-transporting nor electron-transporting properties, as described, for example, in WO 2010/108579.

Particularly preferably, the compound according to formula (1) is used as a matrix material for one or more triplet emitters in combination with a second host material selected from lactam compounds. Particularly preferred are the lactam compound disclosed in WO 2011/116865, WO 2011/137951, in unpublished EP 12007040.7 and in unpublished EP 11008708.7. Most preferred are the compounds shown in the working examples of the above applications.

Examples of preferred lactam compounds to be used in combination with the materials according to formula (1) in the emitting layer are shown in the following table.

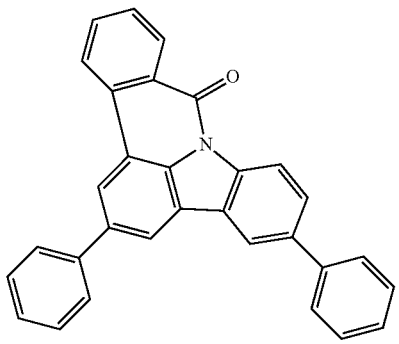 [SMILES: O=c1c2ccccc2c2cc(-c3ccccc3)cc3c4cc(-c5ccccc5)ccc4n1c23]

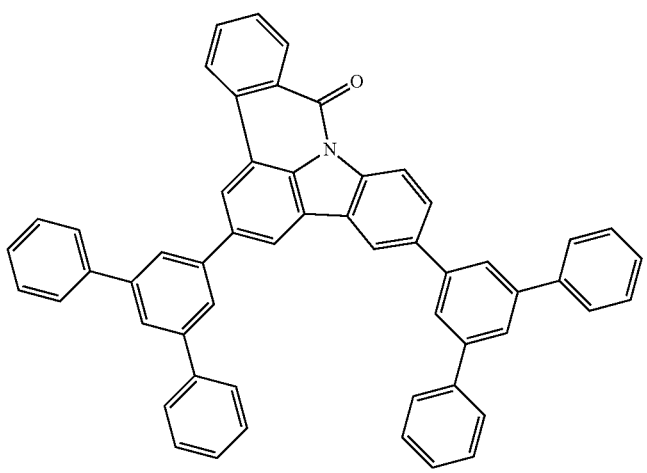 [SMILES: O=c1c2ccccc2c2cc(-c3cc(-c4ccccc4)cc(-c4ccccc4)c3)cc3c4cc(-c5cc(-c6ccccc6)cc(-c6ccccc6)c5)ccc4n1c23]

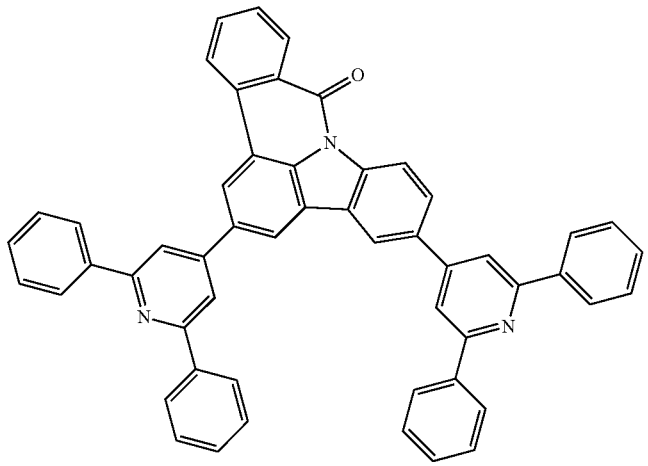 [SMILES: O=c1c2ccccc2c2cc(-c3cc(-c4ccccc4)nc(-c4ccccc4)c3)cc3c4cc(-c5cc(-c6ccccc6)nc(-c6ccccc6)c5)ccc4n1c23]
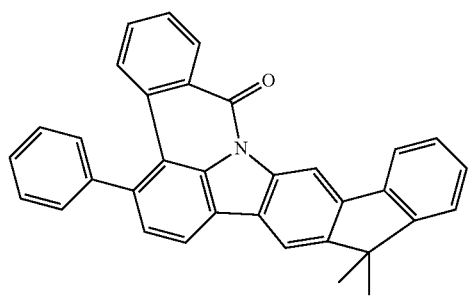 [SMILES: CC1(C)c2ccccc2-c2cc3c(cc21)c1ccc(-c2ccccc2)c2c4ccccc4c(=O)n3c12]
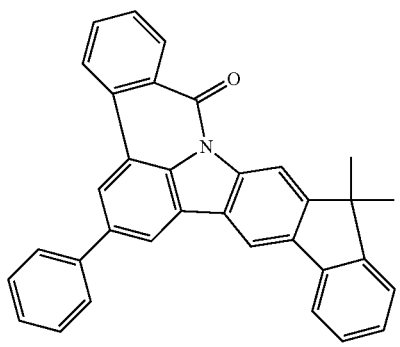 [SMILES: CC1(C)c2ccccc2-c2cc3c4cc(-c5ccccc5)cc5c6ccccc6c(=O)n(c3cc21)c54]
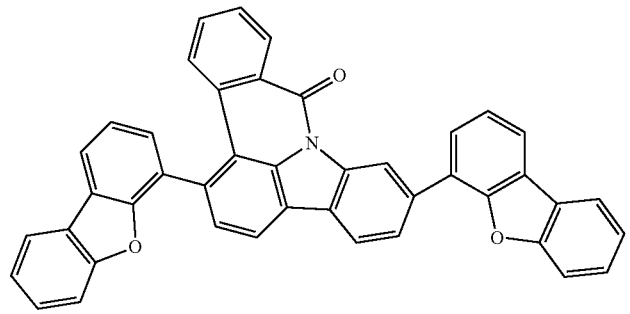 [SMILES: O=c1c2ccccc2c2c(-c3cccc4c3oc3ccccc34)ccc3c4ccc(-c5cccc6c5oc5ccccc56)cc4n1c32]

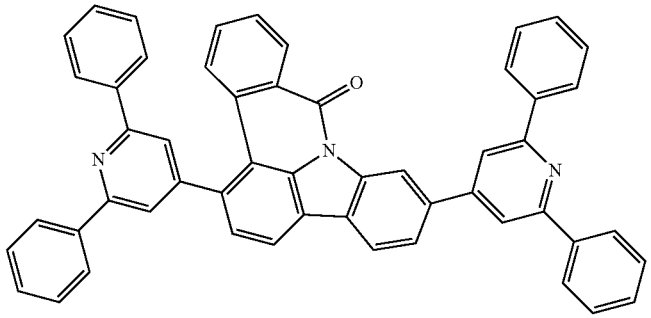 [SMILES: O=c1c2ccccc2c2c(-c3cc(-c4ccccc4)nc(-c4ccccc4)c3)ccc3c4ccc(-c5cc(-c6ccccc6)nc(-c6ccccc6)c5)cc4n1c32]
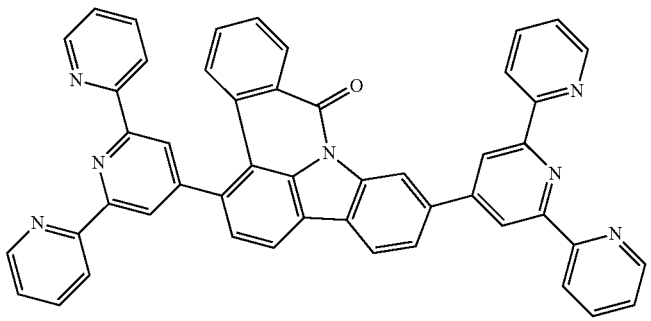 [SMILES: O=c1c2ccccc2c2c(-c3cc(-c4ccccn4)nc(-c4ccccn4)c3)ccc3c4ccc(-c5cc(-c6ccccn6)nc(-c6ccccn6)c5)cc4n1c32]
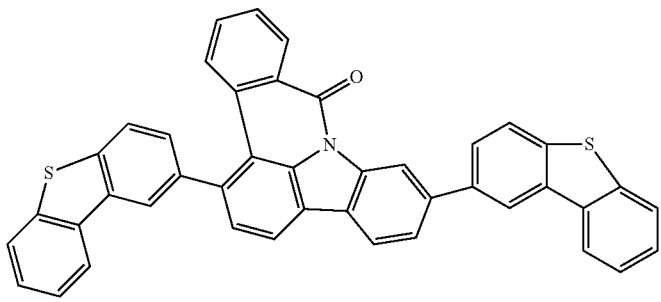 [SMILES: O=c1c2ccccc2c2c(-c3ccc4sc5ccccc5c4c3)ccc3c4ccc(-c5ccc6sc7ccccc7c6c5)cc4n1c32]
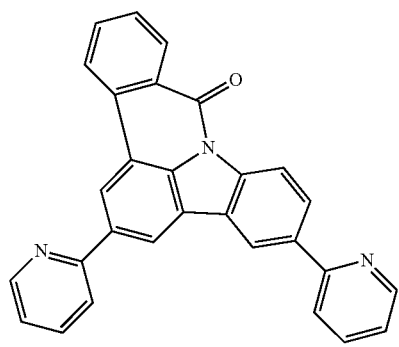 [SMILES: O=c1c2ccccc2c2cc(-c3ccccn3)cc3c4cc(-c5ccccn5)ccc4n1c23]

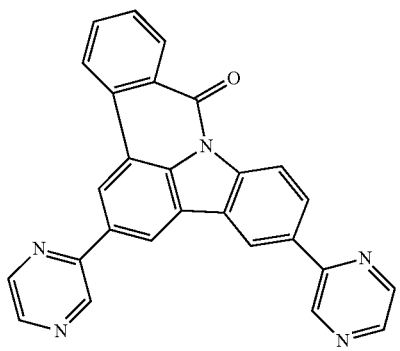 [SMILES: O=c1c2ccccc2c2cc(-c3cnccn3)cc3c4cc(-c5cnccn5)ccc4n1c23]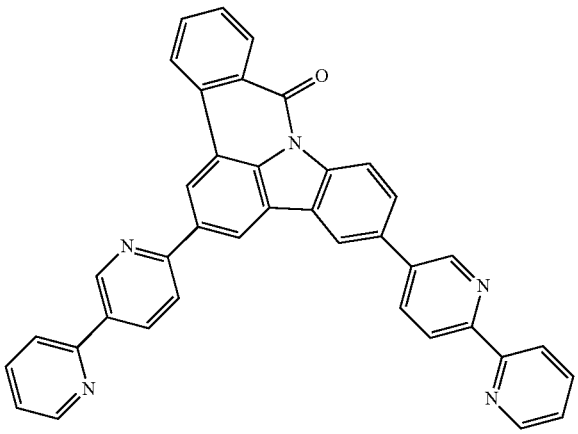 [SMILES: O=c1c2ccccc2c2cc(-c3ccc(-c4ccccn4)cn3)cc3c4cc(-c5ccc(-c6ccccn6)nc5)ccc4n1c23]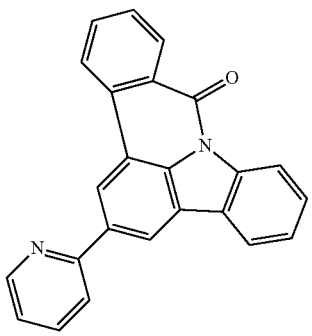 [SMILES: O=c1c2ccccc2c2cc(-c3ccccn3)cc3c4ccccc4n1c23]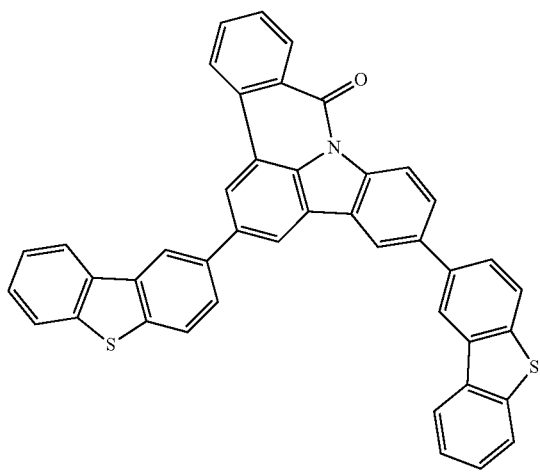 [SMILES: O=c1c2ccccc2c2cc(-c3ccc4sc5ccccc5c4c3)cc3c4cc(-c5ccc6sc7ccccc7c6c5)ccc4n1c23]

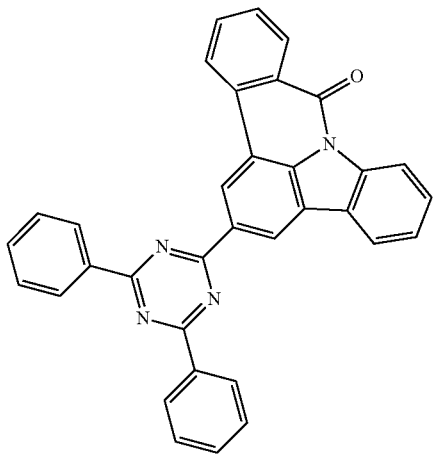 [SMILES: O=c1c2ccccc2c2cc(-c3nc(-c4ccccc4)nc(-c4ccccc4)n3)cc3c4ccccc4n1c23]
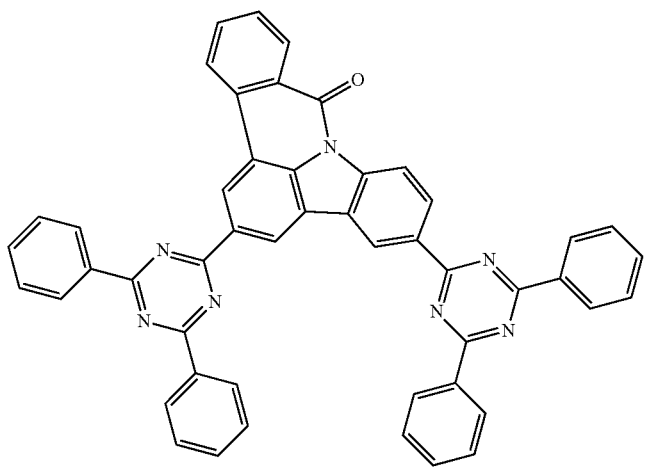 [SMILES: O=c1c2ccccc2c2cc(-c3nc(-c4ccccc4)nc(-c4ccccc4)n3)cc3c4cc(-c5nc(-c6ccccc6)nc(-c6ccccc6)n5)ccc4n1c23]
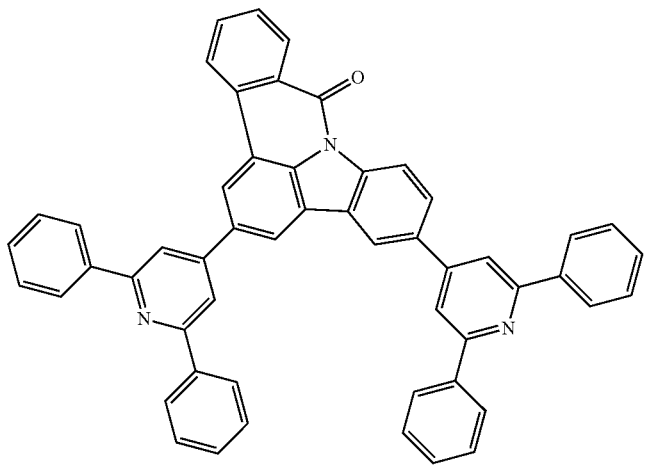 [SMILES: O=c1c2ccccc2c2cc(-c3cc(-c4ccccc4)nc(-c4ccccc4)c3)cc3c4cc(-c5cc(-c6ccccc6)nc(-c6ccccc6)c5)ccc4n1c23]

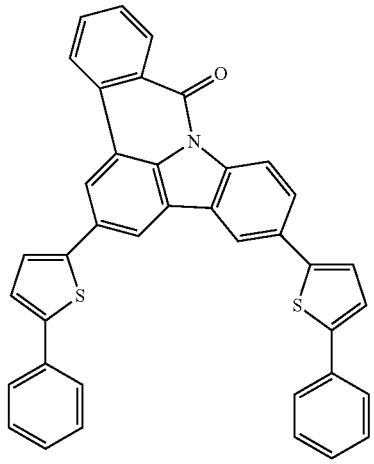 [SMILES: O=c1c2ccccc2c2cc(-c3ccc(-c4ccccc4)s3)cc3c4cc(-c5ccc(-c6ccccc6)s5)ccc4n1c23]
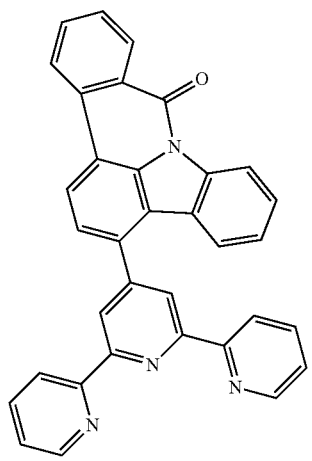 [SMILES: O=c1c2ccccc2c2ccc(-c3cc(-c4ccccn4)nc(-c4ccccn4)c3)c3c4ccccc4n1c23]
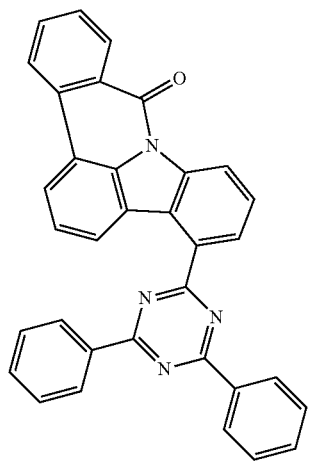 [SMILES: O=c1c2ccccc2c2cccc3c4c(-c5nc(-c6ccccc6)nc(-c6ccccc6)n5)cccc4n1c23]

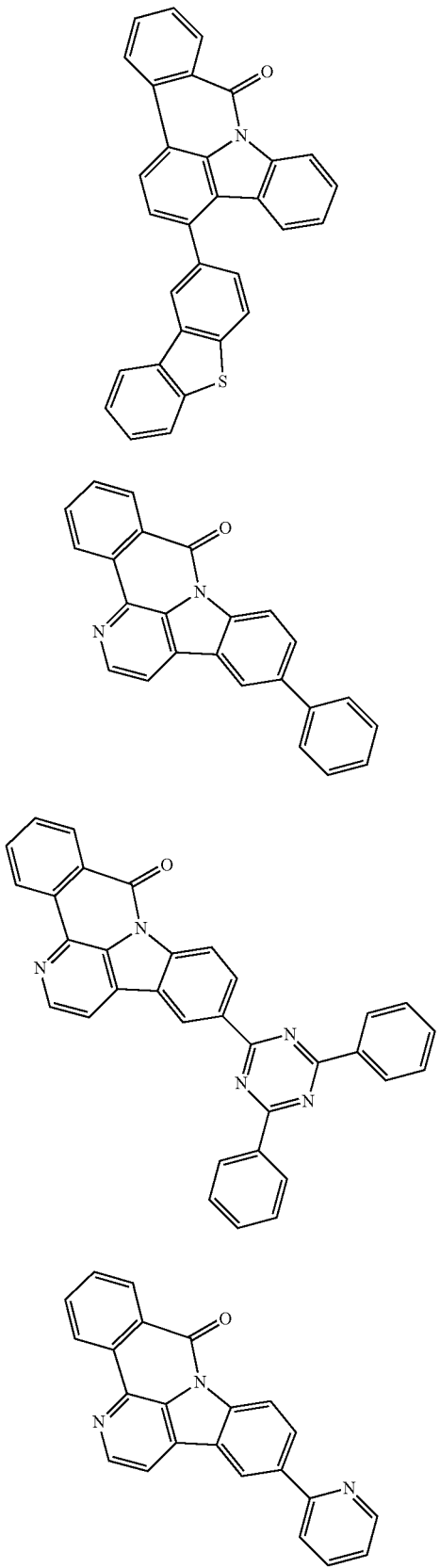

-continued
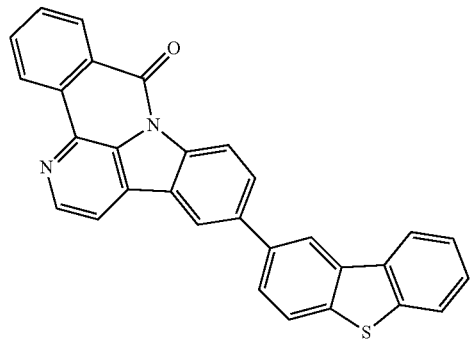 [SMILES: O=c1c2ccccc2c2nccc3c4cc(-c5ccc6sc7ccccc7c6c5)ccc4n1c32]
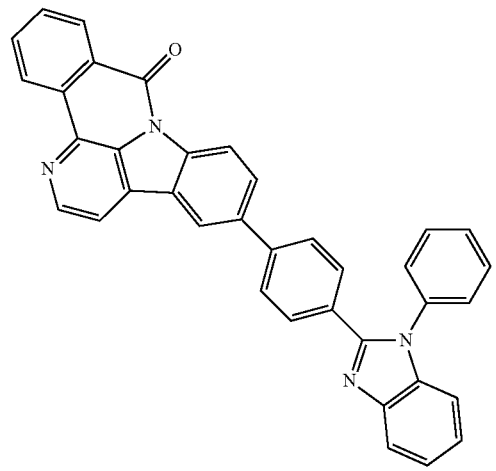 [SMILES: O=c1c2ccccc2c2nccc3c4cc(-c5ccc(-c6nc7ccccc7n6-c6ccccc6)cc5)ccc4n1c32]
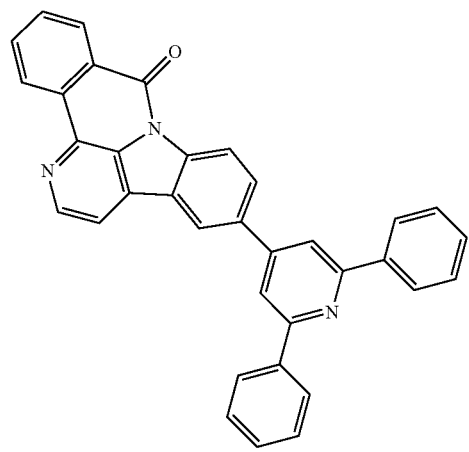 [SMILES: O=c1c2ccccc2c2nccc3c4cc(-c5cc(-c6ccccc6)nc(-c6ccccc6)c5)ccc4n1c32]

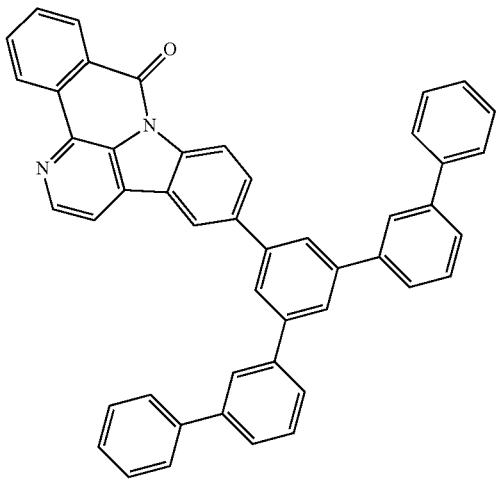 [SMILES: O=c1c2ccccc2c2nccc3c4cc(-c5cc(-c6cccc(-c7ccccc7)c6)cc(-c6cccc(-c7ccccc7)c6)c5)ccc4n1c32]
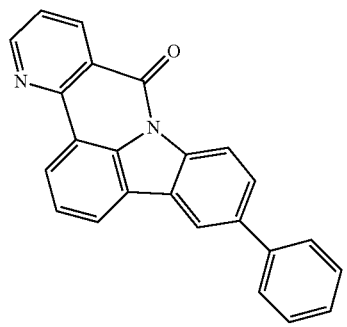 [SMILES: O=c1c2cccnc2c2cccc3c4cc(-c5ccccc5)ccc4n1c32]
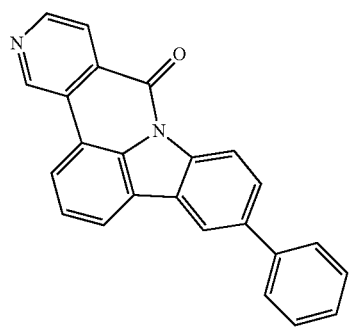 [SMILES: O=c1c2ccncc2c2cccc3c4cc(-c5ccccc5)ccc4n1c23]
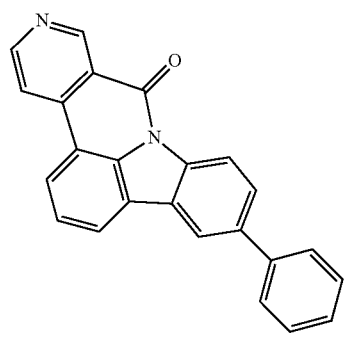 [SMILES: O=c1c2cnccc2c2cccc3c4cc(-c5ccccc5)ccc4n1c23]

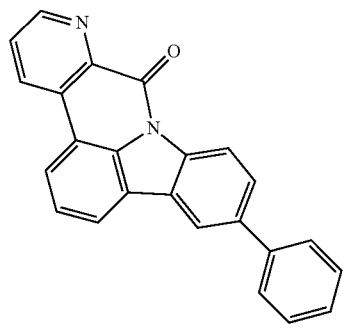 [SMILES: O=c1c2ncccc2c2cccc3c4cc(-c5ccccc5)ccc4n1c23]
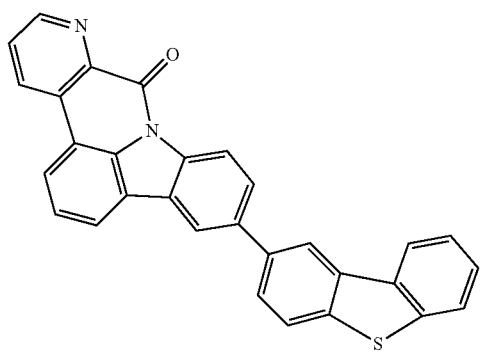 [SMILES: O=c1c2ncccc2c2cccc3c4cc(-c5ccc6sc7ccccc7c6c5)ccc4n1c23]
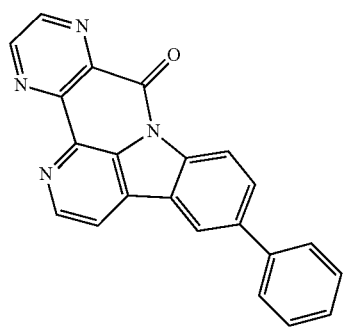 [SMILES: O=c1c2nccnc2c2nccc3c4cc(-c5ccccc5)ccc4n1c32]
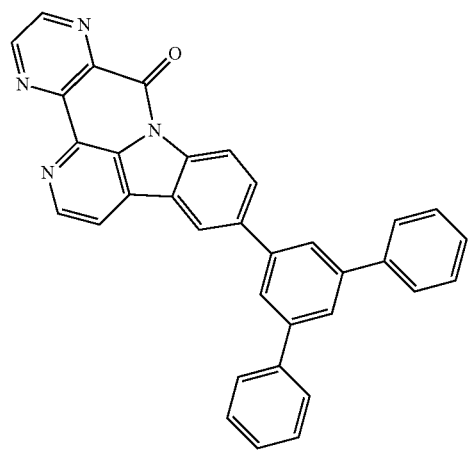 [SMILES: O=c1c2nccnc2c2nccc3c4cc(-c5cc(-c6ccccc6)cc(-c6ccccc6)c5)ccc4n1c32]

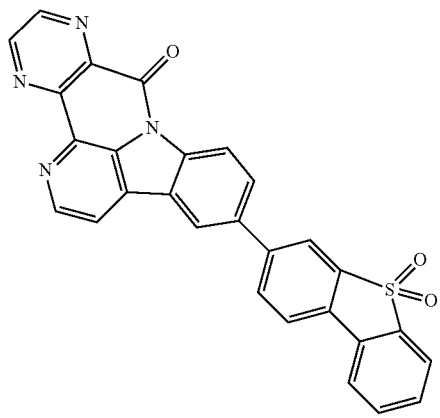 [SMILES: O=c1c2nccnc2c2nccc3c4cc(-c5ccc6c(c5)S(=O)(=O)c5ccccc5-6)ccc4n1c32]
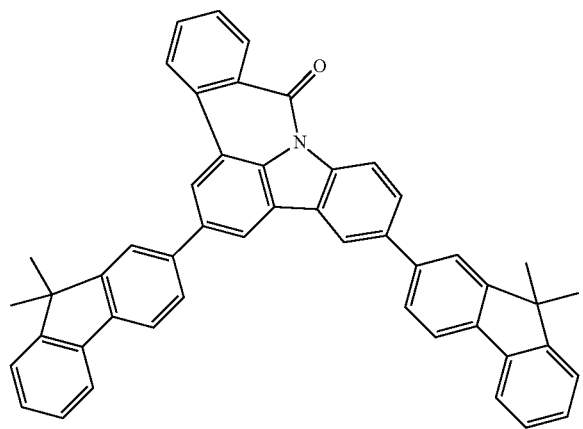 [SMILES: CC1(C)c2ccccc2-c2ccc(-c3ccc4c(c3)c3cc(-c5ccc6c(c5)C(C)(C)c5ccccc5-6)cc5c6ccccc6c(=O)n4c53)cc21]
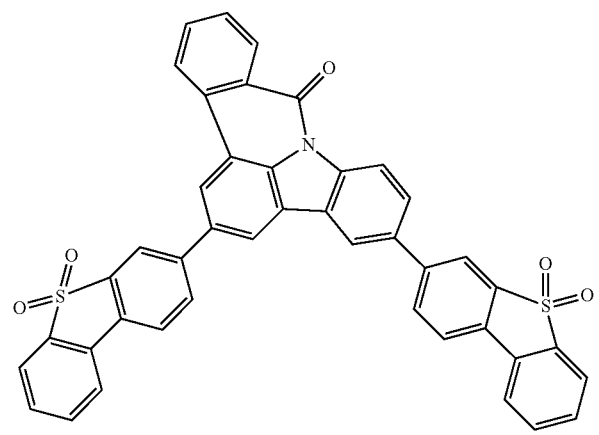 [SMILES: O=c1c2ccccc2c2cc(-c3ccc4c(c3)S(=O)(=O)c3ccccc3-4)cc3c4cc(-c5ccc6c(c5)S(=O)(=O)c5ccccc5-6)ccc4n1c23]

-continued
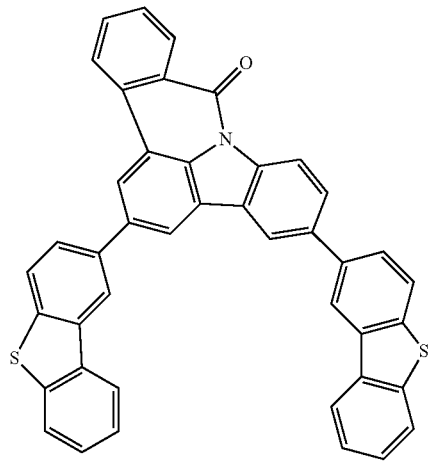 [SMILES: O=c1c2ccccc2c2cc(-c3ccc4sc5ccccc5c4c3)cc3c4cc(-c5ccc6sc7ccccc7c6c5)ccc4n1c23]
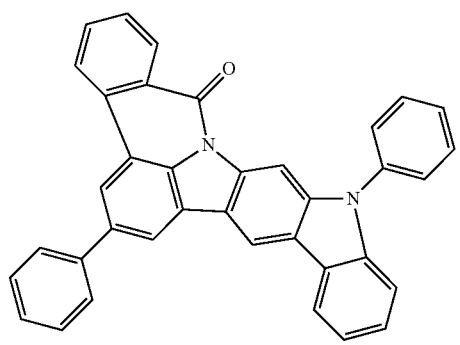 [SMILES: O=c1c2ccccc2c2cc(-c3ccccc3)cc3c4cc5c6ccccc6n(-c6ccccc6)c5cc4n1c23]
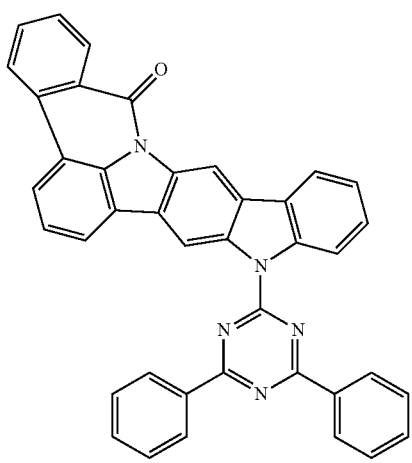 [SMILES: O=c1c2ccccc2c2cccc3c4cc5c(cc4n1c23)c1ccccc1n5-c1nc(-c2ccccc2)nc(-c2ccccc2)n1]

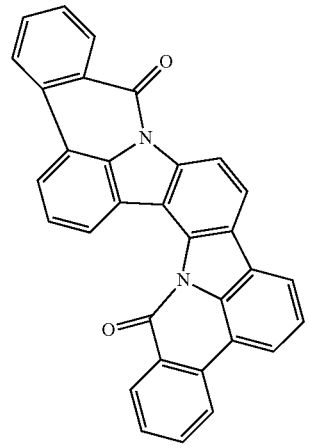 [SMILES: O=c1c2ccccc2c2cccc3c4c(ccc5c6cccc7c8ccccc8c(=O)n(c76)c54)n1c23]
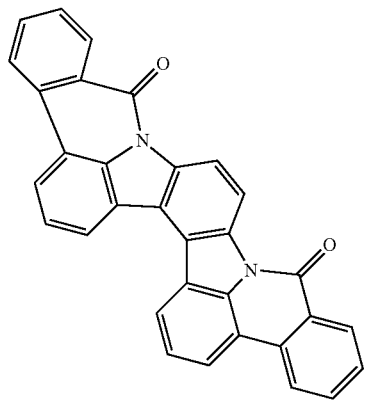 [SMILES: O=c1c2ccccc2c2cccc3c4c5c6cccc7c8ccccc8c(=O)n(c5ccc4n1c23)c76]
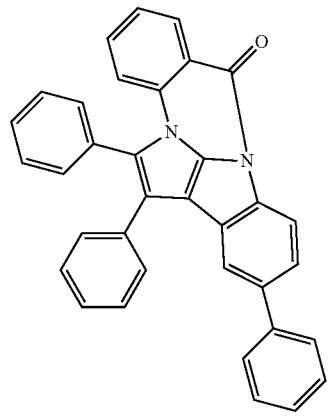 [SMILES: O=c1c2ccccc2n2c(-c3ccccc3)c(-c3ccccc3)c3c4cc(-c5ccccc5)ccc4n1c32]
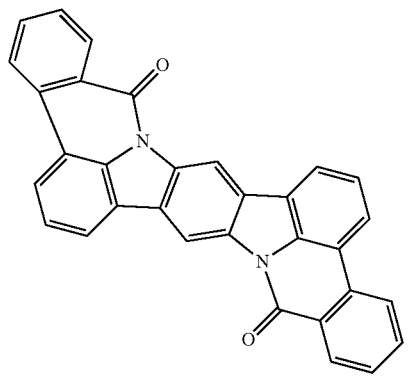 [SMILES: O=c1c2ccccc2c2cccc3c4cc5c(cc4n1c23)c1cccc2c3ccccc3c(=O)n5c21]

-continued
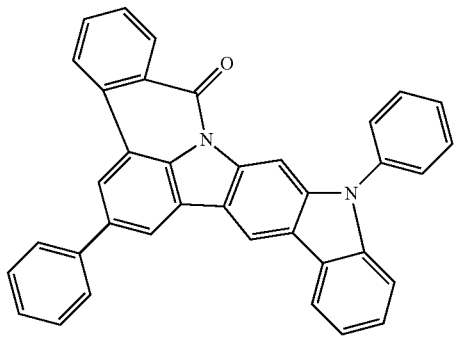 [SMILES: O=c1c2ccccc2c2cc(-c3ccccc3)cc3c4cc5c6ccccc6n(-c6ccccc6)c5cc4n1c23]
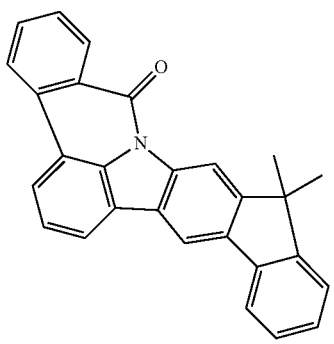 [SMILES: CC1(C)c2ccccc2-c2cc3c4cccc5c6ccccc6c(=O)n(c3cc21)c54]
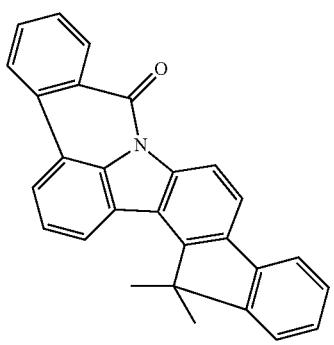 [SMILES: CC1(C)c2ccccc2-c2ccc3c(c21)c1cccc2c4ccccc4c(=O)n3c21]
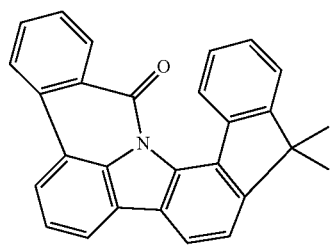 [SMILES: CC1(C)c2ccccc2-c2c1ccc1c3cccc4c5ccccc5c(=O)n(c21)c43]
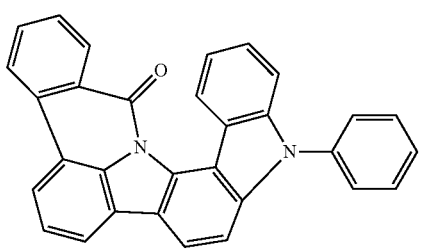 [SMILES: O=c1c2ccccc2c2cccc3c4ccc5c(c6ccccc6n5-c5ccccc5)c4n1c23]

-continued
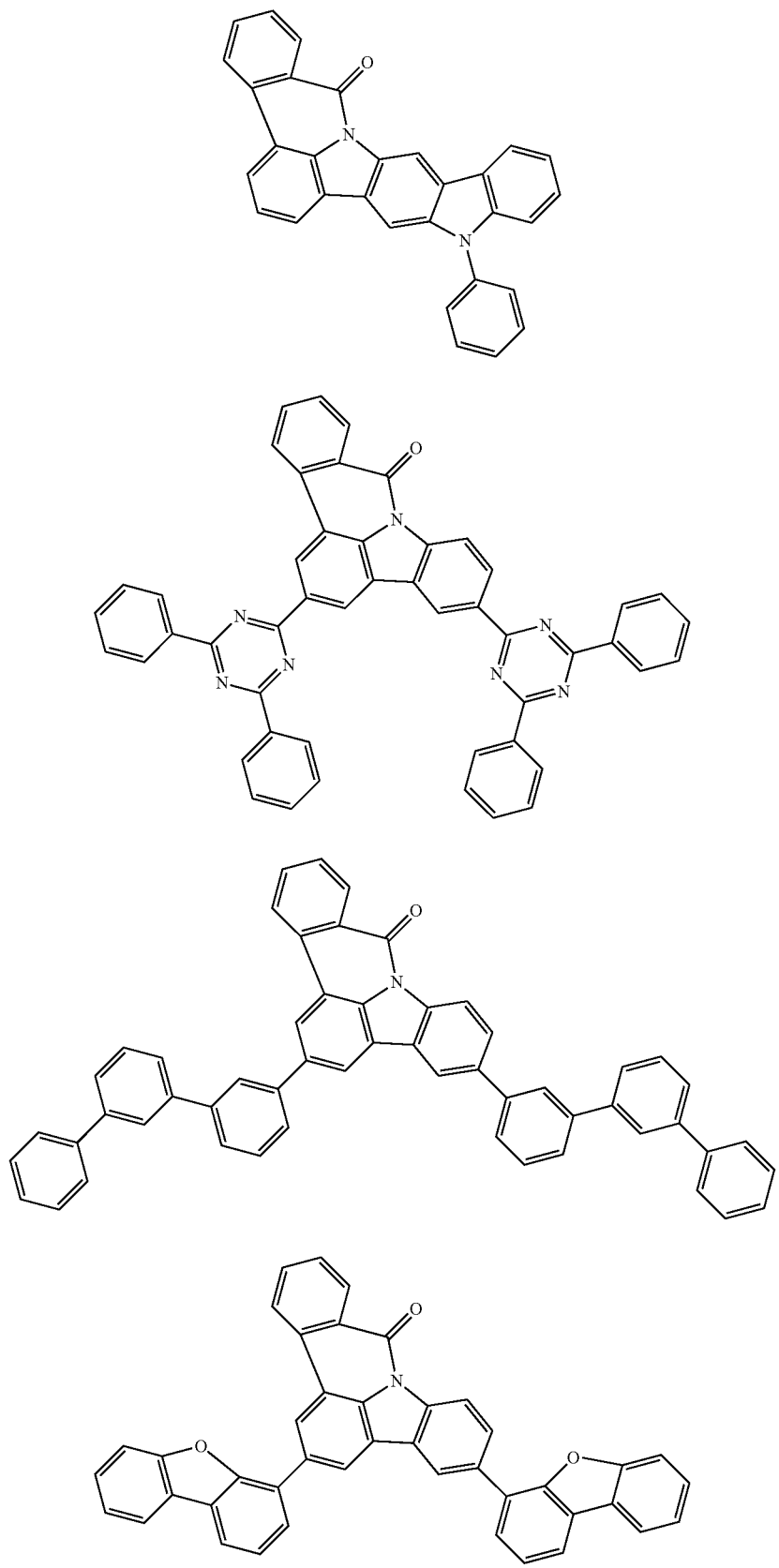

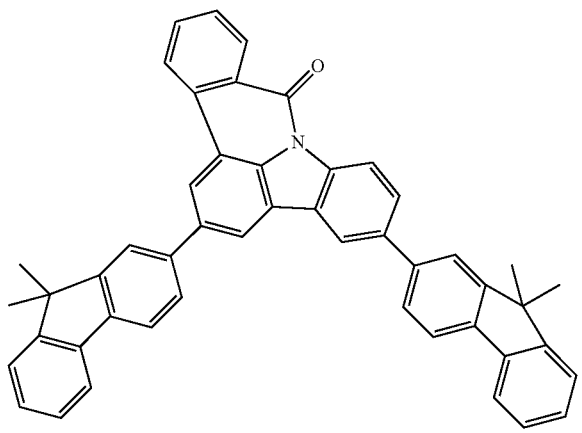 [SMILES: CC1(C)c2ccccc2-c2ccc(-c3ccc4c(c3)c3cc(-c5ccc6c(c5)C(C)(C)c5ccccc5-6)cc5c6ccccc6c(=O)n4c53)cc21]
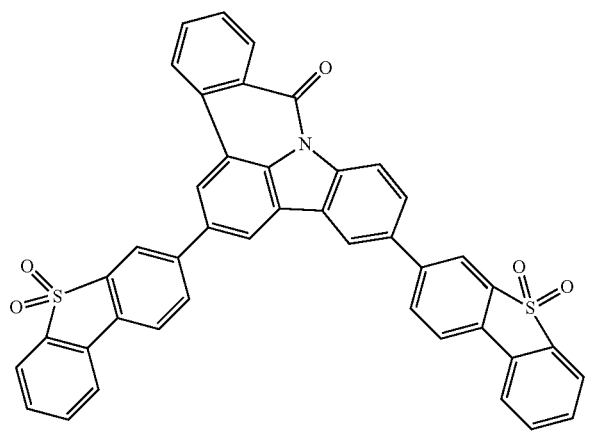 [SMILES: O=c1c2ccccc2c2cc(-c3ccc4c(c3)S(=O)(=O)c3ccccc3-4)cc3c4cc(-c5ccc6c(c5)S(=O)(=O)c5ccccc5-6)ccc4n1c23]
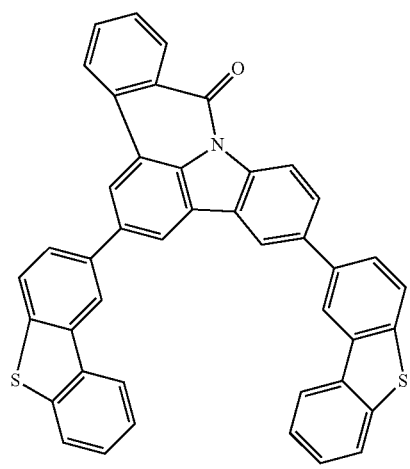 [SMILES: O=c1c2ccccc2c2cc(-c3ccc4sc5ccccc5c4c3)cc3c4cc(-c5ccc6sc7ccccc7c6c5)ccc4n1c23]

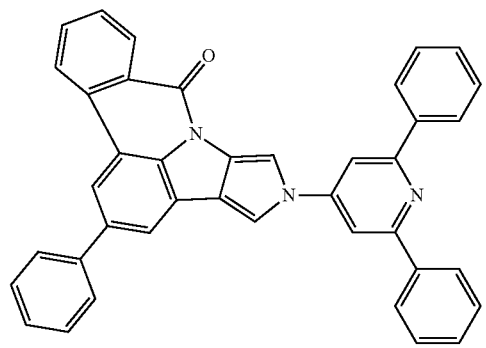 [SMILES: O=c1c2ccccc2c2cc(-c3ccccc3)cc3c4cn(-c5cc(-c6ccccc6)nc(-c6ccccc6)c5)cc4n1c23]
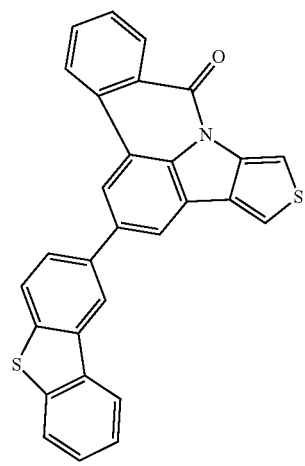 [SMILES: O=c1c2ccccc2c2cc(-c3ccc4sc5ccccc5c4c3)cc3c4cscc4n1c23]
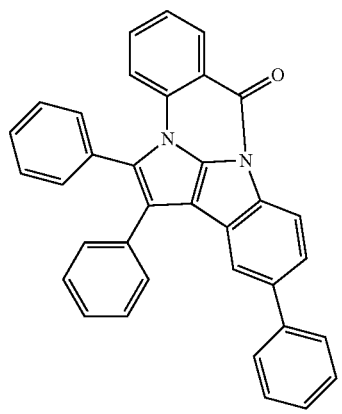 [SMILES: O=c1c2ccccc2n2c(-c3ccccc3)c(-c3ccccc3)c3c4cc(-c5ccccc5)ccc4n1c32]

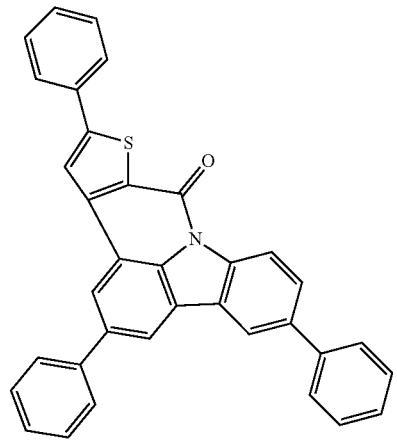 [SMILES: O=c1c2sc(-c3ccccc3)cc2c2cc(-c3ccccc3)cc3c4cc(-c5ccccc5)ccc4n1c23]
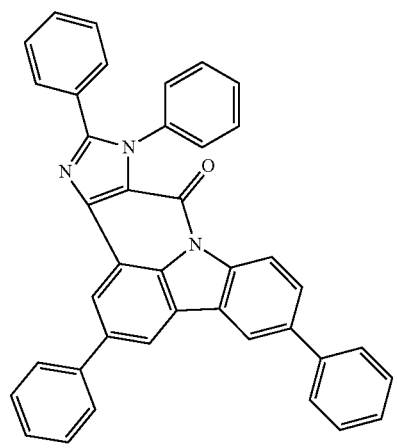 [SMILES: O=c1c2c(nc(-c3ccccc3)n2-c2ccccc2)c2cc(-c3ccccc3)cc3c4cc(-c5ccccc5)ccc4n1c32]
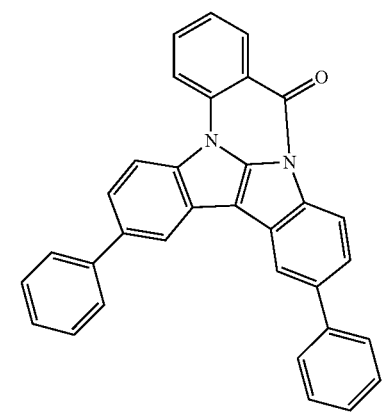 [SMILES: O=c1c2ccccc2n2c3ccc(-c4ccccc4)cc3c3c4cc(-c5ccccc5)ccc4n1c32]

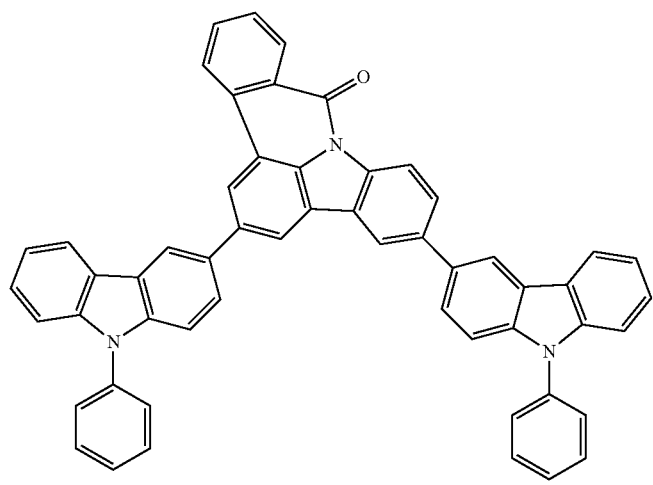 [SMILES: O=c1c2ccccc2c2cc(-c3ccc4c(c3)c3ccccc3n4-c3ccccc3)cc3c4cc(-c5ccc6c(c5)c5ccccc5n6-c5ccccc5)ccc4n1c23]
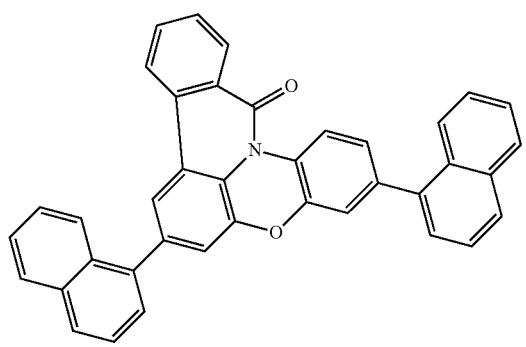 [SMILES: O=c1c2ccccc2c2cc(-c3cccc4ccccc34)cc3c2n1-c1ccc(-c2cccc4ccccc24)cc1O3]
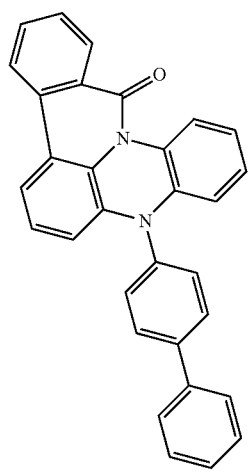 [SMILES: O=c1c2ccccc2c2cccc3c2n1-c1ccccc1N3c1ccc(-c2ccccc2)cc1]

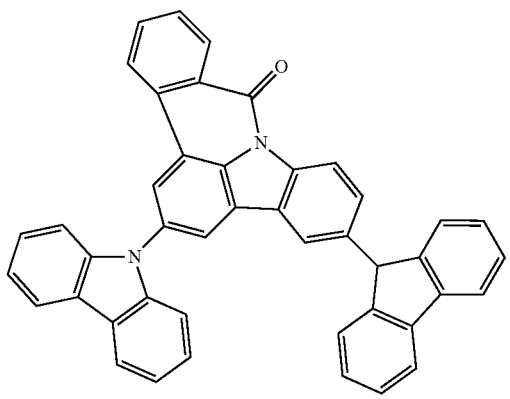 [SMILES: O=c1c2ccccc2c2cc(-n3c4ccccc4c4ccccc43)cc3c4cc(C5c6ccccc6-c6ccccc65)ccc4n1c23]
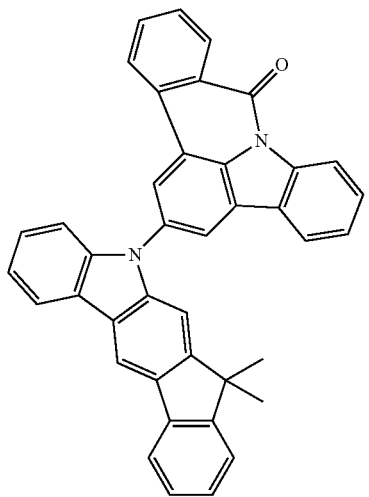 [SMILES: CC1(C)c2ccccc2-c2cc3c4ccccc4n(-c4cc5c6ccccc6c(=O)n6c7ccccc7c(c4)c56)c3cc21]
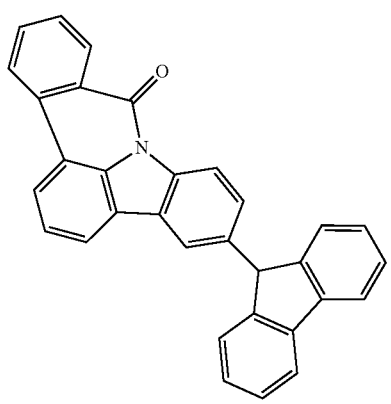 [SMILES: O=c1c2ccccc2c2cccc3c4cc(C5c6ccccc6-c6ccccc65)ccc4n1c23]

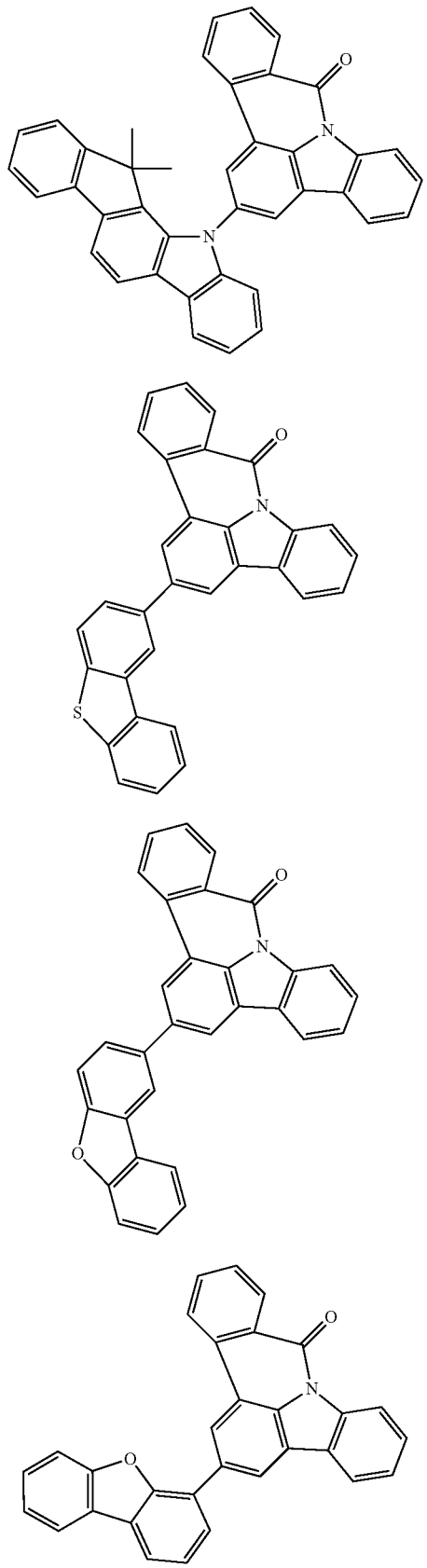

-continued
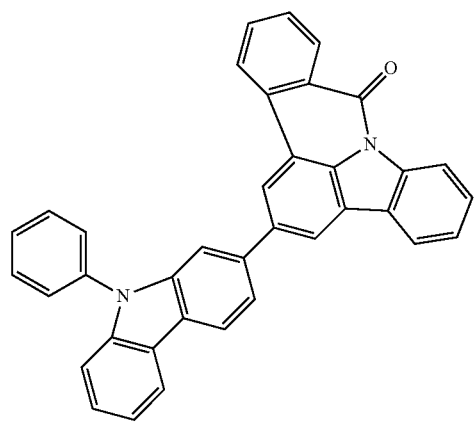 [SMILES: O=c1c2ccccc2c2cc(-c3ccc4c5ccccc5n(-c5ccccc5)c4c3)cc3c4ccccc4n1c23]
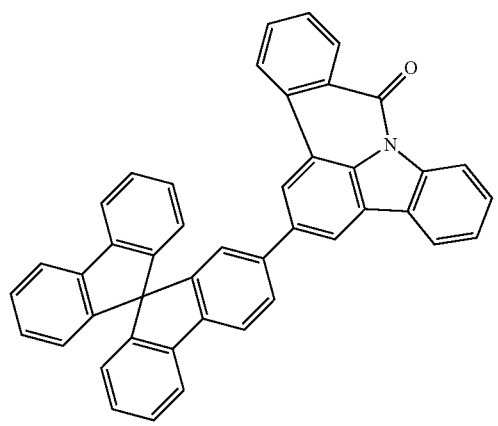 [SMILES: O=c1c2ccccc2c2cc(-c3ccc4c(c3)C3(c5ccccc5-c5ccccc53)c3ccccc3-4)cc3c4ccccc4n1c23]
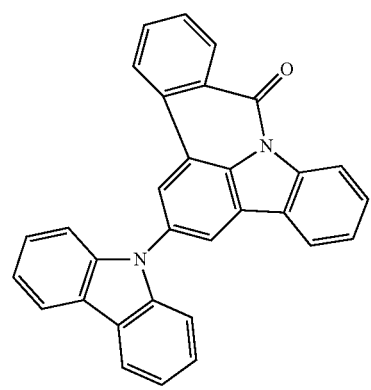 [SMILES: O=c1c2ccccc2c2cc(-n3c4ccccc4c4ccccc43)cc3c4ccccc4n1c23]

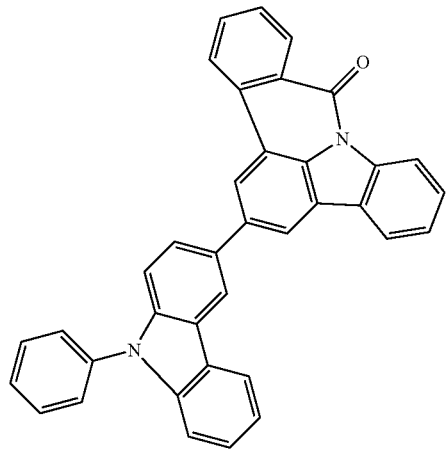 [SMILES: O=c1c2ccccc2c2cc(-c3ccc4c(c3)c3ccccc3n4-c3ccccc3)cc3c4ccccc4n1c23]
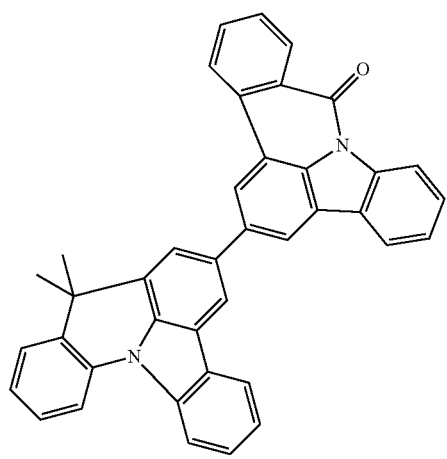 [SMILES: CC1(C)c2ccccc2-n2c3ccccc3c3cc(-c4cc5c6ccccc6c(=O)n6c7ccccc7c(c4)c56)cc1c32]
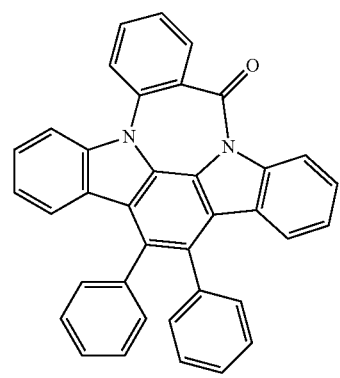 [SMILES: O=c1c2ccccc2n2c3ccccc3c3c(-c4ccccc4)c(-c4ccccc4)c4c5ccccc5n1c4c32]

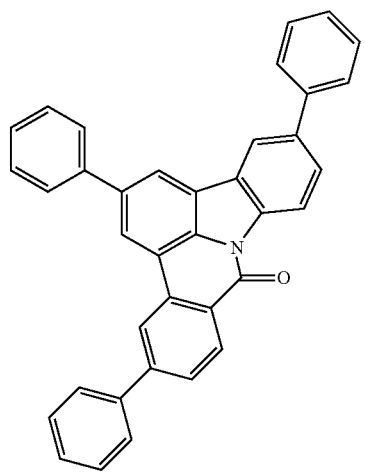 [SMILES: O=c1c2ccc(-c3ccccc3)cc2c2cc(-c3ccccc3)cc3c4cc(-c5ccccc5)ccc4n1c23]
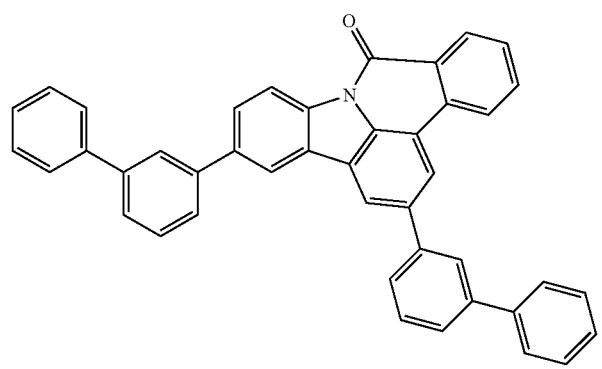 [SMILES: O=c1c2ccccc2c2cc(-c3cccc(-c4ccccc4)c3)cc3c4cc(-c5cccc(-c6ccccc6)c5)ccc4n1c23]
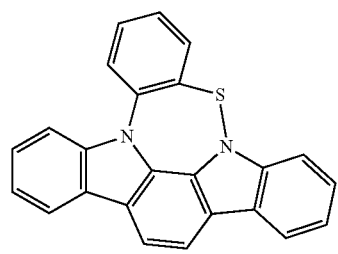 [SMILES: c1ccc2c(c1)sn1c3ccccc3c3ccc4c5ccccc5n2c4c31]
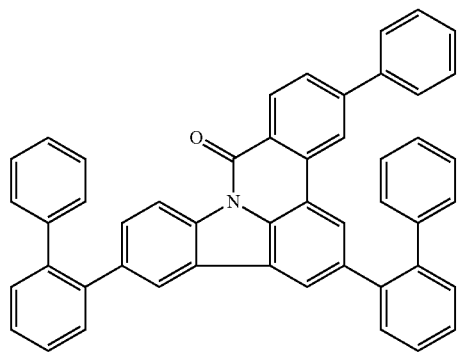 [SMILES: O=c1c2ccc(-c3ccccc3)cc2c2cc(-c3ccccc3-c3ccccc3)cc3c4cc(-c5ccccc5-c5ccccc5)ccc4n1c23]

-continued
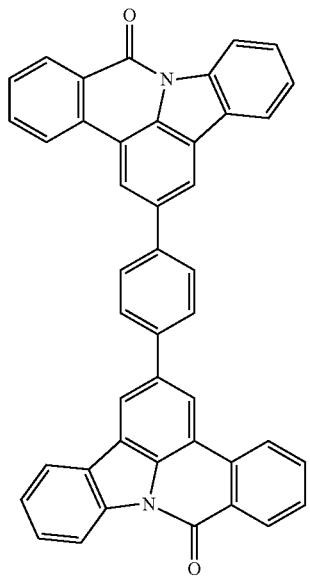 [SMILES: O=c1c2ccccc2c2cc(-c3ccc(-c4cc5c6ccccc6c(=O)n6c7ccccc7c(c4)c56)cc3)cc3c4ccccc4n1c23]
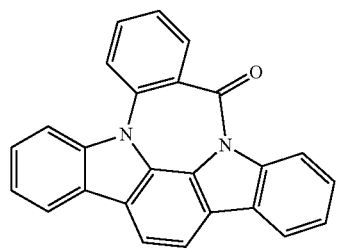 [SMILES: O=c1c2ccccc2n2c3ccccc3c3ccc4c5ccccc5n1c4c32]
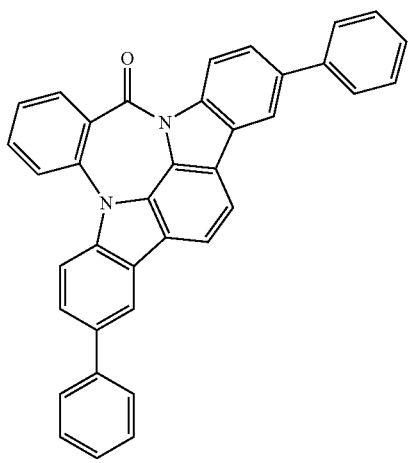 [SMILES: O=c1c2ccccc2n2c3ccc(-c4ccccc4)cc3c3ccc4c5cc(-c6ccccc6)ccc5n1c4c32]
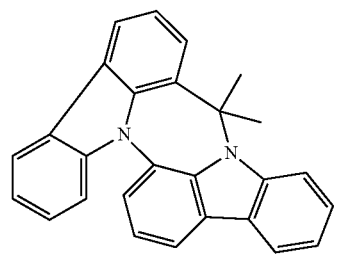 [SMILES: CC1(C)c2cccc3c4ccccc4n(c23)-c2cccc3c4ccccc4n1c23]

-continued
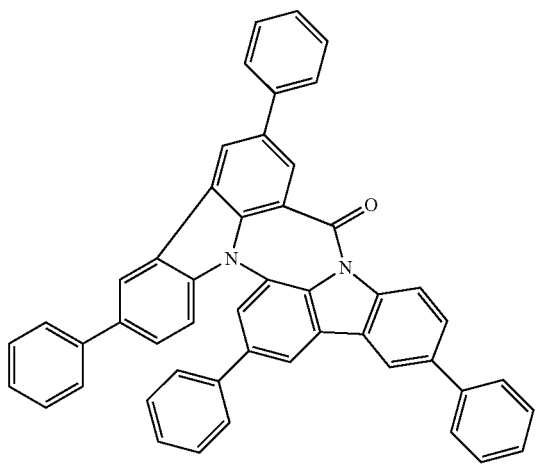 [SMILES: O=c1c2cc(-c3ccccc3)cc3c4cc(-c5ccccc5)ccc4n(c4cc(-c5ccccc5)cc5c6cc(-c7ccccc7)ccc6n1c54)c23]
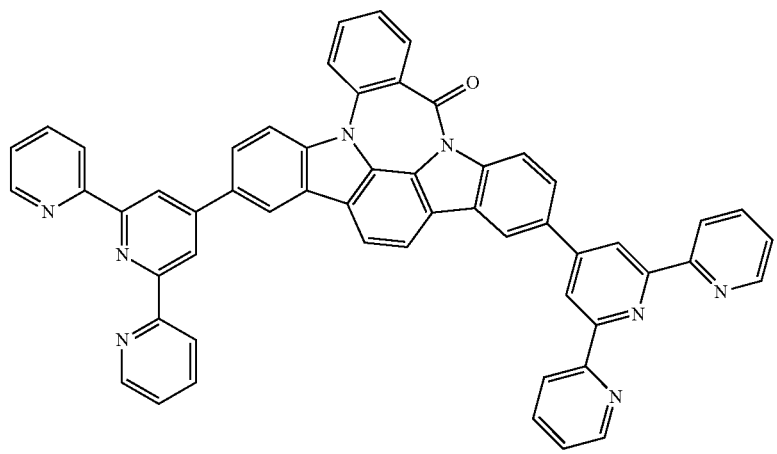 [SMILES: O=c1c2ccccc2n2c3ccc(-c4cc(-c5ccccn5)nc(-c5ccccn5)c4)cc3c3ccc4c5cc(-c6cc(-c7ccccn7)nc(-c7ccccn7)c6)ccc5n1c4c32]
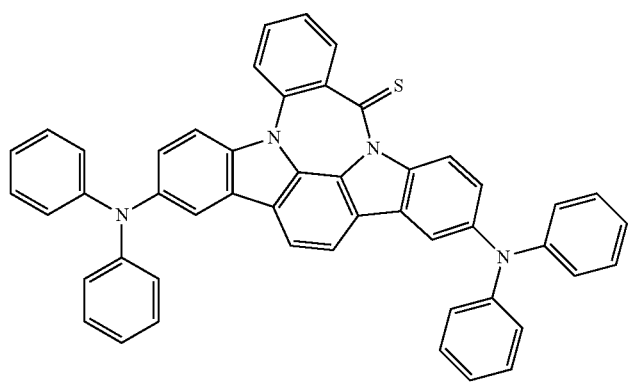 [SMILES: S=c1c2ccccc2n2c3ccc(N(c4ccccc4)c4ccccc4)cc3c3ccc4c5cc(N(c6ccccc6)c6ccccc6)ccc5n1c4c32]

-continued
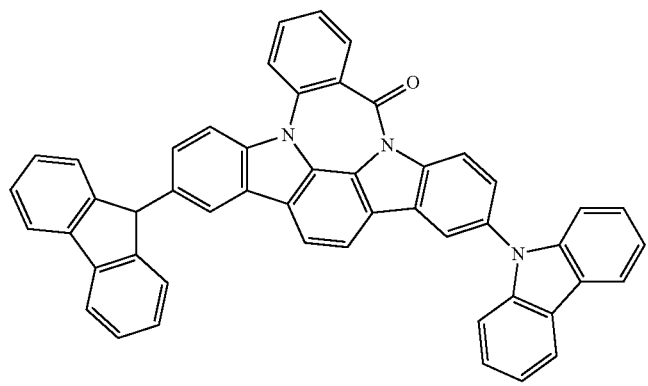 [SMILES: O=c1c2ccccc2n2c3ccc(C4c5ccccc5-c5ccccc54)cc3c3ccc4c5cc(-n6c7ccccc7c7ccccc76)ccc5n1c4c32]
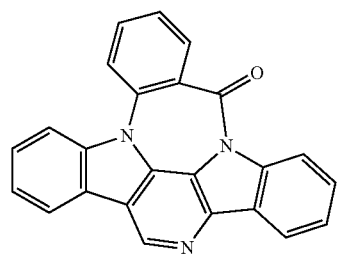 [SMILES: O=c1c2ccccc2n2c3ccccc3c3cnc4c5ccccc5n1c4c32]
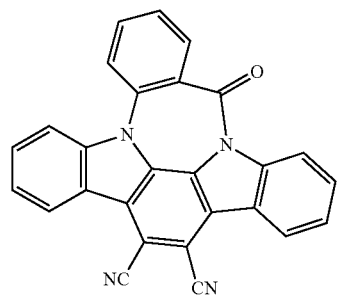 [SMILES: N#Cc1c(C#N)c2c3ccccc3n3c4ccccc4c(=O)n4c5ccccc5c1c4c23]
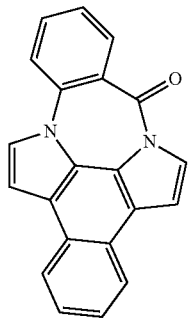 [SMILES: O=c1c2ccccc2n2ccc3c4ccccc4c4ccn1c4c32]
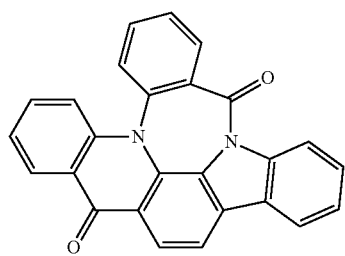 [SMILES: O=c1c2ccccc2n2c3ccccc3c(=O)n3c4ccccc4c4ccc1c2c43]

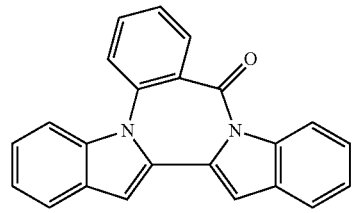 [SMILES: O=c1c2ccccc2n2c3ccccc3cc2c2cc3ccccc3n12]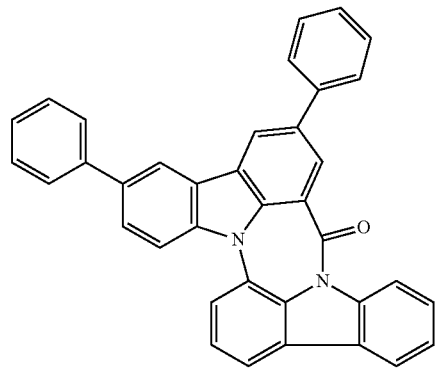 [SMILES: O=c1c2cc(-c3ccccc3)cc3c4cc(-c5ccccc5)ccc4n(c4cccc5c6ccccc6n1c54)c23]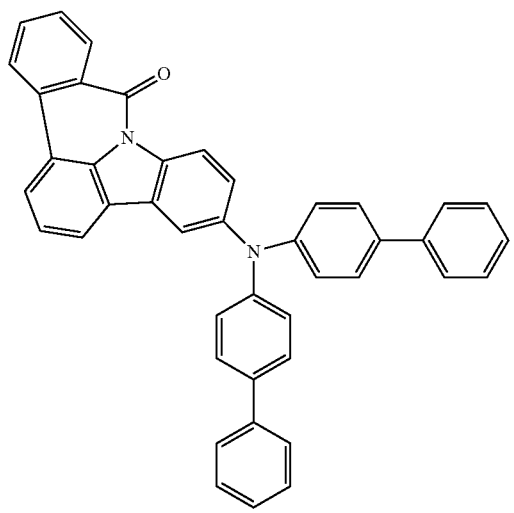 [SMILES: O=c1c2ccccc2c2cccc3c4cc(N(c5ccc(-c6ccccc6)cc5)c5ccc(-c6ccccc6)cc5)ccc4n1c23]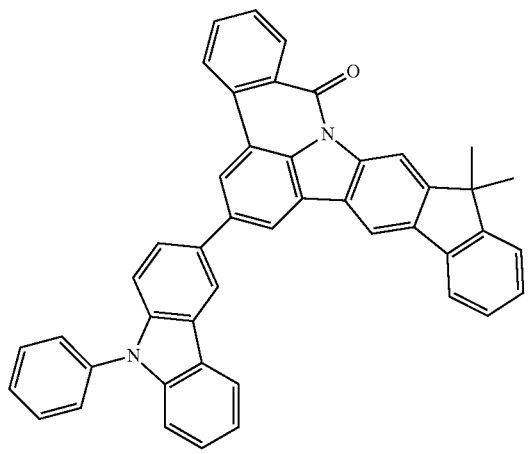 [SMILES: CC1(C)c2ccccc2-c2cc3c4cc(-c5ccc6c(c5)c5ccccc5n6-c5ccccc5)cc5c6ccccc6c(=O)n(c3cc21)c54]

-continued
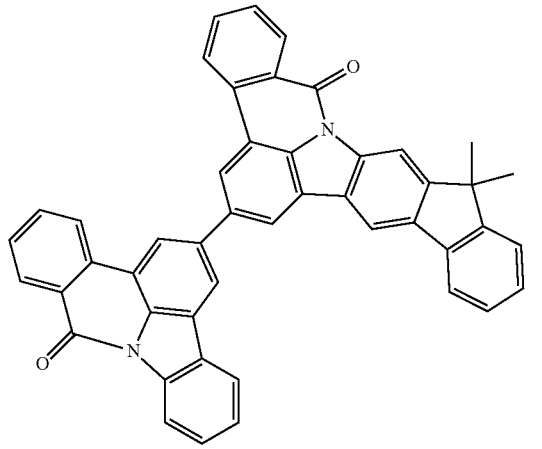 [SMILES: CC1(C)c2ccccc2-c2cc3c4cc(-c5cc6c7ccccc7c(=O)n7c8ccccc8c(c5)c67)cc5c6ccccc6c(=O)n(c3cc21)c54]
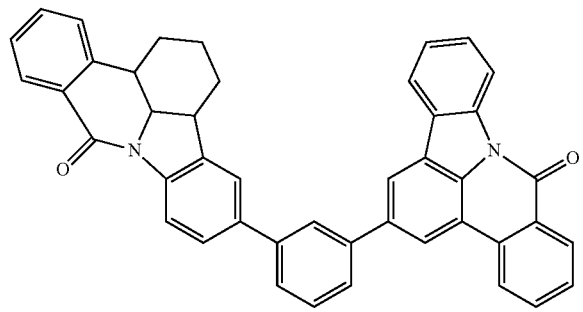 [SMILES: O=C1c2ccccc2C2CCCC3c4cc(-c5cccc(-c6cc7c8ccccc8c(=O)n8c9ccccc9c(c6)c78)c5)ccc4N1C23]
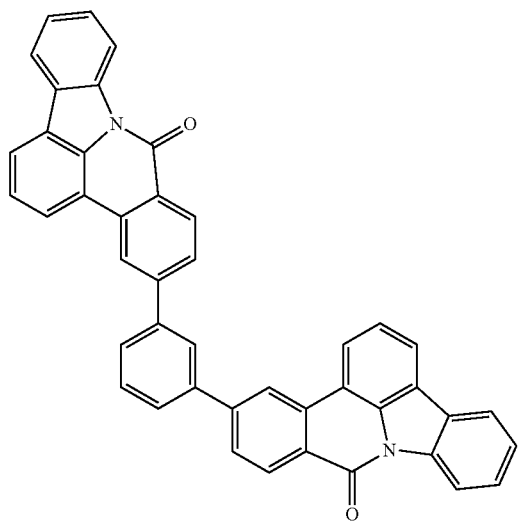 [SMILES: O=c1c2ccc(-c3cccc(-c4ccc5c(=O)n6c7ccccc7c7cccc(c5c4)c76)c3)cc2c2cccc3c4ccccc4n1c23]
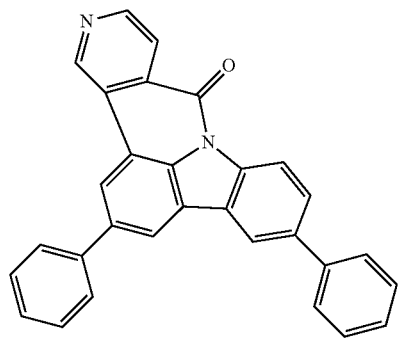 [SMILES: O=c1c2ccncc2c2cc(-c3ccccc3)cc3c4cc(-c5ccccc5)ccc4n1c23]

It is likewise possible to use two or more phosphorescent emitters in the mixture. In this case, the emitter which emits at shorter wavelength acts as co-host in the mixture.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

Examples of the emitters described above are revealed by the applications WO 2000/70655, WO 2001/41512, WO 2002/02714, WO 2002/15645, EP 1191613, EP 1191612, EP 1191614, WO 2005/033244, WO 2005/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/157339 or WO 2012/007086. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

Examples of triplet emitters to be used in the devices according to the present application are shown in the following table.

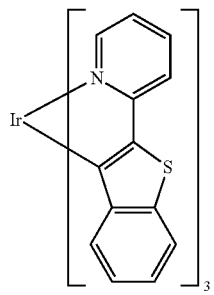

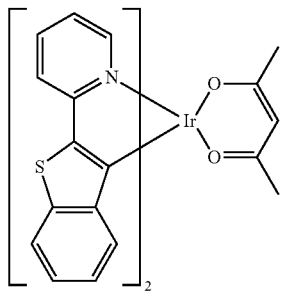

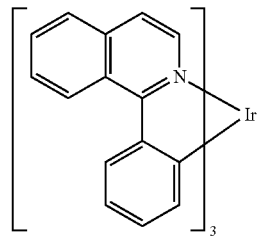

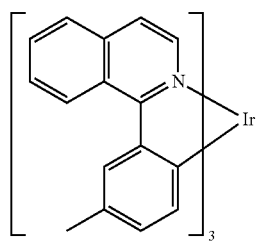

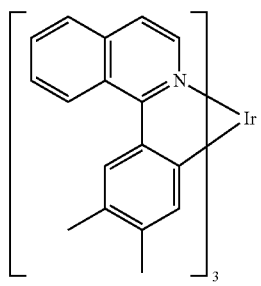

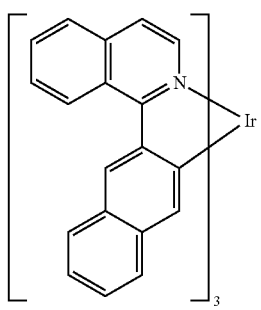

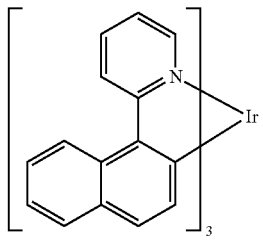

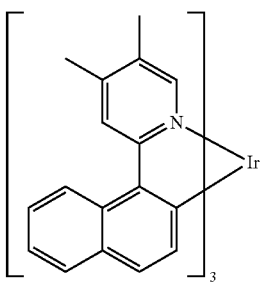

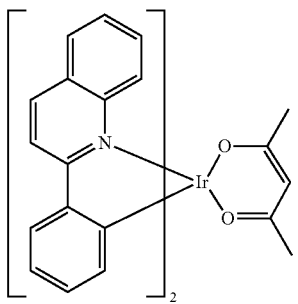
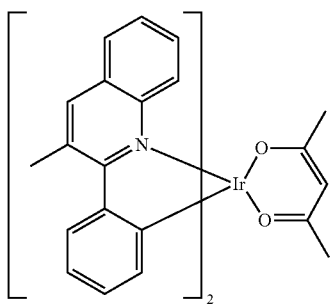
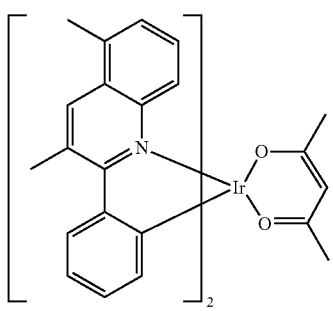
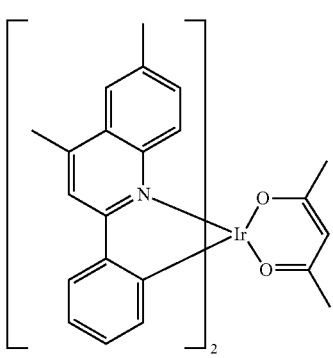
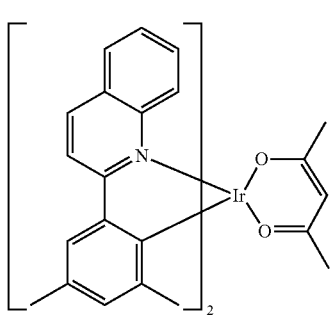
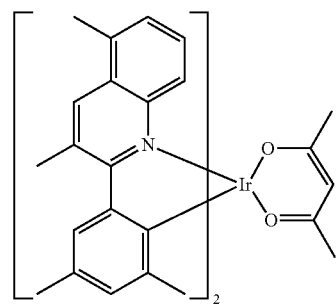
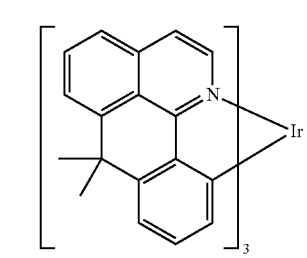
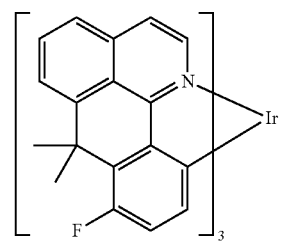
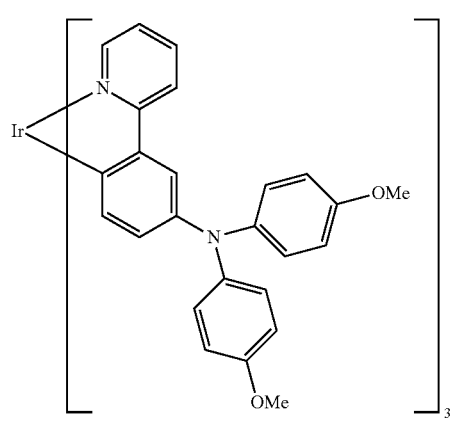
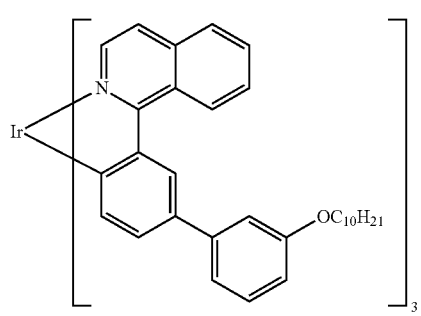

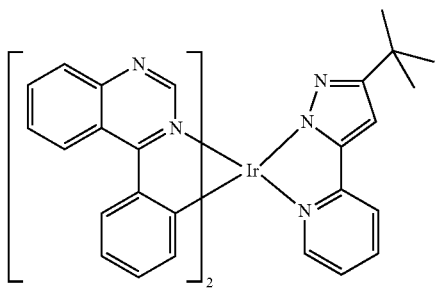
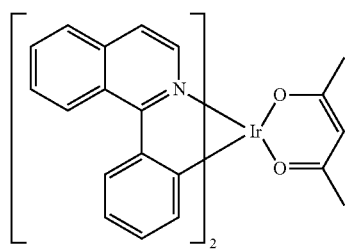
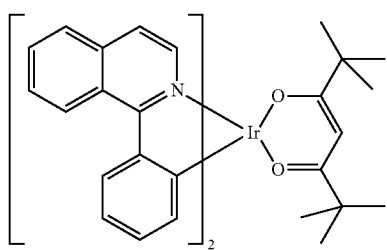
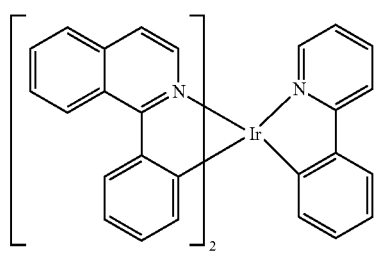
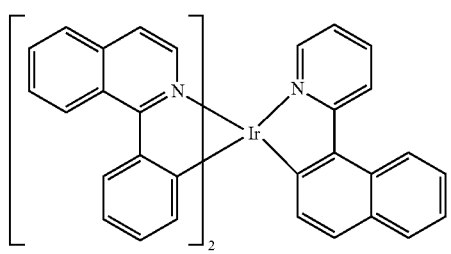
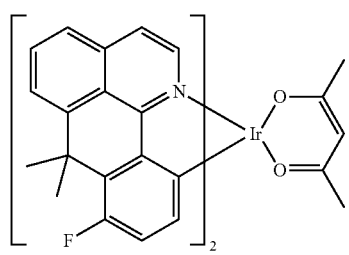
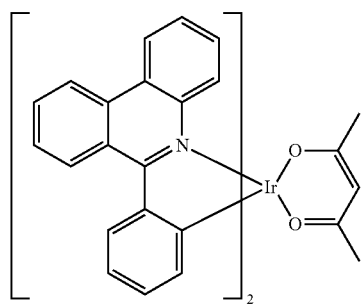
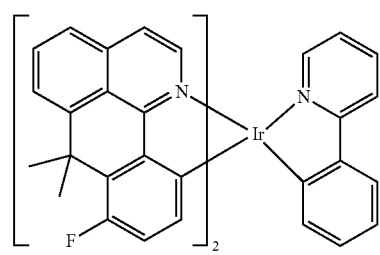
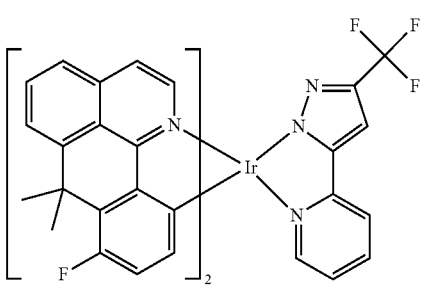
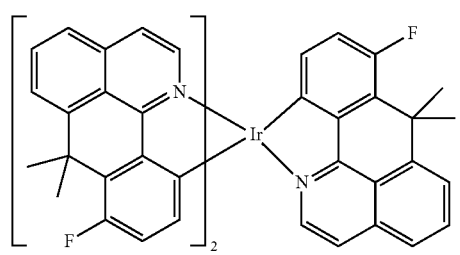
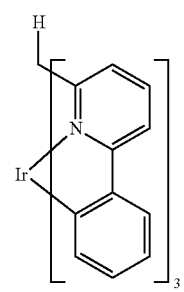

251
-continued
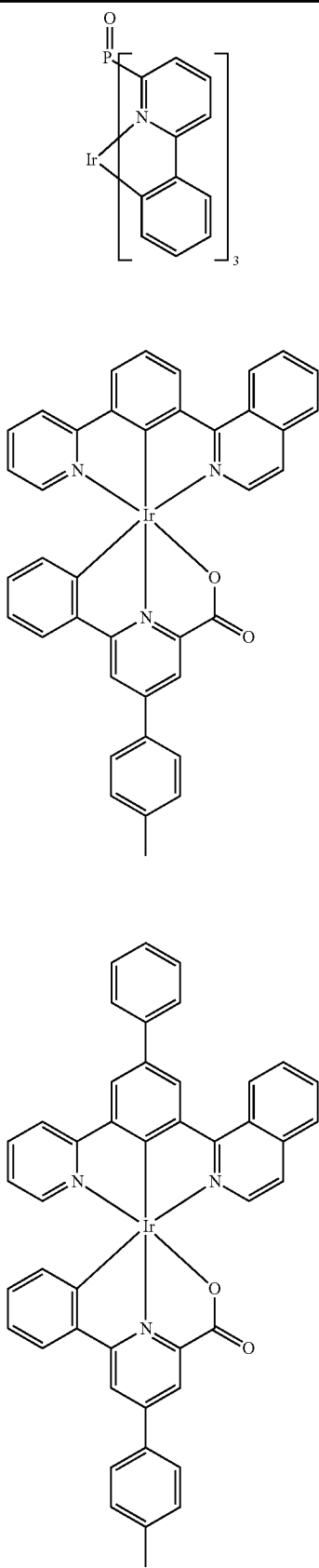
252
-continued
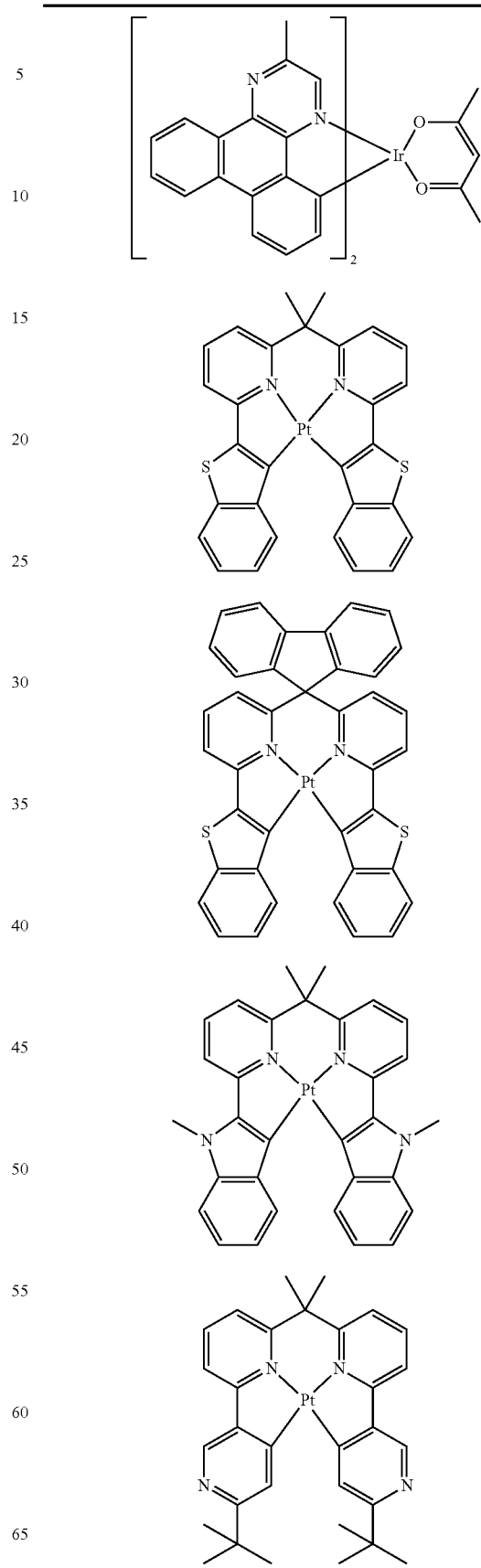

253
-continued
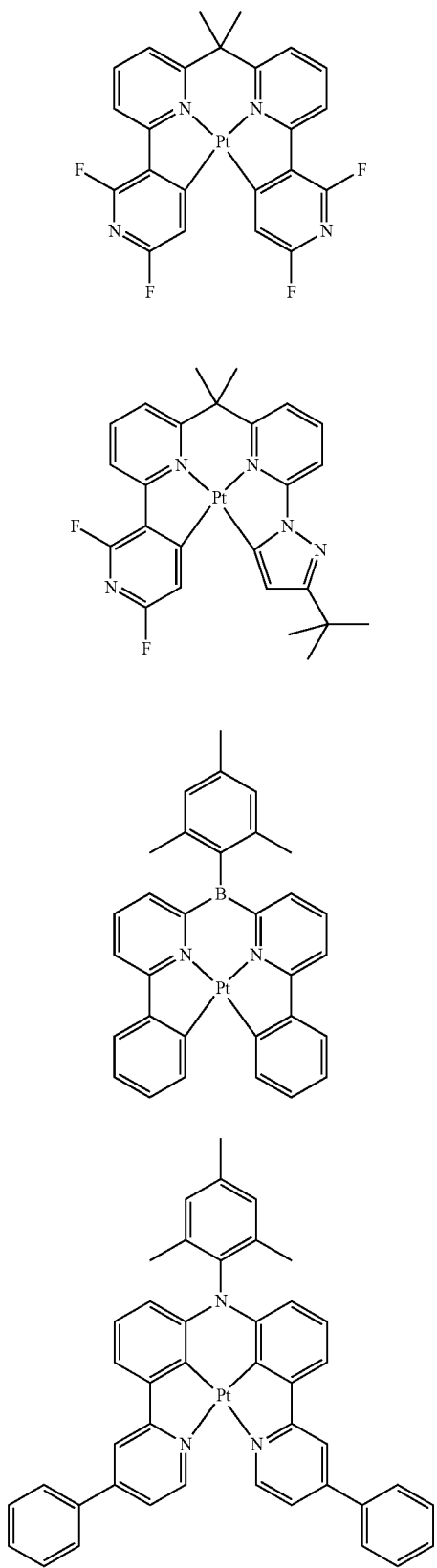
254
-continued
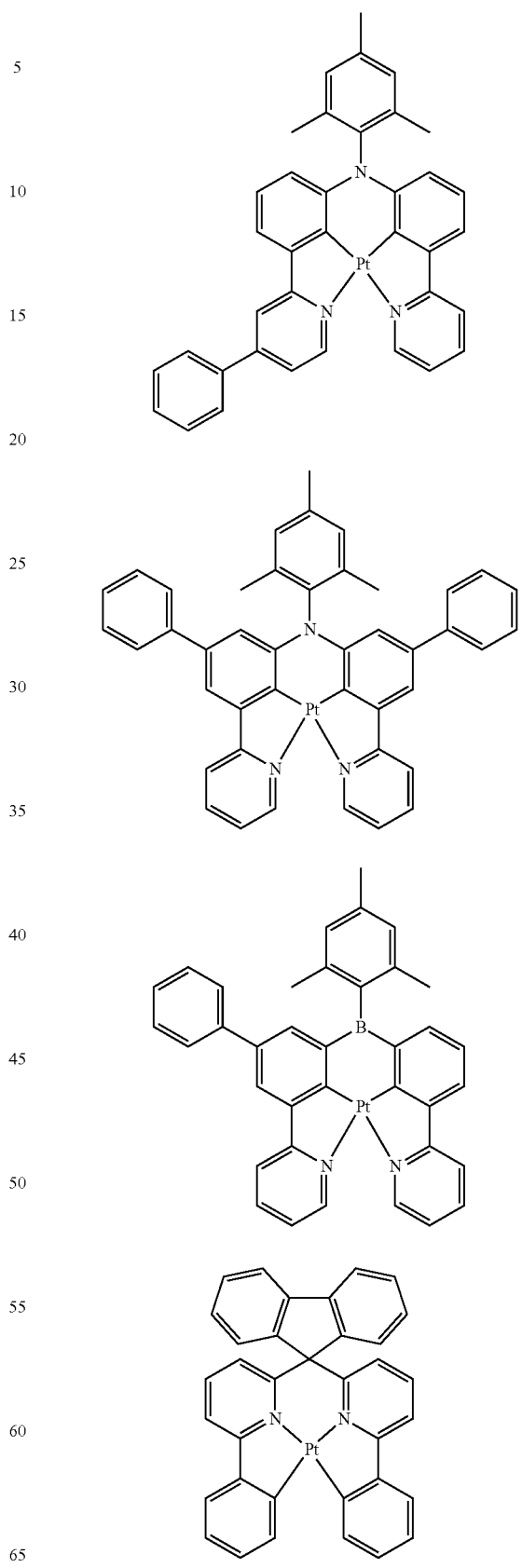

255
-continued
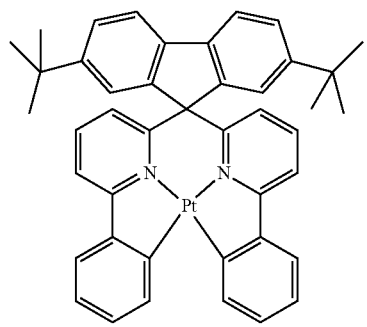
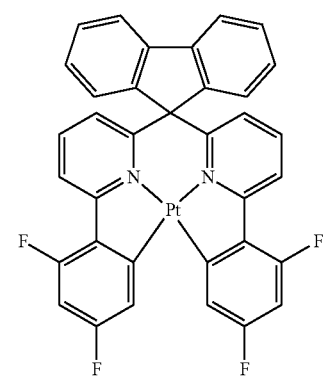
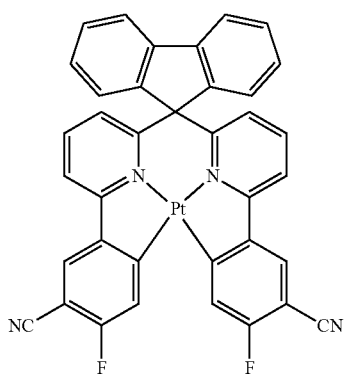
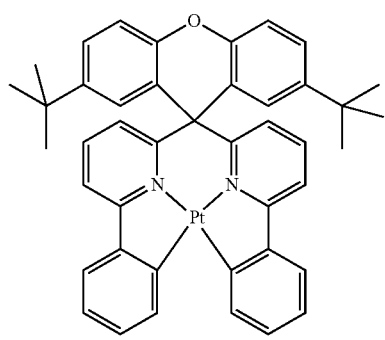
256
-continued
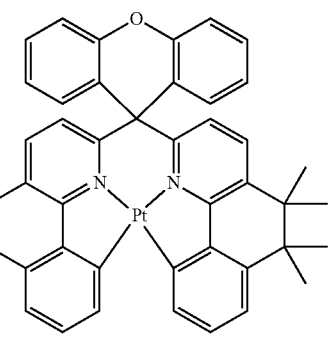
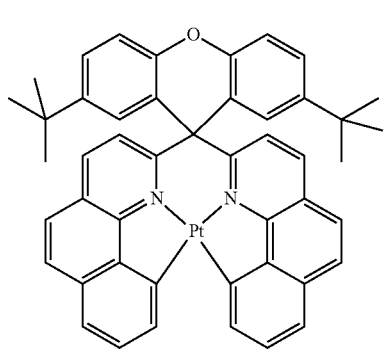
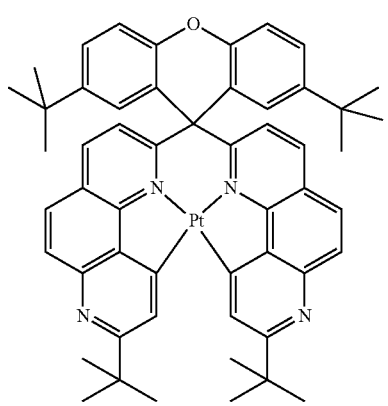
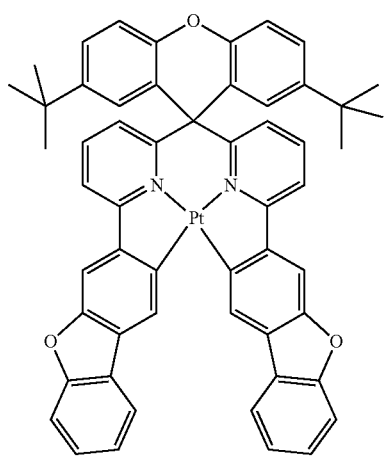

| 257 -continued | 258 -continued |
|---|---|
| 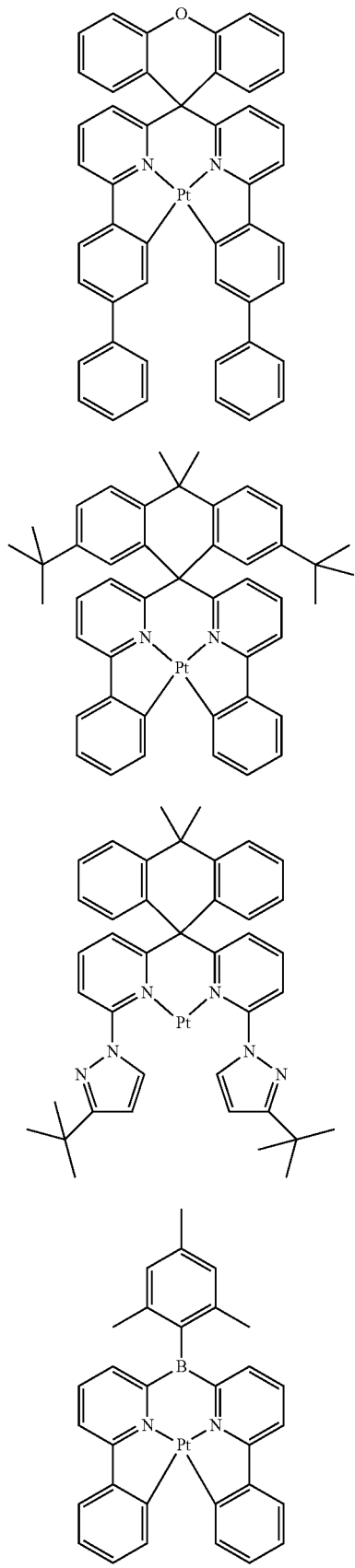 | 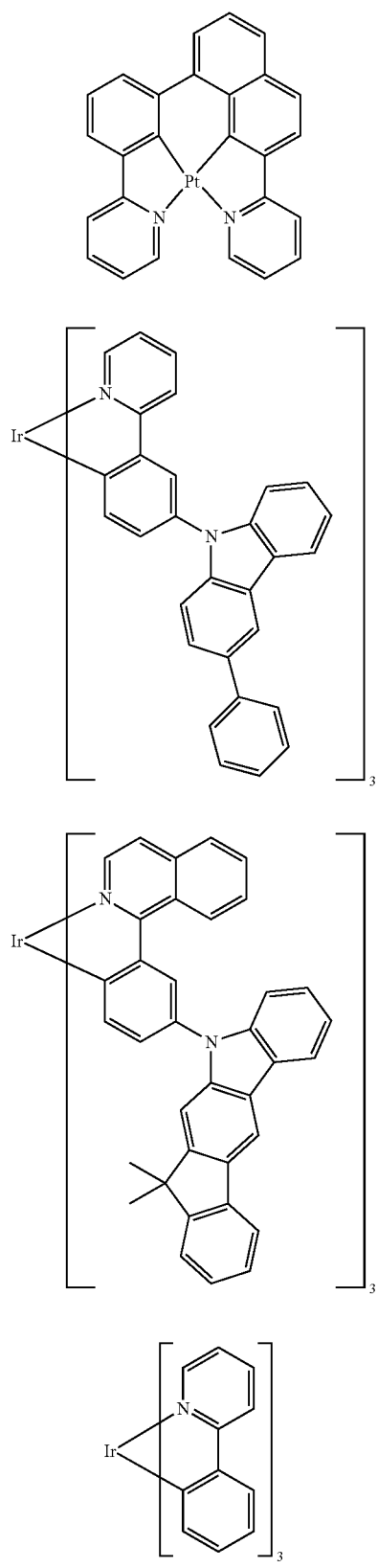 |

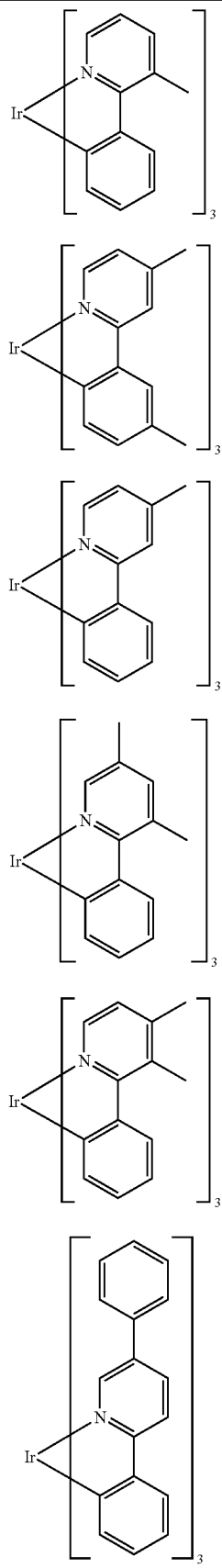
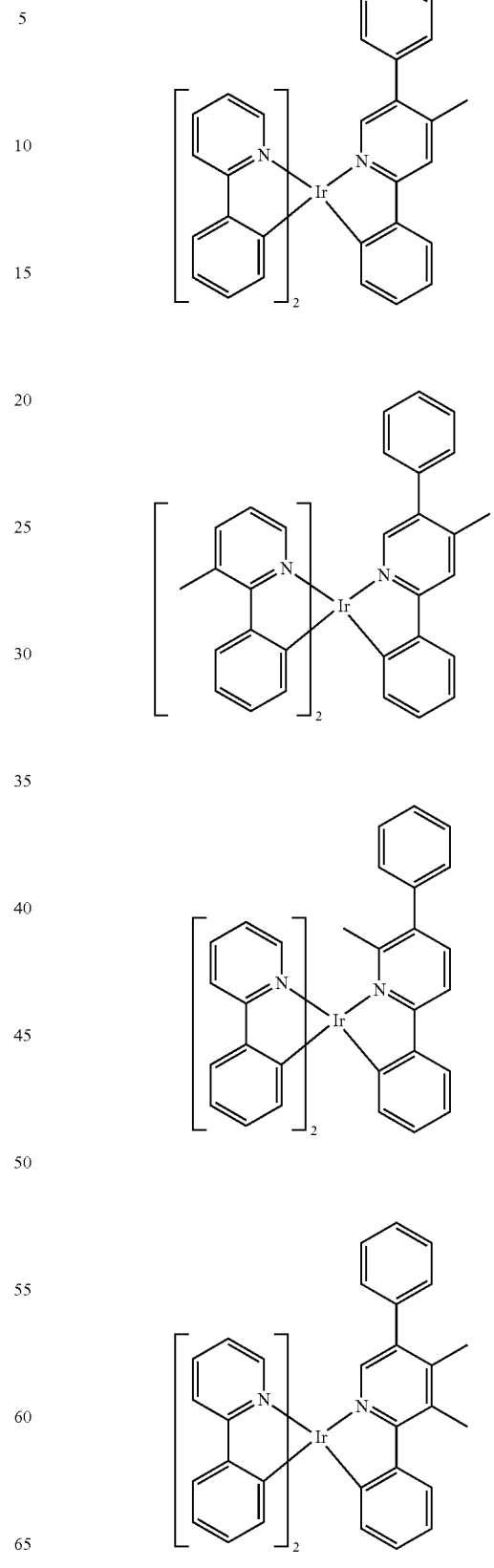

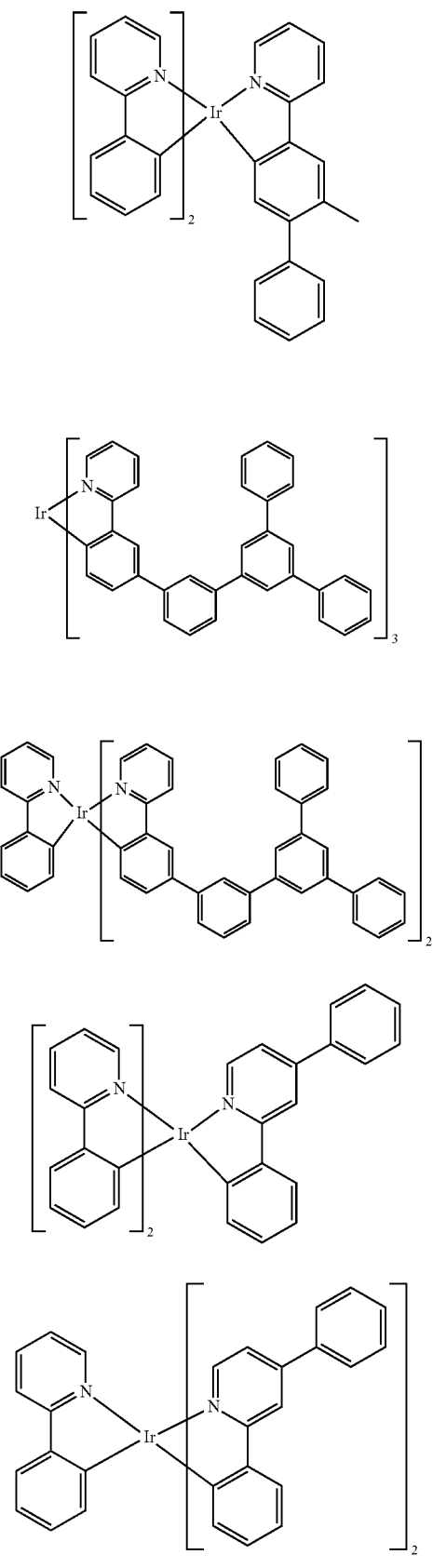
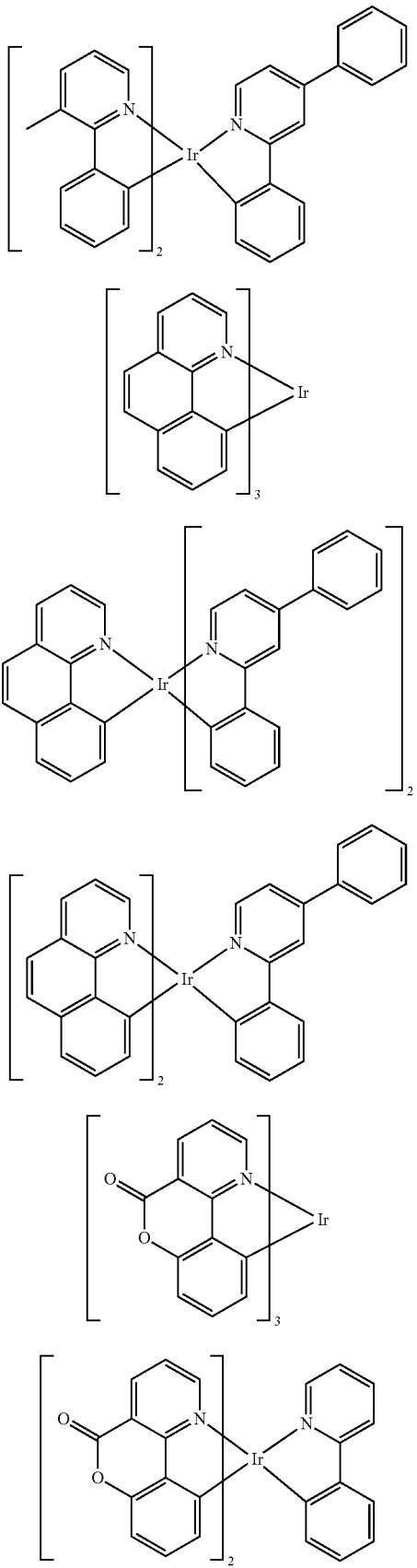

| 263 -continued | 264 -continued |
|---|---|
| 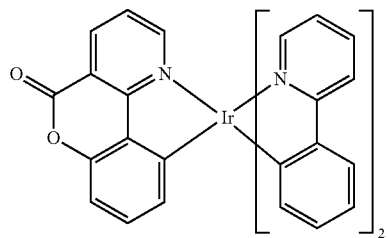 | 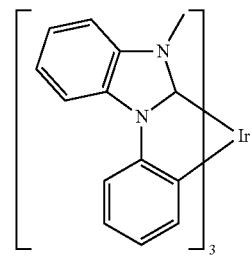 |
| 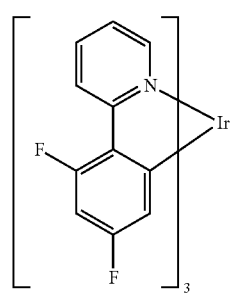 | 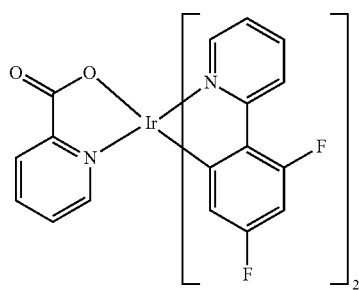 |
| 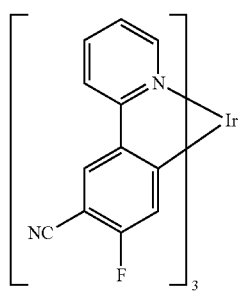 | 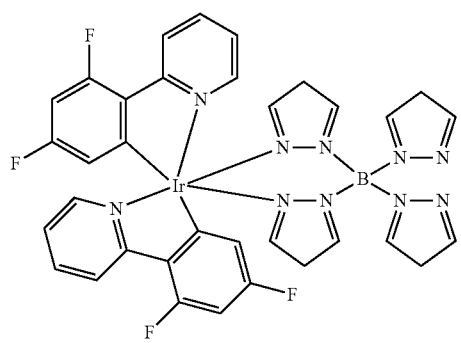 |
| 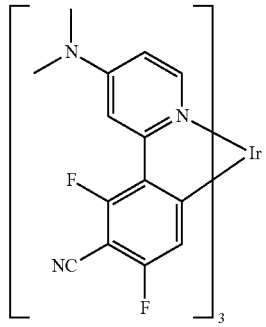 | 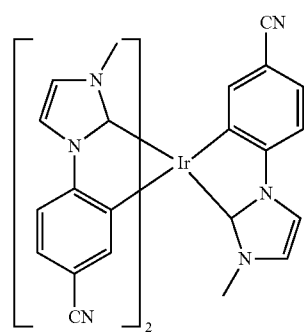 |
| 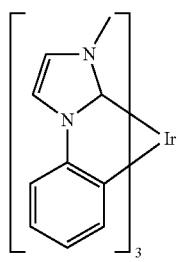 | 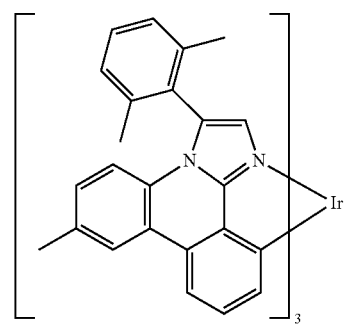 |

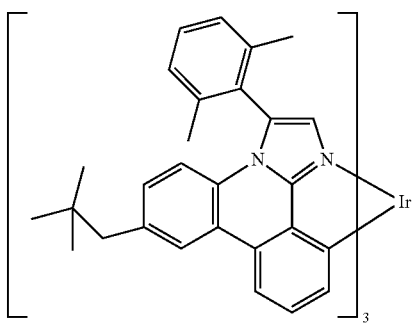
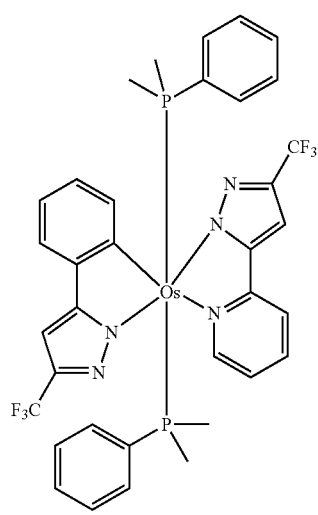
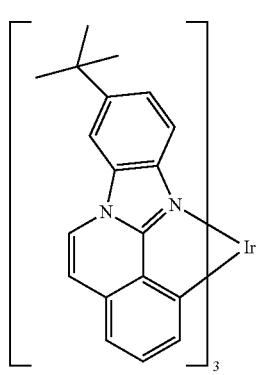
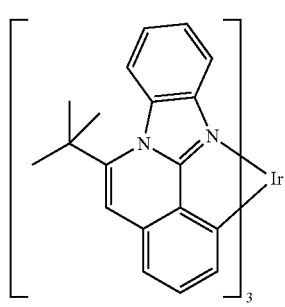
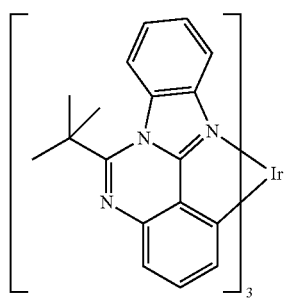

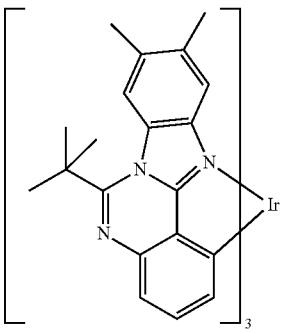

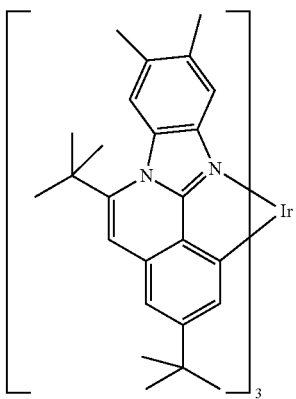

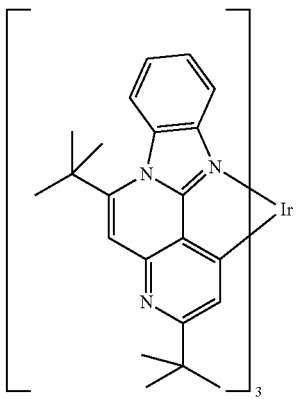

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

It is furthermore possible to use the compound of the formula (1) or the preferred embodiments both in a hole-transport layer or exciton-blocking layer and as matrix in an emitting layer.

In the further layers of the organic electroluminescent device according to the invention, it is possible to use all materials as usually employed in accordance with the prior art. The person skilled in the art will therefore be able, without inventive step, to employ all materials known for organic electroluminescent devices in combination with the compounds of the formula (1) according to the invention or the preferred embodiments.

Preferred fluorescent emitter materials are selected from the class of the arylamines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred emitter materials are selected from indenofluorenamines or indenofluorenediamines, for example in accordance with WO 06/122630, benzoindenofluorenamines or benzoindenofluorenediamines, for example in accordance with WO 08/006449, and dibenzoindenofluoren-amines or dibenzoindenofluorenediamines, for example in accordance with WO 07/140,847. Examples of emitter materials from the class of the styrylamines are substituted or unsubstituted tristilbenamines or the emitter materials described in WO 06/000388, WO 06/058737, WO 06/000389, WO 07/065549 and WO 07/115610. Preference is furthermore given to the condensed hydrocarbons disclosed in the application WO 10/012,328.

Suitable emitter materials are furthermore the structures depicted in the following table, and the derivatives of these structures disclosed in JP 06/001973, WO 04/047499, WO 06/098080, WO 07/065,678, US 2005/0260442 and WO 04/092111.

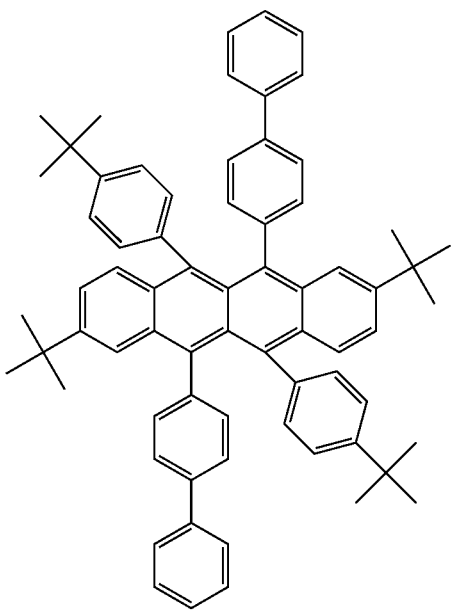 [SMILES: CC(C)(C)c1ccc(-c2c3ccc(C(C)(C)C)cc3c(-c3ccc(-c4ccccc4)cc3)c3c(-c4ccc(C(C)(C)C)cc4)c4ccc(C(C)(C)C)cc4c(-c4ccc(-c5ccccc5)cc4)c23)cc1]
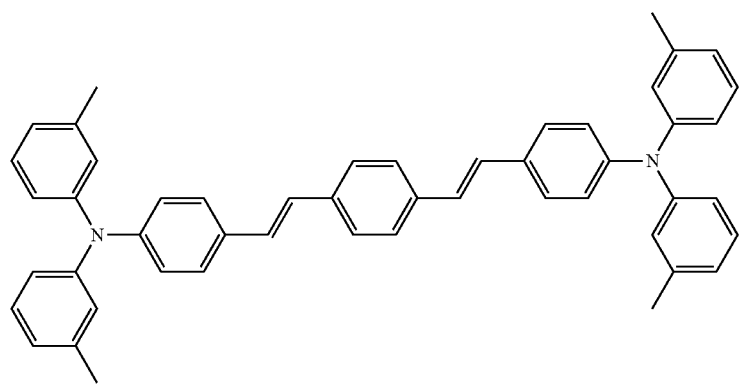 [SMILES: Cc1cccc(N(c2ccc(/C=C/c3ccc(/C=C/c4ccc(N(c5cccc(C)c5)c5cccc(C)c5)cc4)cc3)cc2)c2cccc(C)c2)c1]
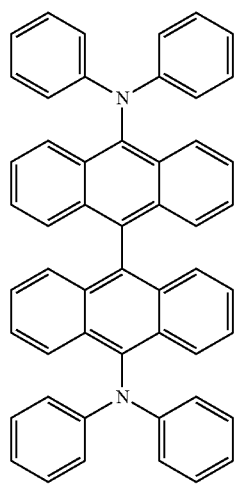 [SMILES: c1ccc(N(c2ccccc2)c2c3ccccc3c(-c3c4ccccc4c(N(c4ccccc4)c4ccccc4)c4ccccc34)c3ccccc23)cc1]

-continued
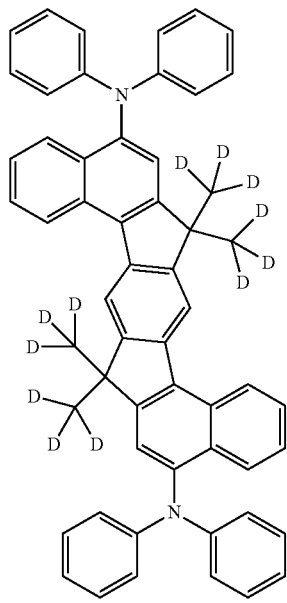 [SMILES: [2H]C([2H])([2H])C1(C([2H])([2H])[2H])c2cc3c(cc2-c2c1cc(N(c1ccccc1)c1ccccc1)c1ccccc21)C(C([2H])([2H])[2H])(C([2H])([2H])[2H])c1cc(N(c2ccccc2)c2ccccc2)c2ccccc2c1-3]
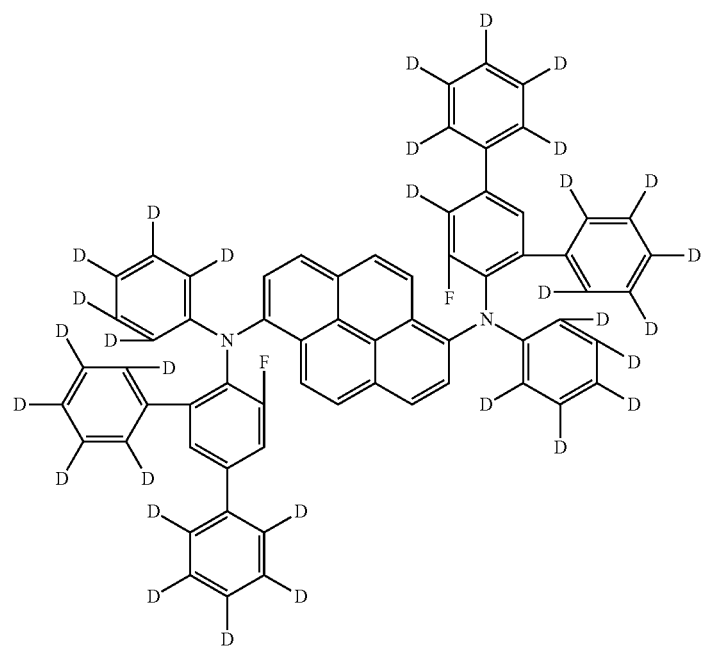 [SMILES: [2H]c1c([2H])c([2H])c(-c2cc(F)c(N(c3c([2H])c([2H])c([2H])c([2H])c3[2H])c3ccc4ccc5c(N(c6c([2H])c([2H])c([2H])c([2H])c6[2H])c6c(-c7c([2H])c([2H])c([2H])c([2H])c7[2H])cc(-c7c([2H])c([2H])c([2H])c([2H])c7[2H])c([2H])c6F)ccc6ccc3c4c65)c(-c3c([2H])c([2H])c([2H])c([2H])c3[2H])c2)c([2H])c1[2H]]
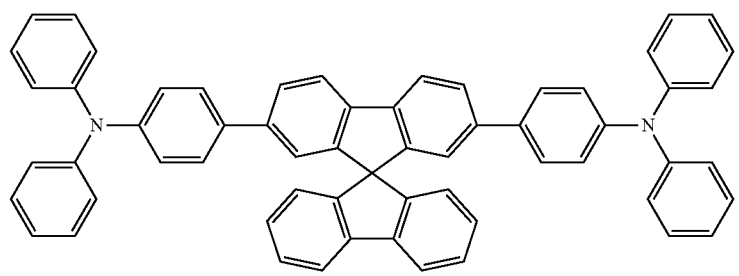 [SMILES: c1ccc(N(c2ccccc2)c2ccc(-c3ccc4c(c3)C3(c5ccccc5-c5ccccc53)c3cc(-c5ccc(N(c6ccccc6)c6ccccc6)cc5)ccc3-4)cc2)cc1]

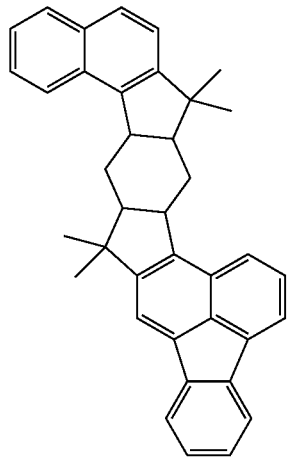 [SMILES: CC1(C)c2ccc3ccccc3c2C2CC3C(CC21)c1c(cc2c4c(cccc14)-c1ccccc1-2)C3(C)C]
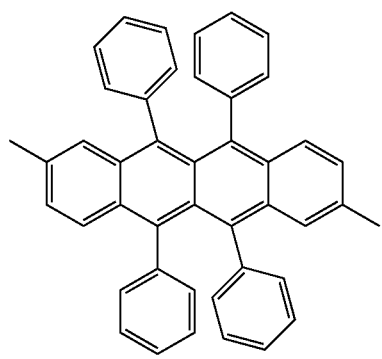
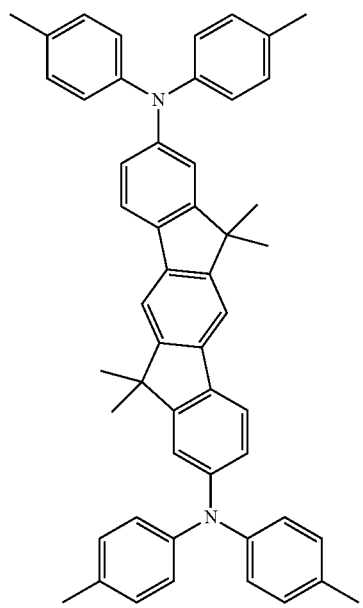

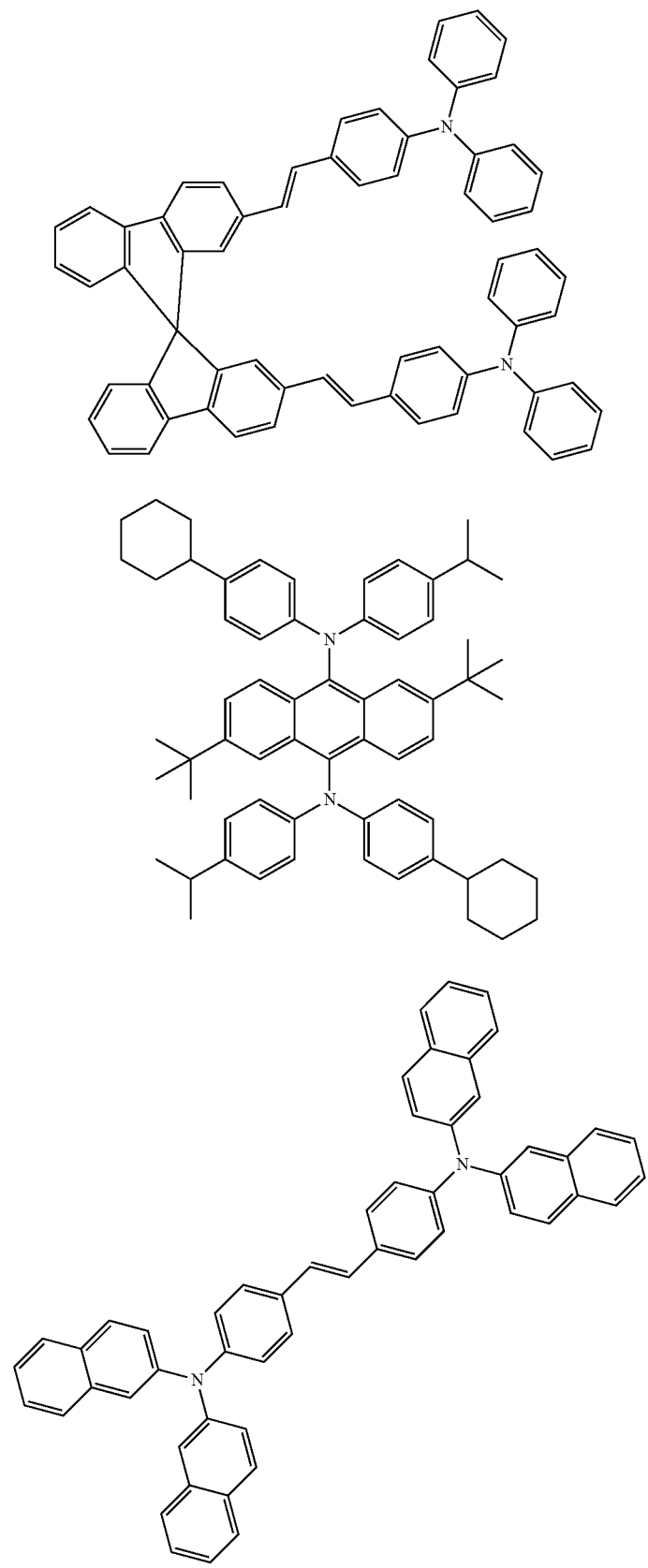

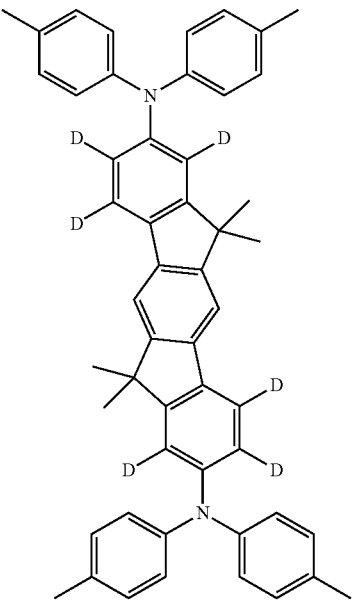
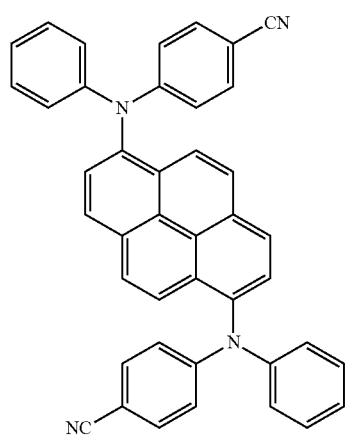 [SMILES: N#Cc1ccc(N(c2ccccc2)c2ccc3ccc4c(N(c5ccccc5)c5ccc(C#N)cc5)ccc5ccc2c3c54)cc1]

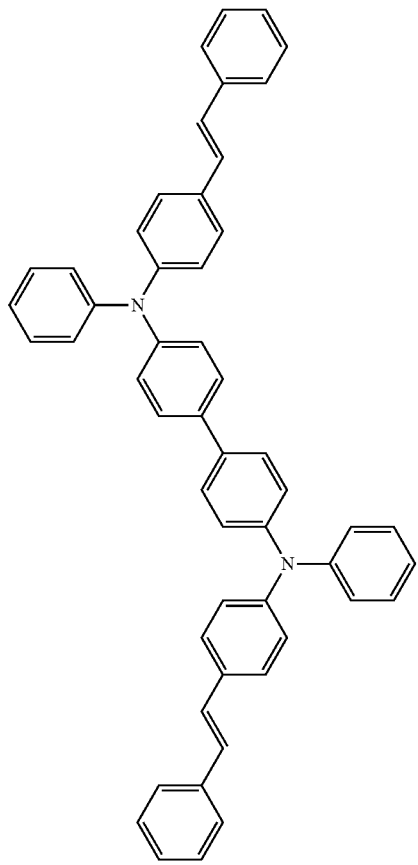 [SMILES: C(=C\c1ccc(N(c2ccccc2)c2ccc(-c3ccc(N(c4ccccc4)c4ccc(/C=C/c5ccccc5)cc4)cc3)cc2)cc1)/c1ccccc1]
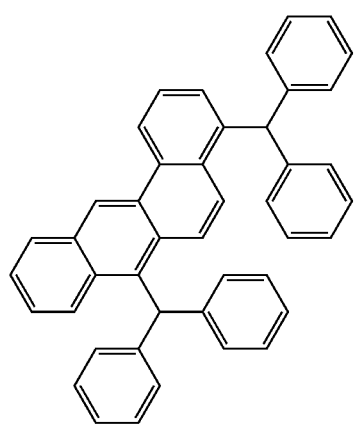 [SMILES: c1ccc(C(c2ccccc2)c2cccc3c2ccc2c(C(c4ccccc4)c4ccccc4)c4ccccc4cc23)cc1]

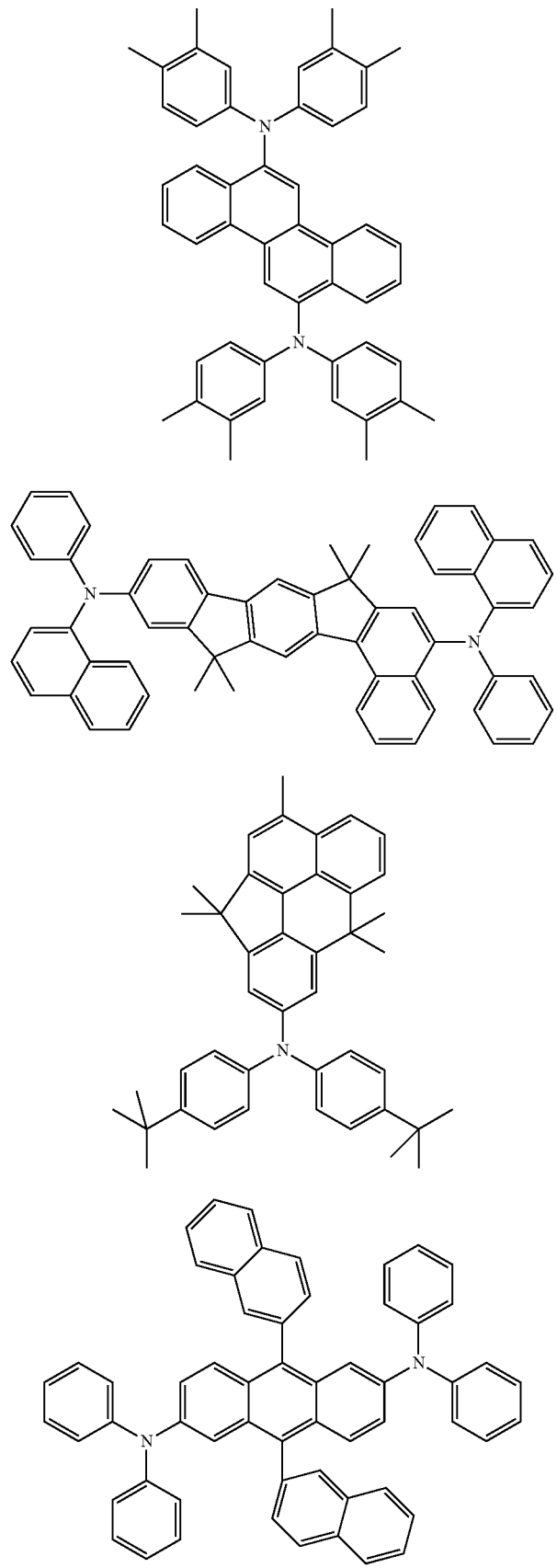

-continued
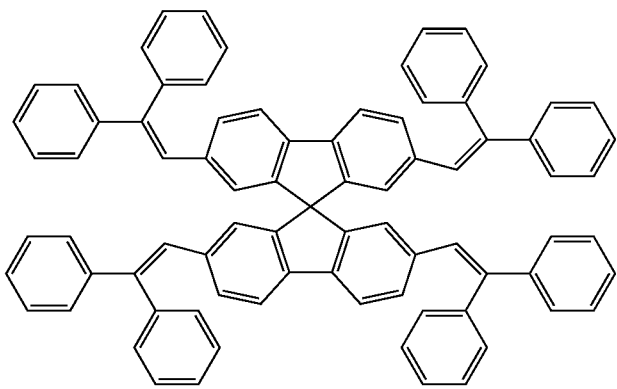 [SMILES: C(=C(c1ccccc1)c1ccccc1)c1ccc2c(c1)C1(c3cc(C=C(c4ccccc4)c4ccccc4)ccc3-2)c2cc(C=C(c3ccccc3)c3ccccc3)ccc2-c2ccc(C=C(c3ccccc3)c3ccccc3)cc21]
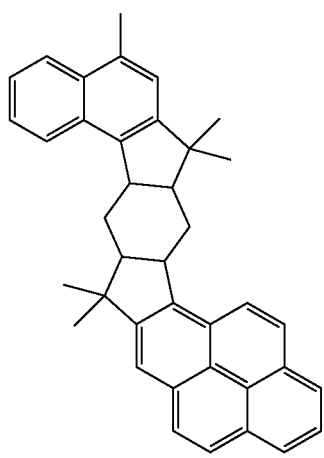 [SMILES: Cc1cc2c(c3ccccc13)C1CC3C(CC1C2(C)C)c1c(cc2ccc4cccc5ccc1c2c45)C3(C)C]
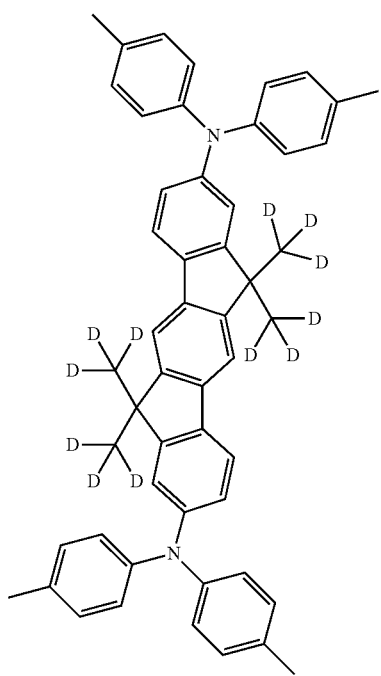

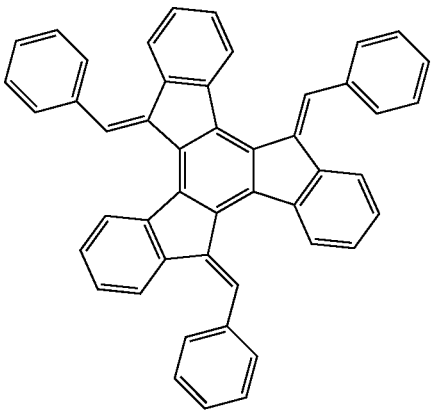 [SMILES: C(=C1/c2ccccc2-c2c1c1c(c3c2/C(=C/c2ccccc2)c2ccccc2-3)/C(=C/c2ccccc2)c2ccccc2-1)/c1ccccc1]
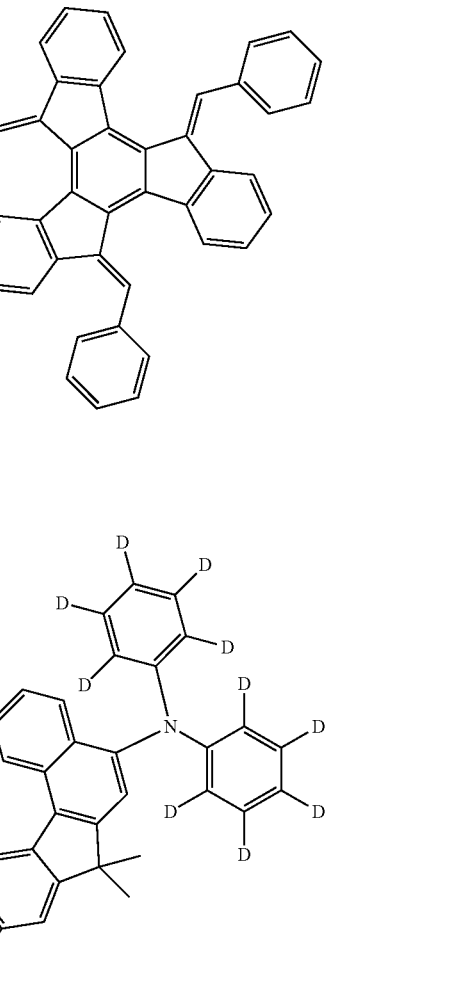
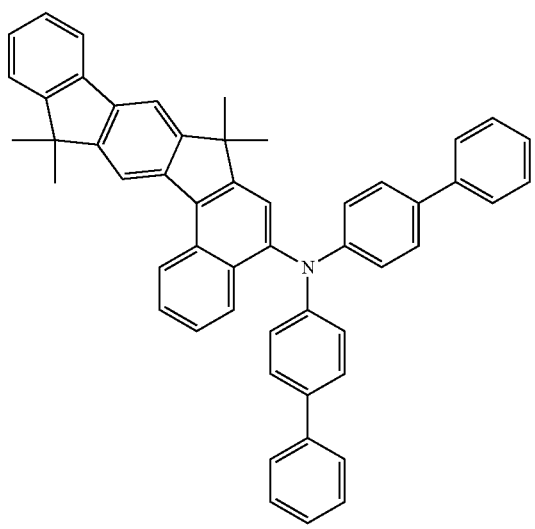 [SMILES: CC1(C)c2ccccc2-c2cc3c(cc21)-c1c(cc(N(c2ccc(-c4ccccc4)cc2)c2ccc(-c4ccccc4)cc2)c2ccccc12)C3(C)C]

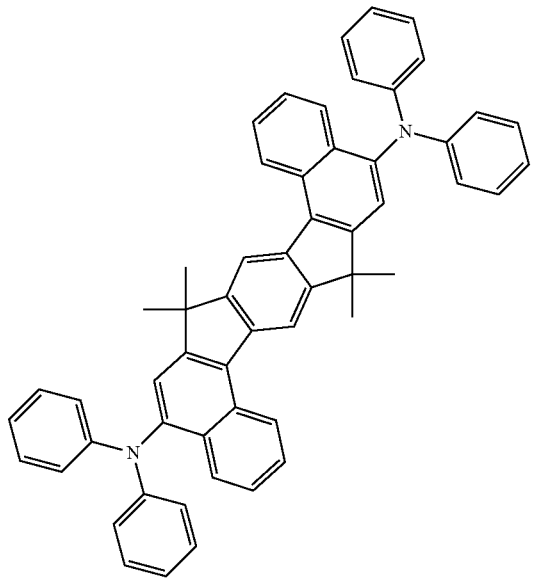 [SMILES: CC1(C)c2cc3c(cc2-c2c1cc(N(c1ccccc1)c1ccccc1)c1ccccc21)C(C)(C)c1cc(N(c2ccccc2)c2ccccc2)c2ccccc2c1-3]
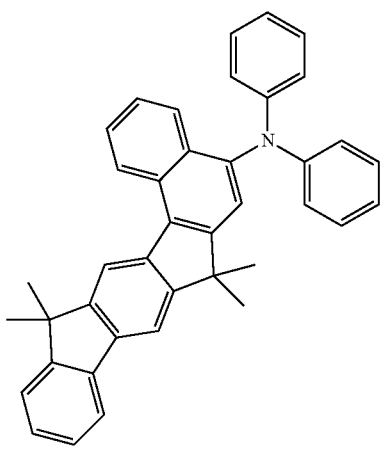 [SMILES: CC1(C)c2ccccc2-c2cc3c(cc21)-c1c(cc(N(c2ccccc2)c2ccccc2)c2ccccc12)C3(C)C]
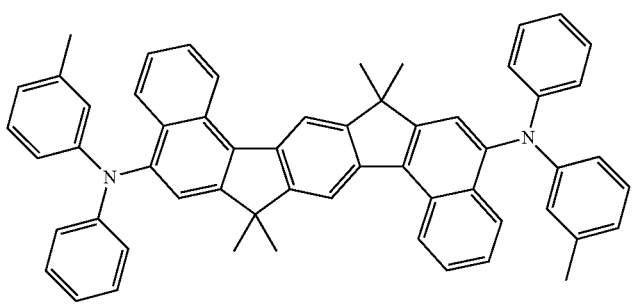 [SMILES: Cc1cccc(N(c2ccccc2)c2cc3c(c4ccccc24)-c2cc4c(cc2C3(C)C)-c2c(cc(N(c3ccccc3)c3cccc(C)c3)c3ccccc23)C4(C)C)c1]

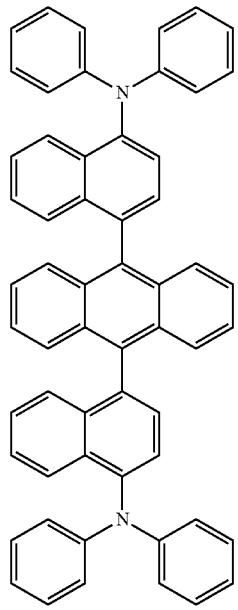 [SMILES: c1ccc(N(c2ccccc2)c2ccc(-c3c4ccccc4c(-c4ccc(N(c5ccccc5)c5ccccc5)c5ccccc45)c4ccccc34)c3ccccc23)cc1]
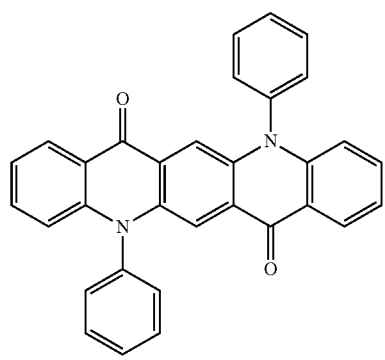 [SMILES: O=c1c2ccccc2n(-c2ccccc2)c2cc3c(=O)c4ccccc4n(-c4ccccc4)c3cc12]
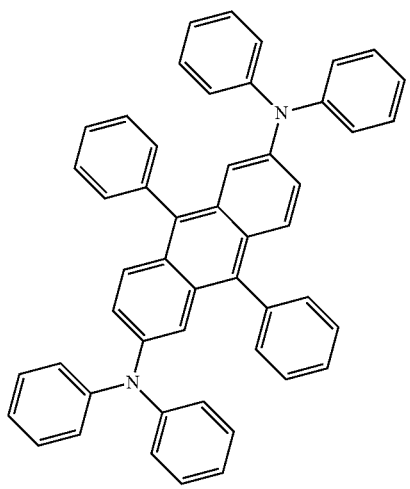 [SMILES: c1ccc(-c2c3ccc(N(c4ccccc4)c4ccccc4)cc3c(-c3ccccc3)c3ccc(N(c4ccccc4)c4ccccc4)cc23)cc1]

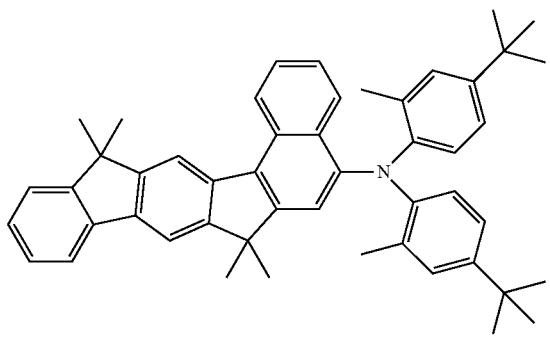 [SMILES: Cc1cc(C(C)(C)C)ccc1N(c1ccc(C(C)(C)C)cc1C)c1cc2c(c3ccccc13)-c1cc3c(cc1C2(C)C)-c1ccccc1C3(C)C]
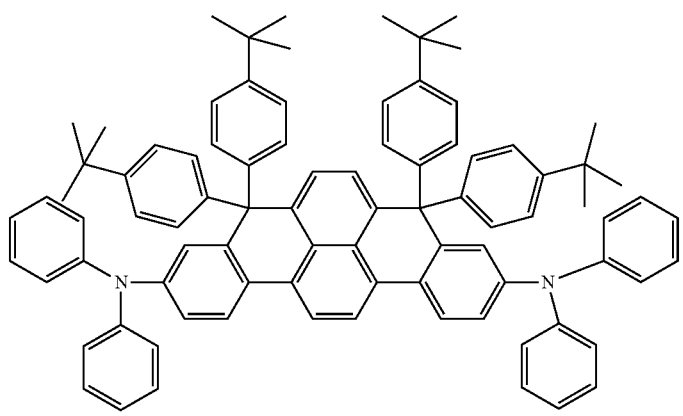 [SMILES: CC(C)(C)c1ccc(C2(c3ccc(C(C)(C)C)cc3)c3cc(N(c4ccccc4)c4ccccc4)ccc3-c3ccc4c5c(ccc2c35)C(c2ccc(C(C)(C)C)cc2)(c2ccc(C(C)(C)C)cc2)c2cc(N(c3ccccc3)c3ccccc3)ccc2-4)cc1]
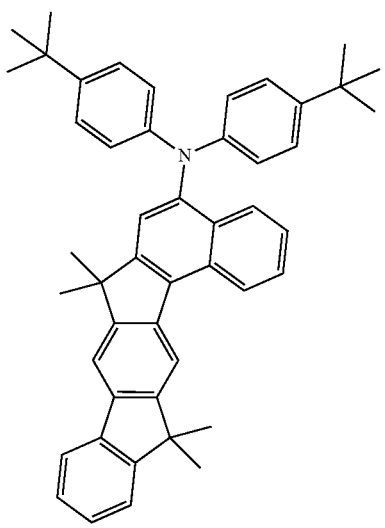 [SMILES: CC(C)(C)c1ccc(N(c2ccc(C(C)(C)C)cc2)c2cc3c(c4ccccc24)-c2cc4c(cc2C3(C)C)-c2ccccc2C4(C)C)cc1]

-continued
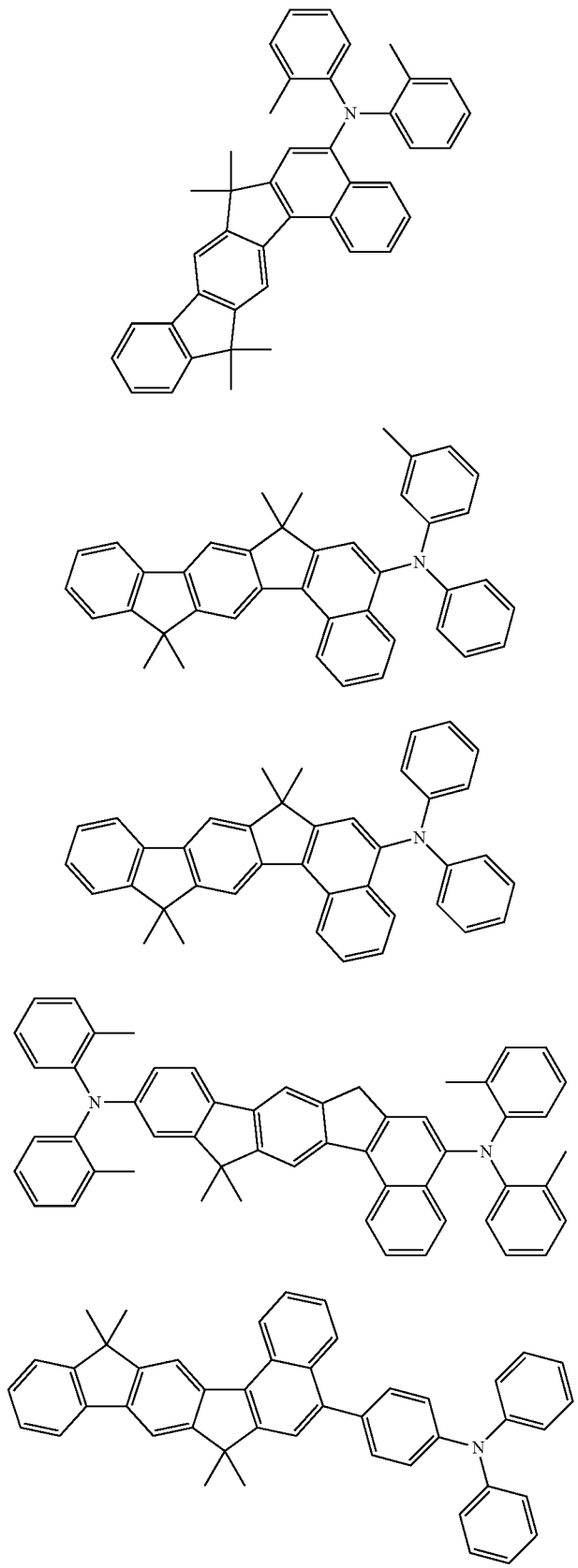

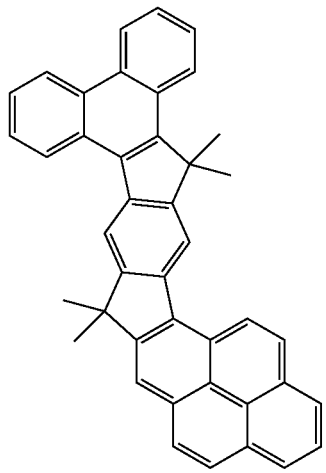 [SMILES: CC1(C)c2cc3c(cc2-c2c1cc1ccc4cccc5ccc2c1c45)C(C)(C)c1c-3c2ccccc2c2ccccc12]
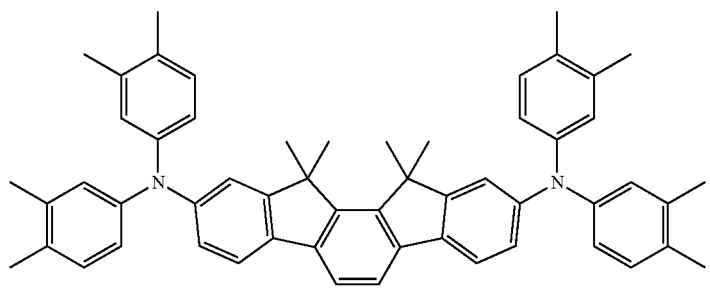
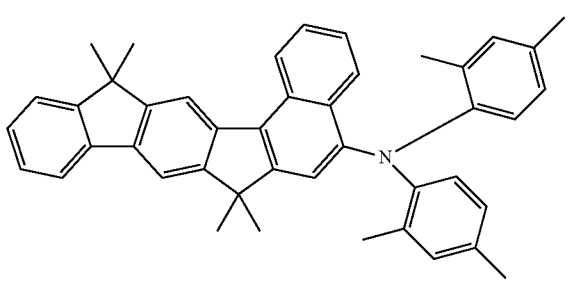 [SMILES: Cc1ccc(N(c2ccc(C)cc2C)c2cc3c(c4ccccc24)-c2cc4c(cc2C3(C)C)-c2ccccc2C4(C)C)c(C)c1]
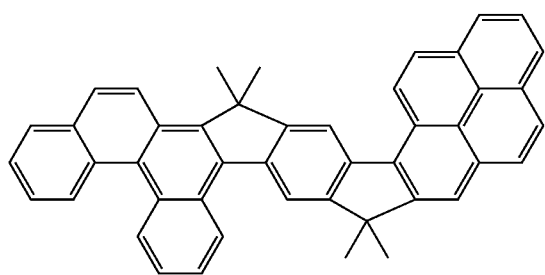 [SMILES: CC1(C)c2cc3c(cc2-c2c1cc1ccc4cccc5ccc2c1c45)C(C)(C)c1c-3c2ccccc2c2c1ccc1ccccc12]

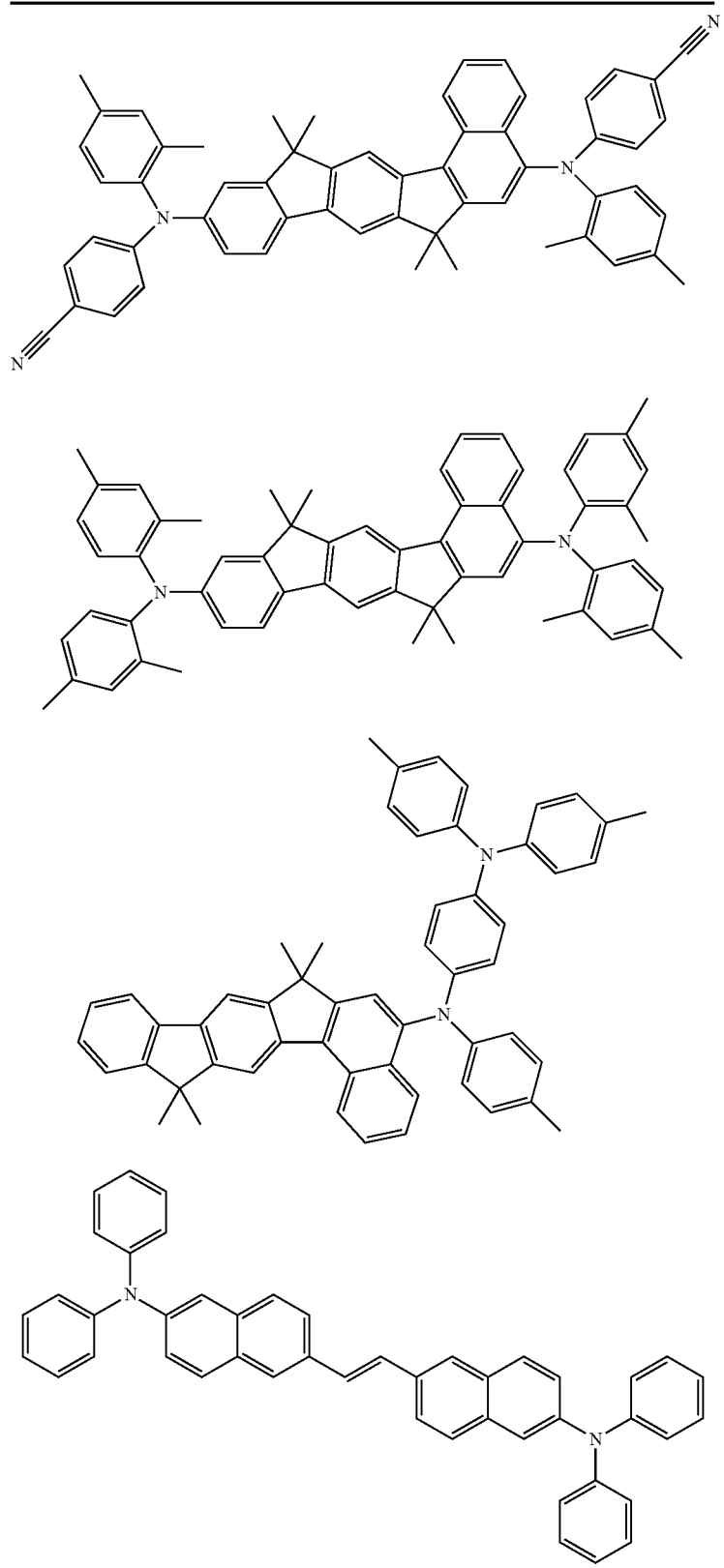
Matrix materials which can be used, preferably for fluorescent dopants, are materials from various classes of substance. Preferred matrix materials are selected from the classes of the oligoarylenes (for example 2,2',7,7'-tetraphenylspirobifluorene in accordance with EP 676461 or dinaphthyl-anthracene), in particular the oligoarylenes containing condensed aromatic groups, the oligoarylenevinylenes (for example DPVBi or spiro-DPVBi in accordance with EP 676461), the polypodal metal complexes (for example in accordance with WO 04/081017), the hole-conducting compounds (for example in accordance with WO 04/058911), the electron-conducting compounds, in particular ketones, phosphine oxides, sulfoxides, etc. (for example in accordance with WO 05/084081 and WO 05/084082), the atropisomers (for example in accordance with WO 06/048268), the boronic acid derivatives (for example in accordance with WO 06/117052) or the benzanthracenes (for example in accordance with WO 08/145,239). Suitable matrix materials are furthermore preferably the compounds according to the invention. Apart from the compounds according to the invention, particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Suitable matrix materials, preferably for fluorescent dopants, are, for example, the materials depicted in the following table, and derivatives of these materials, as disclosed in WO 04/018587, WO 08/006449, U.S. Pat. No. 5,935,721, US 2005/0181232, JP 2000/273056, EP 681019, US 2004/0247937 and US 2005/0211958.

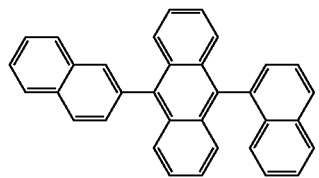

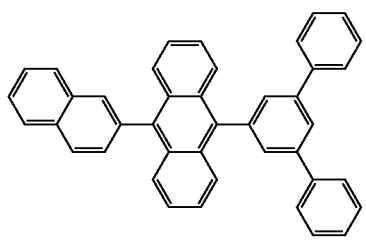

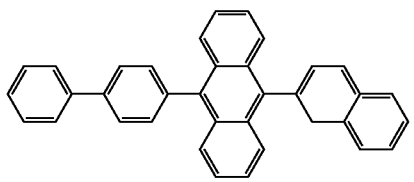

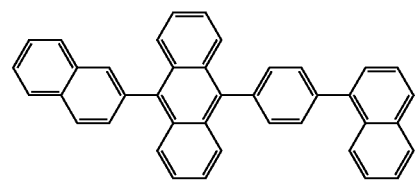 [SMILES: c1ccc2cc(-c3c4ccccc4c(-c4ccc(-c5cccc6ccccc56)cc4)c4ccccc34)ccc2c1]

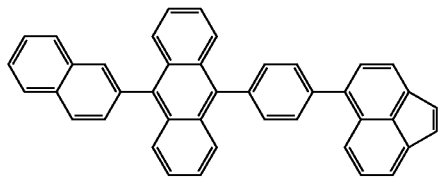 [SMILES: C1=Cc2ccc(-c3ccc(-c4c5ccccc5c(-c5ccc6ccccc6c5)c5ccccc45)cc3)c3cccc1c23]

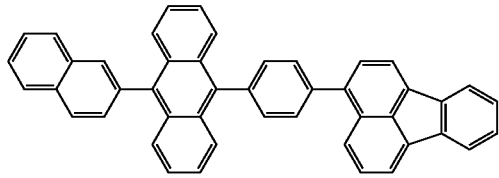 [SMILES: c1ccc2c(c1)-c1cccc3c(-c4ccc(-c5c6ccccc6c(-c6ccc7ccccc7c6)c6ccccc56)cc4)ccc-2c13]

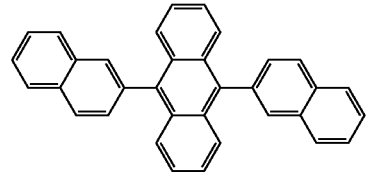 [SMILES: c1ccc2cc(-c3c4ccccc4c(-c4ccc5ccccc5c4)c4ccccc34)ccc2c1]

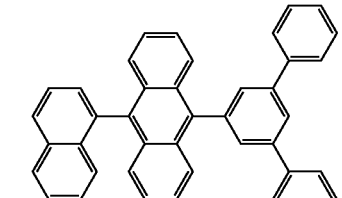

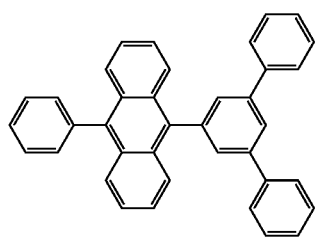 [SMILES: c1ccc(-c2cc(-c3ccccc3)cc(-c3c4ccccc4c(-c4ccccc4)c4ccccc34)c2)cc1]

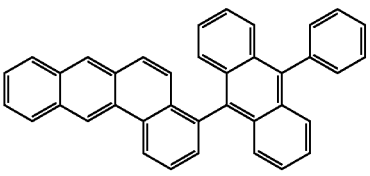 [SMILES: c1ccc(-c2c3ccccc3c(-c3cccc4c3ccc3cc5ccccc5cc34)c3ccccc23)cc1]

| 301 -continued | 302 -continued |
|---|---|
| 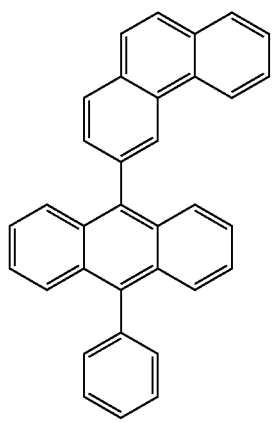 [SMILES: c1ccc(-c2c3ccccc3c(-c3ccc4ccc5ccccc5c4c3)c3ccccc23)cc1] | 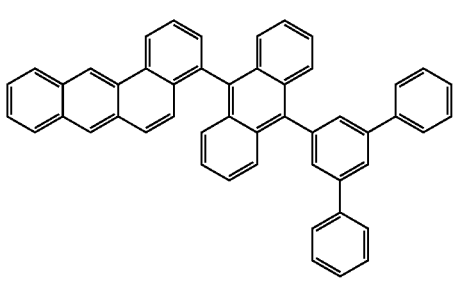 |
| 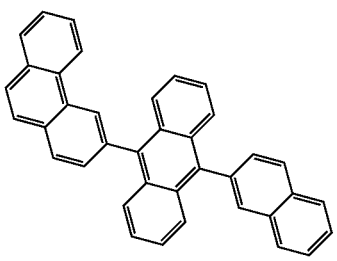 [SMILES: c1ccc2cc(-c3c4ccccc4c(-c4ccc5ccc6ccccc6c5c4)c4ccccc34)ccc2c1] | 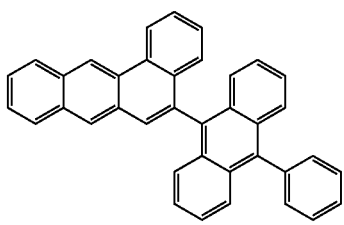 |
| 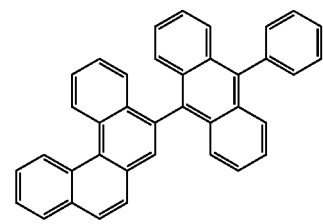 [SMILES: c1ccc(-c2c3ccccc3c(-c3cc4ccc5ccccc5c4c4ccccc34)c3ccccc23)cc1] | 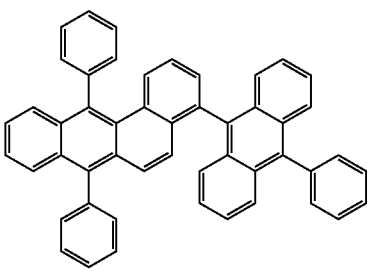 |
| 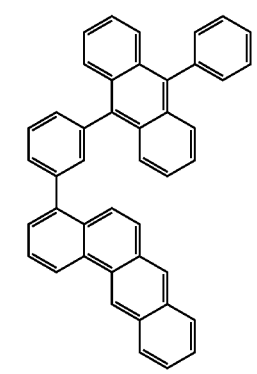 [SMILES: c1ccc(-c2c3ccccc3c(-c3cccc(-c4cccc5c4ccc4cc6ccccc6cc45)c3)c3ccccc23)cc1] | 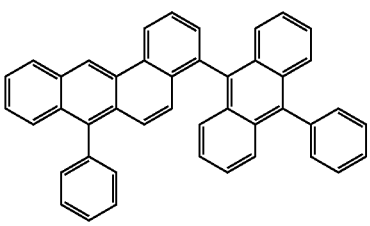 [SMILES: c1ccc(-c2c3ccccc3c(-c3cccc4c3ccc3c(-c5ccccc5)c5ccccc5cc34)c3ccccc23)cc1] |
|  | 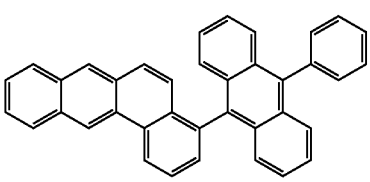 [SMILES: c1ccc(-c2c3ccccc3c(-c3cccc4c3ccc3cc5ccccc5cc34)c3ccccc23)cc1] |

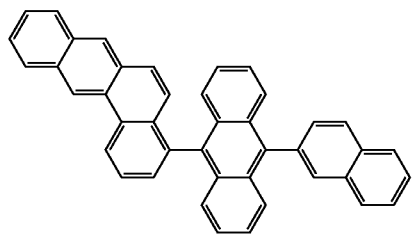 [SMILES: c1ccc2cc(-c3c4ccccc4c(-c4cccc5c4ccc4cc6ccccc6cc45)c4ccccc34)ccc2c1]
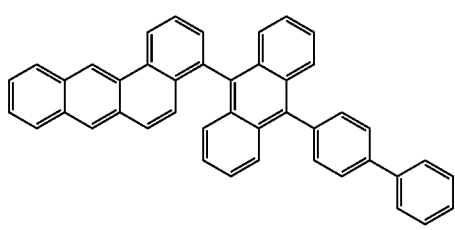 [SMILES: c1ccc(-c2ccc(-c3c4ccccc4c(-c4cccc5c4ccc4cc6ccccc6cc45)c4ccccc34)cc2)cc1]
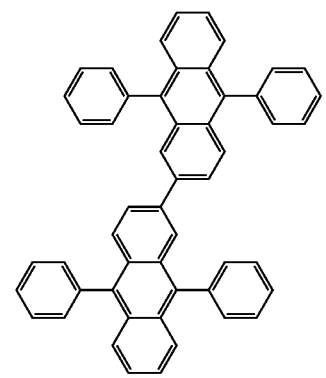 [SMILES: c1ccc(-c2c3ccccc3c(-c3ccccc3)c3cc(-c4ccc5c(-c6ccccc6)c6ccccc6c(-c6ccccc6)c5c4)ccc23)cc1]
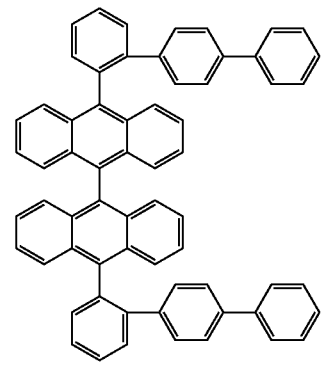 [SMILES: c1ccc(-c2ccc(-c3ccccc3-c3c4ccccc4c(-c4c5ccccc5c(-c5ccccc5-c5ccc(-c6ccccc6)cc5)c5ccccc45)c4ccccc34)cc2)cc1]
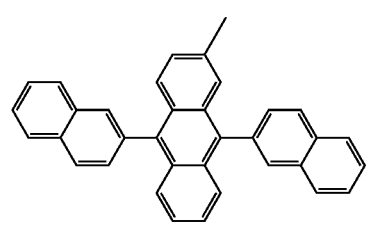 [SMILES: Cc1ccc2c(-c3ccc4ccccc4c3)c3ccccc3c(-c3ccc4ccccc4c3)c2c1]
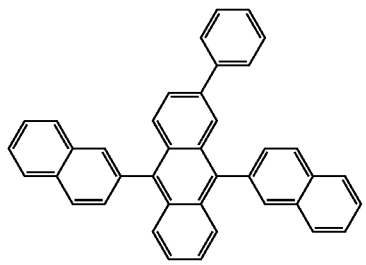 [SMILES: c1ccc(-c2ccc3c(-c4ccc5ccccc5c4)c4ccccc4c(-c4ccc5ccccc5c4)c3c2)cc1]
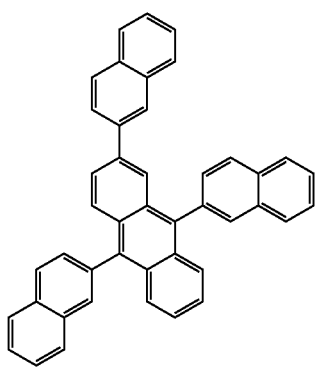 [SMILES: c1ccc2cc(-c3ccc4c(-c5ccc6ccccc6c5)c5ccccc5c(-c5ccc6ccccc6c5)c4c3)ccc2c1]
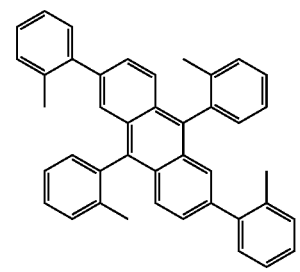 [SMILES: Cc1ccccc1-c1ccc2c(-c3ccccc3C)c3cc(-c4ccccc4C)ccc3c(-c3ccccc3C)c2c1]
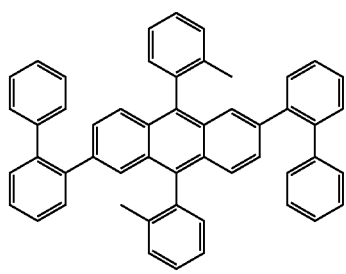 [SMILES: Cc1ccccc1-c1c2ccc(-c3ccccc3-c3ccccc3)cc2c(-c2ccccc2C)c2ccc(-c3ccccc3-c3ccccc3)cc12]
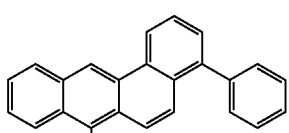
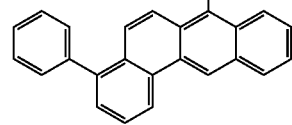

305
-continued
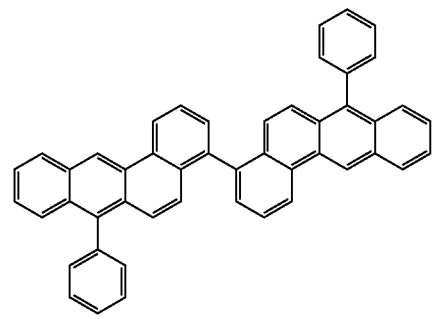 [SMILES: c1ccc(-c2c3ccccc3cc3c2ccc2c(-c4cccc5c4ccc4c(-c6ccccc6)c6ccccc6cc45)cccc23)cc1]
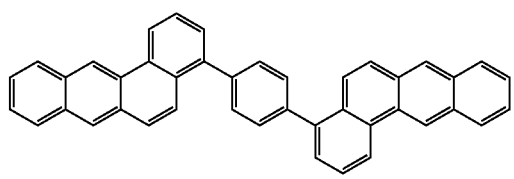 [SMILES: c1ccc2cc3c(ccc4c(-c5ccc(-c6cccc7c6ccc6cc8ccccc8cc67)cc5)cccc43)cc2c1]
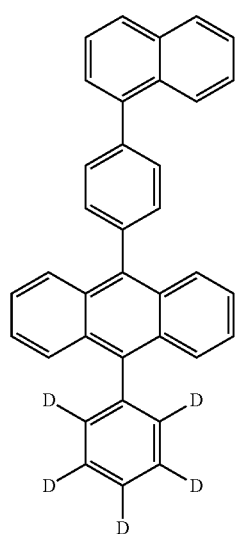 [SMILES: [2H]c1c([2H])c([2H])c(-c2c3ccccc3c(-c3ccc(-c4cccc5ccccc45)cc3)c3ccccc23)c([2H])c1[2H]]
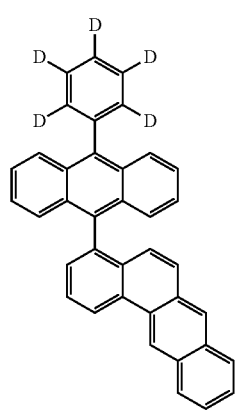 [SMILES: [2H]c1c([2H])c([2H])c(-c2c3ccccc3c(-c3cccc4c3ccc3cc5ccccc5cc34)c3ccccc23)c([2H])c1[2H]]
306
-continued
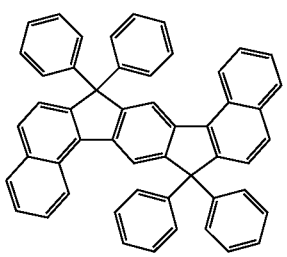 [SMILES: c1ccc(C2(c3ccccc3)c3cc4c(cc3-c3c2ccc2ccccc32)C(c2ccccc2)(c2ccccc2)c2ccc3ccccc3c2-4)cc1]

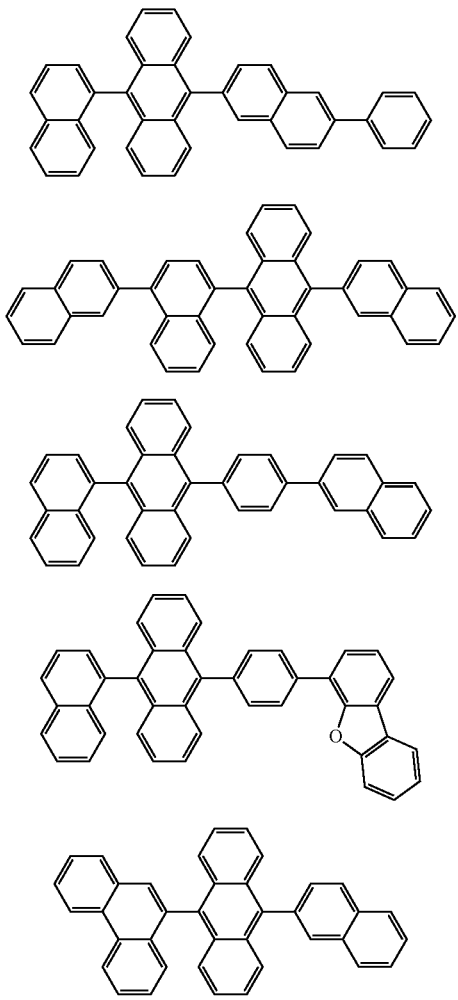

Besides the compounds according to the invention, suitable charge-transport materials, as can be used in the hole-injection or hole-transport layer or in the electron-transport layer of the organic electroluminescent device according to the invention, are, for example, the compounds disclosed in Y. Shirota et al., *Chem. Rev.* 2007, 107(4), 953-1010, or other materials as are employed in these layers in accordance with the prior art.

Preference is furthermore given to an organic electroluminescent device, characterised in that one or more layers are applied by means of a sublimation process, in which the materials are vapour-deposited in vacuum sublimation units at an initial pressure of usually less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *App. Phys. Lett.* 2008, 92, 053301).

Preference is furthermore given to an organic electroluminescent device, characterised in that one or more layers are produced from solution, such as, for example, by spin coating, or by means of any desired printing process, such as, for example, LITI (light induced thermal imaging, thermal transfer printing), ink-jet printing, screen printing, flexographic printing, offset printing or nozzle printing. Soluble compounds, which are obtained, for example, by suitable substitution, are necessary for this purpose. These processes are also particularly suitable for the compounds according to the invention, since these generally have very good solubility in organic solvents.

Also possible are hybrid processes, in which, for example, one or more layers are applied from solution and one or more further layers are applied by vapour deposition. Thus, for example, the emitting layer can be applied from solution and the electron-transport layer by vapour deposition.

These processes are generally known to the person skilled in the art and can be applied by him without inventive step to organic electroluminescent devices comprising the compounds according to the invention.

The processing of the compounds according to the invention from the liquid phase, for example by spin coating or by printing processes, requires formulations of the compounds according to the invention. These formulations can be, for example, solutions, dispersions or mini-emulsions. It may be preferred to use mixtures of two or more solvents for this purpose. Suitable and preferred solvents are, for example, toluene, anisole, o-, m- or p-xylene, methyl benzoate, dimethylanisole, mesitylene, tetralin, veratrol, THF, methyl-THF, THP, chlorobenzene, dioxane or mixtures of these solvents. Preferably, the solvents disclosed in WO 2010/093592 are used for the above purpose.

The present invention therefore furthermore relates to a formulation, in particular a solution, dispersion or mini-emulsion, comprising at least one compound of the formula (1) or the preferred embodiments indicated above and at least one solvent, in particular an organic solvent. The way in which solutions of this type can be prepared is known to the person skilled in the art and is described, for example, in WO 2002/072714, WO 2003/019694, WO 2010/093592 and the literature cited therein.

The present invention furthermore relates to mixtures comprising at least one compound of the formula (1) or the preferred embodiments indicated above and at least one further compound. The further compound can be, for example, a fluorescent or phosphorescent dopant if the compound according to the invention is used as matrix material. The mixture may then also additionally comprise a further material as additional matrix material.

The compounds according to the invention and the organic electroluminescent devices according to the invention are distinguished by the following surprising advantages over the prior art:

1. The compounds according to the invention are very highly suitable for use in a hole-transport or hole-injection layer in an organic electroluminescent device. They are also suitable, in particular, for use in a layer which is directly adjacent to a phosphorescent emitting layer, since the compounds according to the invention do not extinguish the luminescence.
2. The compounds according to the invention, employed as matrix material for fluorescent or phosphorescent emitters, result in very high efficiencies and long lifetimes. This applies, in particular, if the compounds are employed as matrix material together with a further matrix material and a phosphorescent emitter.

3. The compounds according to the invention, employed in organic electroluminescent devices, result in high efficiencies and in steep current/voltage curves with low use and operating voltages.

These above-mentioned advantages are not accompanied by an impairment in the other electronic properties.

The invention is explained in greater detail by the following examples, without wishing to restrict it thereby. On the basis of the descriptions, the person skilled in the art will be able to carry out the invention throughout the range disclosed and prepare further compounds according to the invention without inventive step and use them in electronic devices or use the process according to the invention.

EXAMPLES

A) Synthesis Examples

The following syntheses are carried out under a protective-gas atmosphere, unless indicated otherwise. The starting materials can be purchased from ALDRICH or ABCR. The numbers in square brackets in the case of the starting materials known from the literature are the corresponding CAS numbers.

Example 1

Synthesis of the Brominated Spirobifluorene Derivatives (Starting Materials)

1a) Synthesis of 1-bromospiro-9,9'-bifluorene

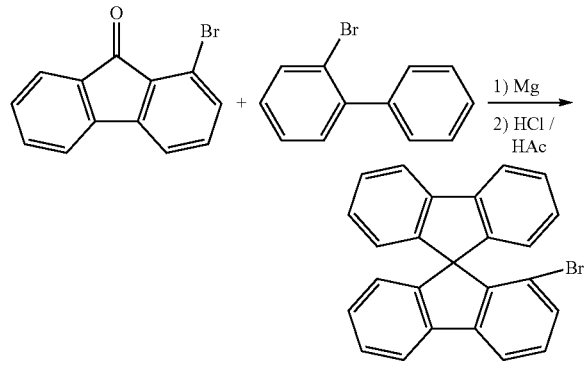

The corresponding Grignard reagent is prepared from 2.7 g (110 mmol) of iodine-activated magnesium turnings and a mixture of 25.6 g (110 mmol) of 2-bromobiphenyl, 0.8 ml of 1,2-dichloroethane, 50 ml of 1,2-dimethoxyethane, 400 ml of THF and 200 ml of toluene with secondary heating using an oil bath at 70° C. When the magnesium has reacted completely, the mixture is allowed to cool to room temperature, and a solution of 25.9 g (100 mmol) of 1-bromofluorenone [36804-63-4] in 500 ml of THF is then added dropwise, the reaction mixture is warmed at 50° C. for 4 h and then stirred at room temperature for a further 12 h. 100 ml of water are added, the mixture is stirred briefly, the organic phase is separated off, and the solvent is removed in vacuo. The residue is suspended in 500 ml of glacial acetic acid at 40° C., 0.5 ml of conc. sulfuric acid is added to the suspension, and the mixture is subsequently stirred at 100° C. for a further 2 h. After cooling, the precipitated solid is filtered off with suction, washed once with 100 ml of glacial acetic acid, three times with 100 ml of ethanol each time and finally recrystallised from dioxane. Yield: 26.9 g (68 mmol), 68%; purity about 98% according to $^1$H-NMR.

1b) Synthesis of 4-bromospiro-9,9'-bifluorene

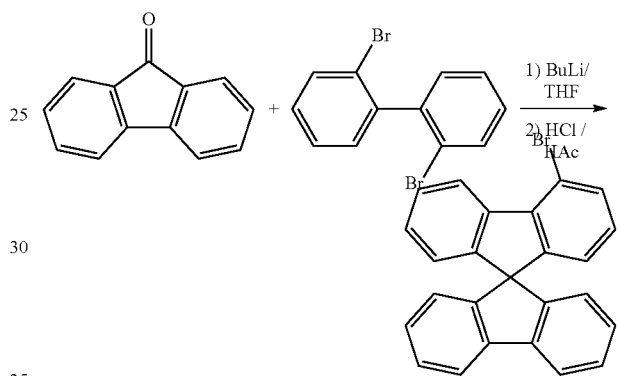

A solution of 2,2'-dibromo-biphenyl (250 g, 785 mmol) in THF (1900 ml) is treated with 318 mL of n-BuLi (2.5 M in hexane, 785 mmol) under argon at −78° C. The mixture is stirred for 30 minutes. A solution of Fluoren-9-one (144 g, 785 mmol) in 1000 mL THF is added dropwise. The reaction proceeds at −78° C. for 30 minutes and then is stirred at room temperature overnight. The reaction is quenched with water and the solid is filtered. Without further purification, a mixture of the alcohol (299 g, 92%), acetic acid (2200 mL) and concentrated HCl (100 mL) is refluxed for 2 hours. After cooling, the mixture is filtered and washed with water and dried under vacuum. The product is isolated in the form of a white solid (280 g, 98% of theory).

The synthesis of further brominated spirobifluorene derivatives is carried out analogously:

| Ex. | Bromo-biphenyl | Bromo-fluorenone | Product: Bromo-Spirobifluorene | Yield |
|---|---|---|---|---|
| 1c | Br-biphenyl structure [2052-07-5] | fluorenone-Br structure | bromospirobifluorene structure [2041-19-2] | 85% |

-continued

| Ex. | Bromo-biphenyl | Bromo-fluorenone | Product: Bromo-Spirobifluorene | Yield |
|---|---|---|---|---|
| 1d | [13029-09-9] | [486-25-9] | [1161009-88-6] | 90% |
| 1e | [2052-07-5] | [216312-73-1] | | 85% |
| 1f | [13029-09-9] | [4269-17-4] | [1257321-41-7] | 90% |
| 1g | [70728-93-7] | [4269-17-4] | | 85% |
| 1h | [70728-89-7] | [4269-17-4] | | 90% |
| 1i | [70728-93-7] | [486-25-9] | | 87% |

-continued
| Ex. | Bromo-biphenyl | Bromo-fluorenone | Product: Bromo-Spirobifluorene | Yield |
|---|---|---|---|---|
| 1j | 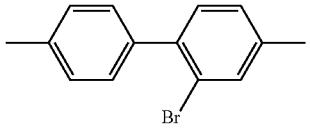 [132462-55-6] | 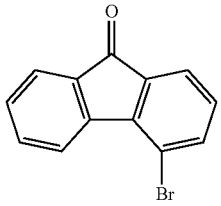 [4269-17-4] | 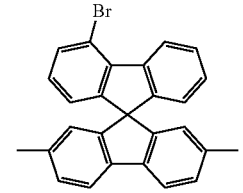 | 85% |
| 1k | 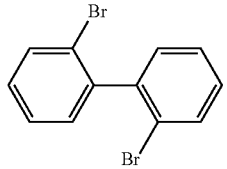 [13029-09-9] | 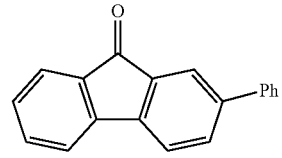 [3096-49-9] | 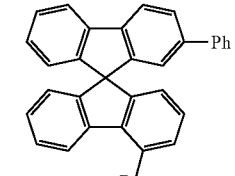 | 80% |
| 1l | 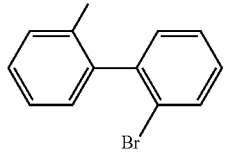 [13029-09-9] | 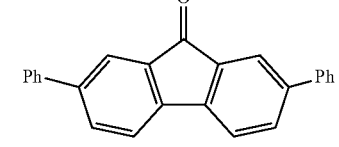 [115033-91-5] | 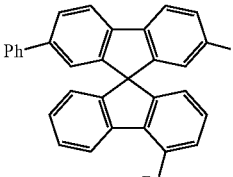 | 80% |
| 1m | 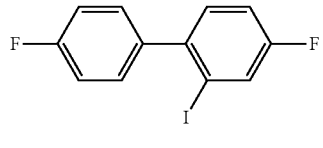 [1214351-66-2] | 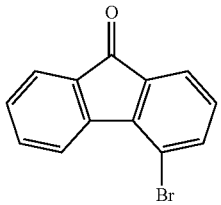 [4269-17-4] | 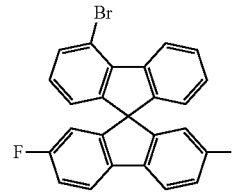 | 90% |
| 1n | 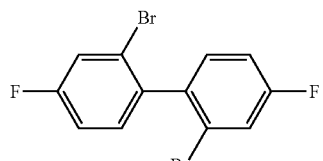 [124445-98-3] | 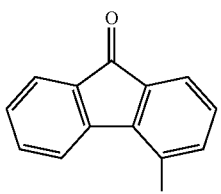 [4269-17-4] | 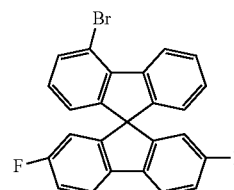 | 80% |

Example 2

Synthesis of 4-biphenyl-2-(9,9'-dimethylfluorenyl)-1-spiro-9,9'-bifluorenylamine Synthesis of 1-(1-biphen-4-yl)-(9,9'-dimethylfluoren-2-yl)amine-9H-Fluoren-9-one

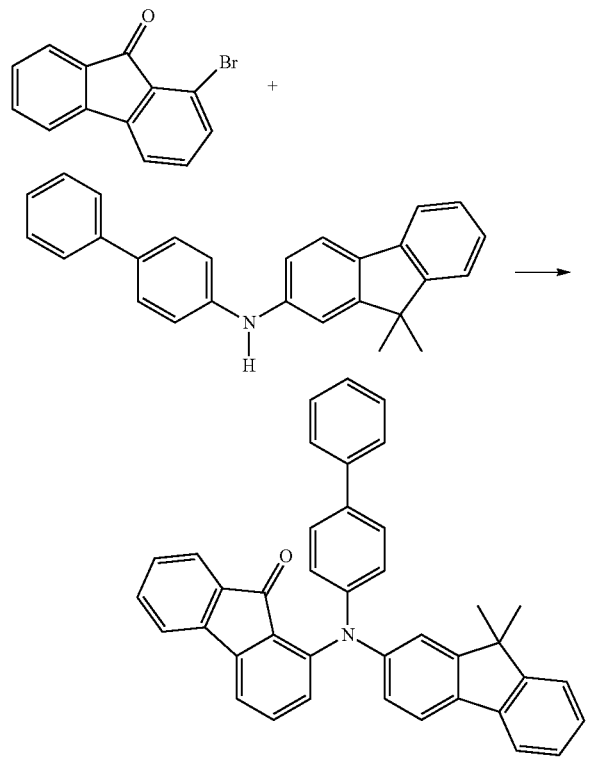

Tri-tert-butylphosphine (4.5 ml of a 1.0 M solution in toluene, 1.9 mmol), palladium acetate (217 mg, 0.97 mmol) and sodium tert-butoxide (13.9 g, 145 mmol) are added to a solution of 1-biphenyl-yl-(9,9-dimethyl-9H-fluoren-2-yl)amine (40.0 g, 111 mmol), 1-Bromo-Fluoren-9-one, (25 g, 96 mmol) in degassed toluene (200 ml), and the mixture is heated under reflux overnight. The reaction mixture is cooled to room temperature, extended with toluene and filtered through Celite. The filtrate is evaporated in vacuo, and the residue is crystallised from toluene/heptane The product is isolated in the form of a pale-yellow solid (43 g, 82% of theory).

Synthesis of 4-biphenyl-2-(9,9'-dimethylfluorenyl)-1-spiro-9,9'-bifluorenylamine

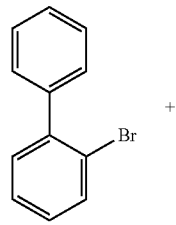

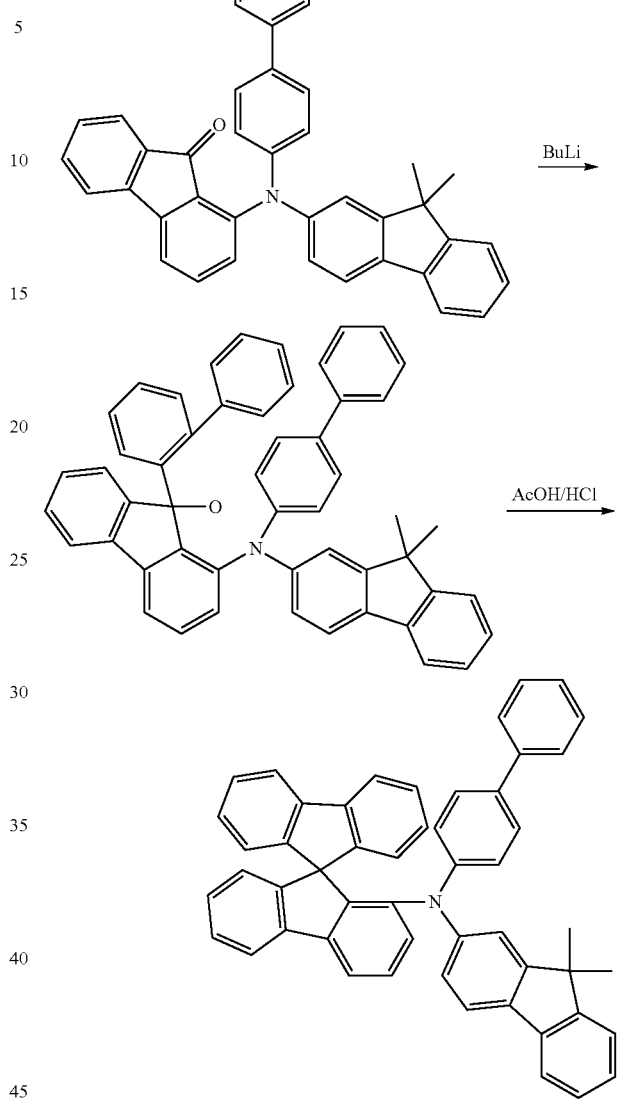

A solution of 2-Bromo-biphenyl (17 g, 70 mmol) in THF (90 ml) is treated with 35 mL of n-BuLi (2.1M in hexane, 70 mmol) under argon at −78° C.

The mixture is stirred for 30 minutes. A solution of 1-(1-biphen-4-yl)-(9,9'-dimethylfluoren-2-yl)amine-9H-Fluoren-9-one (38 g, 70 mmol) in 90 mL THF is added dropwise. The reaction proceeds at −78° C. for 30 minutes and then is stirred at room temperature overnight. The reaction is quenched with water and extracted with ethyl acetate. The intermediate alcohol is obtained after the solvent is removed (31 g, 64%). Without further purification, a mixture of the alcohol, acetic acid (700 mL) and concentrated HCl (62 mL) is refluxed for 2 hours. After cooling, the mixture is filtered and washed with water. The residue is crystallised from toluene. The crude product is extracted in a Soxhlet extractor (toluene) and purified by zone sublimation in vacuo. The product is isolated in the form of a pale-yellow solid (13 g, 43% of theory, purity >99.99% according to HPLC).

Example 3a

Synthesis of 4-biphenyl-2-(9,9'-dimethylfluorenyl)-1-spiro-9,9'-bifluorenylamine

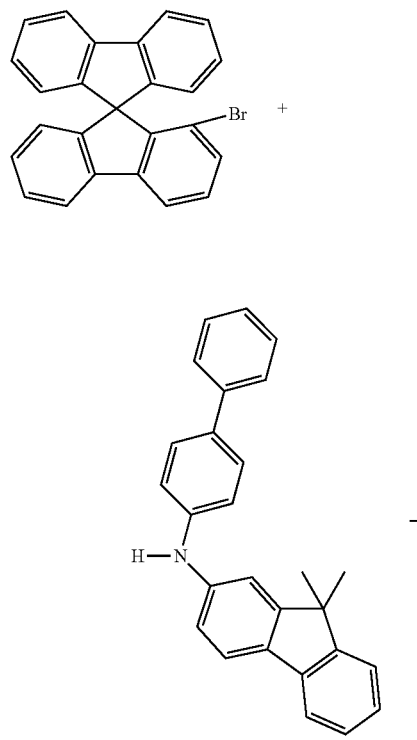

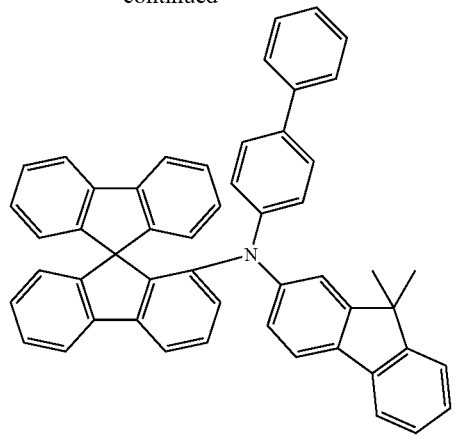

Tri-tert-butylphosphine (4.4 ml of a 1.0 M solution in toluene, 4.4 mmol), palladium acetate (248 mg, 1.1 mmol) and sodium tert-butoxide (16.0 g, 166 mmol) are added to a solution of biphenyl-2-yl-(9,9-dimethyl-9H-fluoren-2-yl)amine (40.0 g, 111 mmol) and 4-bromo-9,9'-spirobifluorene (56.9 g, 144 mmol) in degassed toluene (500 ml), and the mixture is heated under reflux for 2 h. The reaction mixture is cooled to room temperature, extended with toluene and filtered through Celite. The filtrate is evaporated in vacuo, and the residue is crystallised from ethyl acetate/heptane. The crude product is extracted in a Soxhlet extractor (toluene) and purified by zone sublimation in vacuo twice ($p = 3 \times 10^{-4}$ mbar, $T = 298°$ C.). The product is isolated in the form of a pale-yellow solid (20.4 g, 27% of theory, purity >99.99% according to HPLC).

The following compounds are obtained analogously:

| Ex. | Br-spiro | Amine | Product | Yield |
|---|---|---|---|---|
| 3b | (structure) | (structure) [102113-98-4] | (structure) | 43% |
| 3c | (structure) | (structure) [1198395-24-2] | (structure) | 56% |

| Ex. | Br-spiro | Amine | Product | Yield |
|---|---|---|---|---|
| 3d | | [500717-23-7] | | 61% |
| 3e | | [1290039-85-8] | | 72% |
| 3f | | [1267248-54-3] | | 65% |

-continued

| Ex. | Br-spiro | Amine | Product | Yield |
|---|---|---|---|---|
| 3g | | [1354653-33-0] | | 75% |
| 3h | | [1160294-96-1] | | 80% |
| 3i | | [955959-89-4] | | 85% |

-continued
| Ex. | Br-spiro | Amine | Product | Yield |
|---|---|---|---|---|
| 3j | 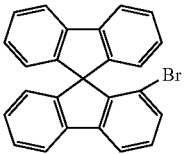 [SMILES: Brc1cccc2c1C1(c3ccccc3-c3ccccc31)c1ccccc1-2] | 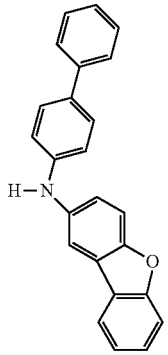 [1300028-94-7] | 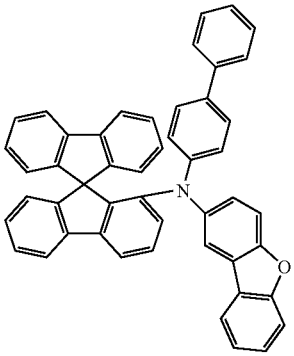 [SMILES: c1ccc(-c2ccc(N(c3ccc4oc5ccccc5c4c3)c3cccc4c3C3(c5ccccc5-c5ccccc53)c3ccccc3-4)cc2)cc1] | 55% |
| 3k | 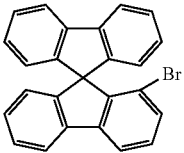 [SMILES: Brc1cccc2c1C1(c3ccccc3-c3ccccc31)c1ccccc1-2] | 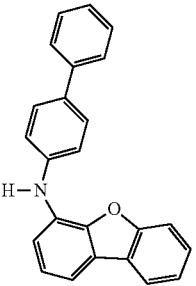 [1318338-47-4] | 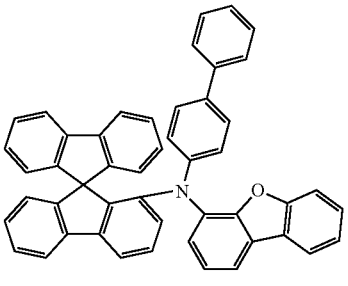 [SMILES: c1ccc(-c2ccc(N(c3cccc4c3C3(c5ccccc5-c5ccccc53)c3ccccc3-4)c3cccc4c3oc3ccccc34)cc2)cc1] | 64% |
| 3l | 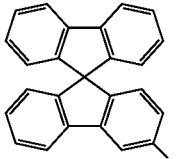 | 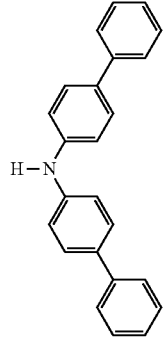 [102113-98-4] | 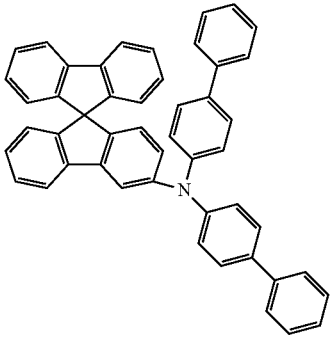 [SMILES: c1ccc(-c2ccc(N(c3ccc(-c4ccccc4)cc3)c3ccc4c(c3)-c3ccccc3C43c4ccccc4-c4ccccc43)cc2)cc1] | 56% |
| 3m | 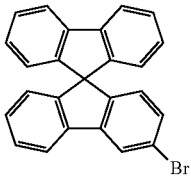 [SMILES: Brc1ccc2c(c1)-c1ccccc1C21c2ccccc2-c2ccccc21] | 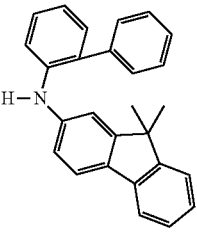 [1198395-24-2] | 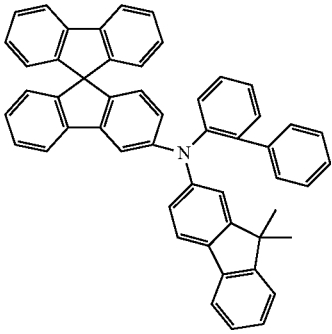 [SMILES: CC1(C)c2ccccc2-c2ccc(N(c3ccc4c(c3)-c3ccccc3C43c4ccccc4-c4ccccc43)c3ccccc3-c3ccccc3)cc21] | 66% |

-continued

| Ex. | Br-spiro | Amine | Product | Yield |
|---|---|---|---|---|
| 3n | | [500717-23-7] | | 46% |
| 3o | | [1267248-54-3] | | 60% |
| 3p | | [1354653-33-0] | | 72% |

-continued

| Ex. | Br-spiro | Amine | Product | Yield |
|---|---|---|---|---|
| 3q | | [1160294-96-1] | | 85% |
| 3r | | [1290039-85-8] | | 50% |
| 3s | | [1300028-94-7] | | 70% |
| 3t | | [1318338-47-4] | | 67% |

-continued

| Ex. | Br-spiro | Amine | Product | Yield |
|---|---|---|---|---|
| 3u | | [955959-89-4] | | 85% |
| 3v | | [102113-98-4] | | 43% |
| 3w | | [1198395-24-2] | | 76% |
| 3x | | [500717-23-7] | | 41% |

-continued

| Ex. | Br-spiro | Amine | Product | Yield |
|---|---|---|---|---|
| 3y | | [1290039-85-8] | | 50% |
| 3z | | [1300028-94-7] | | 59% |
| 3aa | | [1318338-47-4] | | 71% |
| 3ab | | [1267248-54-3] | | 70% |

| Ex. | Br-spiro | Amine | Product | Yield |
|---|---|---|---|---|
| 3ac | | [1354653-33-0] | | 75% |
| 3ad | | [1160294-96-1] | | 80% |
| 3ae | | [955959-89-4] | | 85% |

-continued
| Ex. | Br-spiro | Amine | Product | Yield |
|---|---|---|---|---|
| 3af | <br>1257321-41-7 | 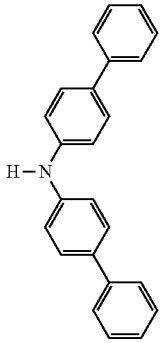<br>102113-98-4 | 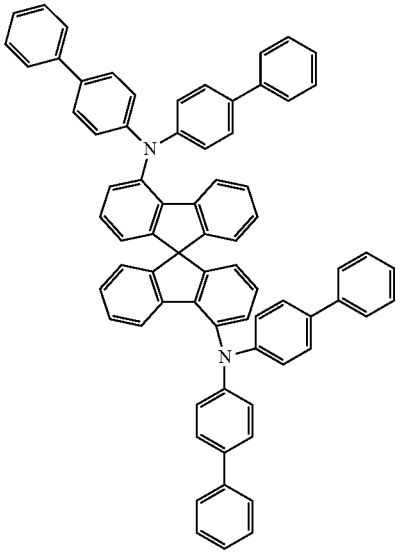 [SMILES: c1ccc(-c2ccc(N(c3ccc(-c4ccccc4)cc3)c3cccc4c3-c3ccccc3C43c4ccccc4-c4c(N(c5ccc(-c6ccccc6)cc5)c5ccc(-c6ccccc6)cc5)cccc43)cc2)cc1] | 48% |
| 3ag | <br>[1257321-41-7] | 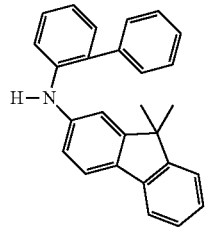<br>[1198395-24-2] | 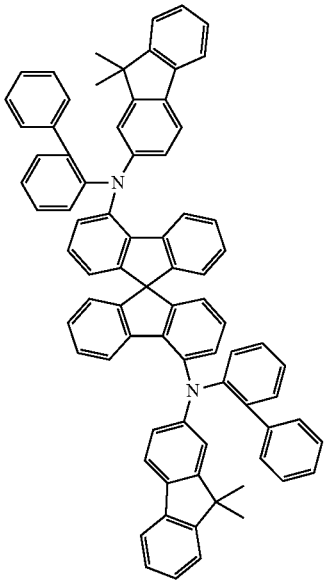 [SMILES: CC1(C)c2ccccc2-c2ccc(N(c3ccccc3-c3ccccc3)c3cccc4c3-c3ccccc3C43c4ccccc4-c4c(N(c5ccc6c(c5)C(C)(C)c5ccccc5-6)c5ccccc5-c5ccccc5)cccc43)cc21] | 46% |

-continued

| Ex. | Br-spiro | Amine | Product | Yield |
|---|---|---|---|---|
| 3ah | [1257321-41-7] | [500717-23-7] | | 41% |
| 3ai | [1257321-41-7] | [1290039-85-8] | | 50% |

-continued
| Ex. | Br-spiro | Amine | Product | Yield |
|---|---|---|---|---|
| 3aj |  [1257321-41-7] | 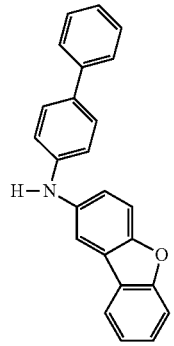 [1300028-94-7] | 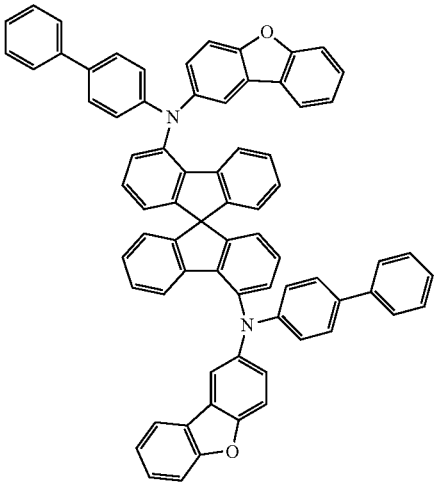 [SMILES: c1ccc(-c2ccc(N(c3ccc4oc5ccccc5c4c3)c3cccc4c3-c3ccccc3C43c4ccccc4-c4c(N(c5ccc(-c6ccccc6)cc5)c5ccc6oc7ccccc7c6c5)cccc43)cc2)cc1] | 43% |
| 3ak | 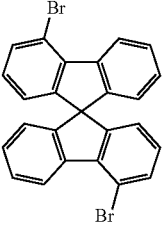 [1257321-41-7] | 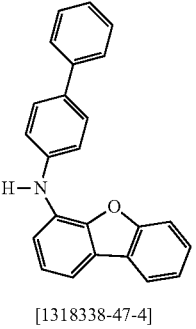 [SMILES: c1ccc(-c2ccc(Nc3cccc4c3oc3ccccc34)cc2)cc1] [1318338-47-4] | 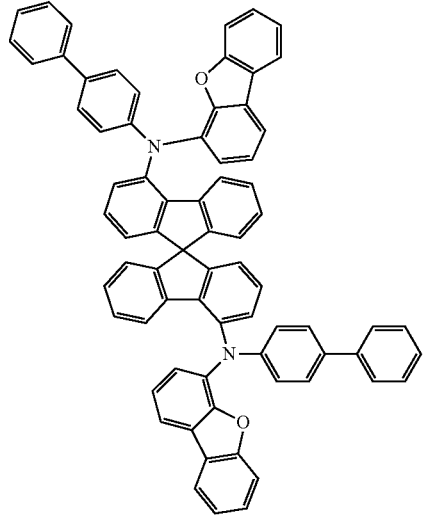 [SMILES: c1ccc(-c2ccc(N(c3cccc4c3-c3ccccc3C43c4ccccc4-c4c(N(c5ccc(-c6ccccc6)cc5)c5cccc6c5oc5ccccc56)cccc43)c3cccc4c3oc3ccccc34)cc2)cc1] | 53% |
| 3al | 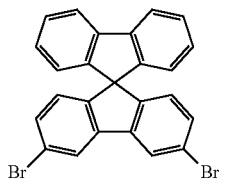 [SMILES: Brc1ccc2c(c1)-c1cc(Br)ccc1C21c2ccccc2-c2ccccc21] | 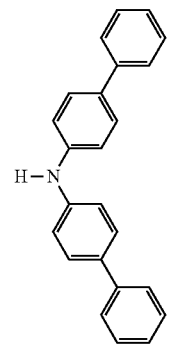 [102113-98-4] | 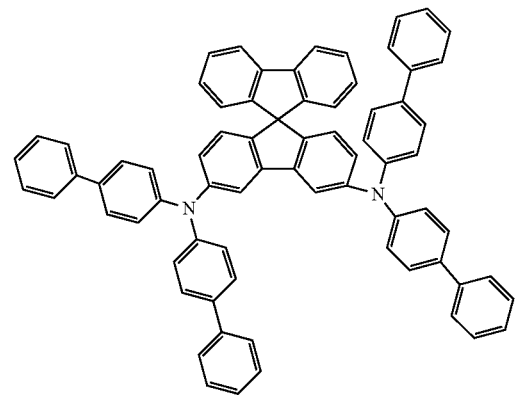 [SMILES: c1ccc(-c2ccc(N(c3ccc(-c4ccccc4)cc3)c3ccc4c(c3)-c3cc(N(c5ccc(-c6ccccc6)cc5)c5ccc(-c6ccccc6)cc5)ccc3C43c4ccccc4-c4ccccc43)cc2)cc1] | 33% |

| Ex. | Br-spiro | Amine | Product | Yield |
|---|---|---|---|---|
| 3am | 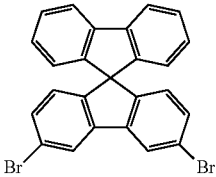 [SMILES: Brc1ccc2c(c1)-c1cc(Br)ccc1C21c2ccccc2-c2ccccc21] | 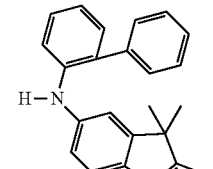 [1198395-24-2] | 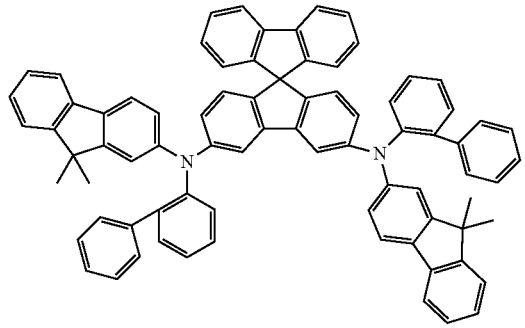 [SMILES: CC1(C)c2ccccc2-c2ccc(N(c3ccc4c(c3)-c3cc(N(c5ccc6c(c5)C(C)(C)c5ccccc5-6)c5ccccc5-c5ccccc5)ccc3C43c4ccccc4-c4ccccc43)c3ccccc3-c3ccccc3)cc21] | 46% |
| 3an | 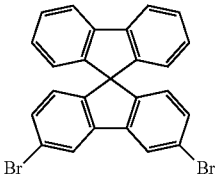 [SMILES: Brc1ccc2c(c1)-c1cc(Br)ccc1C21c2ccccc2-c2ccccc21] | 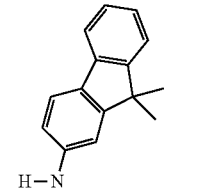 [500717-23-7] | 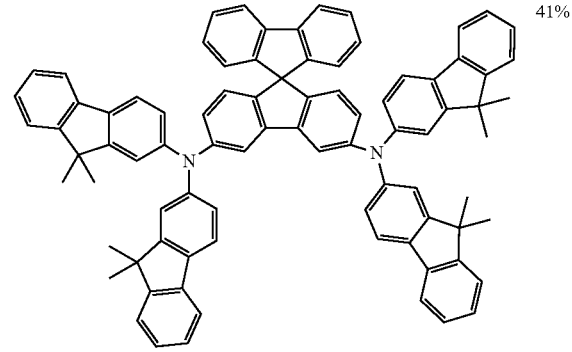 | 41% |
| 3ao | 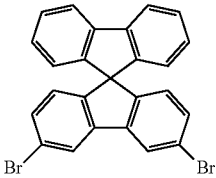 | 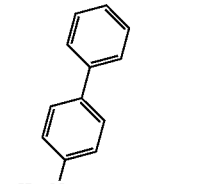 [1290039-85-8] | 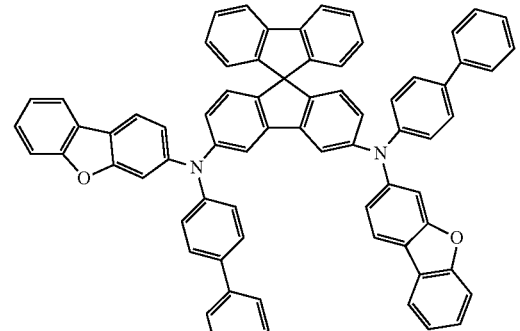 | 40% |
| 3ap | 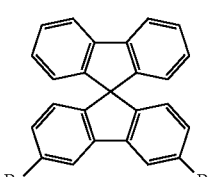 | 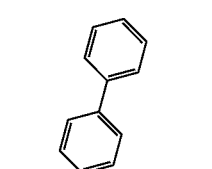 [1300028-94-7] | 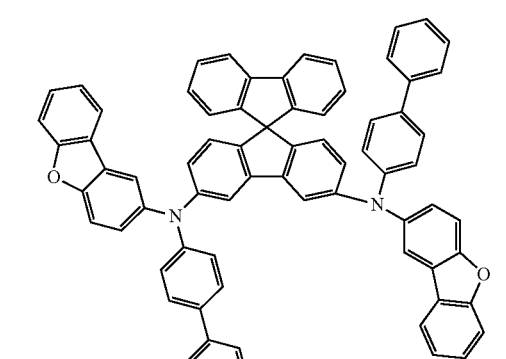 | 51% |

| Ex. | Br-spiro | Amine | Product | Yield |
|---|---|---|---|---|
| 3aq | (3,3'-dibromo-9,9'-spirobifluorene structure) | 4-biphenyl-N-H-(dibenzofuran-4-yl)amine [1318338-47-4] | (product structure) | 47% |

Example 4a

Synthesis of biphenyl-2-yl-(9,9-dimethyl-9H-fluoren-2-yl)-(9,9'-spirobifluoren-4-yl)amine

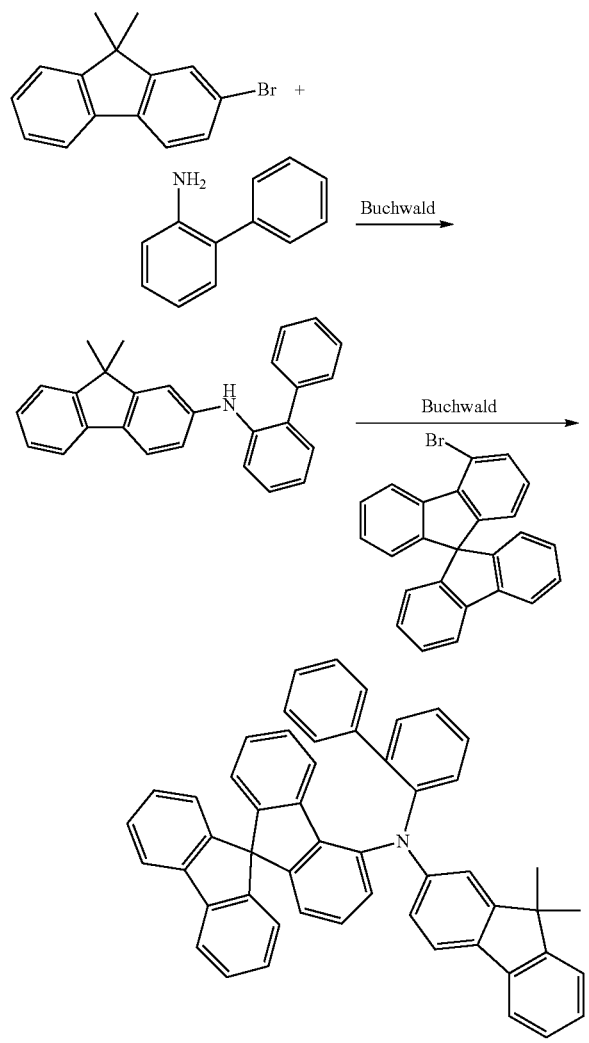

a) Synthesis of biphenyl-2-yl-(9,9-dimethyl-9H-fluoren-2-yl)amine 1,1'-Bis(diphenylphosphino)ferrocene (1.5 g, 2.7 mmol), palladium acetate (616 mg, 2.7 mmol) and sodium tert-butoxide (22.9 g, 238 mmol) are added to a solution of biphenyl-2-ylamine (31.0 g, 183 mmol) and 2-bromo-9,9-dimethyl-9H-fluorene (50.0 g, 183 mmol) in degassed toluene (400 ml), and the mixture is heated under reflux for 20 h. The reaction mixture is cooled to room temperature, extended with toluene and filtered through Celite. The filtrate is extended with water, re-extracted with toluene, and the combined organic phases are dried and evaporated in vacuo. The residue is filtered through silica gel (heptane/dichloromethane) and crystallised from isopropanol. Biphenyl-2-yl-(9,9-dimethyl-9H-fluoren-2-yl)amine is obtained in the form of a pale-yellow solid (63.0 g, 95% of theory).

b) Synthesis of biphenyl-2-yl-(9,9-dimethyl-9H-fluoren-2-yl)-(9,9'-spirobifluoren-4-yl)amine Tri-tert-butylphosphine (4.4 ml of a 1.0 M solution in toluene, 4.4 mmol), palladium acetate (248 mg, 1.1 mmol) and sodium tert-butoxide (16.0 g, 166 mmol) are added to a solution of biphenyl-2-yl-(9,9-dimethyl-9H-fluoren-2-yl)amine (40.0 g, 111 mmol) and 4-bromo-9,9'-spirobifluorene (56.9 g, 144 mmol) in degassed toluene (500 ml), and the mixture is heated under reflux for 2 h. The reaction mixture is cooled to room temperature, extended with toluene and filtered through Celite. The filtrate is evaporated in vacuo, and the residue is crystallised from ethyl acetate/heptane. The crude product is extracted in a Soxhlet extractor (toluene) and purified by zone sublimation in vacuo twice ($p=3\times10^{-4}$ mbar, T=298° C.). The product is isolated in the form of a pale-yellow solid (20.4 g, 27% of theory, purity >99.99% according to HPLC).

The following compounds are obtained analogously:
| Ex. | Starting material 1 | Starting material 2 | Starting material 3 | Product | Yield |
|---|---|---|---|---|---|
| 4b | 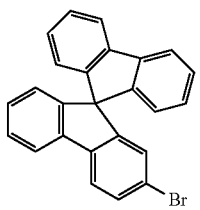 [SMILES: Brc1ccc2c(c1)C1(c3ccccc3-c3ccccc31)c1ccccc1-2] | 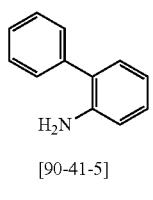 [SMILES: Nc1ccccc1-c1ccccc1]　[90-41-5] | 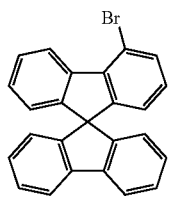　[1161009-88-6] | 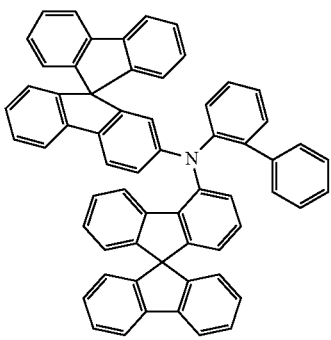 [SMILES: c1ccc(-c2ccccc2N(c2ccc3c(c2)C2(c4ccccc4-c4ccccc42)c2ccccc2-3)c2cccc3c2-c2ccccc2C32c3ccccc3-c3ccccc32)cc1] | 78% |
| 4c | 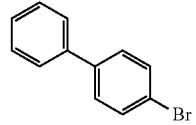 | 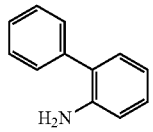 [SMILES: Nc1ccccc1-c1ccccc1] | 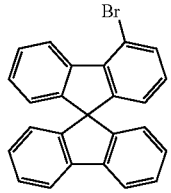 [SMILES: Brc1cccc2c1-c1ccccc1C21c2ccccc2-c2ccccc21] | 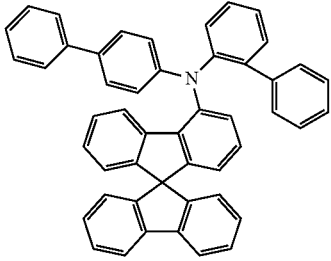 [SMILES: c1ccc(-c2ccc(N(c3ccccc3-c3ccccc3)c3cccc4c3-c3ccccc3C43c4ccccc4-c4ccccc43)cc2)cc1] | 73% |
| 4d | 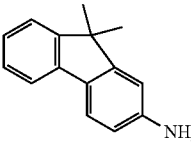 | 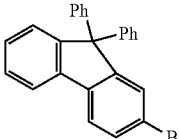 | 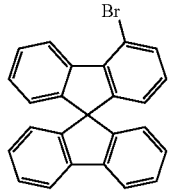 [SMILES: Brc1cccc2c1-c1ccccc1C21c2ccccc2-c2ccccc21] | 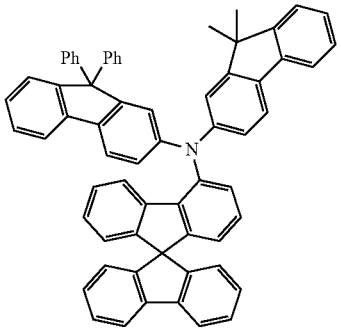 [SMILES: CC1(C)c2ccccc2-c2ccc(N(c3ccc4c(c3)C(c3ccccc3)(c3ccccc3)c3ccccc3-4)c3cccc4c3-c3ccccc3C43c4ccccc4-c4ccccc43)cc21] | 75% |
| 4e | 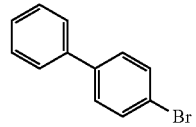 | 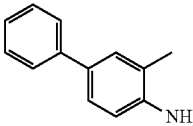　[63019-98-7] | 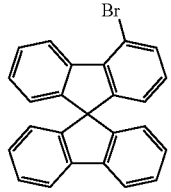 [SMILES: Brc1cccc2c1-c1ccccc1C21c2ccccc2-c2ccccc21] | 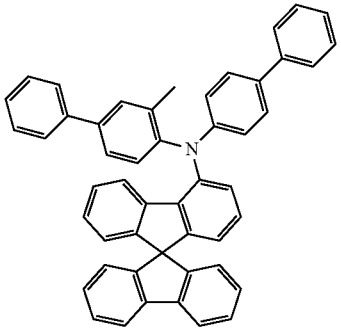 [SMILES: Cc1cc(-c2ccccc2)ccc1N(c1ccc(-c2ccccc2)cc1)c1cccc2c1-c1ccccc1C21c2ccccc2-c2ccccc21] | 79% |

-continued

| Ex. | Starting material 1 | Starting material 2 | Starting material 3 | Product | Yield |
|---|---|---|---|---|---|
| 4f | 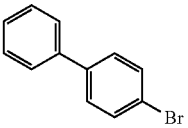 | 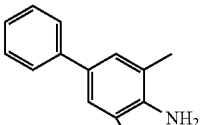  [54810-82-1] | 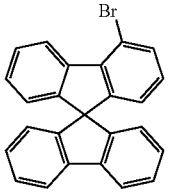 [SMILES: Brc1cccc2c1-c1ccccc1C21c2ccccc2-c2ccccc21] | 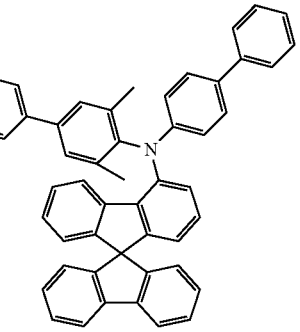 | 78% |

Example 5a

Synthesis of Synthesis of Biphenyl-4-yl-(9,9-dimethyl-9H-fluoren-2-yl)-[4-(9,9'-spiro-bifluoren-4-yl)-phenyl]-amine Synthesis of Biphenyl-4-yl-(9,9-dimethyl-9H-fluoren-2-yl (4,4,5,5tetramethyl-[1,3,2]dioxaborolan-2-yl)-phenyl]-amine 102 g (198 mmol) of Biphenyl-4-yl-(4-bromo-phenyl)-(9,9-dimethyl-9H-fluoren-2-yl)-amine, 4.8 g (5.9 mmol) of Pd(dppf)Cl$_2$, 61.6 g (238 mmol) of bis(pinacolato)diboron and 58.3 g (594 mmol) of potassium acetate are dissolved in 1300 mL of 1,4-dioxane. The reaction mixture is refluxed and agitated under an argon atmosphere for 12 hours and after cooling to room temperature, the mixture is filtered through Celite. The filtrate is evaporated in vacuo, and the residue is crystallised from heptane. The product is isolated in the form of a pale-yellow solid (87 g, 78% of theory).

Synthesis of Biphenyl-4-yl-(9,9-dimethyl-9H-fluoren-2-yl)-[4-(9,9'-spiro-bifluoren-4-yl)-phenyl]-amine

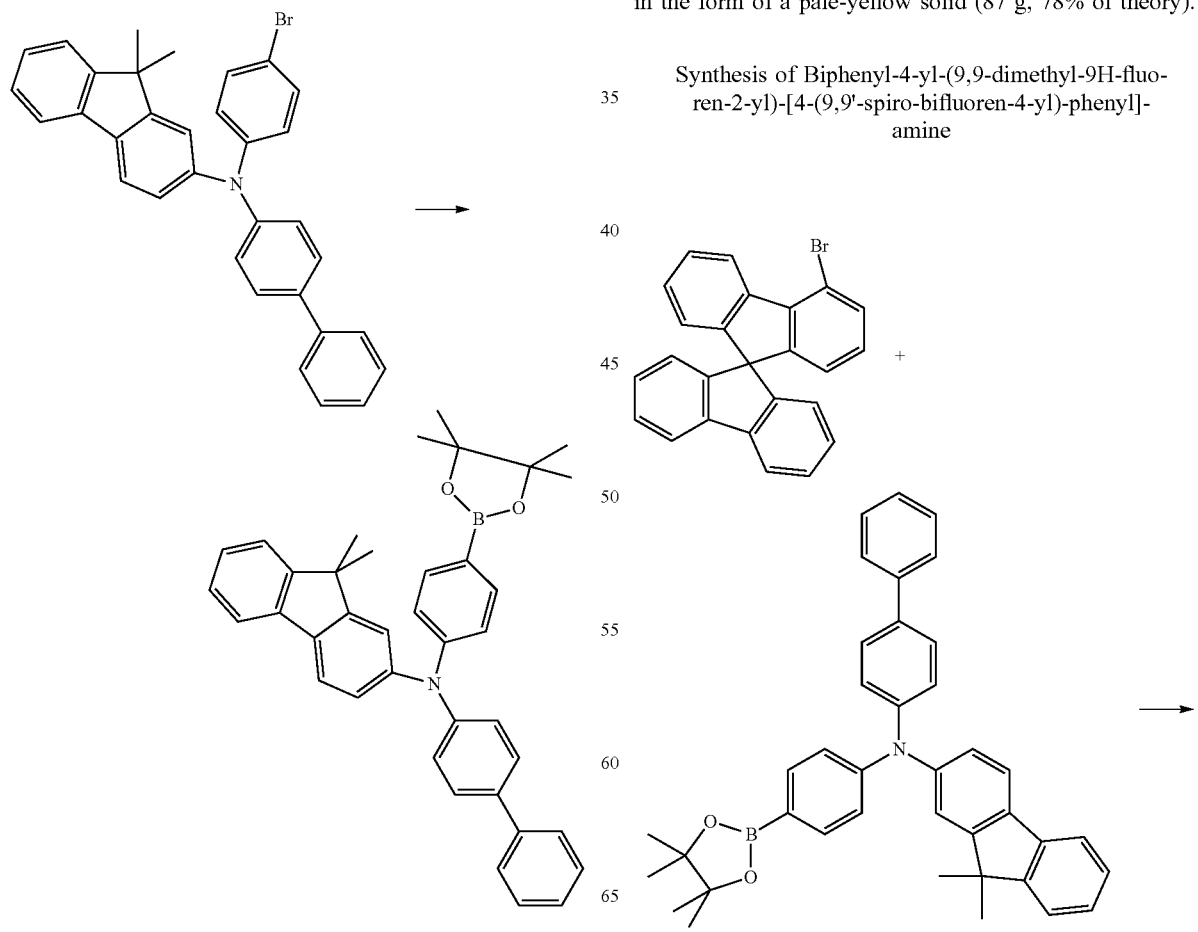

-continued

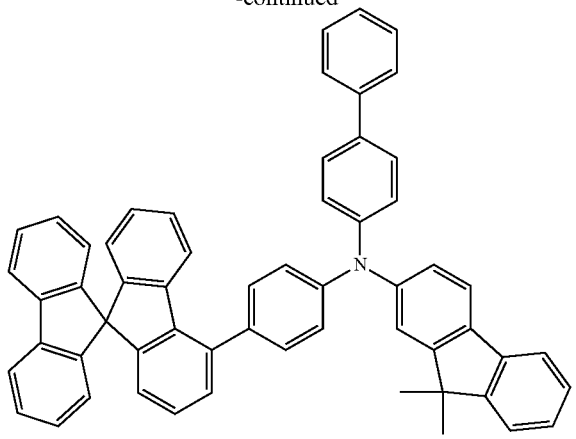

28 g (49.4 mmol) of Biphenyl-4-yl-(9,9-dimethyl-9H-fluoren-2-yl(4,4,5,5-tetramethyl-[1,3,2]dioxaborolan-2-yl)-phenyl]amine, 20 g (49.4 mmol) of 4-bromspirobifluorene, 1.8 g (2.5 mmol) of $PdCl_2(Cy)_3$, 15 g (99 mmol) of cesium fluoride are dissolved in 500 mL of toluene. The reaction mixture is refluxed and agitated under an argon atmosphere for 12 hours and after cooling to room temperature, the mixture is filtered through Celite. The filtrate is evaporated in vacuo, and the residue is crystallised from heptane. The crude product is extracted in a Soxhlet extractor (toluene) and purified by zone sublimation in vacuo twice. The product is isolated in the form of a pale-yellow solid (9 g, 24% of theory, purity >99.99% according to HPLC).

The following compounds are synthesized analogously:

| Ex. | Br-Spiro | Amine | Product | Yield |
|---|---|---|---|---|
| 5b | | | | 43% |
| 5c | | | | 55% |
| 5d | | | | 60% |

-continued

| Ex. | Br-Spiro | Amine | Product | Yield |
|---|---|---|---|---|
| 5e | | | | 63% |
| 5f | | | | 70% |
| 5g | | | | 75% |
| 5h | | | | 55% |

US 9,812,648 B2

353                                                                                              354

-continued

| Ex. | Br-Spiro | Amine | Product | Yield |
|---|---|---|---|---|
| 5i |  |  |  | 64% |
| 5j |  |  |  | 60% |
| 5k |  |  |  | 67% |
| 5l |  |  |  | 58% |

Example 6a

9-Spiro-4-yl-3,6-diphenyl-9H-carbazol

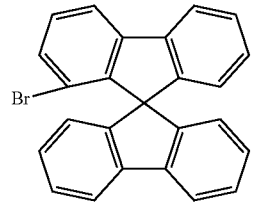

+

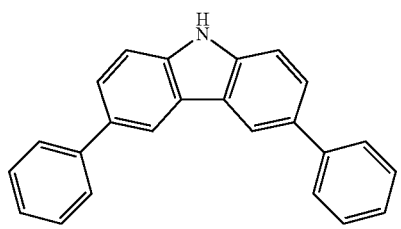

→

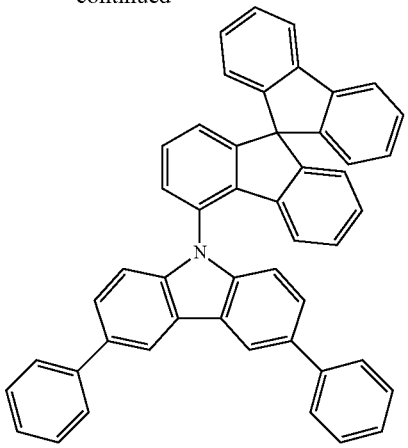

19.2 g (47 mmol) 4-Brom-9-spirobifluorene, 15 g (47 mmol) 3,6-Diphenyl-9-H-carbazole and 29.2 g Rb$_2$CO$_3$ are suspended in 250 mL p-Xylol. To the suspension are given 0.95 g (4.2 mmol) Pd(OAc)$_2$ and 12.6 ml of a 1M solution of Tri-tert-butylphosphine. The mixture is stirred 24 h under reflux. After cooling the organic phase is separated, washed three times with 150 mL water and is subsequently concentrated to dryness in vacuo. The residue is hot extracted with toluene, recrystallized three times from toluene and subsequently sublimated at high vacuum. Yield is 19.6 g (30.9 mmol) corresponding to 66% of theory. Purity is according to HPLC 99.9%.

The following compounds are obtained analogously:

| | starting material 1 | starting material 2 | product | yield |
|---|---|---|---|---|
| 6b | | 1257220-47-5 | | 76% |
| 6c | | 1257220-47-5 | | 65% |

-continued

| starting material 1 | starting material 2 | product | yield |
|---|---|---|---|
| 6d | 1060735-14-9 | | 77% |
| 6e | 103012-26-6 | | 69% |

B) Device Examples

OLEDs according to the invention and OLEDs in accordance with the prior art are produced by a general process in accordance with WO 2004/058911, which is adapted to the circumstances described here (layer-thickness variation, materials).

The data for various OLEDs are presented in the following Examples 1 to 5 below (see Tables 1 to 7).

The substrates used are glass plates coated with structured ITO (indium tin oxide) in a thickness of 50 nm. The OLEDs basically have the following layer structure: substrate/hole-injection layer (IL)/hole-transport layer (HTL)/hole-injection layer (IL)/electron-blocking layer (EBL)/emission layer (EML)/electron-transport layer (ETL) and finally a cathode. In the device structure according to Table 3, the analogous structure is used, only that the first hole injection layer is omitted.

Other examples are presented with the following general device structure shown in Table 6: substrate/p-doped hole transport layer (HIL1)/hole-transport layer (HTL)/p-doped electron blocking layer (HIL2)/electron-blocking layer (EBL)/emission layer (EML)/electron-transport layer (ETL)/electron-injection layer (EIL) and finally a cathode. The cathode is formed by an aluminium layer with a thickness of 100 nm.

Other examples are presented with the following general device structure shown in Table 7. This structure differs from the structure of Examples of Table 6 in that the second p-doped electron blocking layer is omitted, and in that a hole blocking layer (HBL) is present between emitting layer and electron transport layer.

The precise structures of all the OLEDs prepared in the present examples are shown in Tables 1, 3, 6 and 7. The materials required for the production of the OLEDs are shown in Table 5. Data obtained are either in the text and/or shown in Tables 2 and 4.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as H1:SEB1 (95%:5%) here means that material H1 is present in the layer in a proportion by volume of 95% and SEB1 is present in the layer in a proportion of 5%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m$^2$, and the CIE 1931 x and y colour coordinates are calculated therefrom. The expression EQE @ 1000 cd/m$^2$ denotes the external quantum efficiency at an operating luminous density of 1000 cd/m$^2$. LT80 @ 6000 cd/m$^2$ is the lifetime until the OLED has dropped from a luminance of 6000 cd/m² to 80% of the initial intensity, i.e. to 4800 cd/m². LT80 @ 60 mA/cm² is the lifetime until the OLED has dropped from its initial luminance at a constant current of 60 mA to 80% of the initial luminance. The data obtained for the various OLEDs are summarised either in the text and/or shown in Tables 2 and 4.

Use of Compounds According to the Invention as Hole-Transport Materials in Fluorescent and Phosphorescent OLEDs In particular, compounds according to the invention are suitable as HIL, HTL or EBL in OLEDs. They are suitable as a single layer, but also as mixed component as HIL, HTL, EBL or within the EML.

Example 1

Singlet blue devices are shown in Tables 1 and 2, and triplet green devices are shown in Tables 3 and 4.

Compared with devices which comprise NPB as reference (V1, V3), the samples comprising the compounds according to the invention exhibit both higher efficiencies and also significantly improved lifetimes both in singlet blue and also in triplet green devices. Compared with the reference material HTMV1 (V2, V4), the compound according to the invention HTM1 has significantly improved efficiencies and significantly better lifetimes.

TABLE 1

Structure of the OLEDs

| Ex. | IL Thickness/nm | HTL Thickness/nm | IL Thickness/nm | EBL Thickness/nm | EML Thickness/nm | ETL Thickness/nm |
|---|---|---|---|---|---|---|
| V1 | HIL1 5 nm | HIL2 140 nm | HIL1 5 nm | NPB 20 nm | H1(95%):SEB1(5%) 20 nm | ETM1(50%):LiQ(50%) 30 nm |
| V2 | HIL1 5 nm | HIL2 140 nm | HIL1 5 nm | HTMV1 20 nm | H1(95%):SEB1(5%) 20 nm | ETM1(50%):LiQ(50%) 30 nm |
| E1 | HIL1 5 nm | HIL2 140 nm | HIL1 5 nm | HTM1 20 nm | H1(95%):SEB1(5%) 20 nm | ETM1(50%):LiQ(50%) 30 nm |

TABLE 2

Data for the OLEDs

| Ex. | EQE @ 1000 cd/m2 % | LT80 @ 6000 cd/m² [h] | CIE x | CIE y |
|---|---|---|---|---|
| V1 | 4.8 | 70 | 0.14 | 0.17 |
| V2 | 4.3 | 45 | 0.13 | 0.15 |
| E1 | 6.8 | 130 | 0.13 | 0.16 |

TABLE 3

Structure of the OLEDs

| Ex. | HTL Thickness/nm | IL Thickness/nm | EBL Thickness/nm | EML Thickness/nm | ETL Thickness/nm |
|---|---|---|---|---|---|
| V3 | HIL2 70 nm | HIL1 5 nm | NPB 90 nm | H2(88%):TEG(12%) 30 nm | ETM1(50%):LiQ(50%) 40 nm |
| V4 | HIL2 70 nm | HIL1 5 nm | HTMV1 90 nm | H2(88%):TEG(12%) 30 nm | ETM1(50%):LiQ(50%) 40 nm |
| E2 | HIL2 70 nm | HIL1 5 nm | HTM1 90 nm | H2(88%):TEG(12%) 30 nm | ETM1(50%):LiQ(50%) 40 nm |

TABLE 4

Data for the OLEDs

| Ex. | Efficiency @ 1000 cd/m2 | LT80 @ 8000 cd/m² | CIE x | CIE y |
|---|---|---|---|---|
| V3 | 14.4% | 85 h | 0.32 | 0.63 |
| V4 | 16.6% | 60 h | 0.37 | 0.6 |
| E2 | 17.3% | 195 h | 0.37 | 0.61 |

TABLE 5

Structures of the materials used

HIL1

F4TCNQ

TABLE 5-continued
Structures of the materials used
HIL2
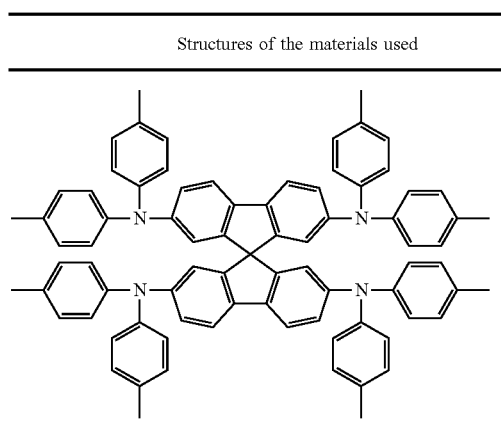
HIL3
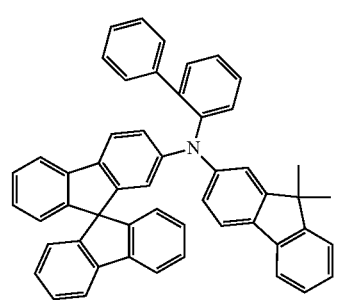 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
H1
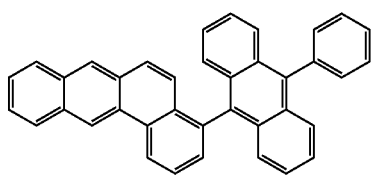
SEB1
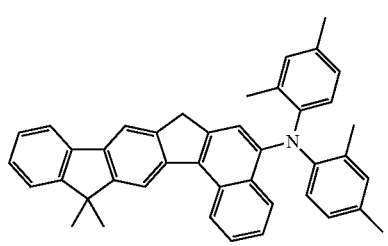 [SMILES: Cc1ccc(N(c2ccc(C)cc2C)c2cc3c(c4ccccc24)-c2cc4c(cc2C3)-c2ccccc2C4(C)C)c(C)c1]
H2
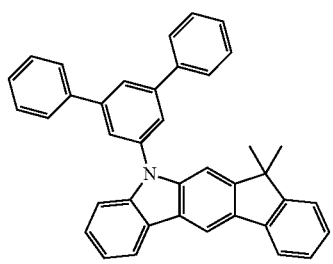 [SMILES: CC1(C)c2ccccc2-c2cc3c4ccccc4n(-c4cc(-c5ccccc5)cc(-c5ccccc5)c4)c3cc21]
TABLE 5-continued
Structures of the materials used
H3
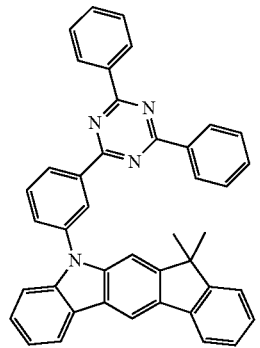 [SMILES: CC1(C)c2ccccc2-c2cc3c4ccccc4n(-c4cccc(-c5nc(-c6ccccc6)nc(-c6ccccc6)n5)c4)c3cc21]
H4
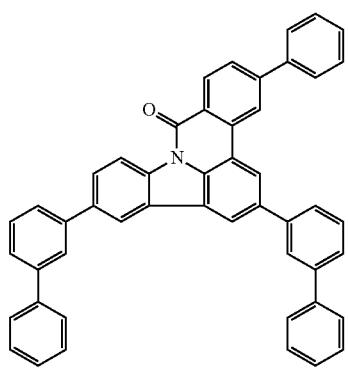 [SMILES: O=c1c2ccc(-c3ccccc3)cc2c2cc(-c3cccc(-c4ccccc4)c3)cc3c4cc(-c5cccc(-c6ccccc6)c5)ccc4n1c23]
TEG
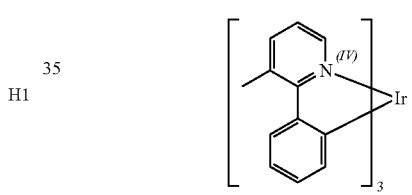
ETM1
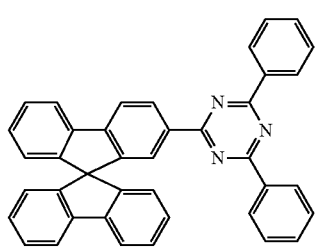 [SMILES: c1ccc(-c2nc(-c3ccccc3)nc(-c3ccc4c(c3)C3(c5ccccc5-c5ccccc53)c3ccccc3-4)n2)cc1]
ETM2
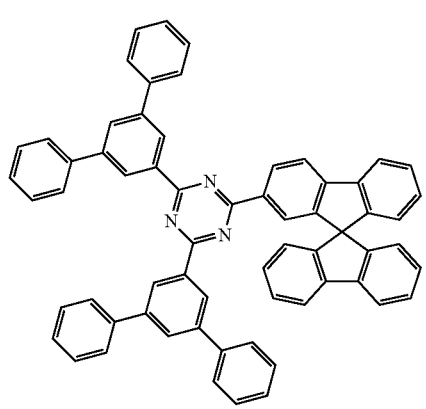 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]

TABLE 5-continued
Structures of the materials used
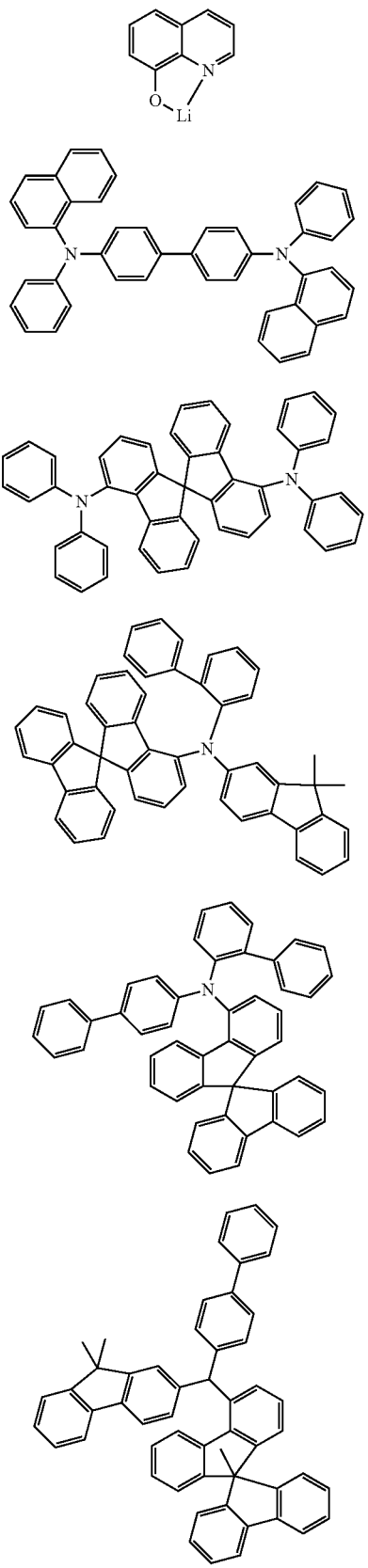
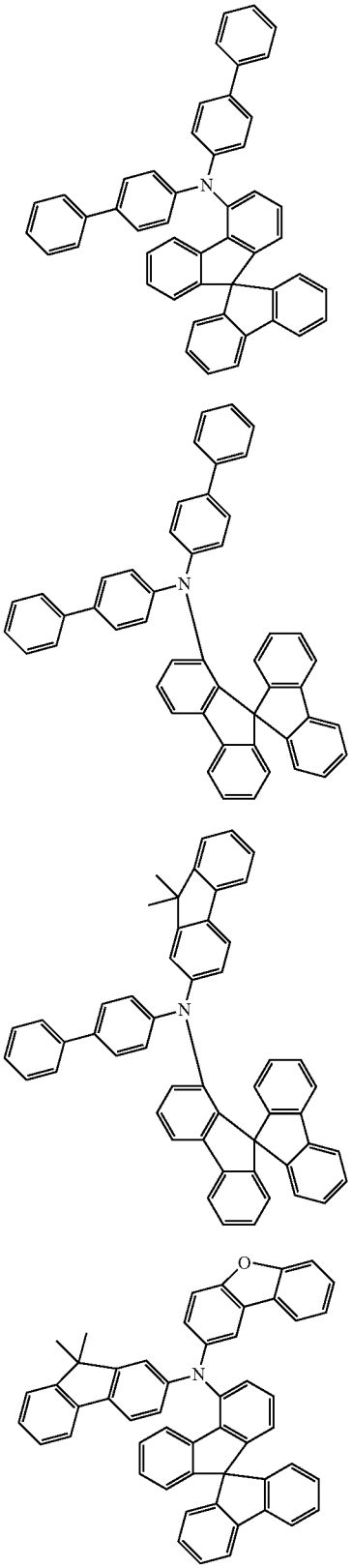

TABLE 5-continued

Structures of the materials used

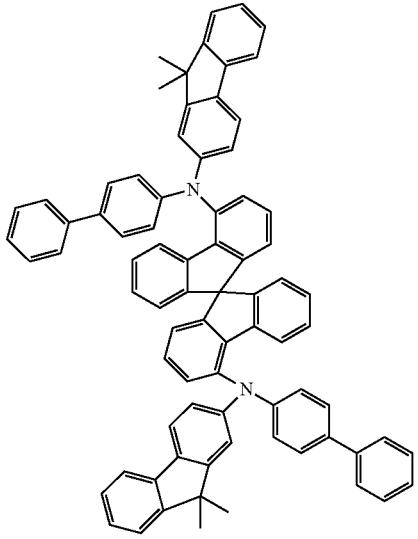 [SMILES: CC1(C)c2ccccc2-c2ccc(N(c3ccc(-c4ccccc4)cc3)c3cccc4c3-c3ccccc3C43c4ccccc4-c4c(N(c5ccc(-c6ccccc6)cc5)c5ccc6c(c5)C(C)(C)c5ccccc5-6)cccc43)cc21]

HTM8

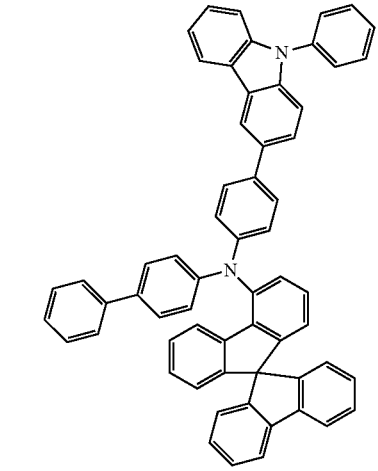 [SMILES: c1ccc(-c2ccc(N(c3ccc(-c4ccc5c(c4)c4ccccc4n5-c4ccccc4)cc3)c3cccc4c3-c3ccccc3C43c4ccccc4-c4ccccc43)cc2)cc1]

HTM9

TABLE 5-continued

Structures of the materials used

HTM10

HTM11

Example 2

In a different blue fluorescent device structure (Table 6) the reference devices V5 and V6, using materials according to the state of the art (NPB and HTMV1), have lower efficiencies (EQE @ 10 mA/cm$^2$ of 6.2% for V5 and 5.8% for V6) compared to the devices comprising the compounds according to the invention E3 (8.5%), E4 (8.3%), E5 (7.9%), E6 (7.6%), E7 (7.8%), E8 (8.9%), E9 (8.4%), E10 (8.1%) and E11 (8.2%).

The reference samples V5 and V6 have also lower lifetimes (V5 of 120 h (LT80 @ 60 mA) and V6 of 105 h) compared to the samples E3 (305 h), E4 (290 h), E5 (320 h), E6 (390 h), E7 (365 h), E8 (165 h), E9 (280 h), E10 (285 h) and E11 (340 h).

Example 3

In a different green phosphorescent device structure (Table 6), the reference device V7 has lower efficiency (EQE @ 2 mA/cm$^2$) of 11.7% compared to the samples comprising the compounds according to the invention E12 (20.0%), E13 (19.6%), E14 (18.9%), E15 (19.2%) and E16 (20.2%). The reference sample V6 has also lower lifetime of 80 h (LT80 @ 20 mA) compared to the samples E12 (90 h), E13 (185 h), E14 (105 h), E15 (205 h) and E16 (185 h).

TABLE 6

Structure of the OLEDs

| Bsp. | HIL1 Dicke/nm | HTL Dicke/nm | HIL2 Dicke/nm | EBL Dicke/nm | EML Dicke/nm | ETL Dicke/nm | EIL Dicke/nm |
|---|---|---|---|---|---|---|---|
| V5 | HIL3:F4TCNQ(3%) 20 nm | HIL3 155 nm | NPB:F4TCNQ(3%) 20 nm | NPB 20 nm | H1:SEB1(5%) 20 nm | ETM2(50%):LiQ(50%) 30 nm | LiQ 1 nm |
| V6 | HIL3:F4TCNQ(3%) 20 nm | HIL3 155 nm | HTMV1:F4TCNQ(3%) 20 nm | HTMV1 20 nm | H1:SEB1(5%) 20 nm | ETM2(50%):LiQ(50%) 30 nm | LiQ 1 nm |
| E3 | HIL3:F4TCNQ(3%) 20 nm | HIL3 155 nm | HTM2:F4TCNQ(3%) 20 nm | HTM2 20 nm | H1:SEB1(5%) 20 nm | ETM2(50%):LiQ(50%) 30 nm | LiQ 1 nm |
| E4 | HIL3:F4TCNQ(3%) 20 nm | HIL3 155 nm | HTM3:F4TCNQ(3%) 20 nm | HTM3 20 nm | H1:SEB1(5%) 20 nm | ETM2(50%):LiQ(50%) 30 nm | LiQ 1 nm |
| E5 | HIL3:F4TCNQ(3%) 20 nm | HIL3 155 nm | HTM4:F4TCNQ(3%) 20 nm | HTM4 20 nm | H1:SEB1(5%) 20 nm | ETM2(50%):LiQ(50%) 30 nm | LiQ 1 nm |
| E6 | HIL3:F4TCNQ(3%) 20 nm | HIL3 155 nm | HTM5:F4TCNQ(3%) 20 nm | HTM5 20 nm | H1:SEB1(5%) 20 nm | ETM2(50%):LiQ(50%) 30 nm | LiQ 1 nm |
| E7 | HIL3:F4TCNQ(3%) 20 nm | HIL3 155 nm | HTM6:F4TCNQ(3%) 20 nm | HTM6 20 nm | H1:SEB1(5%) 20 nm | ETM2(50%):LiQ(50%) 30 nm | LiQ 1 nm |
| E8 | HIL3:F4TCNQ(3%) 20 nm | HIL3 155 nm | HTM7:F4TCNQ(3%) 20 nm | HTM7 20 nm | H1:SEB1(5%) 20 nm | ETM2(50%):LiQ(50%) 30 nm | LiQ 1 nm |
| E9 | HIL3:F4TCNQ(3%) 20 nm | HIL3 155 nm | HTM8:F4TCNQ(3%) 20 nm | HTM8 20 nm | H1:SEB1(5%) 20 nm | ETM2(50%):LiQ(50%) 30 nm | LiQ 1 nm |
| E10 | HIL3:F4TCNQ(3%) 20 nm | HIL3 155 nm | HTM9:F4TCNQ(3%) 20 nm | HTM9 20 nm | H1:SEB1(5%) 20 nm | ETM2(50%):LiQ(50%) 30 nm | LiQ 1 nm |
| E11 | HIL3:F4TCNQ(3%) 20 nm | HIL3 155 nm | HTM10:F4TCNQ(3%) 20 nm | HTM10 20 nm | H1:SEB1(5%) 20 nm | ETM2(50%):LiQ(50%) 30 nm | LiQ 1 nm |
| V7 | HIL3:F4TCNQ(3%) 20 nm | HIL3 210 nm | NPB:F4TCNQ(3%) 20 nm | NPB 20 nm | H2:TEG(10%) 30 nm | ETM2(50%):LiQ(50%) 40 nm | LiQ 1 nm |
| E12 | HIL3:F4TCNQ(3%) 20 nm | HIL3 210 nm | HTM2:F4TCNQ(3%) 20 nm | HTM2 20 nm | H2:TEG(10%) 30 nm | ETM2(50%):LiQ(50%) 40 nm | LiQ 1 nm |
| E13 | HIL3:F4TCNQ(3%) 20 nm | HIL3 210 nm | HTM3:F4TCNQ(3%) 20 nm | HTM3 20 nm | H2:TEG(10%) 30 nm | ETM2(50%):LiQ(50%) 40 nm | LiQ 1 nm |
| E14 | HIL3:F4TCNQ(3%) 20 nm | HIL3 210 nm | HTM4:F4TCNQ(3%) 20 nm | HTM4 20 nm | H2:TEG(10%) 30 nm | ETM2(50%):LiQ(50%) 40 nm | LiQ 1 nm |
| E15 | HIL3:F4TCNQ(3%) 20 nm | HIL3 210 nm | HTM5:F4TCNQ(3%) 20 nm | HTM5 20 nm | H2:TEG(10%) 30 nm | ETM2(50%):LiQ(50%) 40 nm | LiQ 1 nm |
| E16 | HIL3:F4TCNQ(3%) 20 nm | HIL3 210 nm | HTM6:F4TCNQ(3%) 20 nm | HTM6 20 nm | H2:TEG(10%) 30 nm | ETM2(50%):LiQ(50%) 40 nm | LiQ 1 nm |

TABLE 7

Structure of the OLEDs

| Bsp. | HIL1 Dicke/nm | HTL Dicke/nm | EBL Dicke/nm | EML Dicke/nm | HBL Dicke/nm | ETL Dicke/nm | EIL Dicke/nm |
|---|---|---|---|---|---|---|---|
| V8 | HIL3:F4TCNQ(3%) 20 nm | HIL3 230 nm | | H3:TEG(10%) 40 nm | H2 5 nm | ETM2(50%):LiQ(50%) 25 nm | |
| E17 | HIL3:F4TCNQ(3%) 20 nm | HIL3 230 nm | | H3:HTM3(60%):TEG(10%) 40 nm | H2 5 nm | ETM2(50%):LiQ(50%) 25 nm | |
| V9 | HIL3:F4TCNQ(3%) 20 nm | HIL3 220 nm | HTM3 10 nm | H4:TEG(10%) 40 nm | | ETM2(50%):LiQ(50%) 30 nm | LiQ 1 nm |
| E18 | HIL3:F4TCNQ(3%) 20 nm | HIL3 220 nm | HTM3 10 nm | H4:HTM4(10%):TEG(10%) 40 nm | | ETM2(50%):LiQ(50%) 30 nm | LiQ 1 nm |
| E19 | HIL3:F4TCNQ(3%) 20 nm | HIL3 220 nm | HTM3 10 nm | H4:HTM11(45%):TEG(10%) 40 nm | | ETM2(50%):LiQ(50%) 30 nm | LiQ 1 nm |

Use of Compounds According to the Invention as Matrix Materials in Phosphorescent OLEDs Example 4

In a different green phosphorescent device structure (Table 7), the reference device V8, which does not have the compound according to the invention as a matrix material of the emitting layer, has lower efficiency (EQE @ 2 mA/cm$^2$ of 14.4%) compared to the sample E17 comprising the compound according to the invention HTM3 (EQE @ 2 mA/cm$^2$ of 16.1%), used as a mixed matrix component in the EML. The reference sample V8 has also lower lifetime of 305 h (LT80 @ 20 mA) compared to sample E17 of 330 h.

Example 5

In a different green phosphorescent device structure (Table 7) it is shown that the compounds according to the invention show favorable effects as a mixed matrix component in the emitting layer, in combination with a lactam compound H4. The reference device V9 has an efficiency (EQE @ 2 mA/cm$^2$) of 17.6% and a lifetime of 255 h. Lifetime can be improved by adding a compound according to the invention to the emitting layer as a co-matrix material, as shown by examples E18 and E19 compared to V9. Device E18 shows an efficiency of 13.4% and a lifetime of 400 h, and device E19 shows an efficiency of 17.9% and a lifetime of 270 h, which are both improvements compared to reference device V9.

The invention claimed is:
1. A compound of the formula

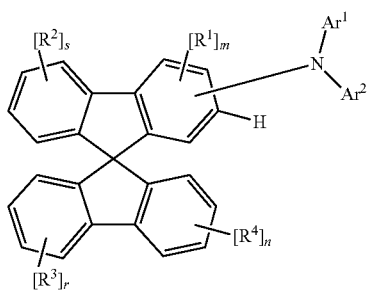

where the following applies to the symbols and indices used:

$Ar^1$ is selected from the group consisting of fluorene, biphenyl, terphenyl, quaterphenyl, dibenzofuran and dibenzothiophene, each of which is optionally substituted by one or more radicals $R^5$;

$Ar^2$ is selected from any one of formulae (11) to (27)

formula (11)
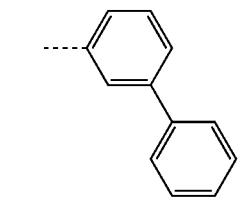

formula (12)
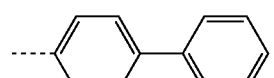

formula (13)

formula (14)
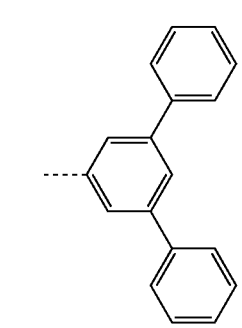

formula (15)
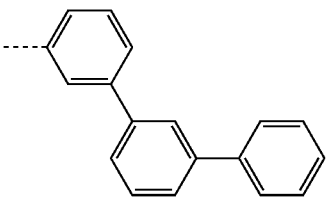

formula (16)
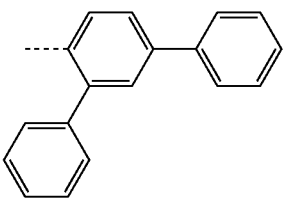

formula (17)
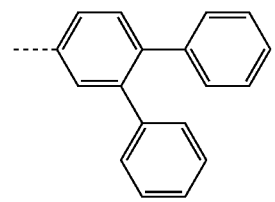

formula (18)
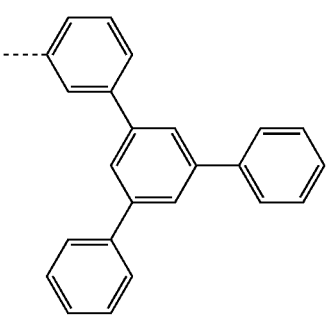

formula (19)
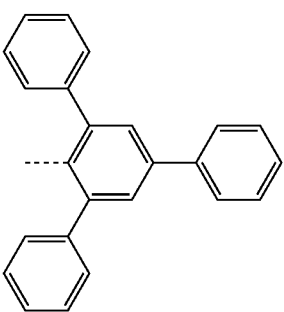

formula (20)
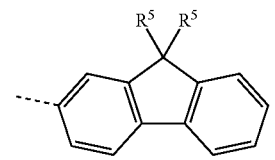

formula (21)
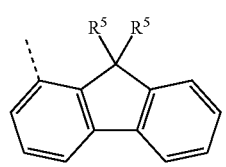

-continued formula (22)
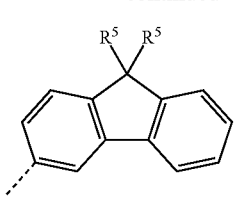

formula (23)
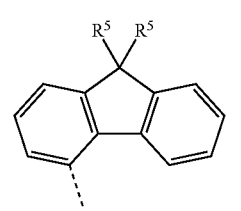

formula (24)
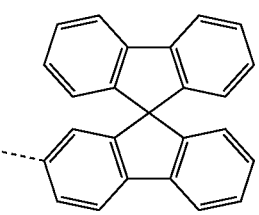

formula (25)
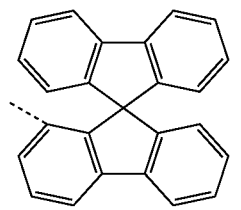

formula (26)
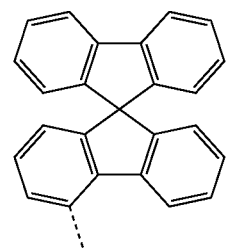

formula (27)
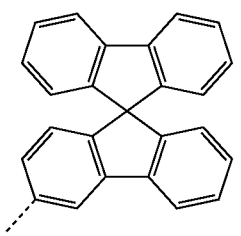

where the dashed bond indicates the bond to the nitrogen, and the groups are optionally substituted by one or more radicals $R^5$;

$R^1$, $R^2$, $R^3$, $R^4$ are on each occurrence, identically or differently, selected from the group consisting of H, D, F, Cl, Br, I, CN, $Si(R^6)_3$, a straight-chain alkyl, alkoxy or thioalkyl group having 1 to 40 C atoms, and a branched alkyl, alkoxy or thioalkyl group having 3 to 40 C atoms, and a cyclic alkyl group having 3 to 40 C atoms, each of which optionally is substituted by one or more radicals $R^6$, where in each case one or more non-adjacent $CH_2$ groups optionally is replaced by $Si(R^6)_2$, $C=NR^6$, $P(=O)(R^6)$, SO, $SO_2$, $NR^6$, O, S or $CONR^6$ and where one or more H atoms optionally is replaced by D, F, Cl, Br or I, an aromatic ring system having 6 to 60 C atoms, which may in each case be substituted by one or more radicals $R^6$, an aryloxy or heteroaryloxy group having 5 to 60 aromatic ring atoms, which optionally is substituted by one or more radicals $R^6$, or an aralkyl or heteroaralkyl group having 5 to 60 aromatic ring atoms, which may in each case be substituted by one or more radicals $R^6$, where two or more adjacent substituents $R^1$ or $R^2$ or $R^3$ or $R^4$ may optionally form a mono- or polycyclic, aliphatic ring system, which optionally is substituted by one or more radicals $R^6$;

$R^5$ is on each occurrence, identically or differently, selected from the group consisting of H, D, F, Cl, Br, I, CN, $Si(R^6)_3$, a straight-chain alkyl, alkoxy or thioalkyl group having 1 to 40 C atoms or a branched alkyl, alkoxy, and thioalkyl group having 3 to 40 C atoms, and a cyclic alkyl group having 3 to 40 C atoms, each of which optionally is substituted by one or more radicals $R^6$, where in each case one or more non-adjacent $CH_2$ groups optionally is replaced by $Si(R^6)_2$, $C=NR^6$, $P(=O)(R^6)$, SO, $SO_2$, $NR^6$, O, S or $CONR^6$ and where one or more H atoms optionally is replaced by D, F, Cl, Br or I, an aromatic ring system having 6 to 60 C atoms, which may in each case be substituted by one or more radicals $R^6$, an aryloxy or heteroaryloxy group having 5 to 60 aromatic ring atoms, which optionally is substituted by one or more radicals $R^6$, or an aralkyl or heteroaralkyl group having 5 to 60 aromatic ring atoms, which may in each case be substituted by one or more radicals $R^6$;

$R^6$ is selected from H, D, F, an aliphatic hydrocarbon radical having 1 to 20 C atoms, or an aromatic, or heteroaromatic, ring system having 5 to 30 C atoms, in which one or more H atoms optionally is replaced by D or F, where two or more adjacent substituents $R^6$ may form a mono- or polycyclic, aliphatic ring system with one another;

m is 0, 1 or 2;

n is on each occurrence, identically or differently, 0, 1, 2, 3 or 4; and r, s are on each occurrence, identically or differently, 0, 1, 2, 3 or 4.

2. The compound according to claim 1, wherein $Ar^2$ is selected from the groups of formulae (11), (20) or (24), which are optionally substituted by one or more radicals $R^5$.

3. The compound according to claim 1, wherein the groups $Ar^1$ and $Ar^2$ are different from one another.

4. The compound according to claim 1, wherein $R^1$ to $R^4$ are selected, identically or differently on each occurrence, from the group consisting of H, F, CN, a straight-chain alkyl or alkoxy group having 1 to 10 C atoms, a branched alkyl or alkoxy group having 3 to 10 C atoms, and a cyclic alkyl group having 3 to 10 C atoms, each of which optionally is substituted by one or more radicals $R^6$, where one or more non-adjacent $CH_2$ groups optionally is replaced by O and where one or more H atoms optionally is replaced by F, and an aromatic ring system having 6 to 24 aromatic ring atoms, which may in each case he substituted by one or more radicals $R^6$.

5. The compound according to claim 1, wherein the radical $R^5$ which is bonded to $Ar^1$ or $Ar^2$ is identically or differently on each occurrence, selected from the group consisting of H, F, CN, a straight-chain alkyl group having 1 to 10 C atoms, a branched or cyclic alkyl group having 3 to 10 C atoms, and an aromatic system having 5 to 24 aromatic ring atoms, each of which optionally is substituted by one or more radicals $R^6$.

6. The compound according to claim 1, wherein $R^1$, $R^2$, $R^3$, $R^4$ are on each occurrence, identically or differently, selected from the group consisting of H, D, F, Cl, Br, I, CN, $Si(R^6)_3$, a straight-chain alkyl, alkoxy or thioalkyl group having 1 to 40 C atoms, a branched alkyl, alkoxy or thioalkyl group having 3 to 40 C atoms, and a cyclic alkyl group having 3 to 40 C atoms, each of which optionally is substituted by one or more radicals $R^6$, where in each case one or more non-adjacent $CH_2$ groups optionally is replaced by $Si(R^6)_2$, $C=NR^6$, $P(=O)(R^6)$, SO, $SO_2$, $NR^6$, O, S or $CONR^6$ and where one or more H atoms optionally is replaced by D, F, Cl, Br or I, an aromatic ring system having 6 to 60 C atoms, which may in each case be substituted by one or more radicals $R^6$, an aryloxy or heteroaryloxy group having 5 to 60 aromatic ring atoms, which optionally is substituted by one or more radicals $R^6$, and an aralkyl or heteroaralkyl group having 5 to 60 aromatic ring atoms, which may in each case be substituted by one or more radicals $R^6$; and $R^6$ is selected from H, D, F, an aliphatic hydrocarbon radical having 1 to 20 C atoms, or an aromatic or heteroaromatic ring system having 5 to 30 C atoms, in which one or more H atoms optionally is replaced by D or F.

7. A process for the preparation of the compound according to claim 1, which comprises introducing the diarylamino group $—NAr^1 Ar^2$ by a C—N coupling reaction between a 1- or 3- or 4-halogenated spirobifluorene of the formula

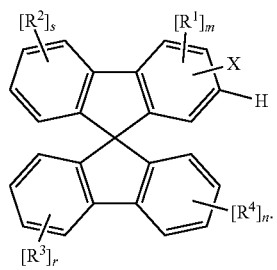

wherein X is halogen, and
a diarylamine of the formula $HNAr^1Ar^2$.

8. An electronic device which comprises the compound according to claim 1.

9. The electronic device as claimed in claim 8, wherein the device is selected from the group consisting of an organic electroluminescent device, an organic integrated circuit, an organic field-effect transistor, an organic thin-film transistor, an organic light-emitting transistor, an organic solar cell, an organic dye-sensitised solar cell, an organic optical detector, an organic photoreceptor, an organic field-quench device, a light-emitting electrochemical cell, an organic laser diode and an organic plasmon emitting device.

10. An organic electroluminescent device which comprises the compound according to claim 1 comprised as hole-transport material in a hole-transport or hole-injection or exciton-blocking or electron-blocking layer, or as matrix material for fluorescent or phosphorescent emitters in an emitting layer.

* * * * *